(12) United States Patent
Kanderian, Jr. et al.

(10) Patent No.: US 6,589,190 B2
(45) Date of Patent: Jul. 8, 2003

(54) QUANTIFICATION OF MUSCLE TONE

(75) Inventors: Sami S. Kanderian, Jr., Northbridge, CA (US); Randal P. Goldberg, Mountain View, CA (US); Katrina Rieflin Ubell, Ann Arbor, MI (US); Barbara J. De Lateur, Baltimore, MD (US); Louis L. Whitcomb, Baltimore, MD (US); Fred A. Lenz, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 0 days.

(21) Appl. No.: 09/949,411

(22) Filed: Sep. 6, 2001

(65) Prior Publication Data

US 2002/156399 A1 Oct. 24, 2002

Related U.S. Application Data

(60) Provisional application No. 60/230,314, filed on Sep. 6, 2000.

(51) Int. Cl.$^7$ ............ A61B 5/103; A61B 5/117
(52) U.S. Cl. ............................................. 600/587
(58) Field of Search .................... 600/587, 300, 600/595, 594; 73/379.01, 379.02; 601/33, 40, 23; 482/44

(56) References Cited

U.S. PATENT DOCUMENTS

| 5,050,618 A | 9/1991 | Larsen ............... 128/774 |
| 5,170,777 A | 12/1992 | Reddy et al. ............ 128/25 |
| 5,713,370 A | 2/1998 | Cook ................. 128/774 |
| 5,720,711 A | 2/1998 | Bond et al. ............. 601/23 |
| 5,738,636 A | 4/1998 | Saringer et al. .......... 601/5 |
| 5,788,607 A | 8/1998 | Baker ................. 482/44 |

OTHER PUBLICATIONS

PCT Search Report.

*Primary Examiner*—Max F. Hindenburg
*Assistant Examiner*—Brian Scott Szmal
(74) *Attorney, Agent, or Firm*—Peter F. Corless; Lisa S. Hazzard; Edwards & Angell, LLP

(57) ABSTRACT

A method and device for the quantification of muscle tone, particularly the wrist, wherein non-sinusoidal and non ramp trajectories are used to drive the wrist. Equation 1 is utilized determine the stiffness, viscosity and inertial parameters.

$$\tau_s(t) = K_H \theta(t) + B_H \dot\theta(t) + J_T \ddot\theta(t) + \tau_{off} \quad [\text{Eq. 1}]$$

wherein where $\tau_s$ is the total torque, $\tau_{off}$ is the offset torque, $K_H$ and $B_H$ are the angular stiffness and viscosity of the combined flexor and extensor muscle groups that act on the joint, $J_T$ is the combined inertia of the oscillating appendage, $\theta$ is the angular displacement of the system, and $\dot\theta$ and $\ddot\theta$ are the velocity and acceleration. In accordance with the method, the trajectory $\theta(t)$ is controlled, the torque response $\tau(t)$ is measured and the stiffness, viscosity, and inertial parameters are determined using Equation 1. The method and device are particularly suitable for use on patients with spacisity.

12 Claims, 167 Drawing Sheets

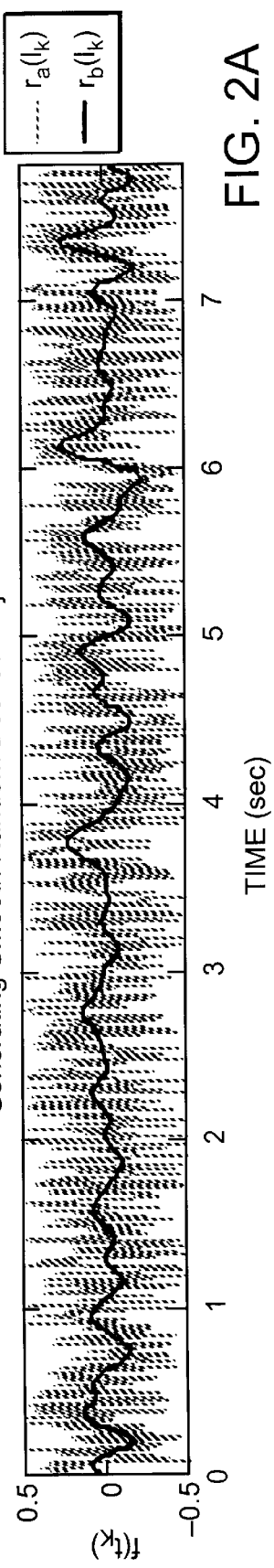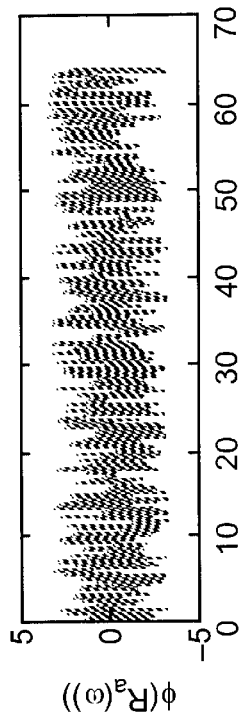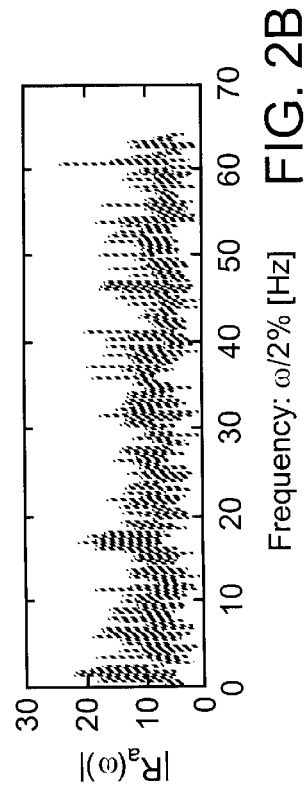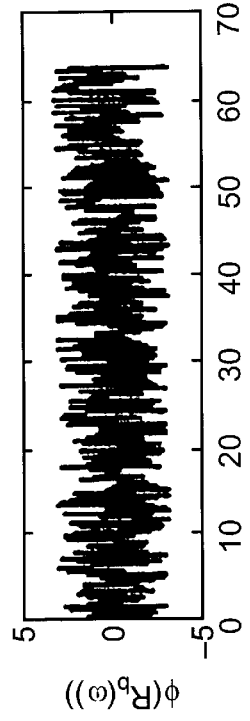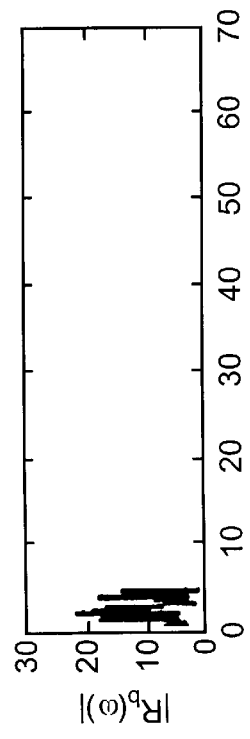

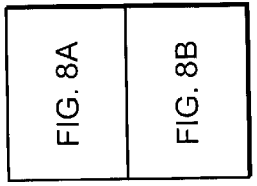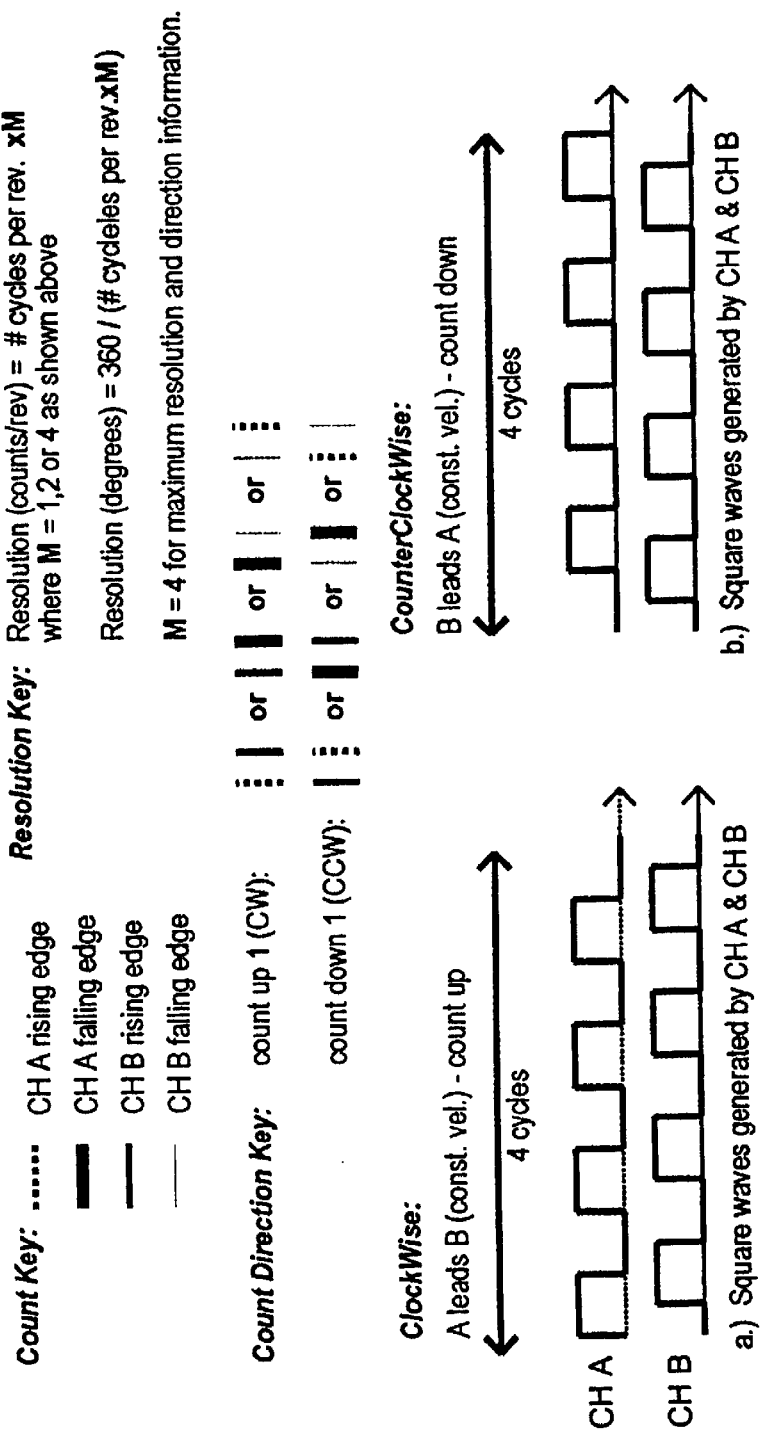
FIG. 8
FIG. 8A

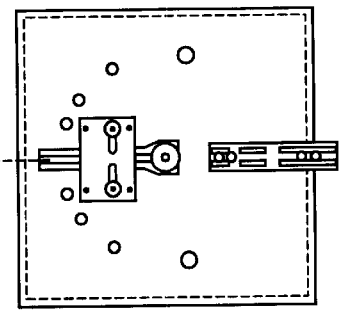
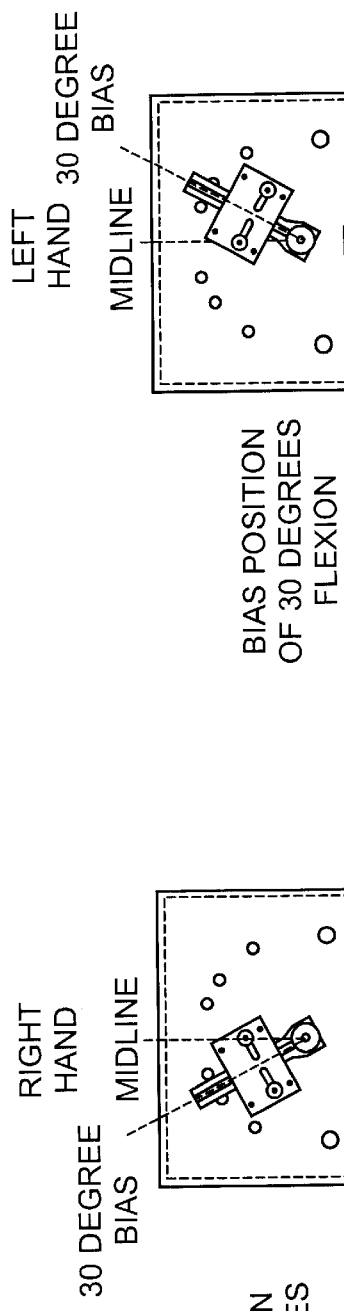
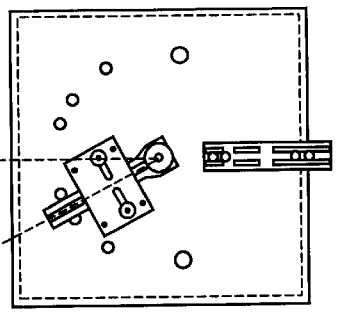
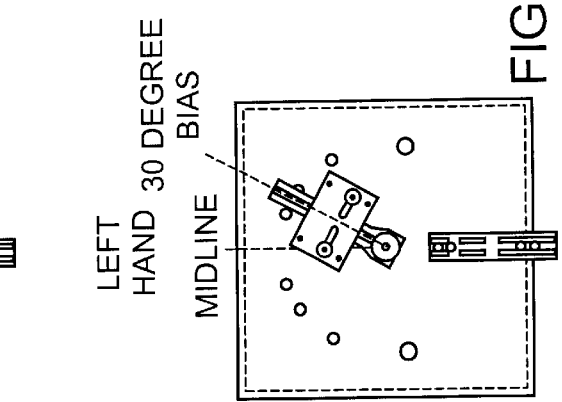
FIG. 17A  BIAS POSITION OF 0 DEGREES  RIGHT HAND MIDLINE & 0 DEGREE BIAS
FIG. 17B  BIAS POSITION OF 0 DEGREES  LEFT HAND MIDLINE & 0 DEGREE BIAS
FIG. 17C  BIAS POSITION OF 30 DEGREES FLEXION  RIGHT HAND MIDLINE  30 DEGREE BIAS
FIG. 17D  BIAS POSITION OF 30 DEGREES FLEXION  LEFT HAND 30 DEGREE BIAS  MIDLINE

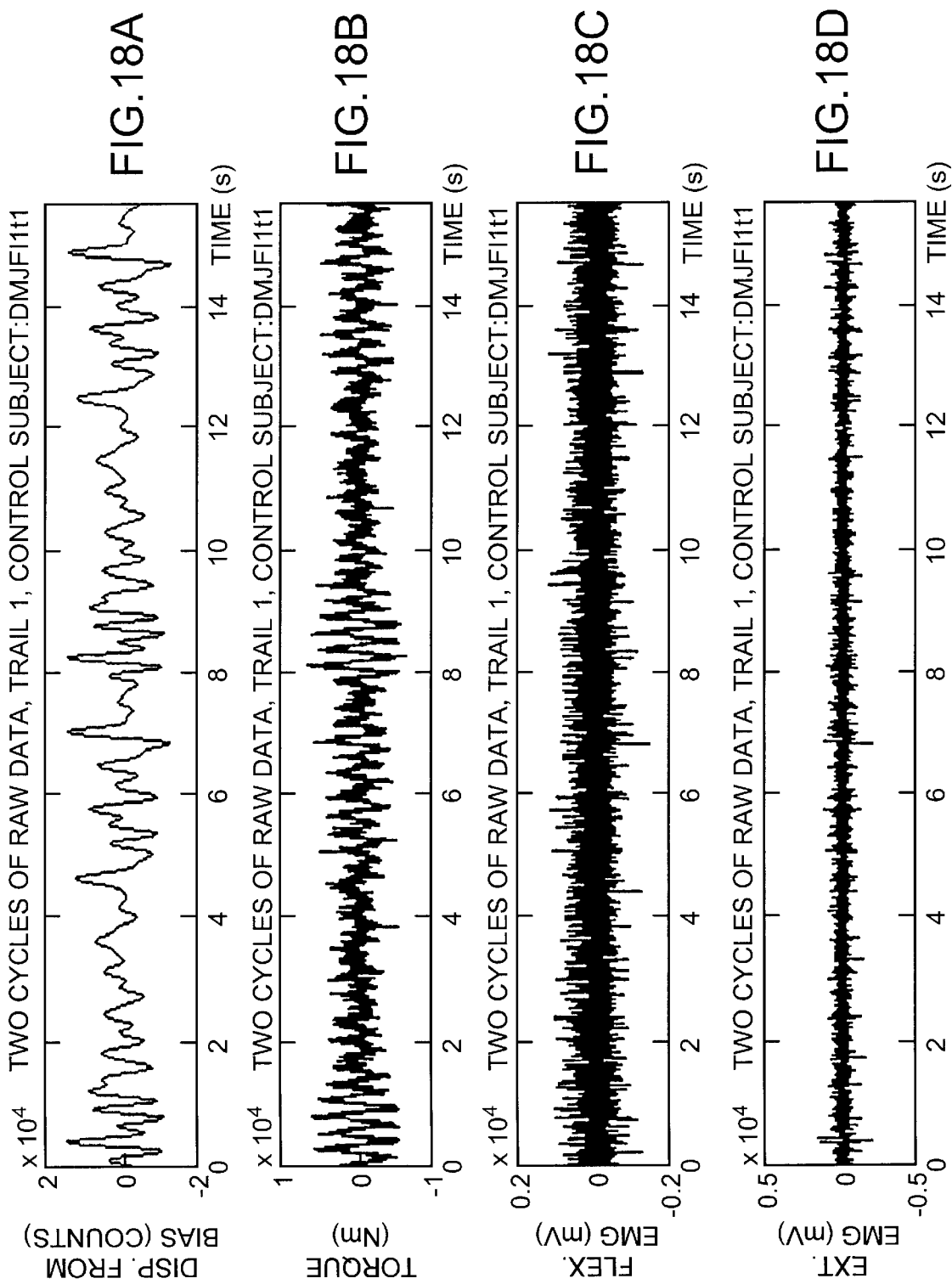

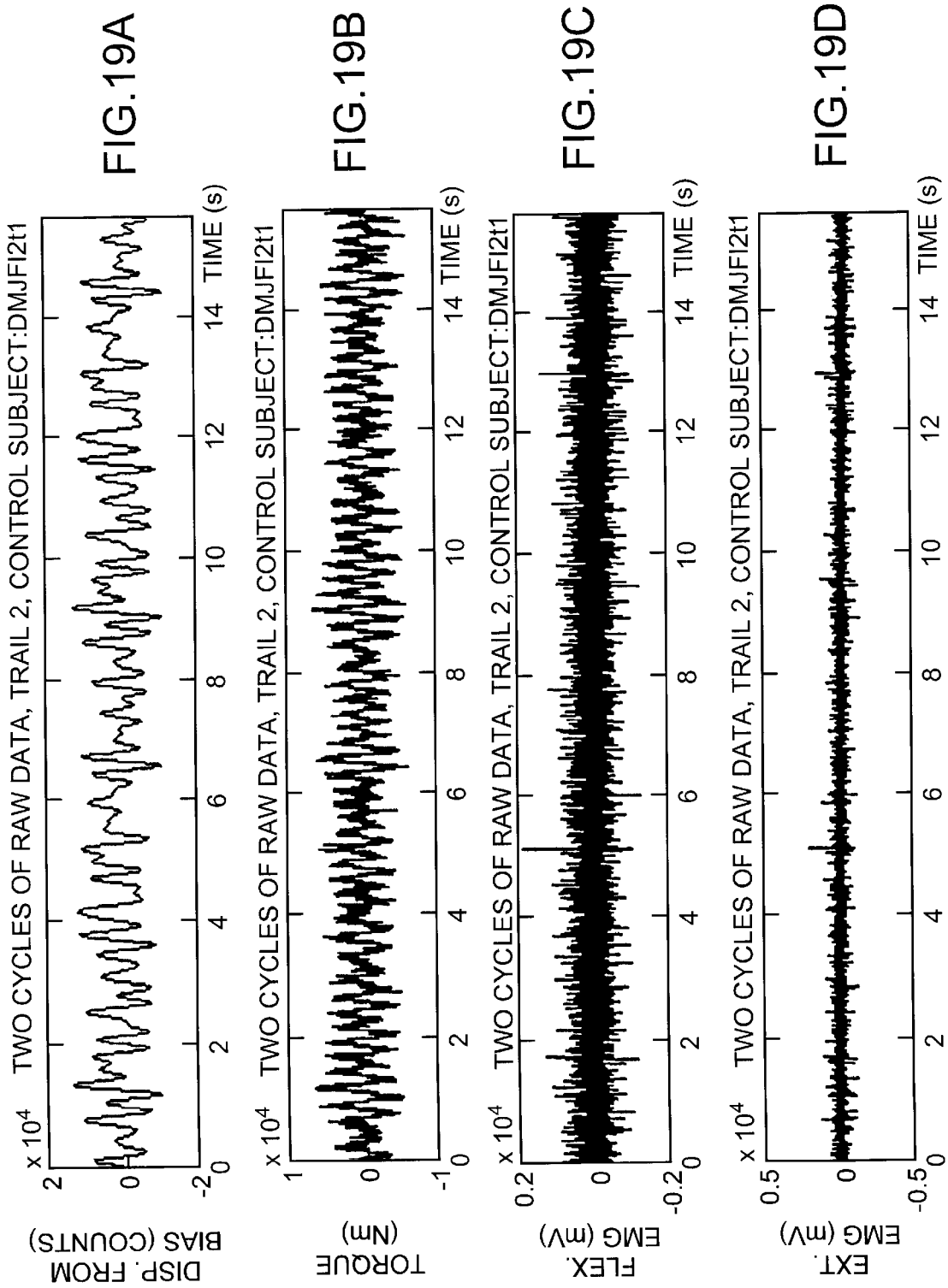

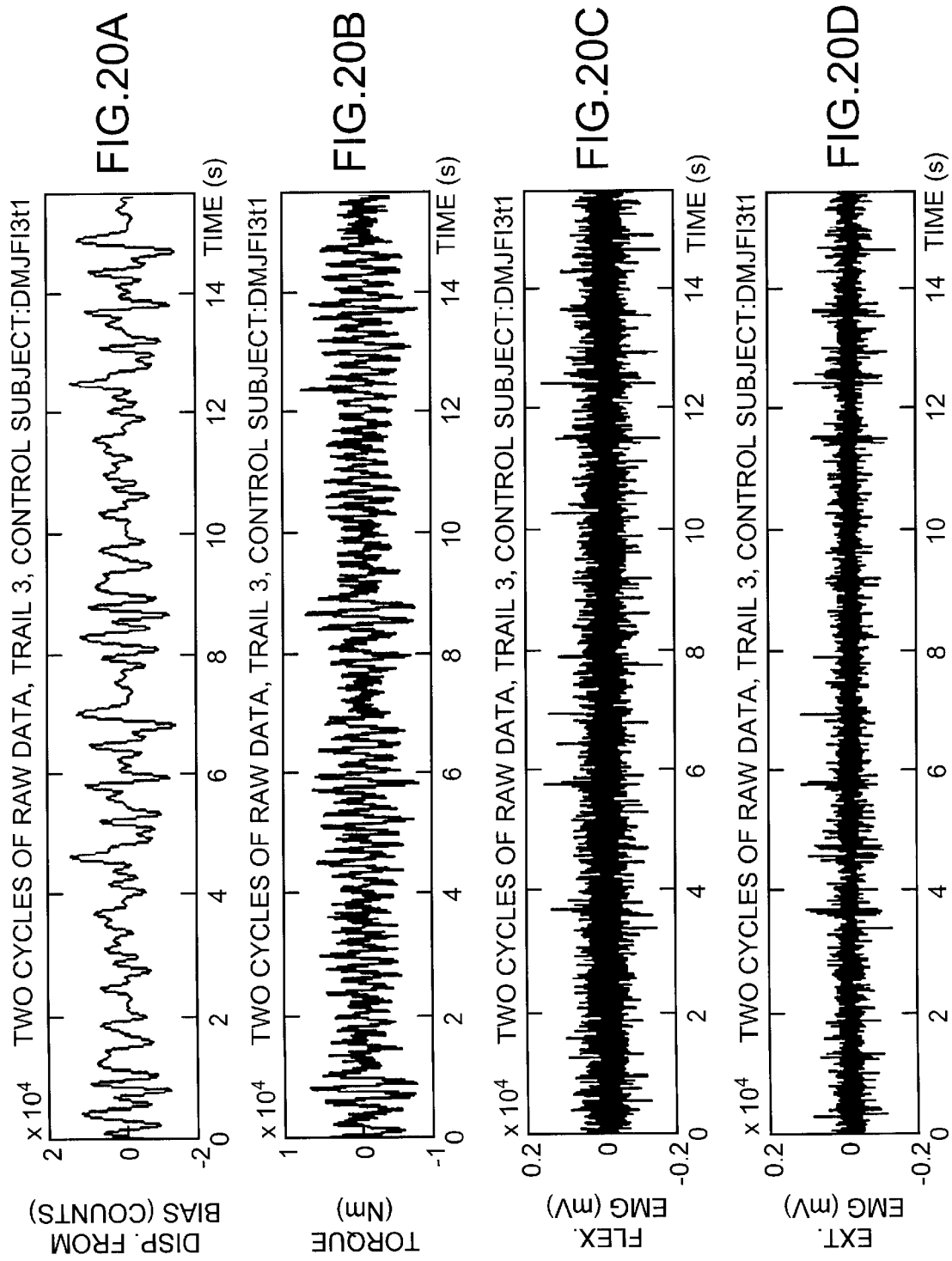

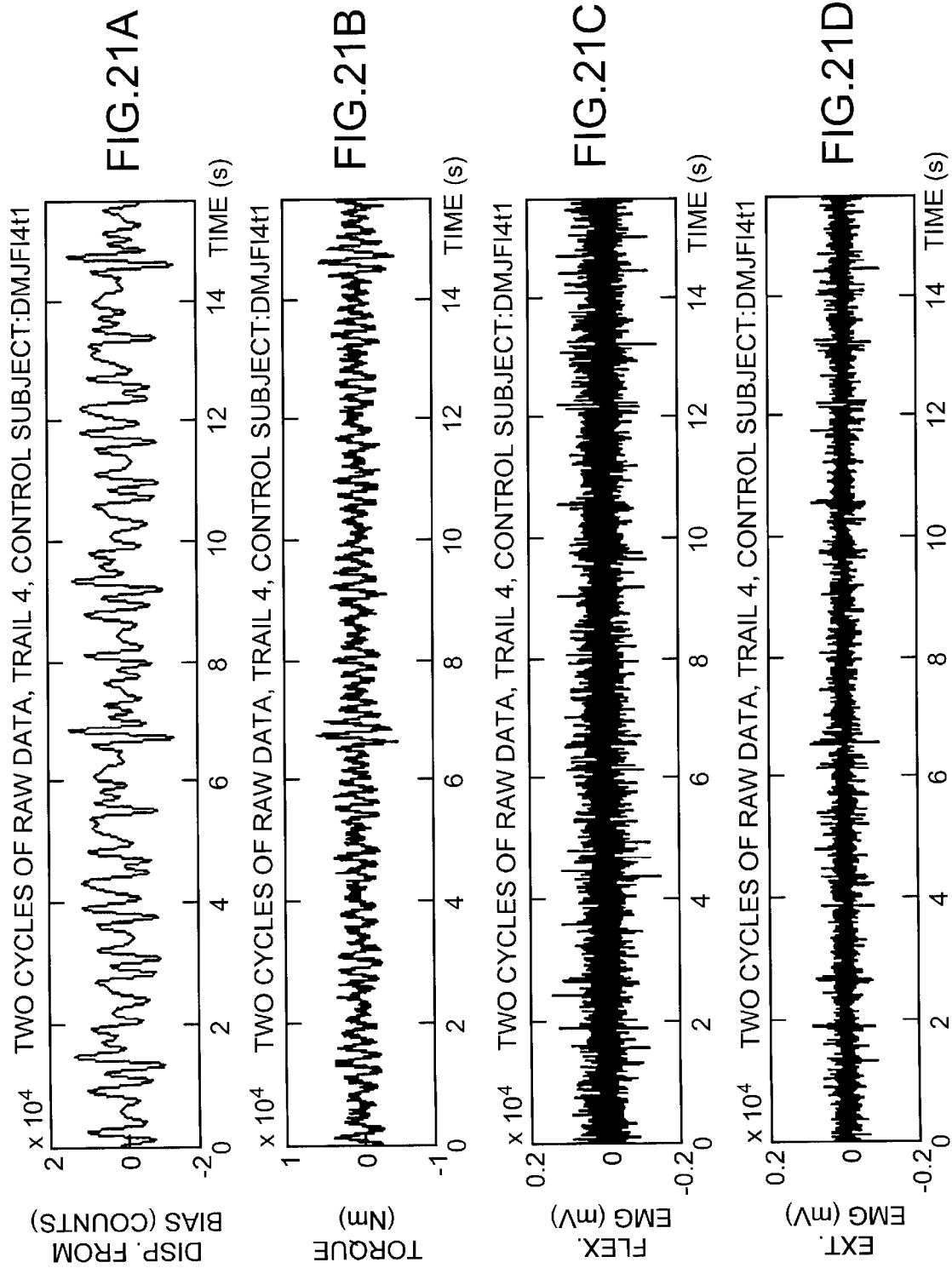

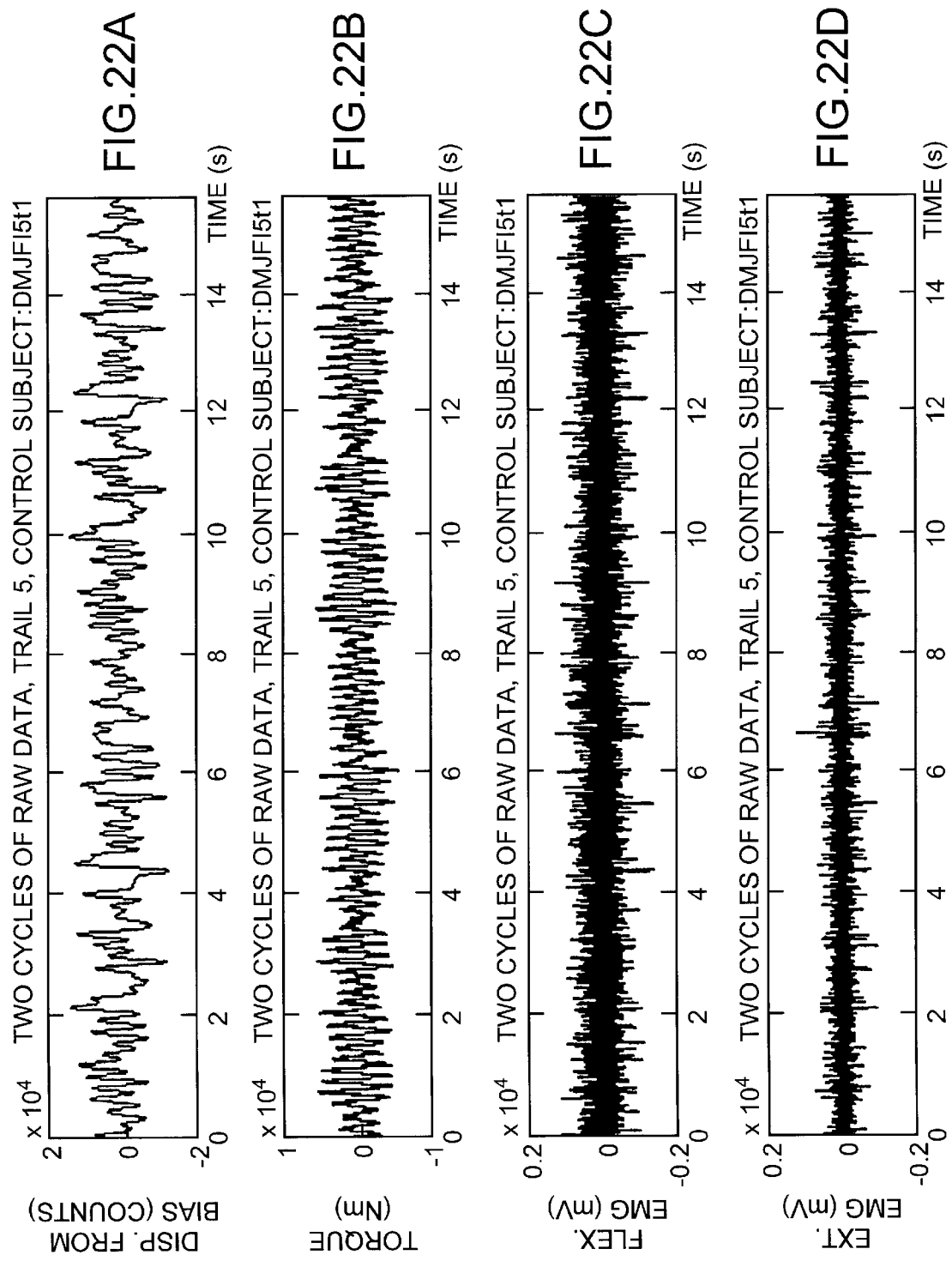

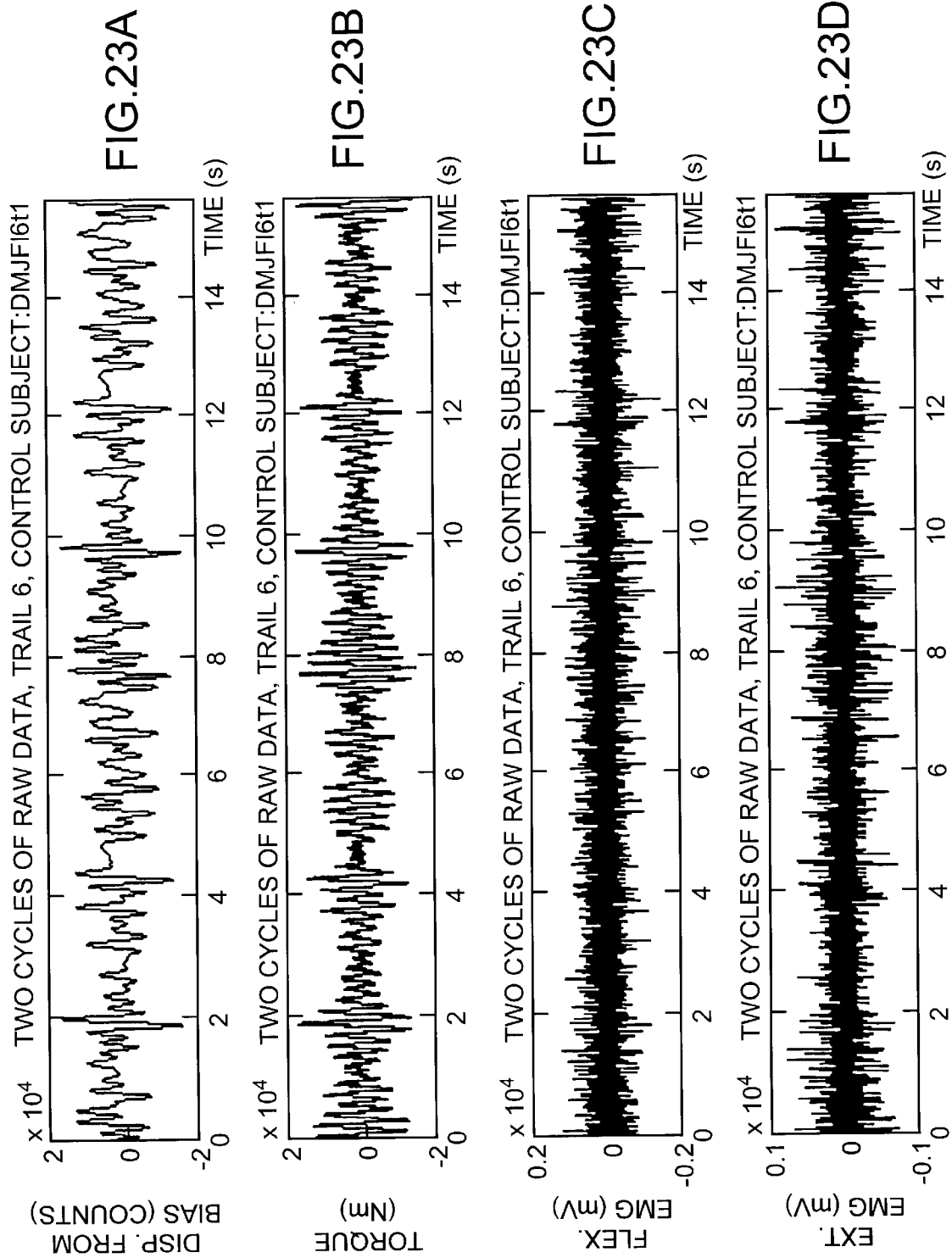

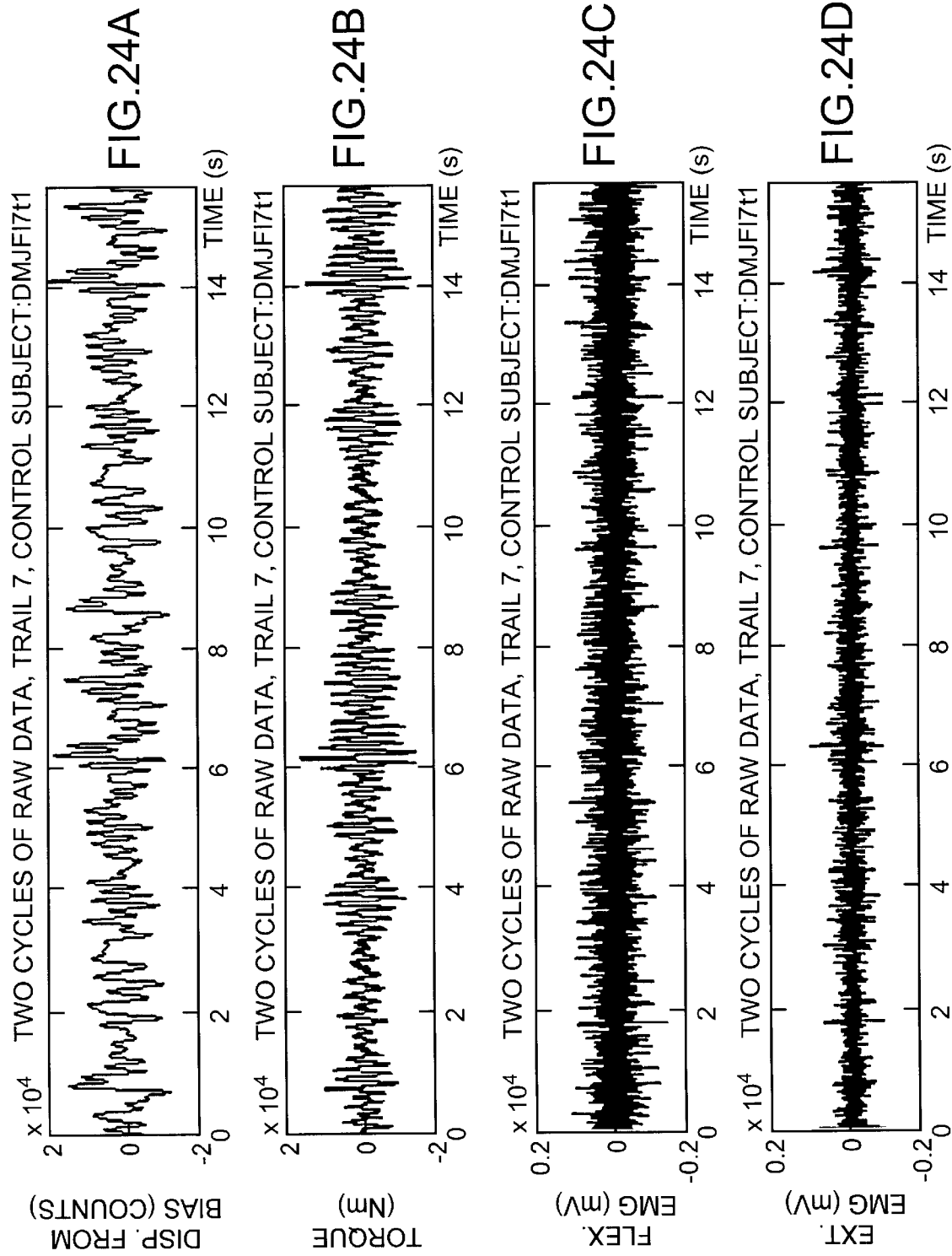

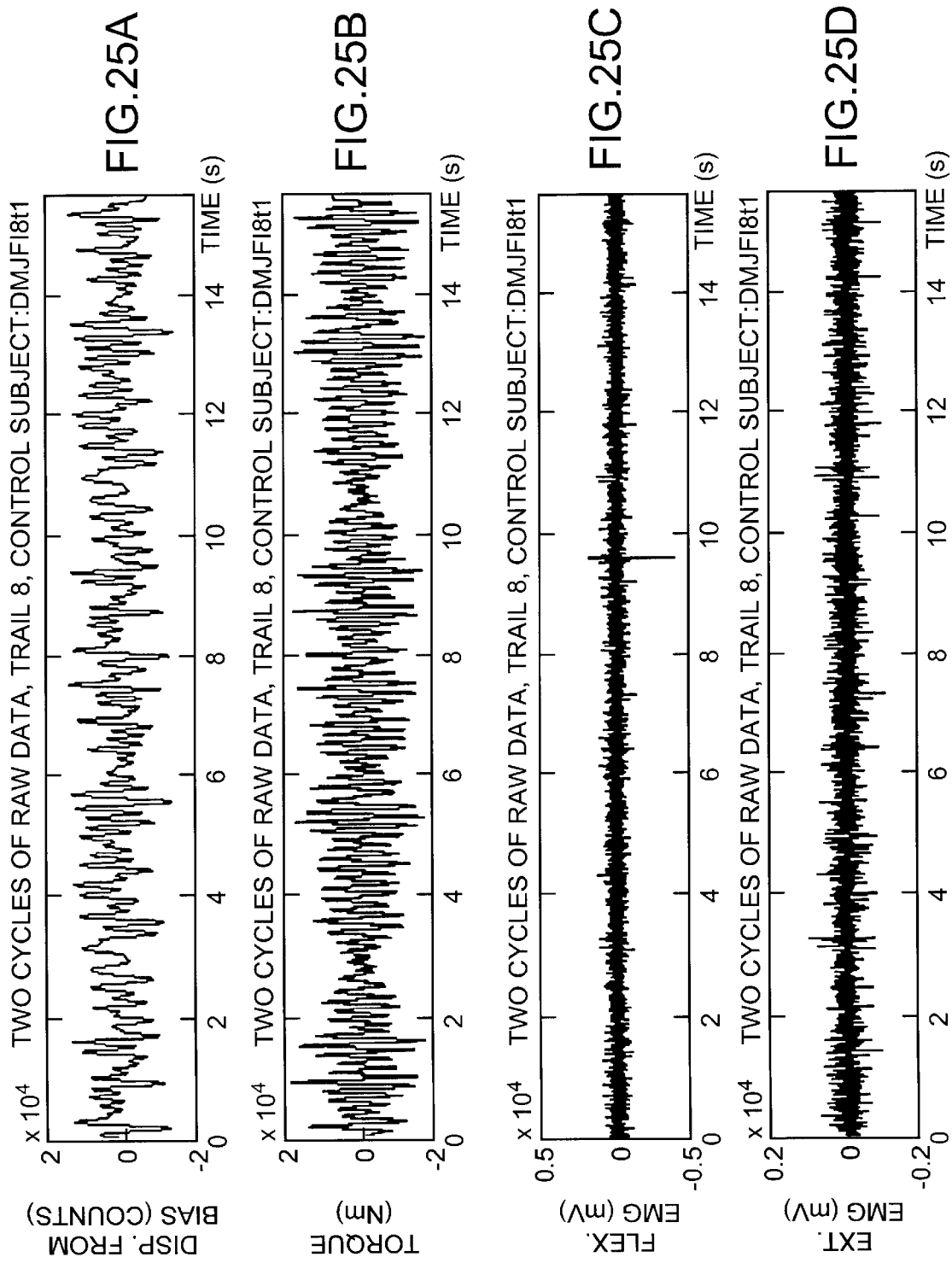

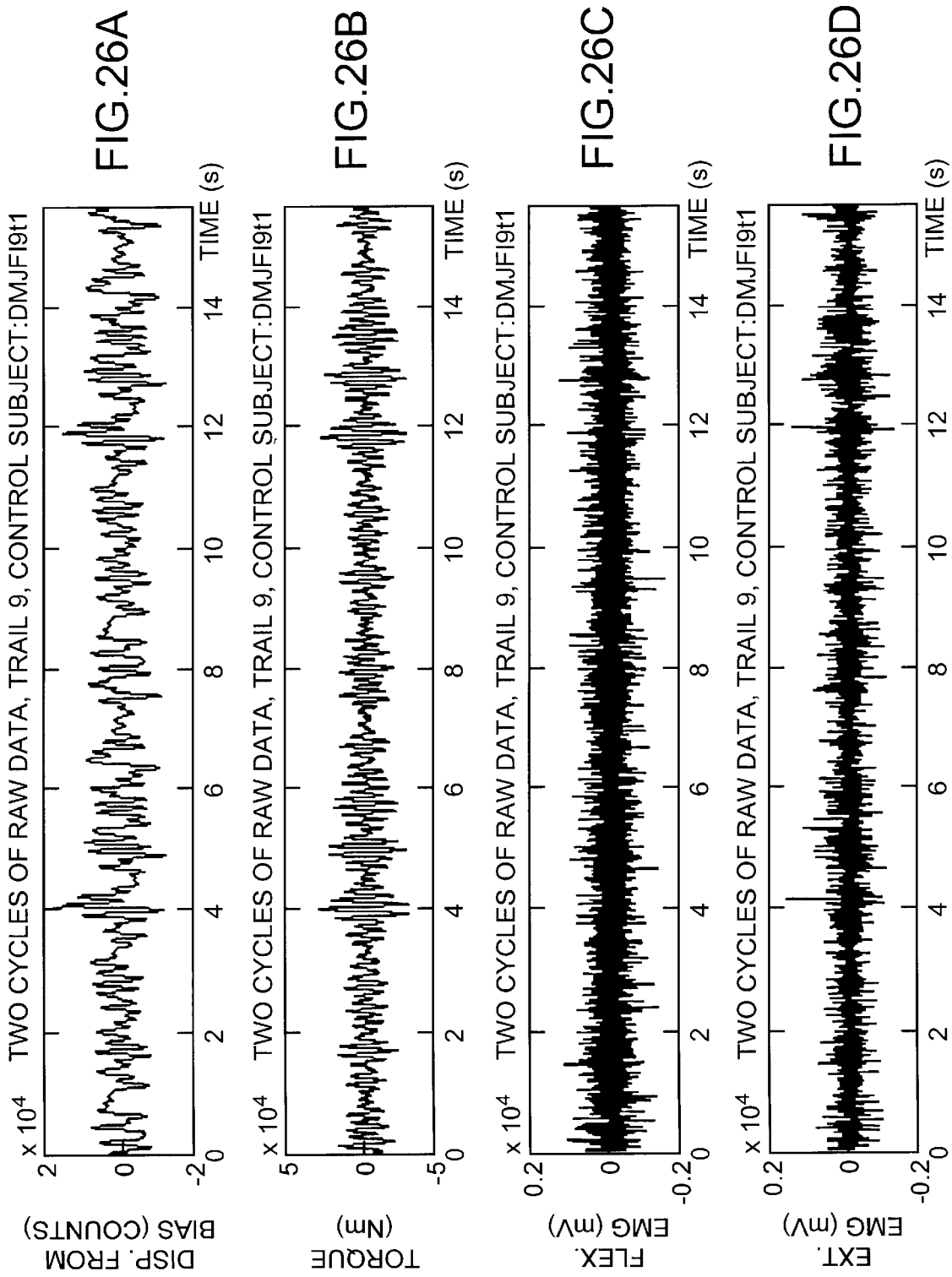

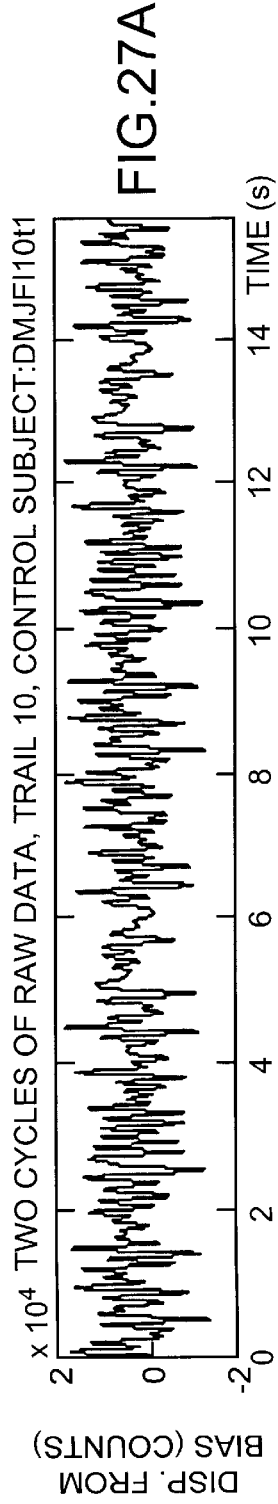
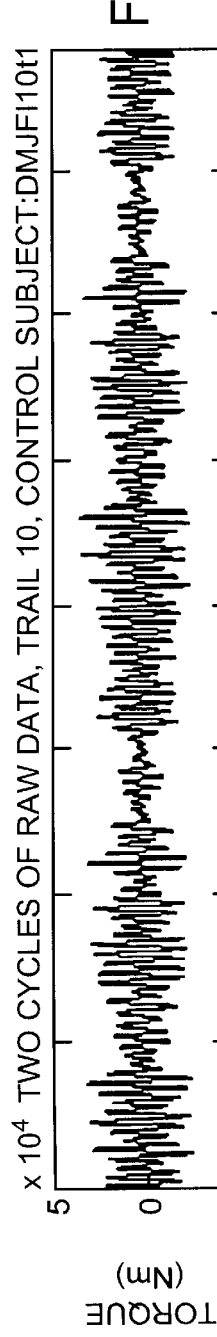
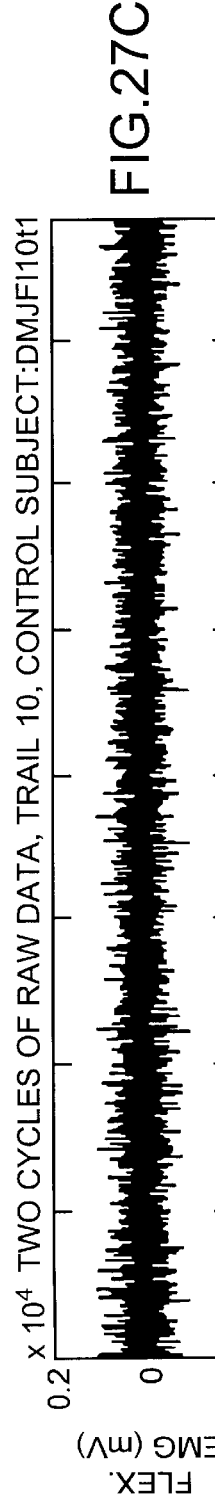
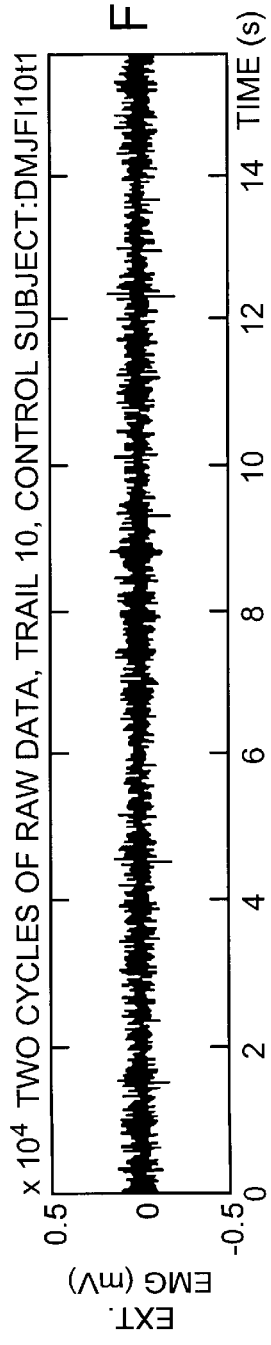
FIG. 27A
FIG. 27B
FIG. 27C
FIG. 27D

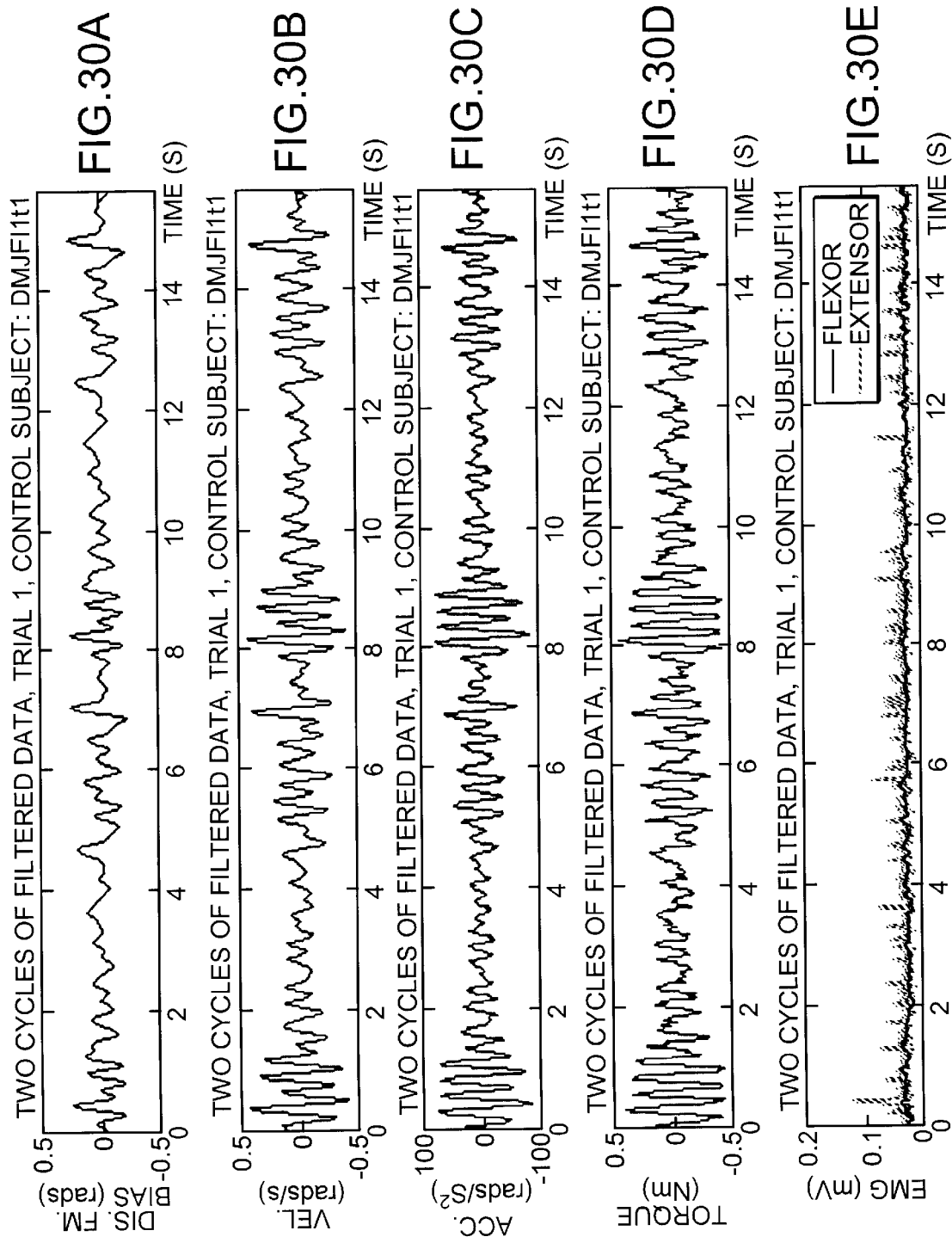

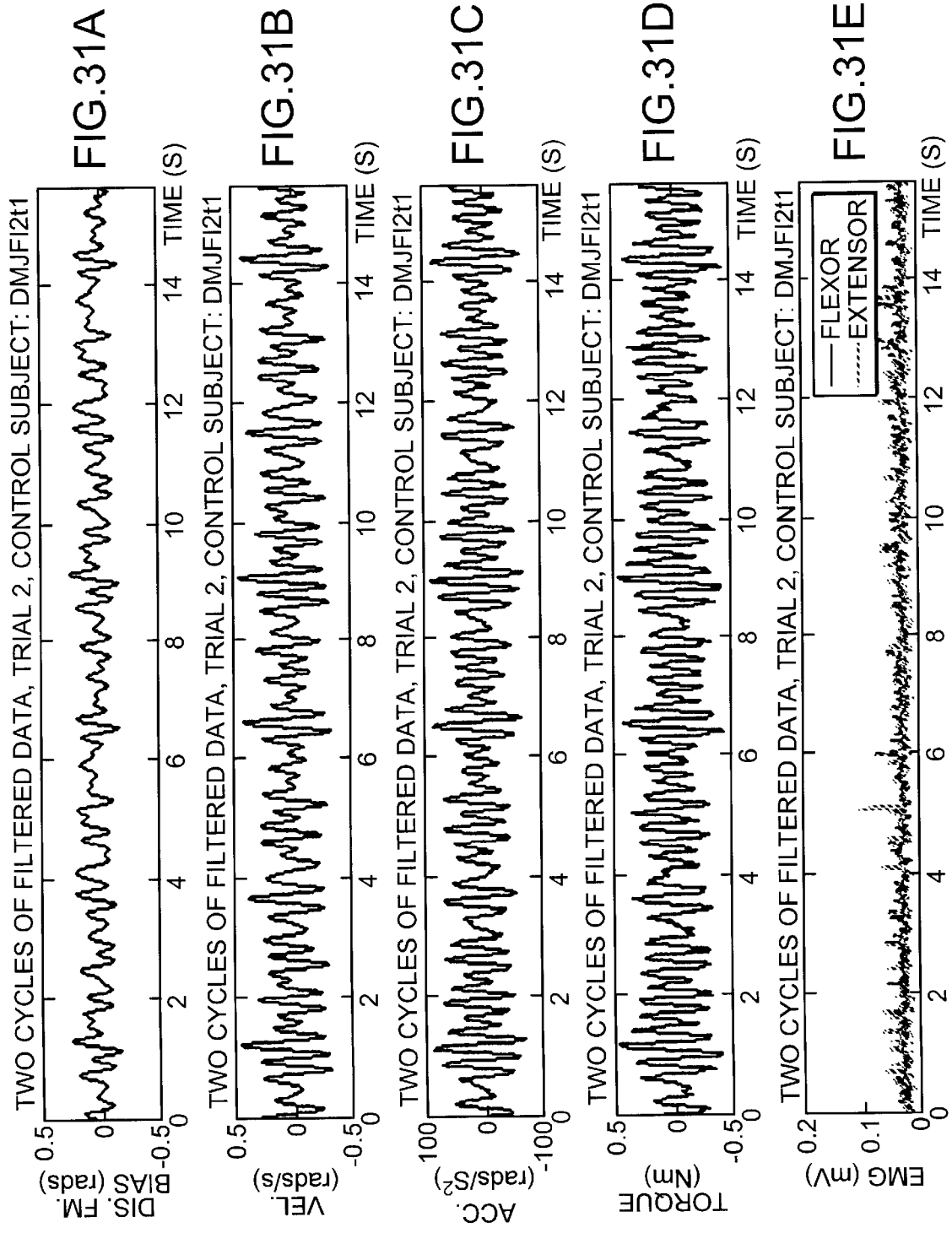

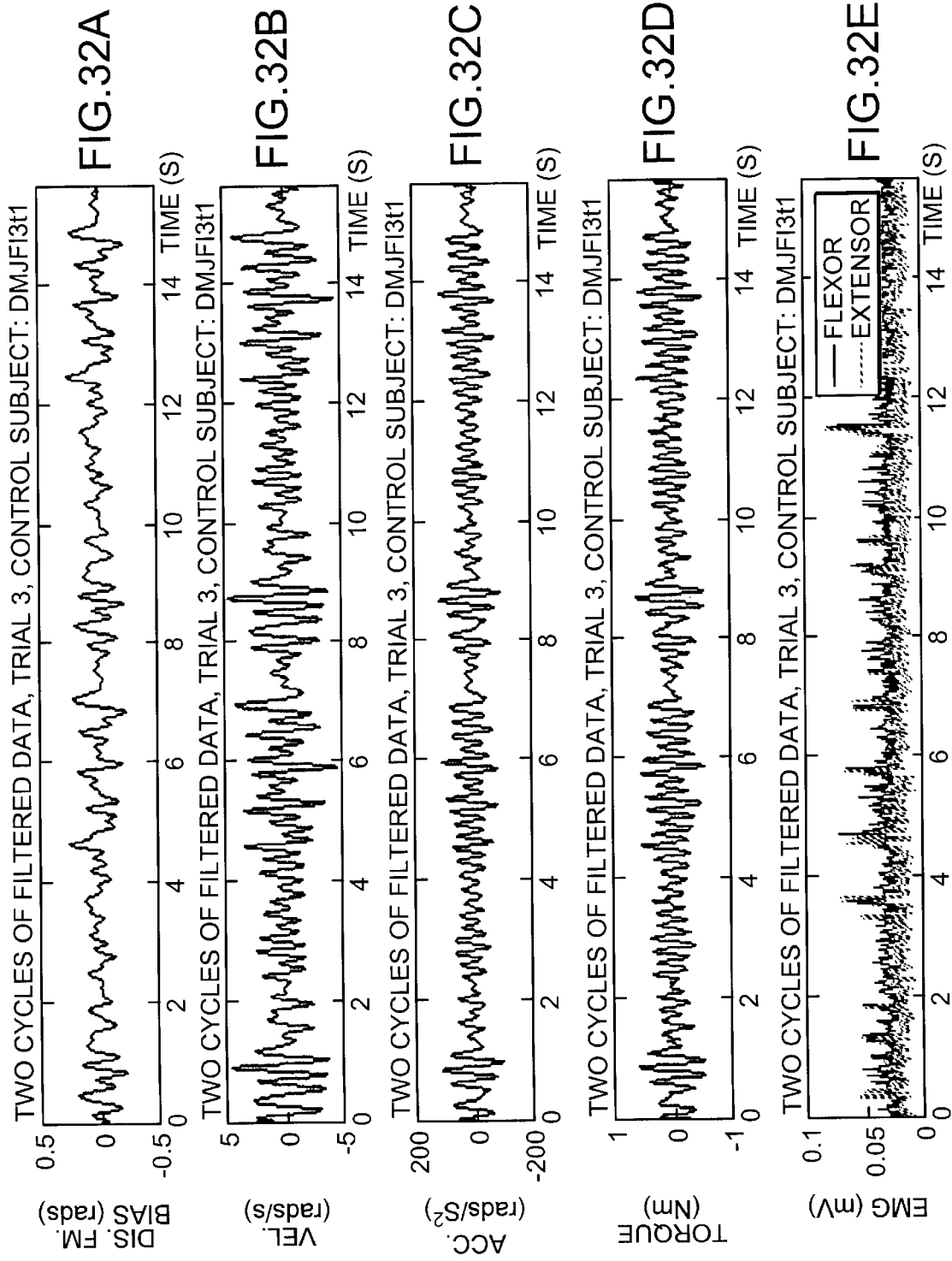

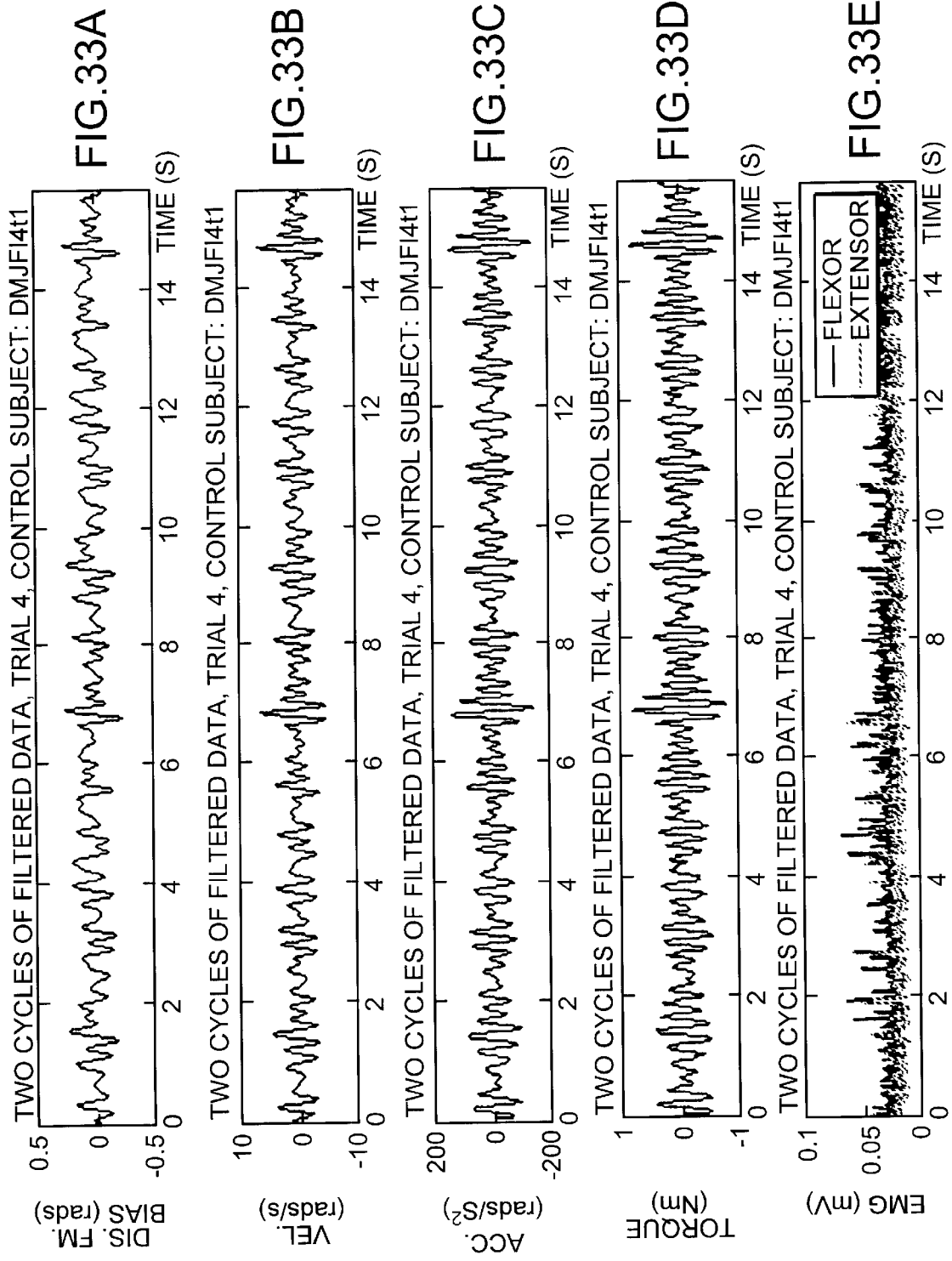

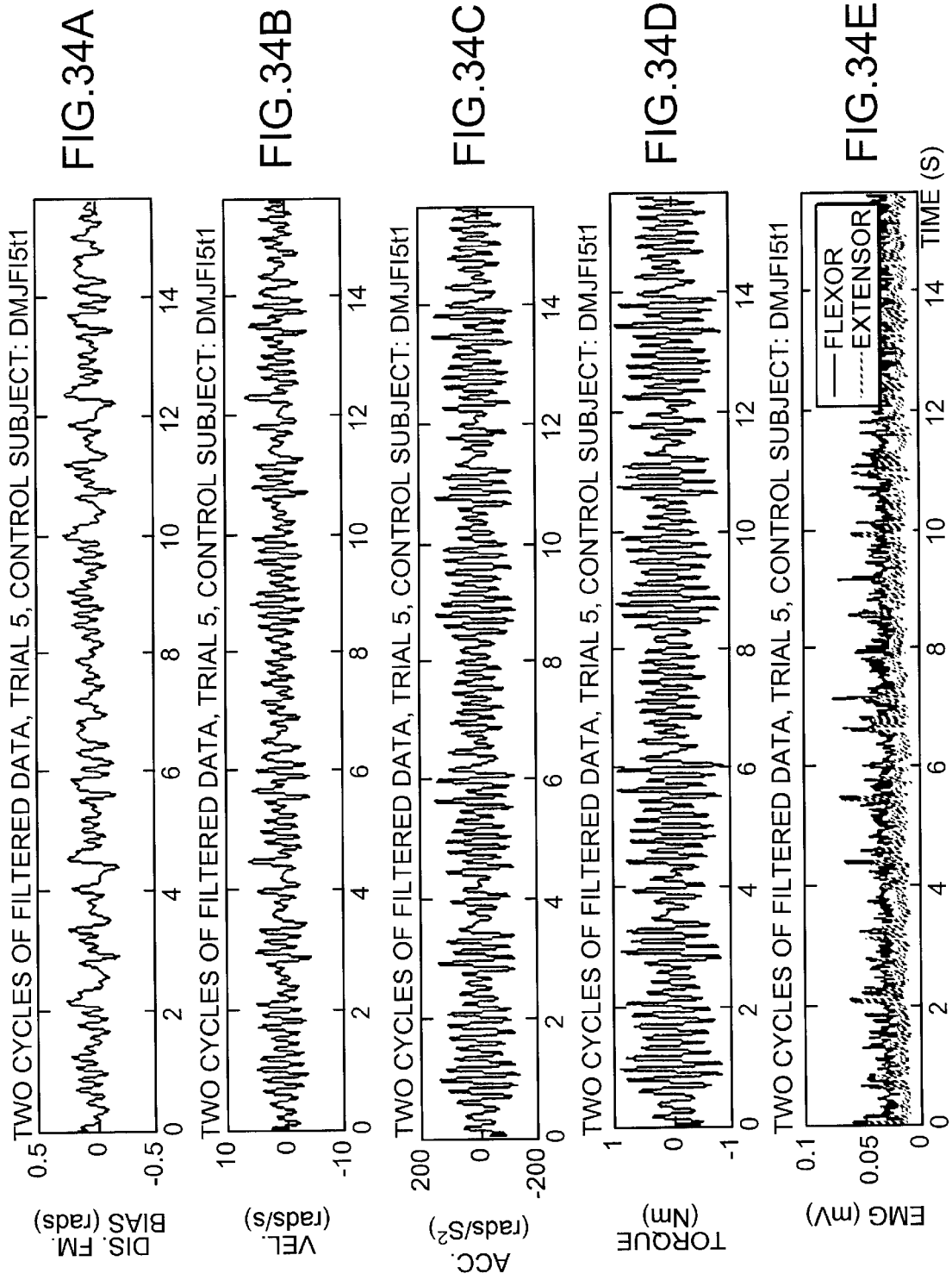

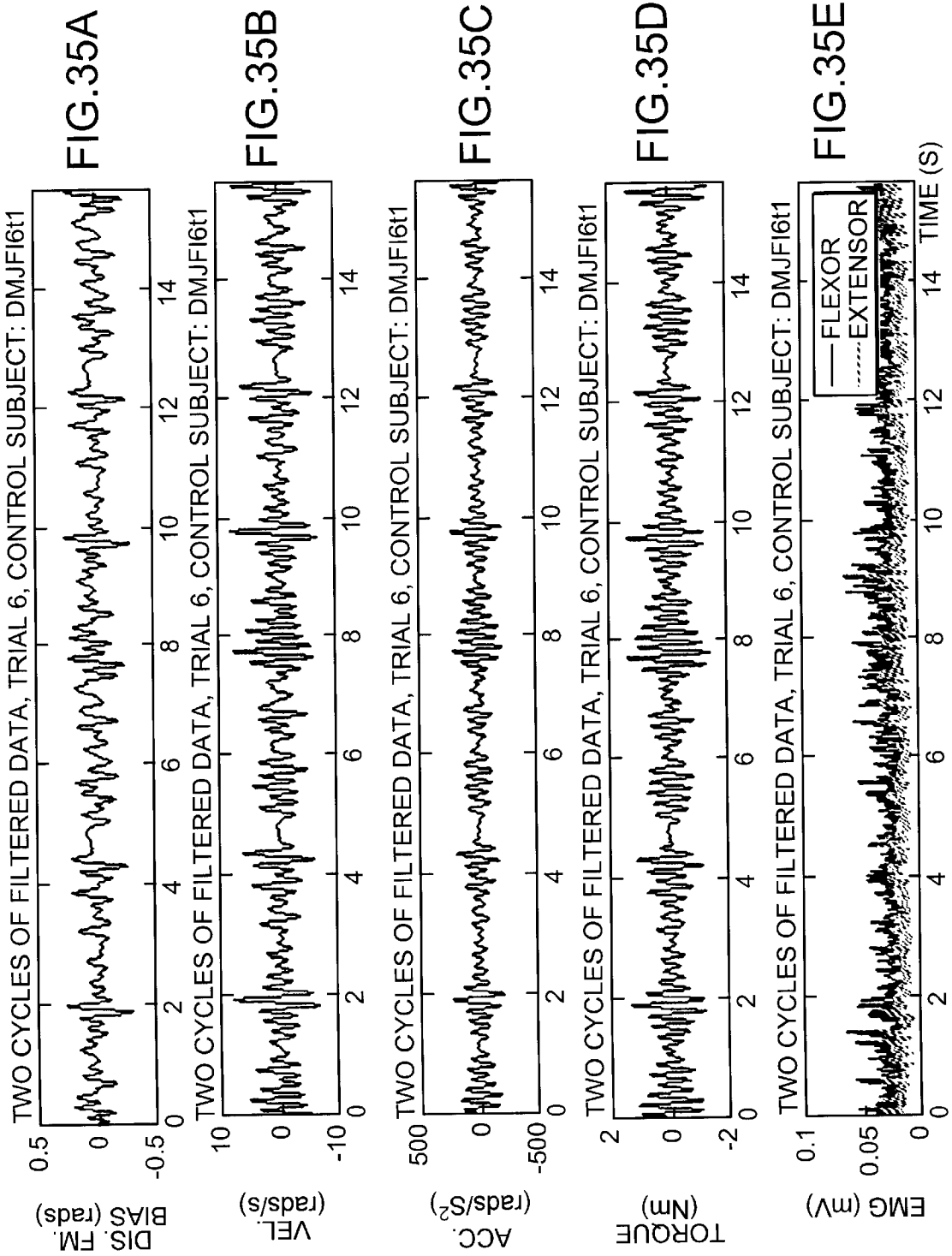

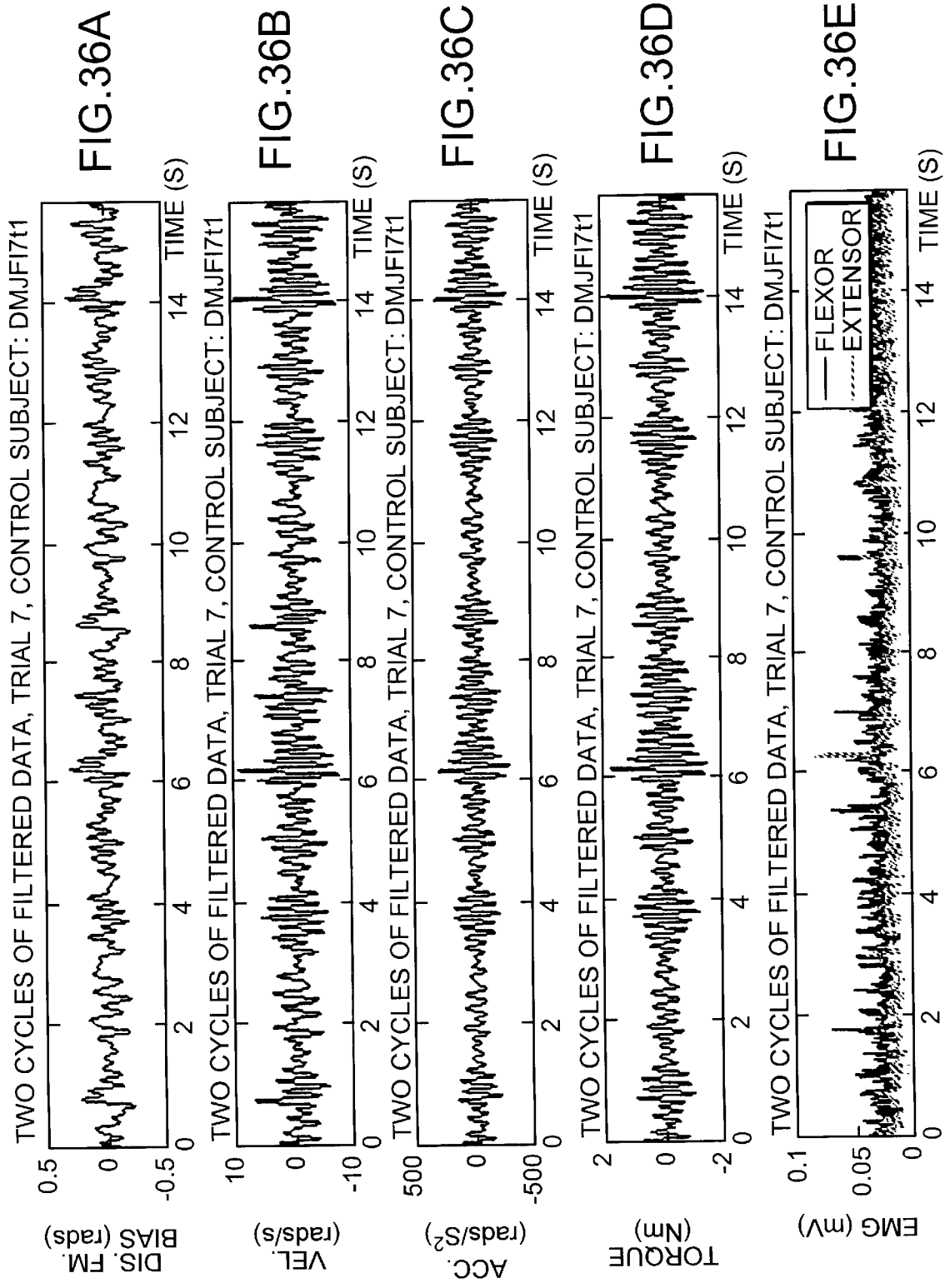

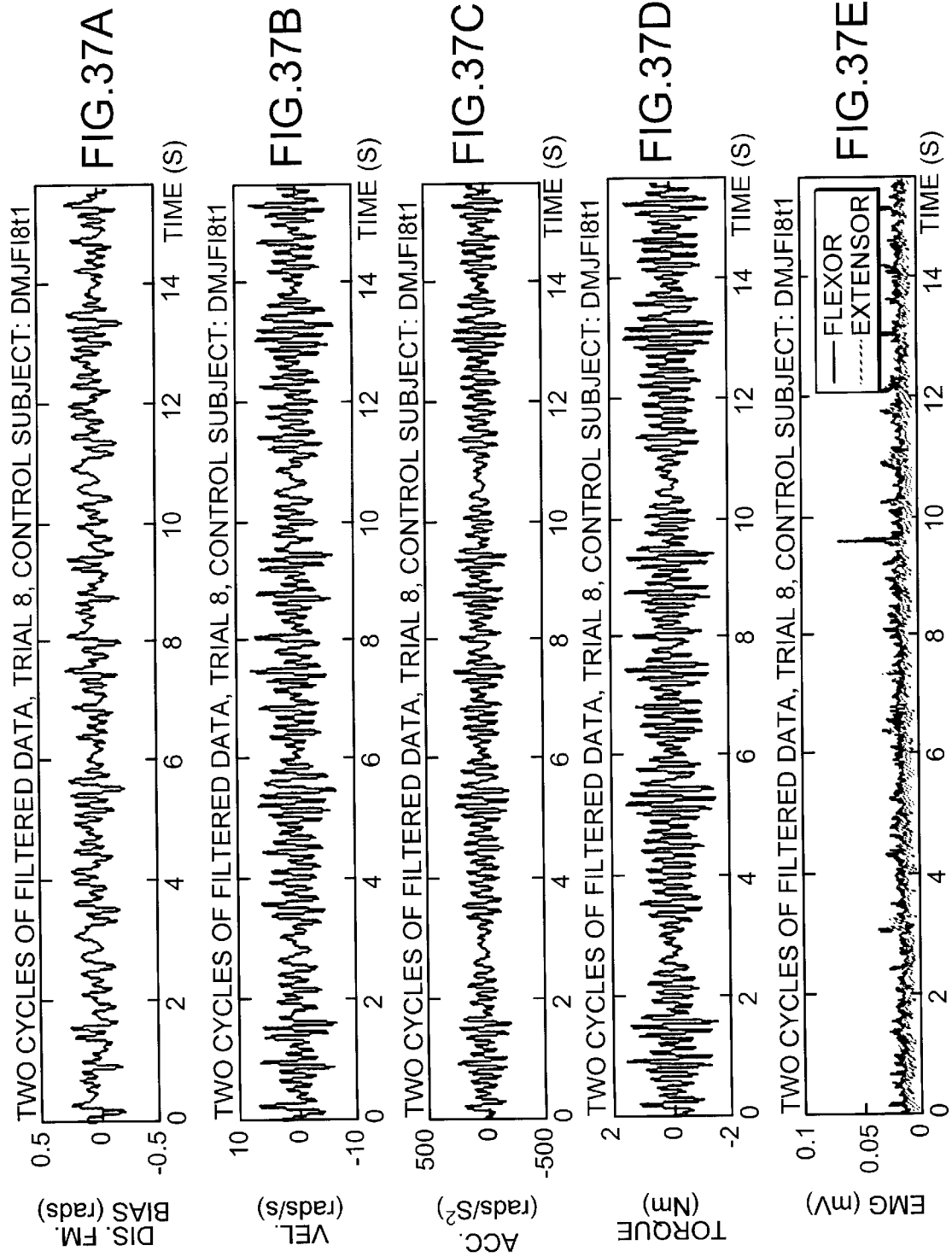

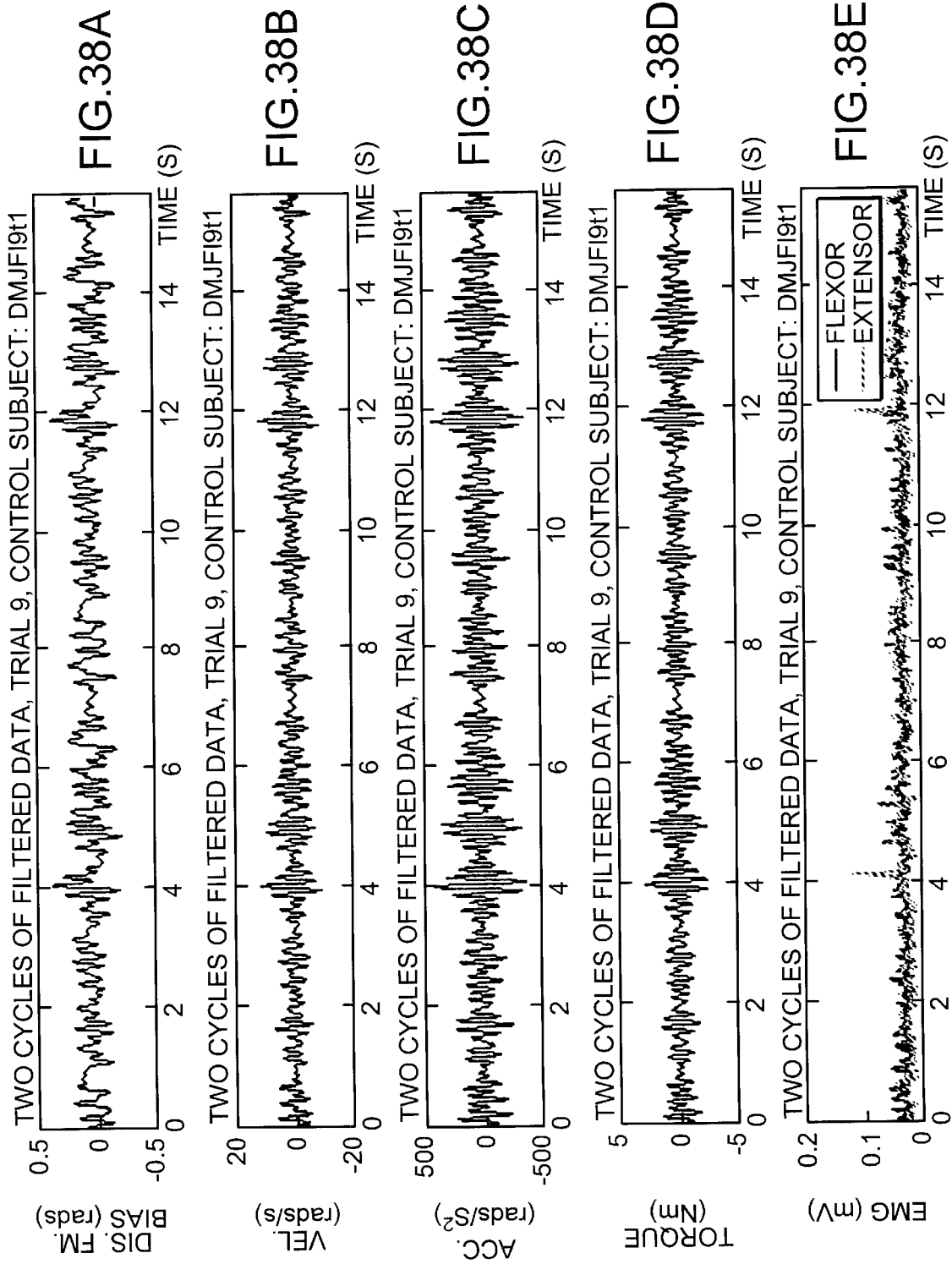

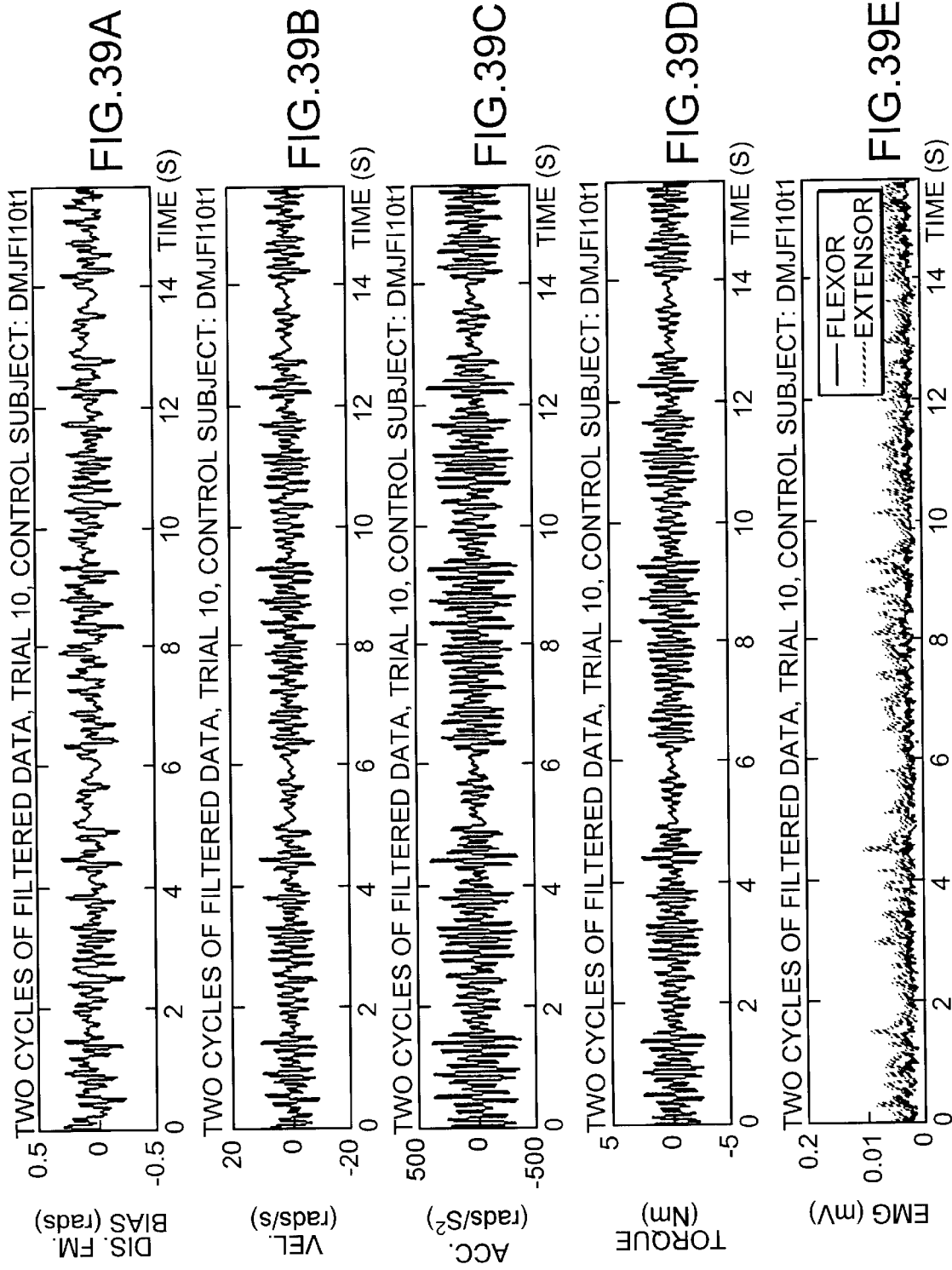

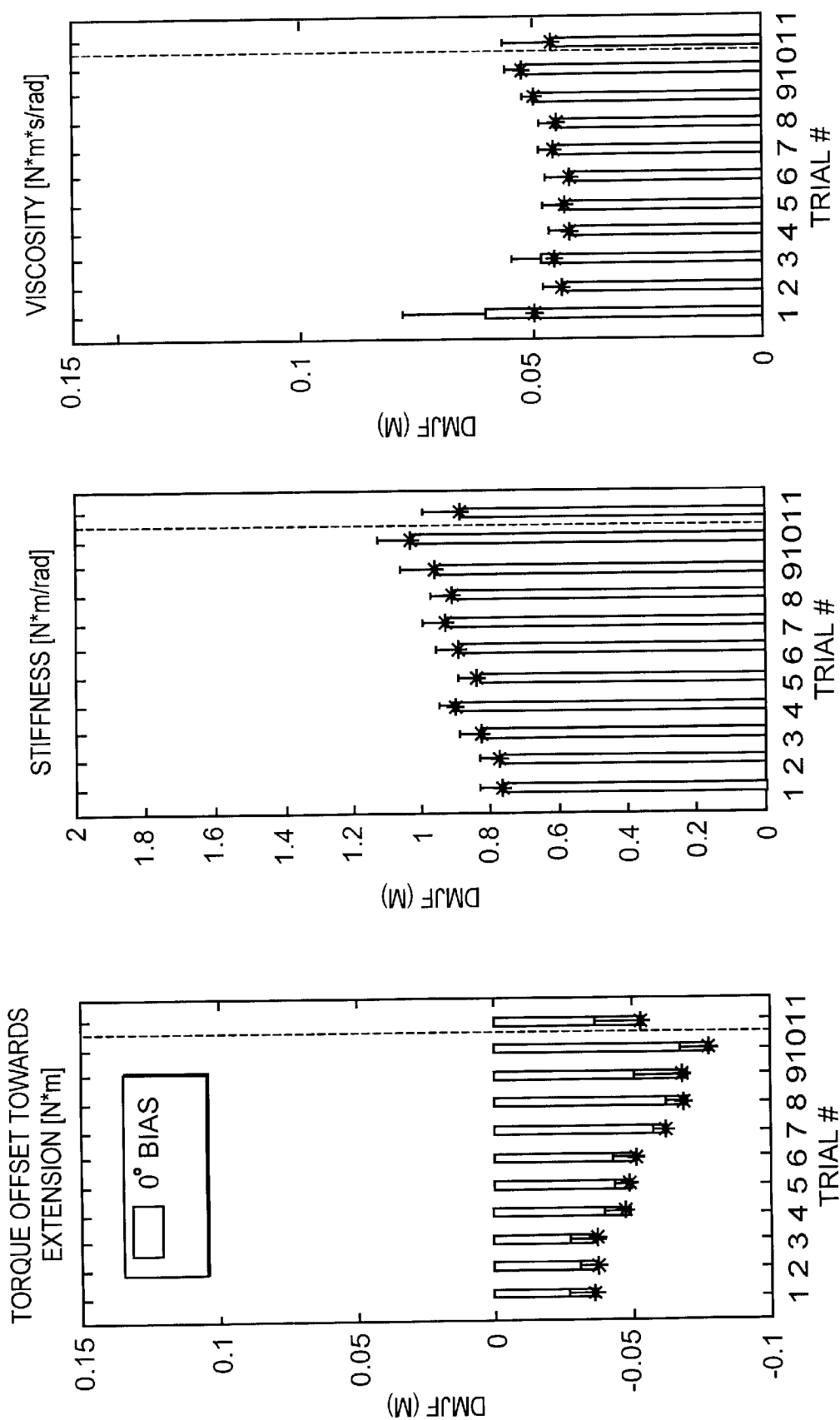

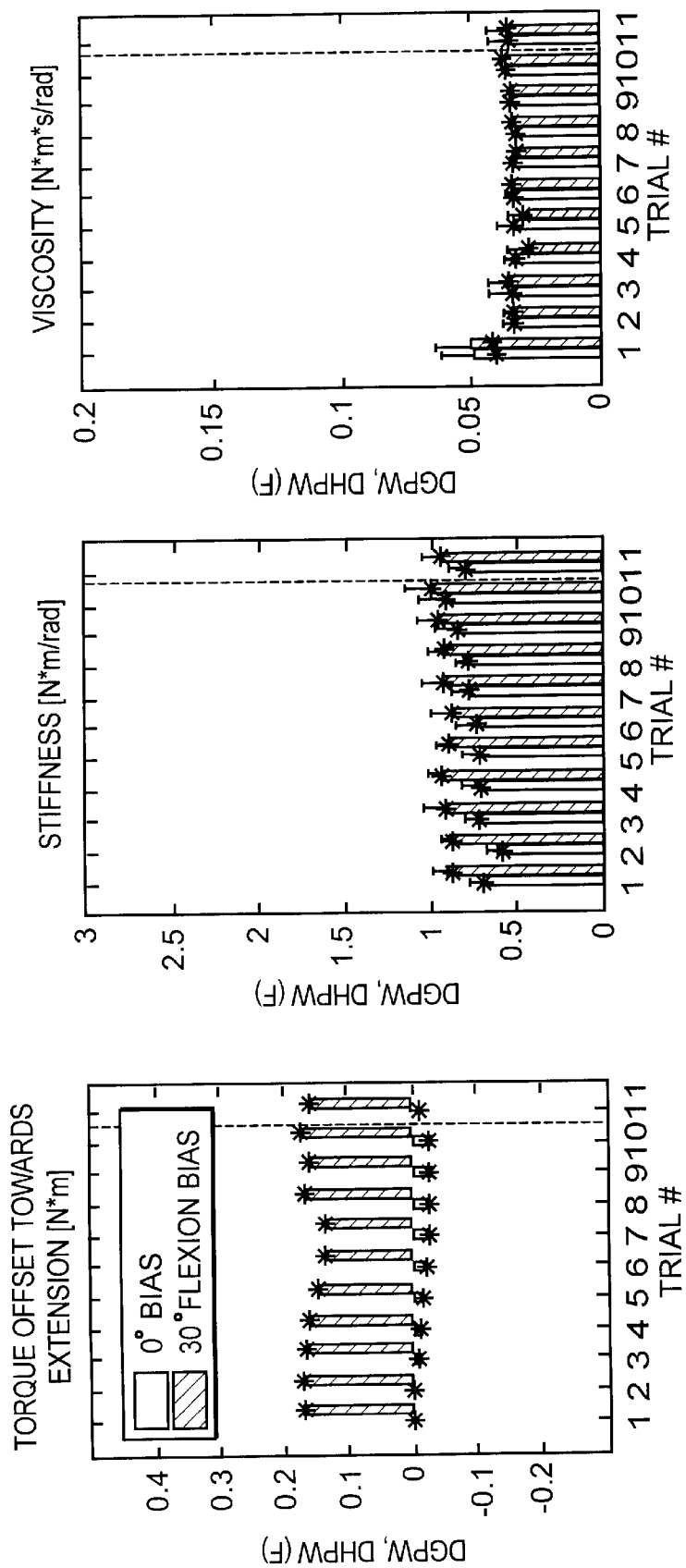

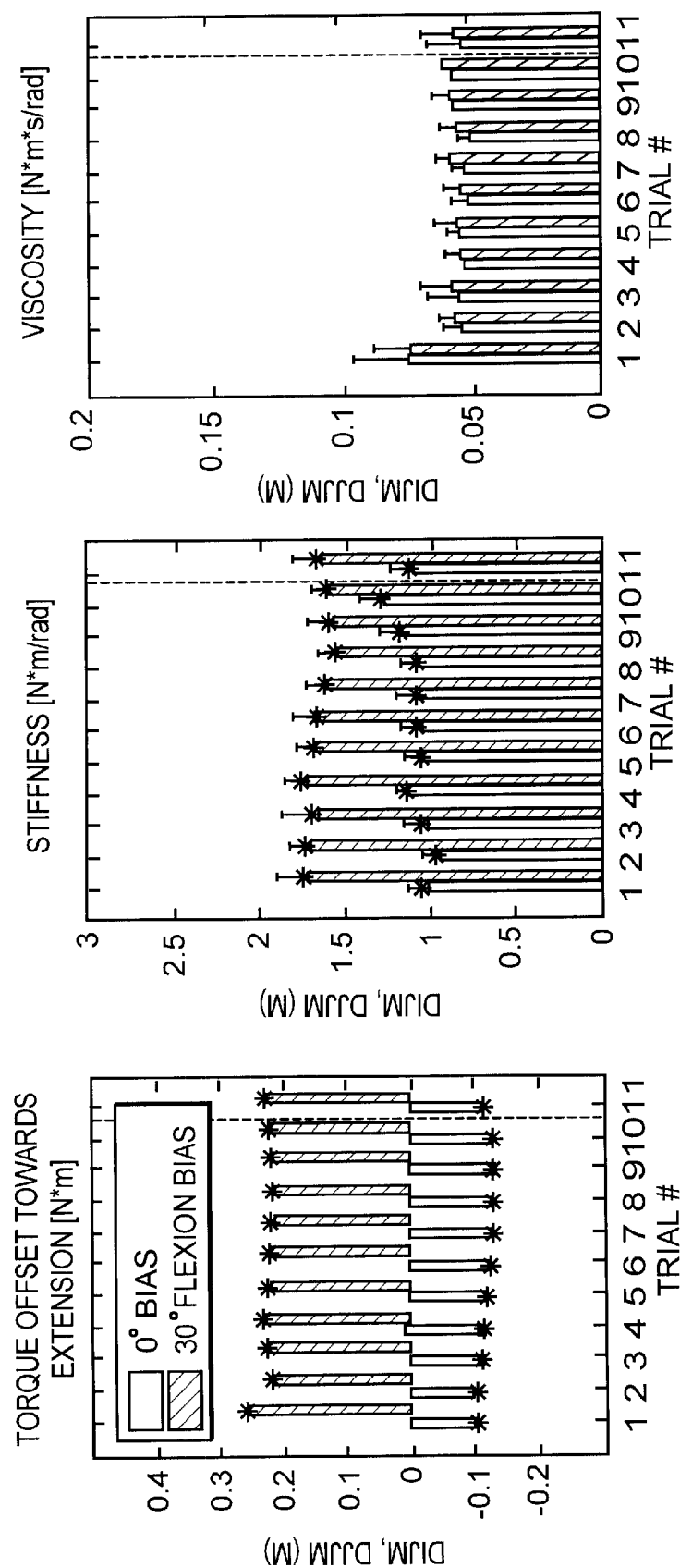

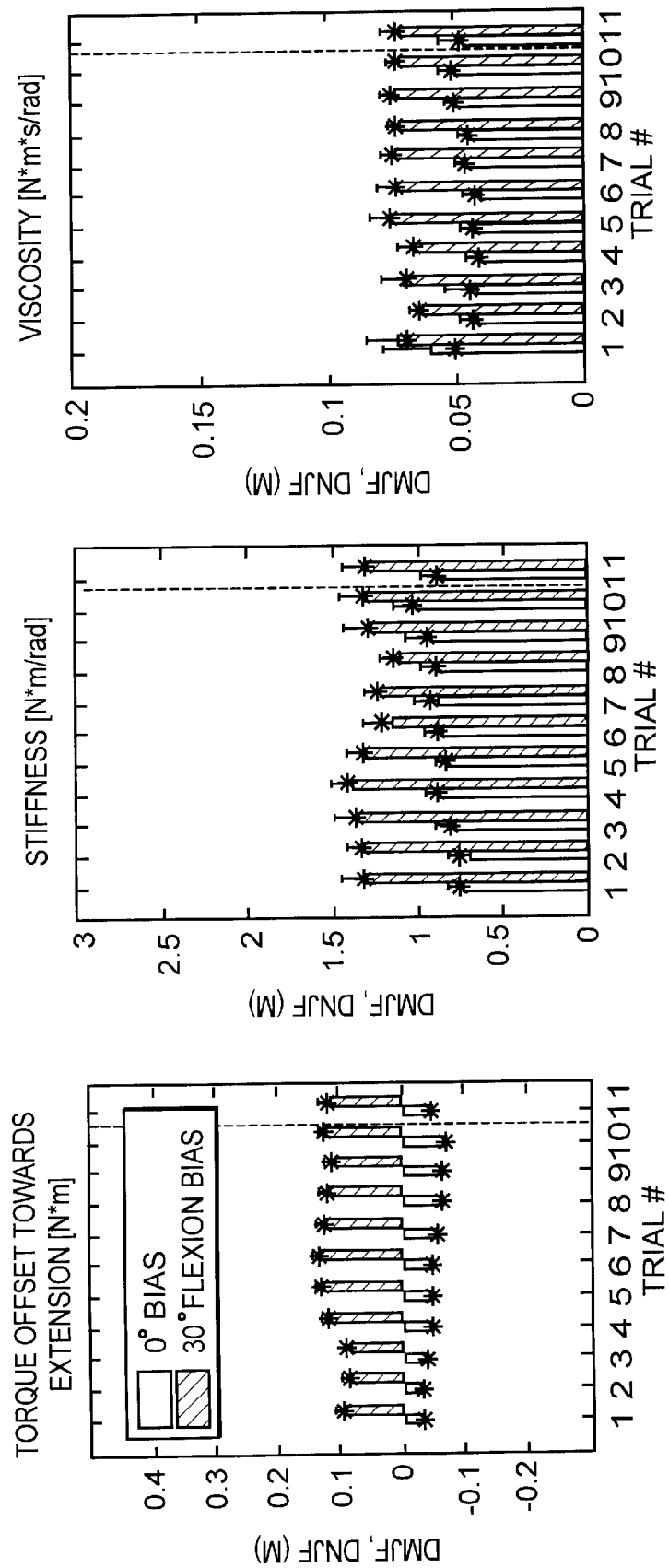

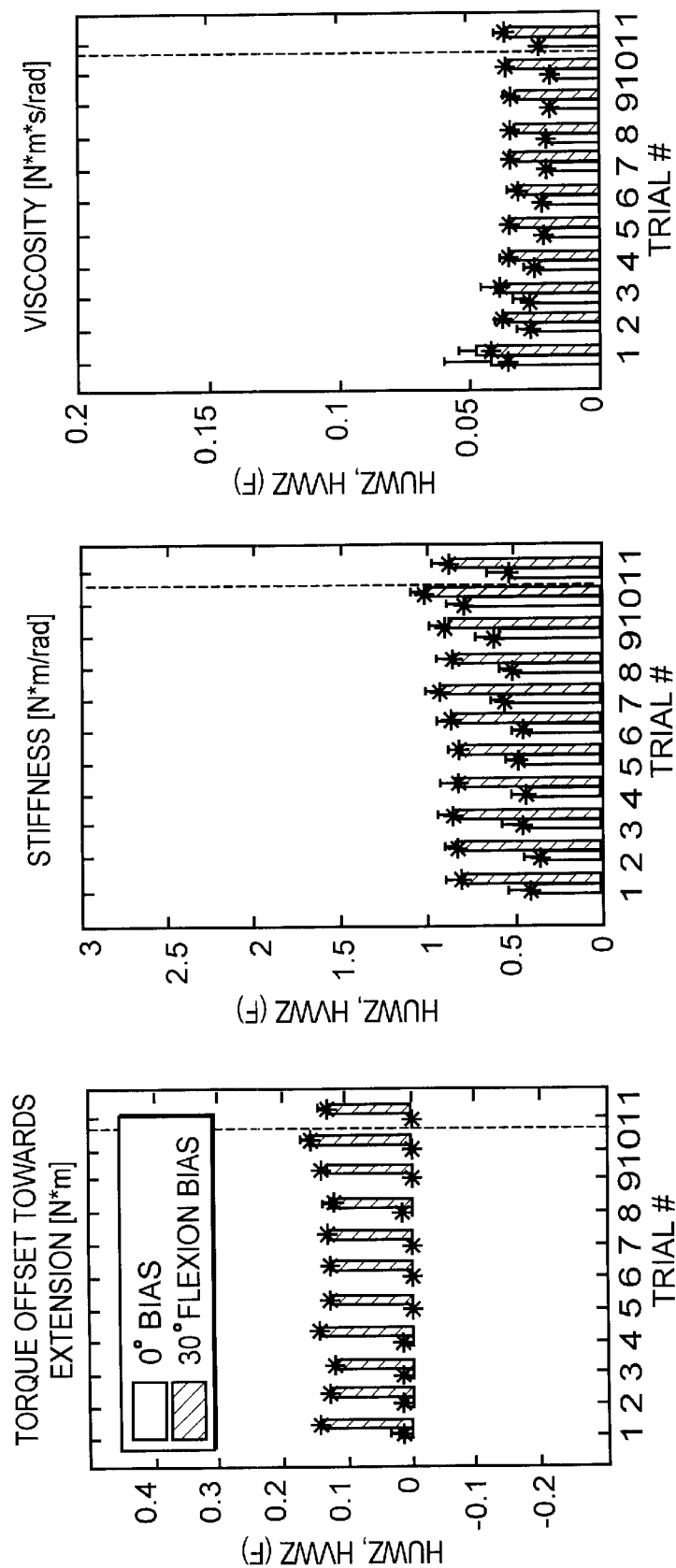

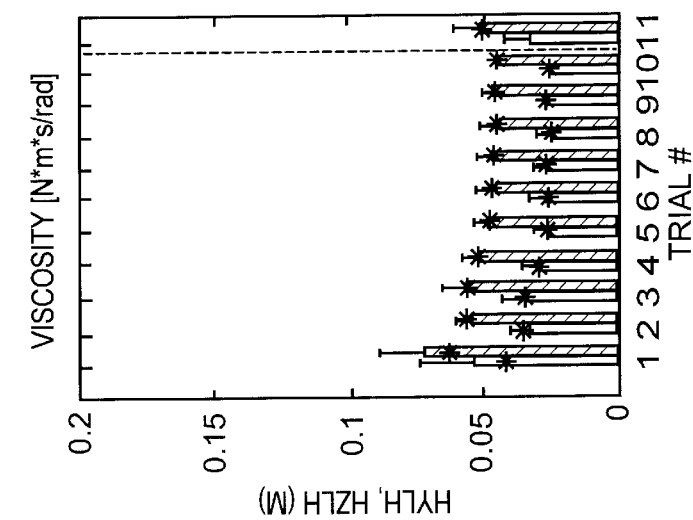
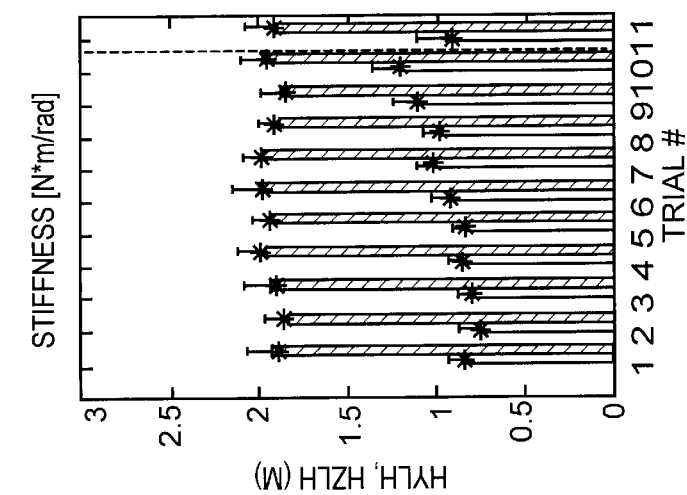
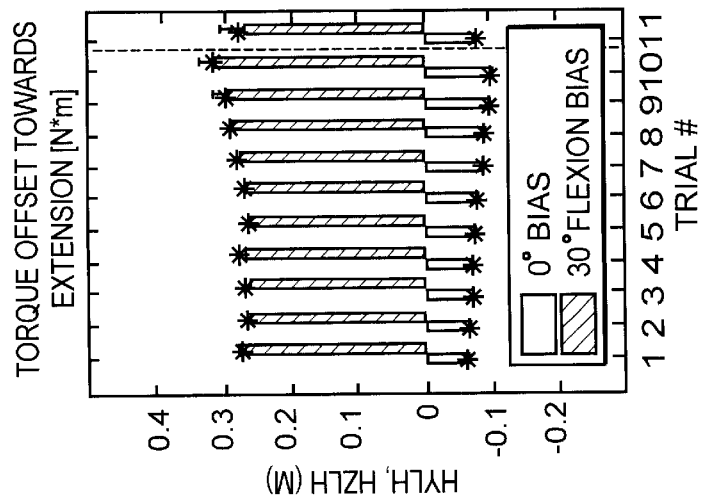
FIG. 51C
FIG. 51B
FIG. 51A

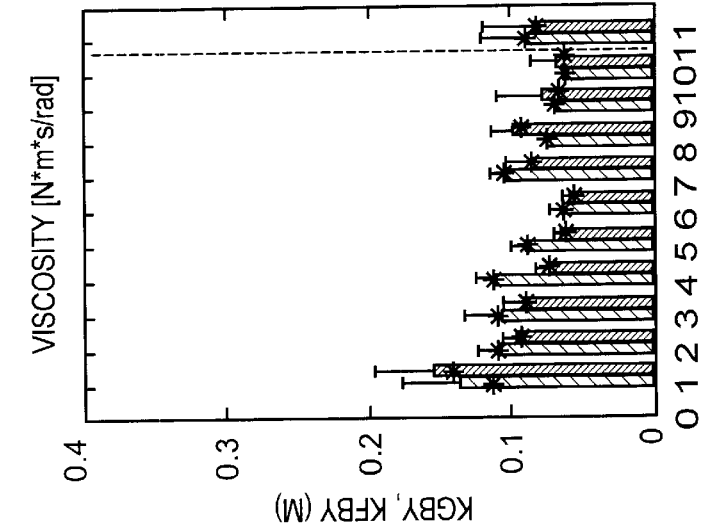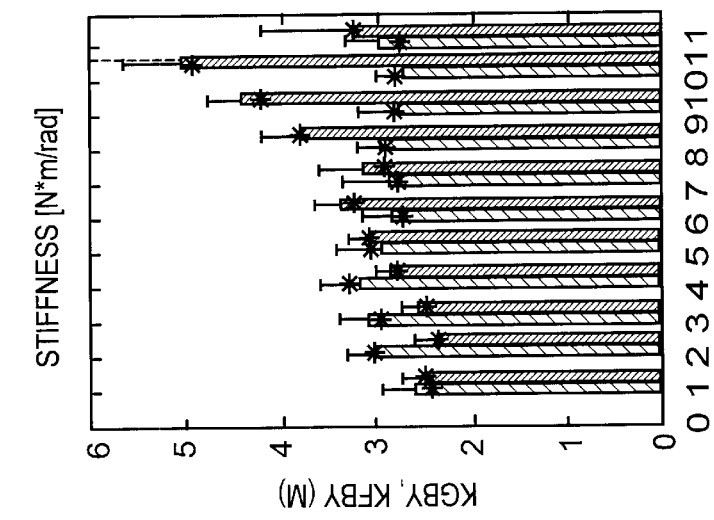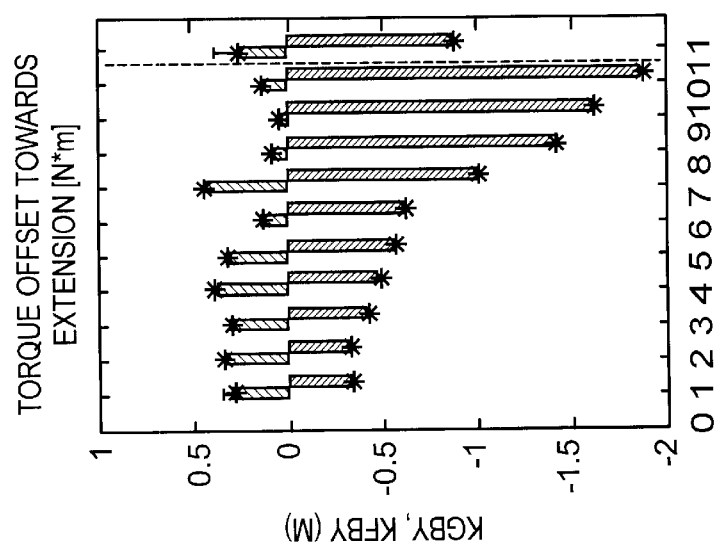
FIG. 55C
FIG. 55B
FIG. 55A

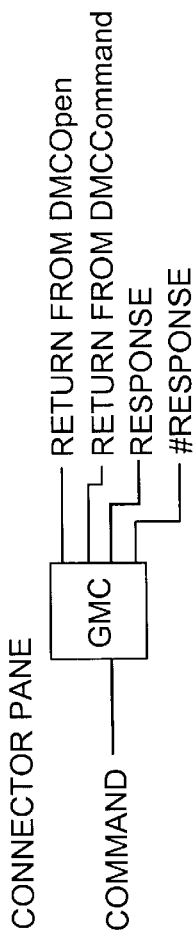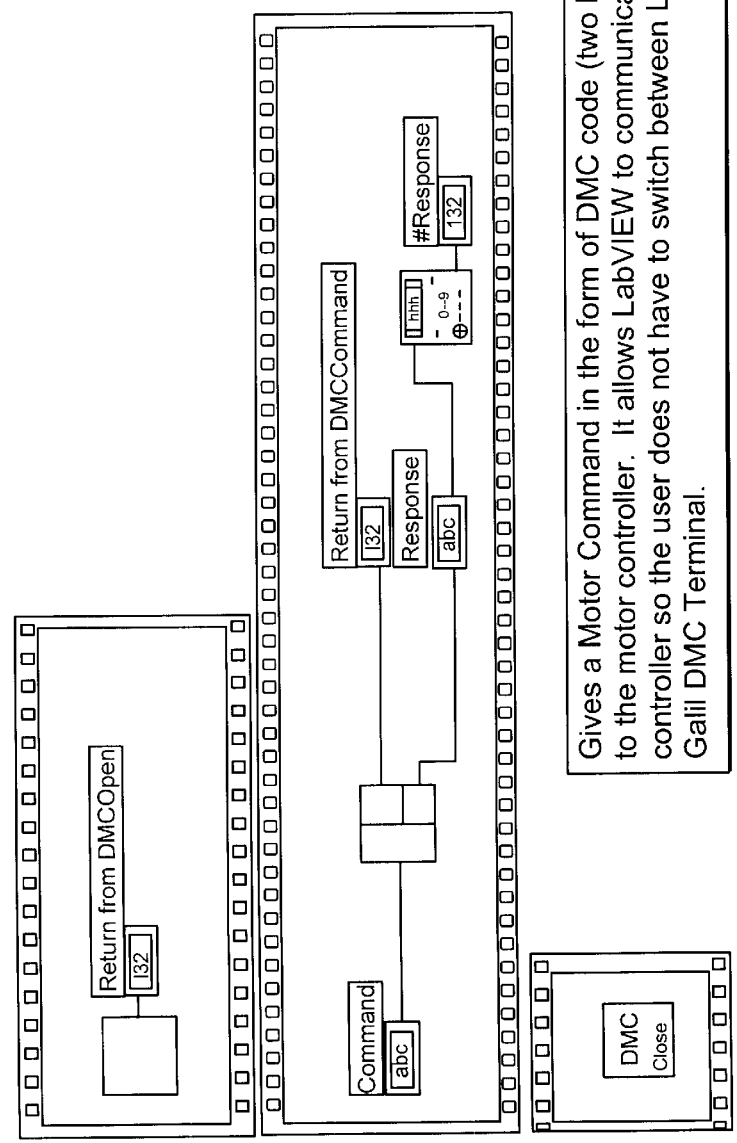
FIG. 84

LabVIEW VIRTUAL INSTRUMENT NAME: Input info.vi

LabVIEW VIRTUAL INSTRUMENT NAME: GOTO BP.vi
CONNECTOR PANE

LabVIEW VIRTUAL INSTRUMENT NAME: Calibrate.vi
CONNECTOR PANE
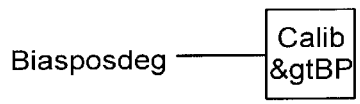
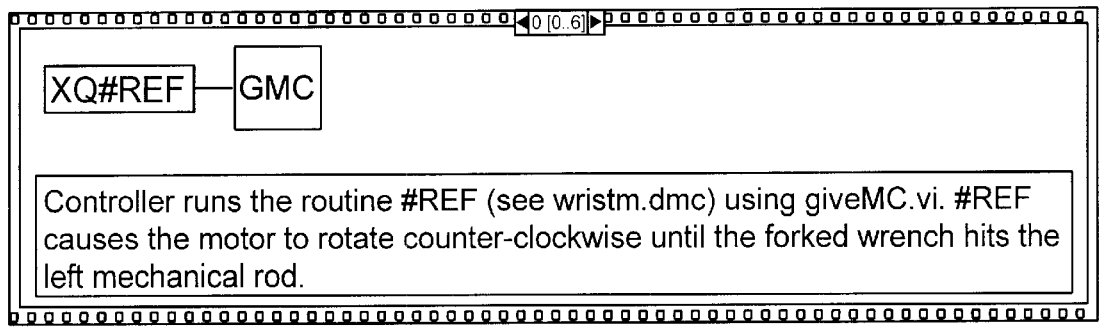
FIG. 96
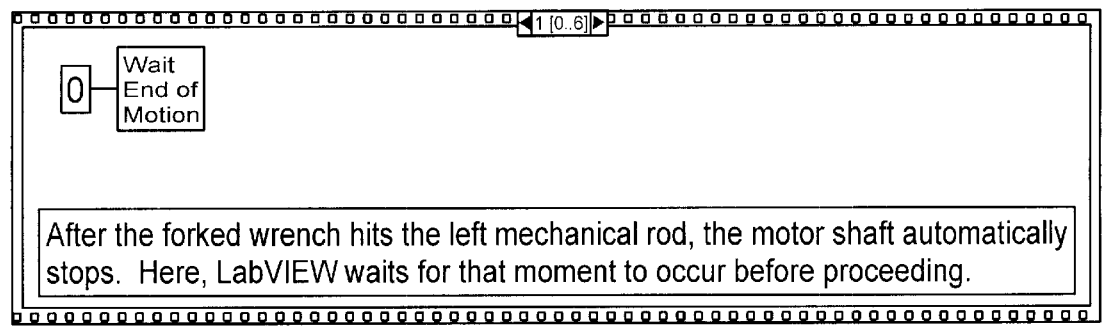
FIG. 97
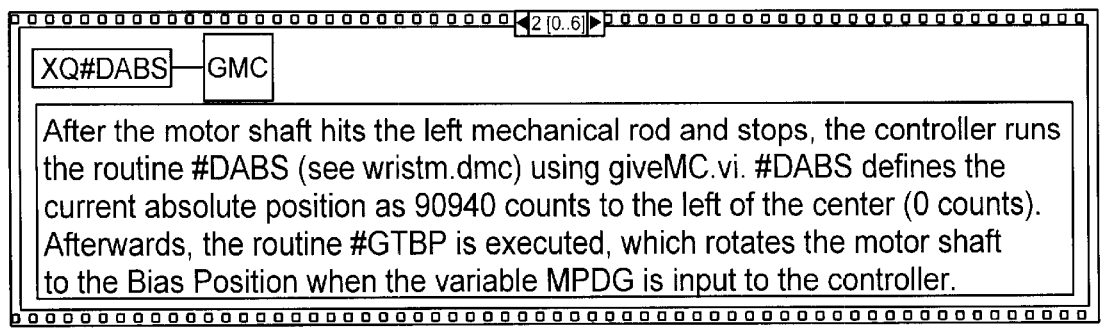
FIG. 98

LabVIEW VIRTUAL INSTRUMENT NAME: Halt.vi
CONNECTOR PANE
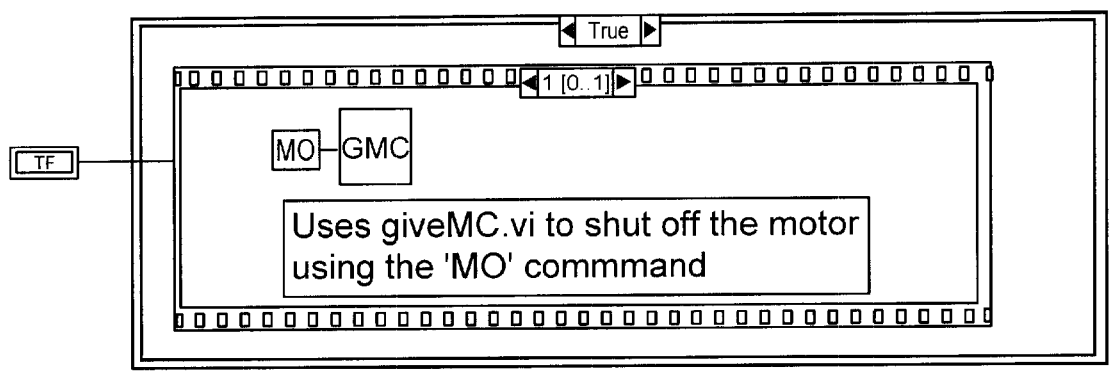
If the boolean input is 'True' then the motor is shut off and the execution of the program is halted.
FIG. 111
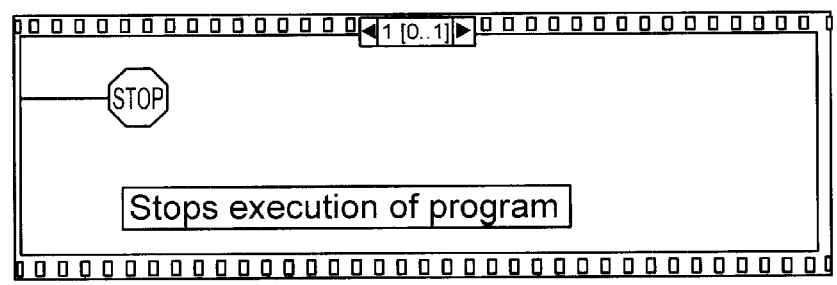
FIG. 112

LabVIEW VIRTUAL INSTRUMENT NAME: GoSin.vi
CONNECTOR PANE
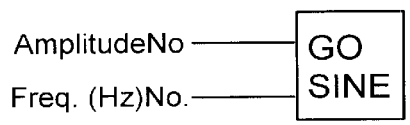
BLOCK DIAGRAM
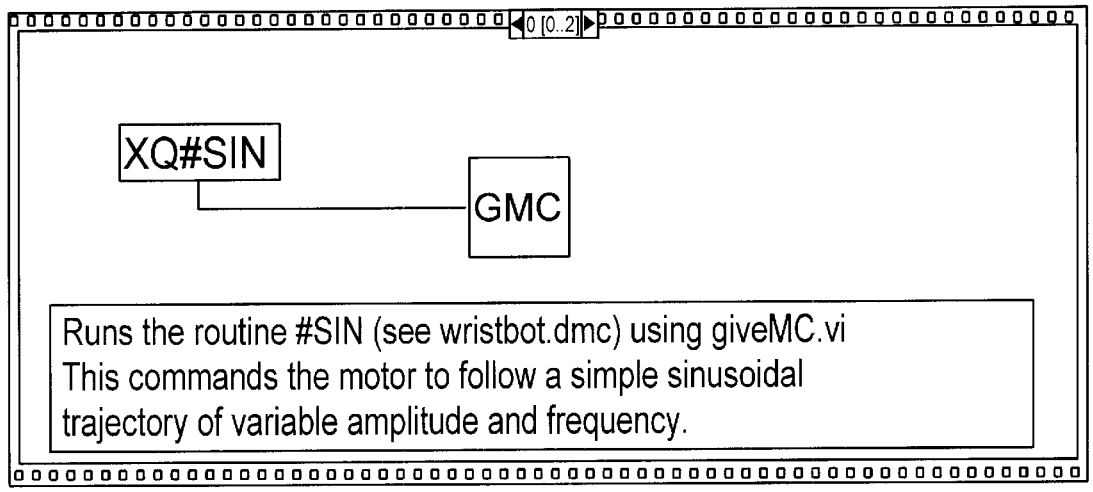
FIG. 122
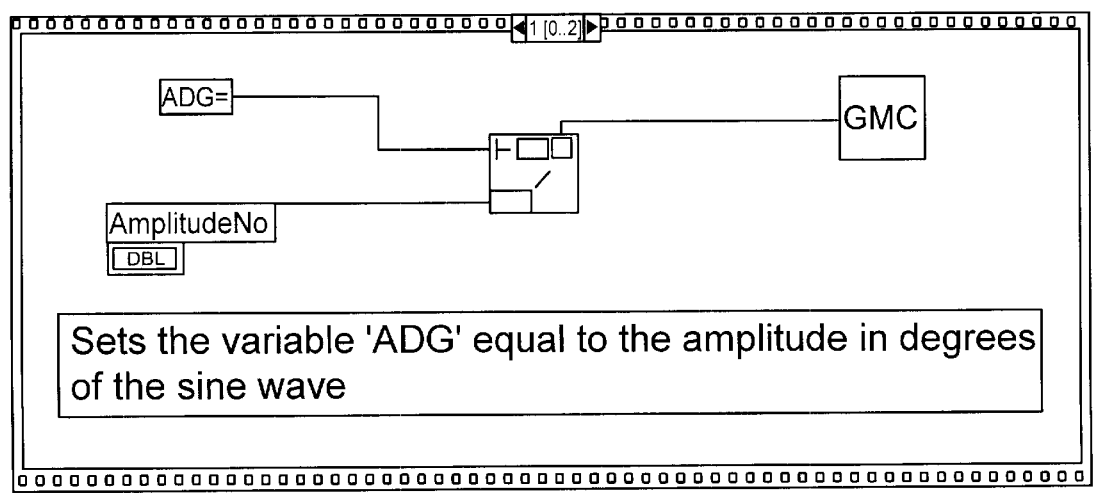
FIG. 123

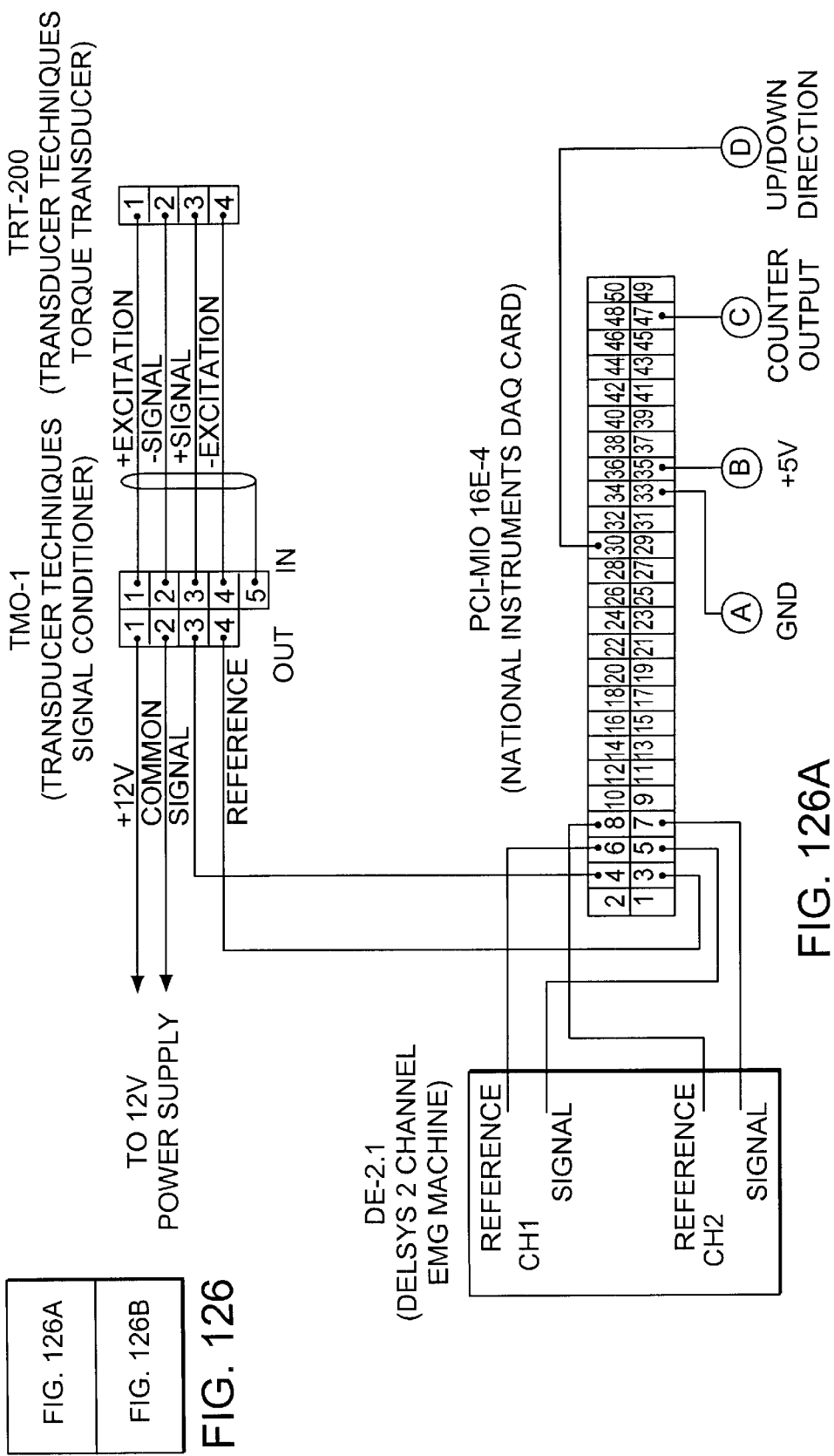

NOTES:
1. HOLES TO SURFACE OF BASE TO FIT SCREWS
2. HOLES TO FIT TORQUE TRANSDUCER
3. HOLE TO FIT MOTOR SHAFT

DETAIL 1

DETAIL 1

NOTES:
1. ALL FOUR HOLES ARE IDENTICAL AND MATCH WITH TORQUE TRANSDUCER
2. THIS MUST FIT INSIDE OF THE SHAFT (FIG. 131A-D)

NOTES:
1. THIS 1.00" WIDTH MUST SLIDE FREELY IN 1.00 SLOT IN BOTTOM OF FIG.132A-D
2. THIS 0.250" WILL HAVE A FREE SLIDING FIT WITH A 1/4"-20 ALL THREAD ROD

FIG. 132A  —2 PLACES 10-24 TAPPED HOLE 1/2" DEEP

FIG. 132C  —1/4"-20 TAPPED HOLE 3/4" DEEP

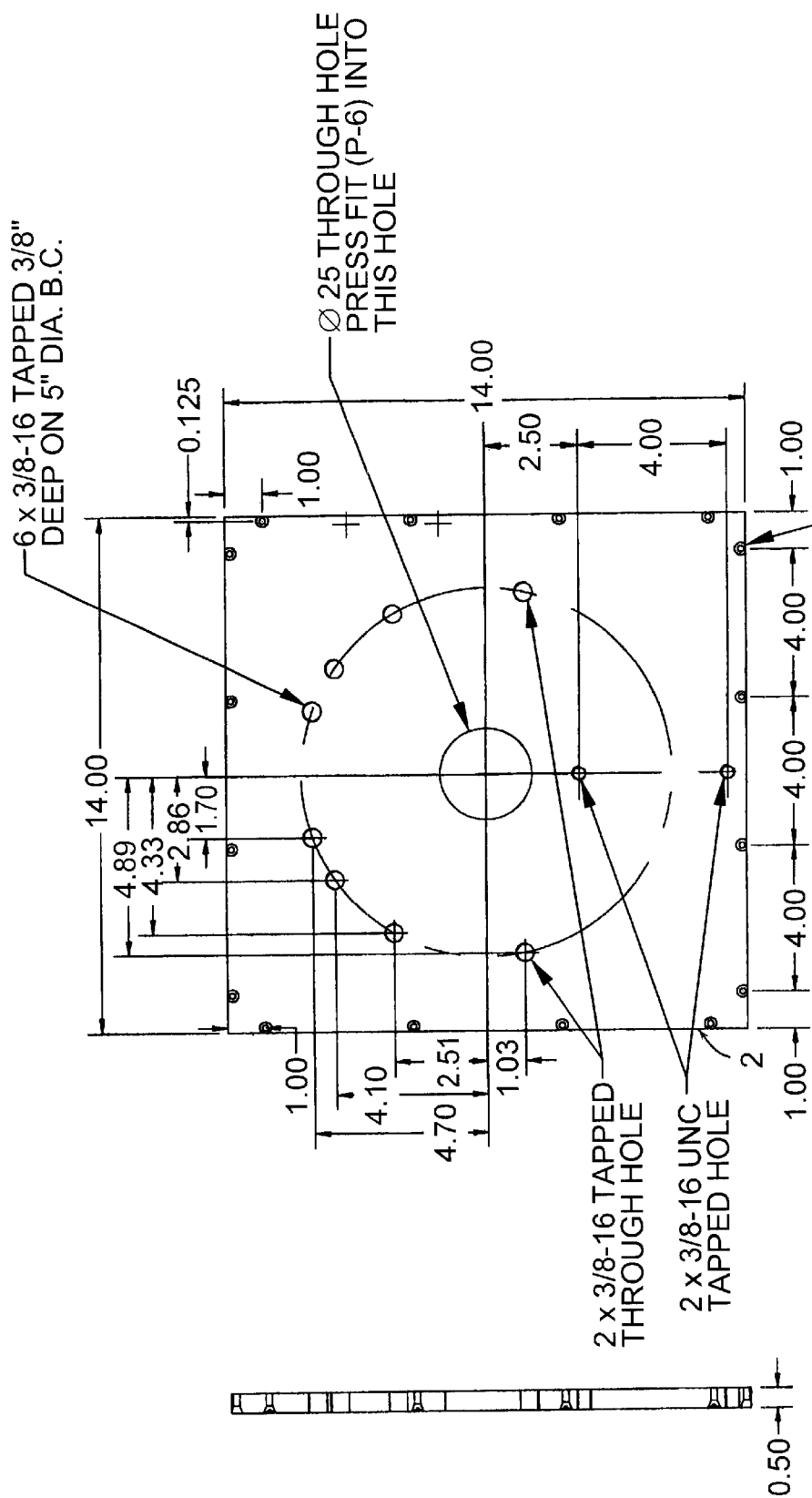

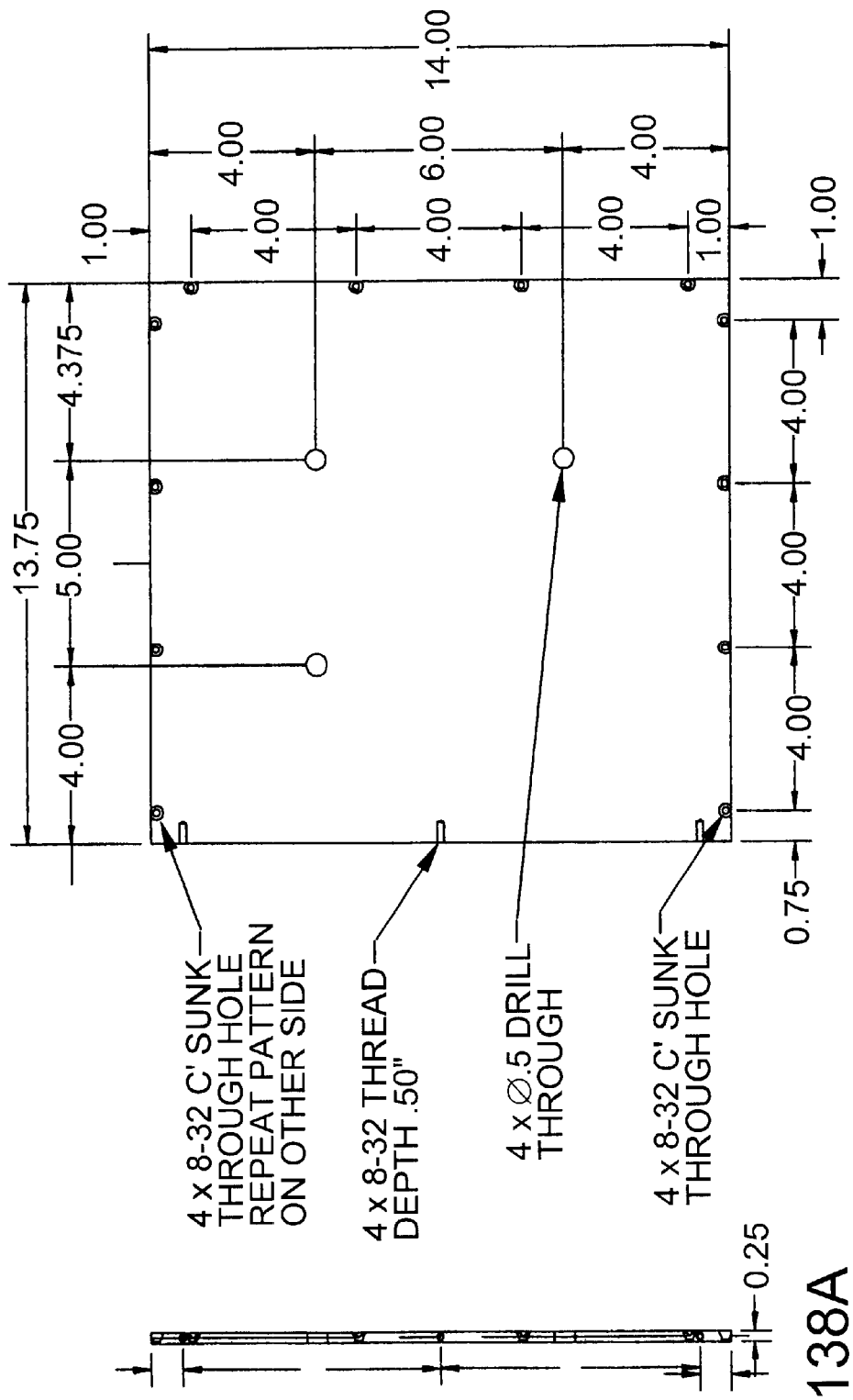

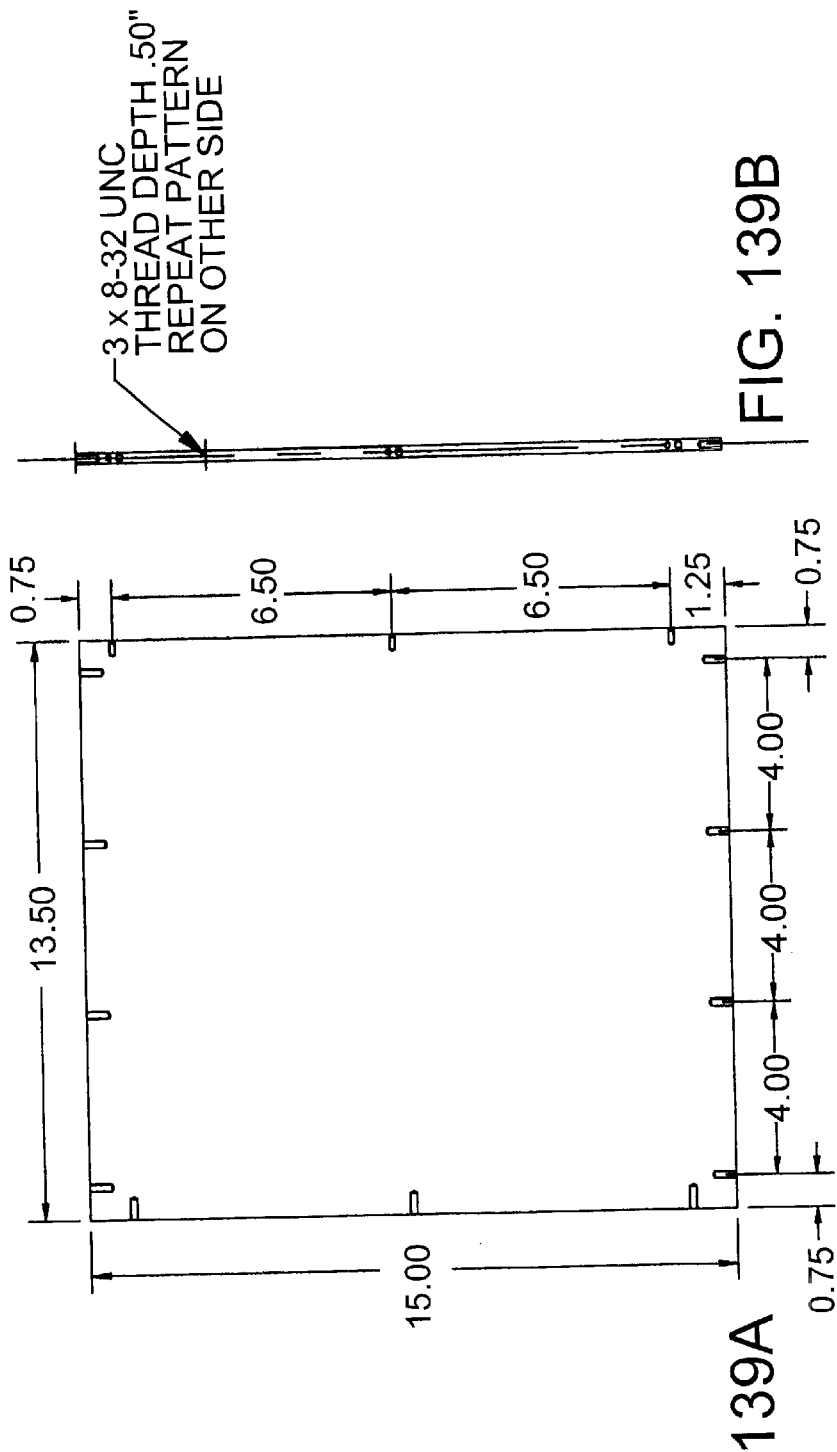
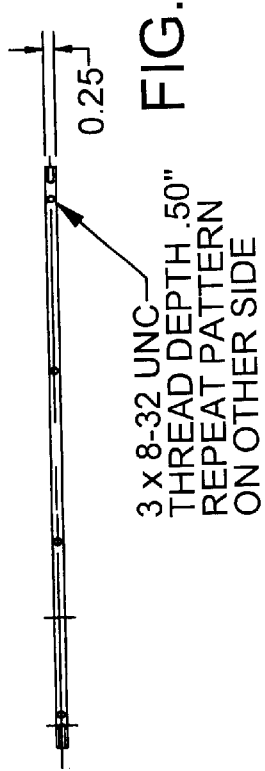
FIG. 139A
FIG. 139B
FIG. 139C

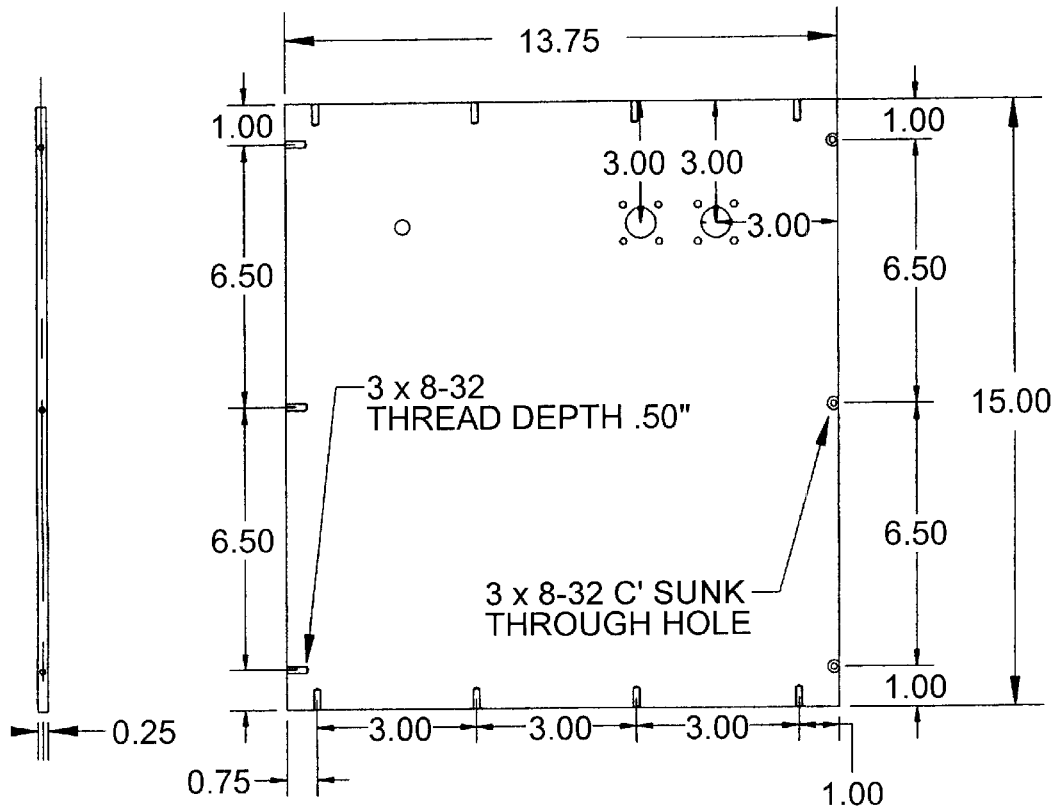
FIG. 141A  FIG. 141B
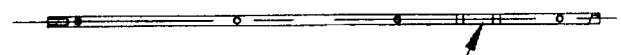
TAPPED DEPTH .50"
REPEAT PATTERN
ON OPPOSITE SIDE    FIG. 141C

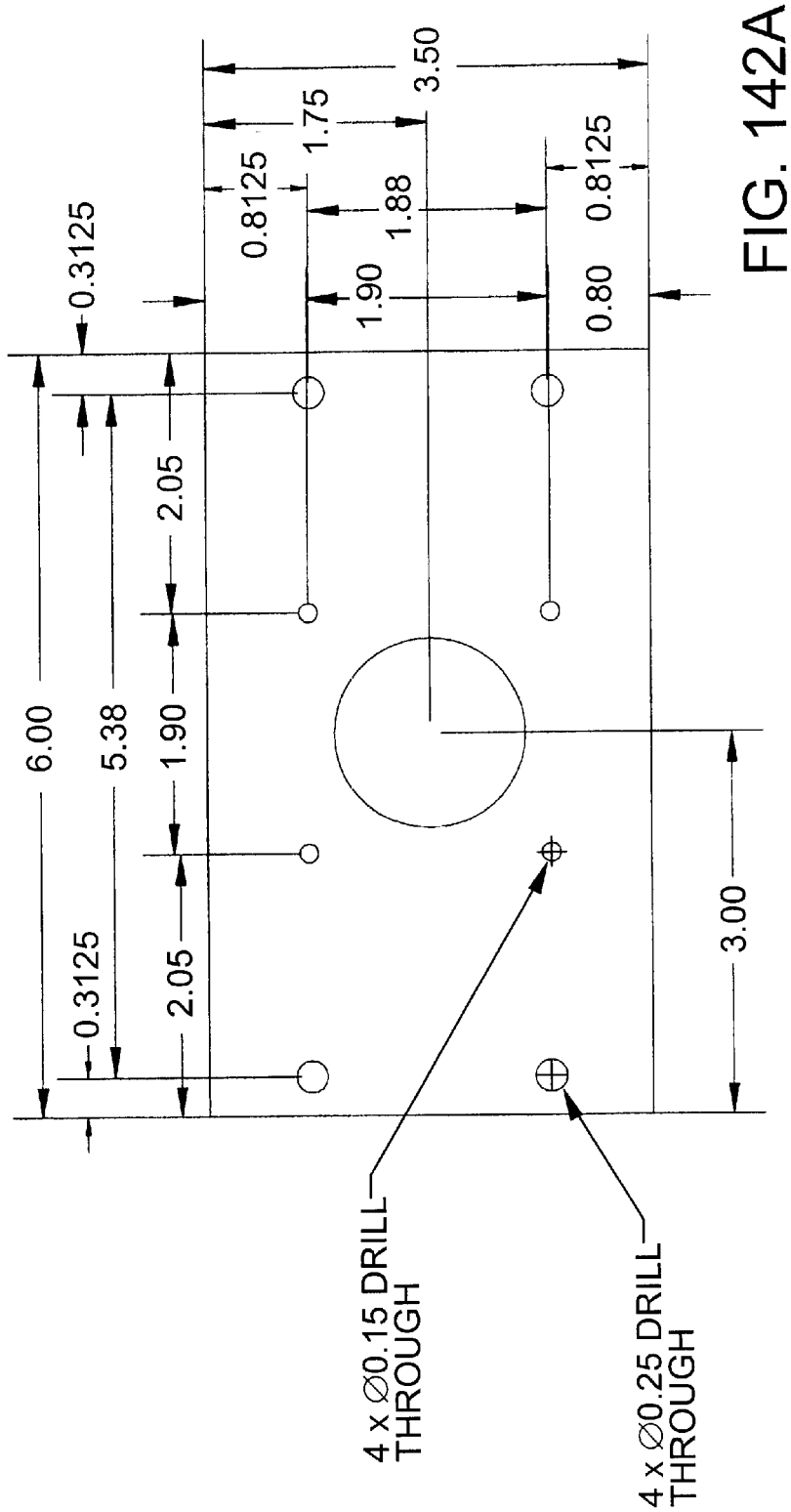
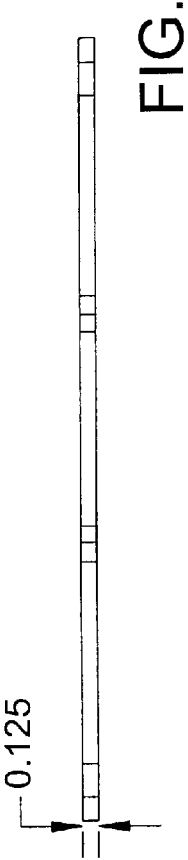
FIG. 142A
FIG. 142B

NOTES:
1. MATCH HOLES TO ENCODER MOUNTING COLUMNS (D-17)
2. MATCH HOLES TO MOTOR FACE (P-1)

NOTES:
1. BOTH D-5's WILL HAVE 1/4" -20 ALL-THREAD ROD AND WILL SECURE TO D-4 BY THREE-ARM KNOBS.
2. BOTH D-7's WILL HAVE 1/4" -20 ALL-THREAD ROD AND WILL SECURE TO D-6 BY BAR KNOBS. THE BAR KNOBS WILL BE SECURED TO THE ALL-THREAD BY A PIN AND THE POLE WILL SCREW DOWN FROM THE TOP.
3. THE D-5's WILL EACH HAVE ONE 1/4" i.d. FLAT WASHER BETWEEN THE KNOB AND D-4. THE D-7's WILL EACH HAVE ONE 1/4" i.d. WAVE WASHER FOLLOWED BY ANOTHER 1/4" i.d. FLAT WASHER BETWEEN THE KNOB AND D-6.

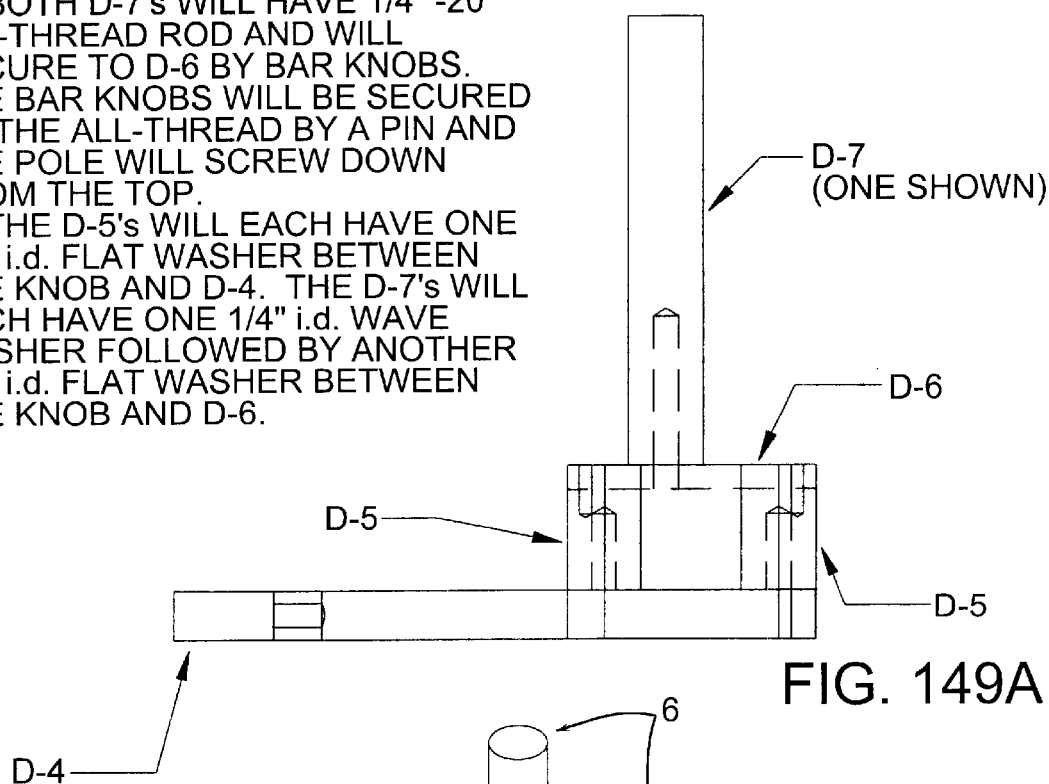

FIG. 149A

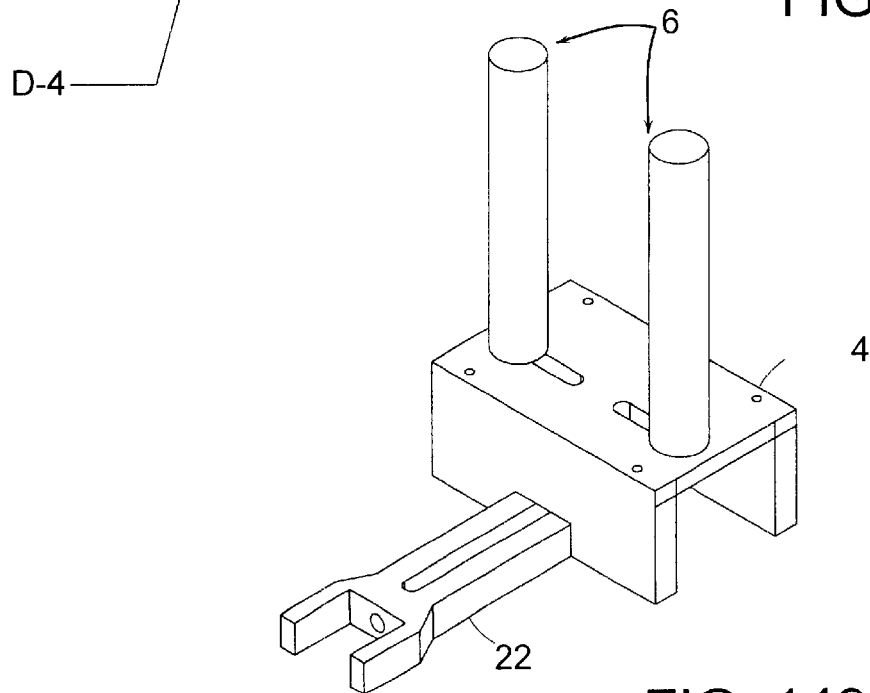

FIG. 149B

QUANTIFICATION OF MUSCLE TONE

The present application claims the benefit of U.S. provisional application No. 60/230,314, filed on Sep. 6, 2000, incorporated herein by reference.

FIELD OF THE INVENTION

The present invention relates to a method and apparatus for the quantification of muscle tone. More particularly, the present invention relates to a method and device that utilize non-sinusoidal perturbations to quantify muscle tone. The device is, and method are particularly useful in quantifying muscle tone in a spastic patient.

BACKGROUND OF THE INVENTION

Individual skeletal muscle cells are mechanically and anatomically arranged in parallel. The total force produced by a muscle is equal to the sum of the forces generated by its constituent cells. In the normal subject, muscles that comprise the wrist flexors and extensors are normally relaxed and are usually recruited to generate force and movement.

Lower motor neuron paralysis occurs when muscles are deprived of their immediate nerve supply from the spinal cord. This occurs when a nerve between the spinal cord and a muscle is cut or when cell bodies of the ventral horn are destroyed as in poliomyelitis. Muscles become soft and atrophic, and reflex response to sensory stimuli is lost. Most nerve disorders that affect limb function are due to upper motor neuron paralysis, wherein damage is present somewhere in the corticospinal tract that originates in the brain and travels through the spinal cord.

Spasticity is defined as abnormal involuntary contraction of a muscle or group of muscles due to a rate-dependent reflex mechanism. The spindle elicits the reflex response upon deformation. To a certain extent, these reflexes are normal and important. In normal operation, these reflexes are suppressed to a certain extent to allow flexibility and motion of joints. In spasticity however, there is a disruption in the normal behavior of the stretch reflex that causes muscles, particularly the flexors, to be extremely resistive to passive stretch (i.e. high in tone). As a result, motor control is severely impaired and stiffness or tightness of the muscles may interfere with gait, movement, and speech. Spasticity is usually found in people with some sort of upper motor neuron paralysis, such as those with cerebral palsy, traumatic brain injury, spinal cord injury and stroke patients.

Common symptoms of spasticity may include hypertonicity (increased muscle tone), clonus (a series of rapid muscle contractions), exaggerated deep tendon reflexes, muscle spasms, scissoring (involuntary crossing of the legs) and fixed joints. The degree of spasticity varies from mild muscle stiffness to severe, painful, and uncontrollable muscle spasms. The condition can interfere with rehabilitation in patients with certain disorders, and often interferes with daily activities.

Many forms of intervention are available to reduce muscle tone in spasticity. Biochemical pharmaceuticals such as Botox (Botulinum Toxin Type A), Intrethecal Baclofen, and Zanaflex (tizanidine) may be used as a biochemical form of intervention. (See R. W. Armstrong, P. Steinbok, D. D. Cochrane, et al. *Intrathecally administered baclofen for treatment of children with spasticity of cerebral origin*. J Neurosurg; 87(3):409–414, Sep 1997; J. V. Basmajian, K. Shankardass, D. Russel: *Ketazolam Once Daily for Spasticity: Double-Blind Cross-Over Study*. Arch. Phys. Med. Rehabil. Vol. 67, pp556–557, 1986; P. J. Delwaide: *Electrophysiological Analysis of the Mode of Action of Muscle Relaxants in Spasticity*. Annals of Neurology, Vol. 17, No. 1, January 1985, pp 90–950). These chemicals are used either to destroy nerve endings at the neuromuscular junction, or they are used as blocking agents which depress neuromuscular transmission by competing with acetylcholine for receptors, thus suppressing nerve conduction. In severe cases, microsurgery is also an option, where incisions are made in the brainstem or anywhere in the stretch reflex pathway. The safest form of intervention is physical therapy, such as training, stretching exercises and casting. (J. C. Otis, L. Root, M. A. Kroll: *Measurement of Plantar Flexor Spasticity During Treatment with Tone-Reducing Casts*. Journal of Pediatric Orthopedics 5:682–686, 1985).

Tone is defined as the degree of resistance to stretch from an external source. An assessment of tone is important in evaluating the degree of spasticity that a patient has. This assessment is imperative for the clinician to decide what form of intervention to take and to what degree. Further, continued assessment throughout intervention is important to assess the effectiveness of the intervention. For example, if the Botox dosage administered is too low, it may have little or no effect in reducing a patient's spasticity. Conversely, if the dosage is too high, then the patient may lose the ability to control his or her limb, as blocking too many neuromuscular junctions at the muscle site may prevent the central nervous system from having any control over the muscle. An assessment of tone before and after intervention is also important as it can demonstrate the effectiveness of the treatment.

Probably the most widely accepted clinical test for the evaluation of tone in spasticity is the Ashworth scale shown below in Table 1.

TABLE 1

| Grade | Description |
|---|---|
| 0 | No increase in muscle tone. |
| 1 | Slight increase in muscle tone, manifested by a catch and release or by minimal resistance at the end of the range of motion when the affected part(s) is(are) moved in flexion or extension. |
| 2 | Slight increase in muscle tone, manifested by a catch followed by minimal resistance through the remainder of the range of motion but the affected part(s) is(are) easily moved. |
| 3 | More marked increase in muscle tone through most of the range of movement, but affected part(s) easily moved. |
| 4 | Considerable increase in muscle tone, passive movement difficult. |
| 5 | Affected part(s) is(are) rigid in flexion or extension. |

TABLE 1: Modified Ashworth scale. The Ashworth scale is a popular, and widely accepted method of evaluating muscle tone among clinicians. Though the grades are numeric, they are based on a qualitative "feel" of resistance to passive stretch movements performed by the clinician on the patient. (Taken from Arch. Phys. Med. Rehabili. Vol 80, September 1999).

The clinician moves the subject's limbs about the joints and then assigns a grade based on a "touchy feely" assessment of how much resistance the clinician feels. One can easily see the problem here. Since the test is a qualitative one, different clinicians may assign different grades to the same test. Even the same clinician's evaluation may change due to lack of consistency or depending on whether he or she is optimistic or pessimistic at the time of the test. The clinician may also be biased and may, for example, assign a better grade if he or she has knowledge of interventions being performed on the patient. Even putting all these issues aside, it is difficult to get an absolute measure of tone using the Ashworth scale. As stated in a review article "The quantification of spasticity has been a difficult and challenging problem, and has been based primarily on highly observer-dependent measurements. The lack of effective measurement techniques has been restrictive, since quantification is necessary to evaluate various modes of treatment." (R. T. Katz, W. Rymer: *Spastic hypertonia; mechanisms and measurement. Archives of Physical Medicine and Rehabilitation.* 1989; 70:144–145).

In attempt to quantify muscle tone, some have used Electromyography (EMG) information. (See P. J. Delwaide: *Electrophysiological Analysis of the Mode of Action of Muscle Relaxants in Spasticity.* Annals of Neurology, Vol. 17, No. 1, January 1985, pp 90–95; A. Eisen: *Electromyography in Disorders of Muscle Tone.* Le Journal Canadien des Sciences Neurologiques, Vol. 14, No. 3. August 1987, pp 501–505; W. G. Tatton, P. Bawa, I. C. Bruce, R. G. Lee: *Long Loop Reflexes in Monkeys: An Interpretative Base for Human Reflexes. Cerebral Motor Control in Man.: Long Loop Mechanisms.* Prog. clin. Neurophysiol., vol 4, Ed. J. E. Desmedt, pp 229–245, Krager Basel, 1978). EMG electrodes measure and amplify actual action potentials sent to the muscles. Thus, they can monitor the stretch reflex in action and the active force of muscles can be monitored.

However, the total force of muscles is a combination of both the active and passive forces. Active tension is due to muscle stimulation and contraction due to crossbridge cycling. Independent of muscle stimulation and crossbridge cycling, muscles also experience passive tension. Like all materials, muscles experience a passive tension when they are stretched beyond their resting lengths. This is due to the inherent mechanical properties of connective tissue in the muscles, such as elastin. The total force of the muscle is the sum of the active and passive tensions, as shown in FIG. 1. If muscles were de-innervated, then there would be no active force and the total force would just be the passive force.

EMG electrodes cannot monitor passive tension. Thus, the EMG signal is correlated to the active force exhibited by the muscle but not the total force. The most common definition of spasticity is "a motor disorder characterized by a velocity-dependent increase in muscle tonic stretch reflexes (muscle tone) with exaggerated tendon jerks, resulting from hyperexcitability of the stretch reflex, as one component of the upper motor neuron syndrome." (J. W. Lance: *Symposium Synopsis: Disordered Motor Control*, R. G. Feldman, R. R. Young, W. P. Koella, Chicago, Year Book Pulishers, 1980, pp. 485–494). However, it has also been proposed that an increase in tone is largely caused by changes in the intrinsic mechanical properties of the muscle tissue that causes an increase in the passive stiffness of the muscle. This contribution of muscle tone is independent of the stretch reflex and is not encapsulated in the EMG signal. Still further, EMG signals are extremely noisy, particularly if surface electrodes are used. EMG signals measured with surface electrodes can also be influenced by hair, oil, or lotions, and dead skin, thereby i yielding erroneous results. Though the amplitude of the EMG signal is correlated with the active force produced by the muscle, it is extremely difficult to find the proper transformation between the two quantities. This relationship differs from person to person due to physiological differences. It is also sensitive to changes in location of the electrode within the same subject. Thus, the use of an EMG machine is not a good option for quantifying muscle tone, but, rather, is more useful for monitoring the timing of reflex responses.

Still other tests, such as the pendulum test, measure the range of motion and rate of change of motion of the joint in response to a tendon jerk test. Though such tests may give an indication of tone, the trajectory of a joint does not give a full picture of muscle tone.

Tone describes the relationship of torque produced by the muscles in response to an induced trajectory perturbation, or the resulting trajectory given a torque perturbation. Either way, the relationship between torque and trajectory can be described using a mathematical model where parameters quantify tone in terms of the viscoelastic properties of the muscles. However, it is difficult to quantify these parameters. Unlike heart rate or blood pressure, which are inherently physical quantities that can be measured, tone describes a relationship between torque and displacement, as well as the first derivative of angular displacement or velocity of the joint based on the viscoelastic properties of the muscles. Also, inertia of the limb has influence on the torque, which needs to be properly isolated when determining the viscoelastic properties of the muscles acting on a joint.

In the past, simple DC motors have been used to oscillate an appendage about its joint while measuring the torque response due to the external perturbation. The response of appendage movements about the joint of rotation can be explained in terms of elastic and viscous parameters. These parameters are dependent upon the passive mechanical properties of muscles and the active stretch reflex response, which has some inherent delay. A certain amount of torque is required to move the appendage and to move the parts of the apparatus, as every mass has a rotational inertia. Thus, the torque response measured can be written as equation 1 shown below:

$$\tau_s(t) = K_H \Delta\theta(t) + B_H \dot\theta(t) + J_T \ddot\theta(t) \quad [\text{Eq. 1}]$$
$$\tau_s(t) = K_H (\theta(t) - \theta_{RP}) + B_H \dot\theta(t) + J_T \ddot\theta(t)$$
$$\tau_s(t) = K_H \theta(t) + B_H \dot\theta(t) + J_T \ddot\theta(t) - K_H \theta_{EQ}$$
$$\tau_s(t) = K_H \theta(t) + B_H \dot\theta(t) + J_T \ddot\theta(t) + \tau_{off}$$

where $\tau_s$ is the total torque sensed by the transducer. $\tau_{off}$ is the offset torque and tells the angular position the hand prefers to be in relative to the origin or bias position. $K_H$ and $B_H$ are the angular stiffness and viscosity of the combined flexor and extensor muscle groups that act on the joint. $J_T$ is the combined inertia of oscillating appendage, $J_H$ and the rotating components of the apparatus, $J_A$. $J_T=J_H+J_A$. $\theta$ is the angular displacement of the system.

$\dot\theta$ and $\ddot\theta$ are the velocity and acceleration which are the first and second derivatives of displacement respectively. $\theta_{RP}$ is the angular position of the resting hand.

This second order differential equation has previously been used as a model by many including Evans at al (C. M. Evans, S. J. Fellows, P. M. H. Rack, H. F. Ross and D. K. W. Walters: *Response of the Normal Human Ankle Joint to Imposed Sinusoidal Movements.* J. Physiol. (1983), 344, pp. 483–502), Rack et al. (P. M. H. Rack, H. F. Ross and T. I. H. Brown: *Reflex Response during Sinusoidal Movements of Human Limbs.* Prog. Clin. Neurophysiol., vol. 4, Ed. J. E. Desmedt, pp 216–228, 1978), Lehmann et al. (J. F. Lehmann, R. Price, B. J. DeLateur, S. Hinderer, C. Traynor: *Spasticity: Quantitative Measurements as a Basis for Assessing Effectiveness of Therapeutic Intervrntion.* Arch. Phys. Med. Rehabil. Vol 70. pp 6–15, 1989), Prince et al. (R.

Price, K. F. Bjornson, J. F. Lehmann, J. F. McLaughlin, R. M. Hays: *Quantitative Measurement of Spasticity in Children with Cerebral Palsy*. Developemental Medicine and Child Neurology, 33, pp.585–595, 1991), Minders et al. (M. Meinders, R. Price, J. F. Lehmann, K. A. Questad: *The Stretch Reflex Response in the Normal and Spastic Ankle: Effect of Ankle Position*. Arch. Phys. Med. Rehabili. Vol 77. pp 487–491, 1996). In each case, simple sinusoidal displacements of the ankle or finger joint were used at various frequencies. The technique of measuring the frequency response to sinusoidal inputs to investigate properties of second order electromechanical systems is common and easy to do. The goal is to compute $K_H$ and $B_H$ at various frequencies of oscillation. Since the activation stretch reflex loop in the central nervous system is rate-dependent, one would expect that $K_H$ and $B_H$ vary at different perturbation speeds. Sinusouds have been chosen because they are easy to generate by means of a unidirectional rotating wheel and crank. No feedback loop is necessary. It has been argued that since sinusoidal movements are continuous and smooth, they involve no sudden impulsive movements that might synchronize a large number of sensory receptors in an artificial or unphysiological way.

However, there is a fundamental mathematical problem in isolating the inertia from the elastic stiffness of the muscles when using simple sinusoidal displacements.

In this case, the displacement, $\theta(t)=A \cdot \sin(\omega t)$, where A is the amplitude of the sinusoid in radians and $\omega$ is the frequency of the oscillation in rads/sec. The velocity, $$\dot\theta(t) = d\theta/dt = A\omega \cdot \cos(\omega t)$$

and the acceleration $$\ddot\theta(t) = d^2\theta/dt^2 = -A\omega^2 \cdot \sin(\omega t).$$

Substituting these state variables into equation 1 and rearranging, we get:

$\tau_s - \tau_{off} = K_H A \sin(\omega t) + B_H A\omega \cos(\omega t) - J_T A\omega^2 \sin(\omega t)$ $\tau_s - \tau_{off} = (K_H - J_T\omega^2)(A \sin(\omega t)) + B_H \omega (A \cos(\omega t))$    [Eq. 2]

The dominant waveform of the torque response is a sinusoid of the same frequency but $\phi$ radians out of phase with the displacement wave as shown in equation 3. After data acquisition, A, M and $\phi$ are obtained by looking at the transfer functions of the displacement and torque signals in the frequency domain to obtain the magnitude and phases at the forced frequency $\omega$ $\tau_s - \tau_{off} = M \sin(\omega t + \phi)$    [Eq. 3]

From the sum formula:

$\tau_s - \tau_{off} = M \sin(\phi)\cos(\omega t) + M \cos(\omega)\sin(\omega t)$ If $M_1 = M \sin(\phi)$ and $M_2 = M \cos(\phi)$ Then:

$\tau_s - \tau_{off} = M_1 \cos(\omega t) + M_2 \sin(\omega t)$    [Eq. 4]

Substituting equation 4 into equation 2:

$M_1 \cos(\omega t) + M_2 \sin(\omega t) = (K_s - J_T\omega^2)(A \sin(\omega t)) + B_H\omega(A \cos(\omega t))$ Thus, the total torque measured can be isolated as a component in phase with the displacement wave and a component quadrature with the displacement wave.

$M_1/A = K_H - J_T\omega^2$    [Eq. 5]

and $M_2/A = B_H\omega$    [Eq. 6]

The amplitude of the in phase component contains both elastic and inertial terms. Researchers have argued that a least squares (error) fit of the in phase component and displacement amplitude with frequency squared yields a linear relationship of slope intercept form; y=mx+b, where y is $M_1/A$, x is $\omega^2$, m is the slope and b is the intercept. They have assumed that the slope is the total inertial and this "total inertia" value has been used to evaluate the stiffness by manipulating equation 5 to solve for $K_H$ at each frequency.

At first glance of equation 5, this assumption may seem correct. After all, the total inertia does remain constant. However, the assumption is false because the least squares fit yields an intercept, b, that is a single approximation of $K_H$ across all frequencies. Since the goal is to find a pair of varying stiffness and viscosity values at each frequency, this analysis is self-contradictory. This analysis forces the $K_H$ values to be trendless (uncorrelated) across frequencies whose variance depends on how well equation 5 fits to a straight line. To put it simply, there are more unknowns than equations. If N sinusoids are used, each at a different forcing frequency, we are looking for N different stiffness values and one inertia value. Thus, there are N+1 unknowns and N number of equations that resemble equation 5. With more unknowns than equations, the system is indeterminate and it is impossible to isolate the stiffness values from the inertia value when only sinusoids are used.

Another way to show this problem that prevents isolation of the stiffness and inertial values from the in phase component can be shown using least squares regression analysis. Usually, we can obtain the linear parameters of the model in equation 1 by performing a least squares regression fit on the data. Given any set of data values obtained from a given perturbation trial:

$$T_s = \begin{vmatrix} \tau_s(t_1) \\ \tau_s(t_2) \\ \vdots \\ \tau_s(t_n) \end{vmatrix}_{n \times 1} \quad \text{and}$$

$$\Psi = \begin{vmatrix} 1 & \theta(t_1) & \dot\theta(t_1) & \ddot\theta(t_1) \\ 1 & \theta(t_2) & \dot\theta(t_2) & \ddot\theta(t_2) \\ \vdots & \vdots & \vdots & \vdots \\ 1 & \theta(t_n) & \dot\theta(t_n) & \ddot\theta(t_n) \end{vmatrix}_{n \times 4}$$

It is possible to obtain the set of four parameters, $$\tilde N = \begin{vmatrix} \tau_{off} \\ K_H \\ B_H \\ J_T \end{vmatrix}_{4 \times 1}$$

that describes the model in equation 1

$\tau_s(t) = K_H \theta(t) + B_H \dot\theta(t) + J_T \ddot\theta(t) + \tau_{off}$    [eq.1]

using the pseudo-inverse which minimizes the sum squared error $$SE=(\hat{O}_s-\emptyset\tilde{N})^T(\hat{O}_s-\emptyset\tilde{N})$$

$$V_{emf}=K_e$$

Typically, the pseudo-inverse (denoted by the function pinv in equation 7), can be used to obtain the vector of unknowns, P, as follows:

$$\tilde{N}=pinv(\emptyset)\hat{O}_s=(\emptyset^T\emptyset)^{-1}\emptyset^T\hat{O}_s \quad \text{[eq. 7]}$$

However, this can usually but not always be done because, in the case of sinusoidal perturbation at a given frequency, the acceleration waveform is always a constant multiple of the displacement waveform by the scalar quantity $-A\omega^2$ for all time. Thus the displacement values and acceleration values are linearly dependent. Since the first and third rows of $\Psi$ are linearly dependent, the product of the matrices $\Psi^T\Psi$ is singular or very close to singular. All singular matrices are noninvertible, thus P cannot be obtained, or the obtained values are inaccurate.

SUMMARY OF THE INVENTION

The present invention provides a method and apparatus that quantifies muscle by using non-sinusoidal perturbations. More particularly, the device and method move the upper or lower extremities of a patient in a non-sinusoidal trajectory, $\theta(t)$, while measuring the torque response $\tau_s(t)$ and utilizing Equation 1 to determine the stiffness $K_H$, viscosity $B_H$ and inertial $J_T$ parameters.

$$\tau_s(t) = K_H\theta(t) + B_H\dot{\theta}(t) + J_T\ddot{\theta}(t) + \tau_{off} \quad \text{[Eq. 1]}$$

In an exemplary embodiment, as set out herein in more detail, the device and method of the present invention can be utilized to quantify the forearm muscle tone, the wrist in particular. The device is particularly useful for quantifying muscle tone in a spastic patient. However, it is to be understood that the present method and device are not limited to quantification of forearm muscle tone or to the spastic patient. Rather, the device and method are useful on both the upper and lower extremities including, for example, the ankle. Further, the method and device can be used to measure muscle tone in the non-spastic patient. For example, the method and device are useful in evaluating patients with various types of upper or lower motor neuron paralysis that affects skeletal muscles, such as patients with cerebral palsy, traumatic brain injury, spinal cord injury, stroke, or Parkinson's Disease patients. Further, the method and device could be used in analyzing a patient's muscle tone in line with, for example, physical therapy that the patient is undergoing to regain control of the muscles in the legs after a spinal accident.

More specifically, in accordance with an exemplary method of the present invention, the wrist is driven with an arbitrary trajectory that is neither sinusoidal nor ramp. By controlling the trajectory $\theta(t)$ and measuring the torque response $\tau(t)$, the stiffness, viscosity, and inertial parameters in equation 1 can then be determined.

In general, the device in accordance with the present invention is an automated tone assessment device that non-invasively and properly quantifies tone. The device properly determines the muscle tone of a person's flexors and extensors about a appendage non-invasively. The appendage is perturbed with arbitrary trajectories by virtue of a robotic design that uses a closed loop automated feedback direct drive device that tracks any arbitrary desired trajectory. The device perturbs an appendage with any desired trajectory to properly determine the stiffness of the flexors and extensors of an appendage. More particularly, a desired displacement of the wrist is first determined using a set of conditions detailed herein. A discrete set of finite points defining this trajectory is then input into a controller, and a motor shaft tracks these points at a certain sampling rate.

Other aspects and embodiments of the invention are discussed infra.

BRIEF DESCRIPTION OF THE DRAWINGS

It should be understood that the drawings are provided for the purpose of illustration only and are not intended to define the limits of the invention. The foregoing and other objects and advantages of the embodiments described herein will become apparent with reference to the following detailed description when taken in conjunction with the accompanying drawings in which:

FIG. 6 shows an optical encoder in the form of a code wheel with a series of slits followed by opaque radial lines. The two LED/Phototransistor pairs measure the amount of rotation by keeping count of the number of slits that go by.

FIG. 17 shows four possibilities of bias positions that subjects were tested at in accordance with the present invention.

FIG. 18 shows raw data collected from optical encoder, torque transducer and EMG electrodes in trial 1 of experiment DMJF.

FIG. 19 shows raw data collected from optical encoder, torque transducer and EMG electrodes in trial 2 of experiment DMJF.

FIG. 20 shows raw data collected from optical encoder, torque transducer and EMG electrodes in trial 3 of experiment DMJF.

FIG. 21 shows raw data collected from optical encoder, torque transducer and EMG electrodes in trial 4 of experiment DMJF.

FIG. 22 shows raw data collected from optical encoder, torque transducer and EMG electrodes in trial 5 of experiment DMJF.

FIG. 23 shows raw data collected from optical encoder, torque transducer and EMG electrodes in trial 6 of experiment DMJF.

FIG. 24 shows raw data collected from optical encoder, torque transducer and EMG electrodes in trial 7 of experiment DMJF.

FIG. 25 shows raw data collected from optical encoder, torque transducer and EMG electrodes in trial 8 of experiment DMJF.

FIG. 26 shows raw data collected from optical encoder, torque transducer and EMG electrodes in trial 9 of experiment DMJF.

FIG. 27 shows raw data collected from optical encoder, torque transducer and EMG electrodes in trial 10 of experiment DMJF.

FIG. 30 shows rectified data filtered from the optical encoder, torque transducer and EMG electrodes in trial 1 of experiment DMJF.

FIG. 31 shows rectified data filtered from the optical encoder, torque transducer and EMG electrodes in trial 2 of experiment DMJF.

FIG. 32 shows rectified data filtered from the optical encoder, torque transducer and EMG electrodes in trial 3 of experiment DMJF.

FIG. 33 shows rectified data filtered from the optical encoder, torque transducer and EMG electrodes in trial 4 of experiment DMJF.

FIG. 34 shows rectified data filtered from the optical encoder, torque transducer and EMG electrodes in trial 5 of experiment DMJF.

FIG. 35 shows rectified data filtered from the optical encoder, torque transducer and EMG electrodes in trial 6 of experiment DMJF.

FIG. 36 shows rectified data filtered from the optical encoder, torque transducer and EMG electrodes in trial 7 of experiment DMJF.

FIG. 37 shows rectified data filtered from the optical encoder, torque transducer and EMG electrodes in trial 8 of experiment DMJF.

FIG. 38 shows rectified data filtered from the optical encoder, torque transducer and EMG electrodes in trial 9 of experiment DMJF.

FIG. 39 shows rectified data filtered from the optical encoder, torque transducer and EMG electrodes in trial 10 of experiment DMJF.

FIG. 55 shows the results for adult subject BY with hemiplegic spasticity. The affected and unaffected arms were tested at a bias of 30 degrees flexion at each of the ten filtered, random trajectories.

FIG. 137 shows an AutoCAD mechanical design drawing of one embodiment of the top surface of the housing in accordance with the present invention.

FIG. 138 shows an AutoCAD mechanical design drawing of one embodiment of the bottom surface of the housing in accordance with the present invention.

FIG. 139 shows an AutoCAD mechanical design drawing of one embodiment of the back surface of the housing in accordance with the present invention.

FIG. 141 shows an AutoCAD mechanical design drawing of one embodiment of the right side surface of the housing in accordance with the present invention.

FIG. 142 shows an AutoCAD mechanical design drawing of one embodiment of the encoder mount in accordance with the present invention.

FIG. 149 shows an AutoCAD mechanical design drawing of one embodiment of the hand sub assembly in accordance with the present invention.

DETAILED DESCRIPTION OF THE INVENTION

Figure 1:
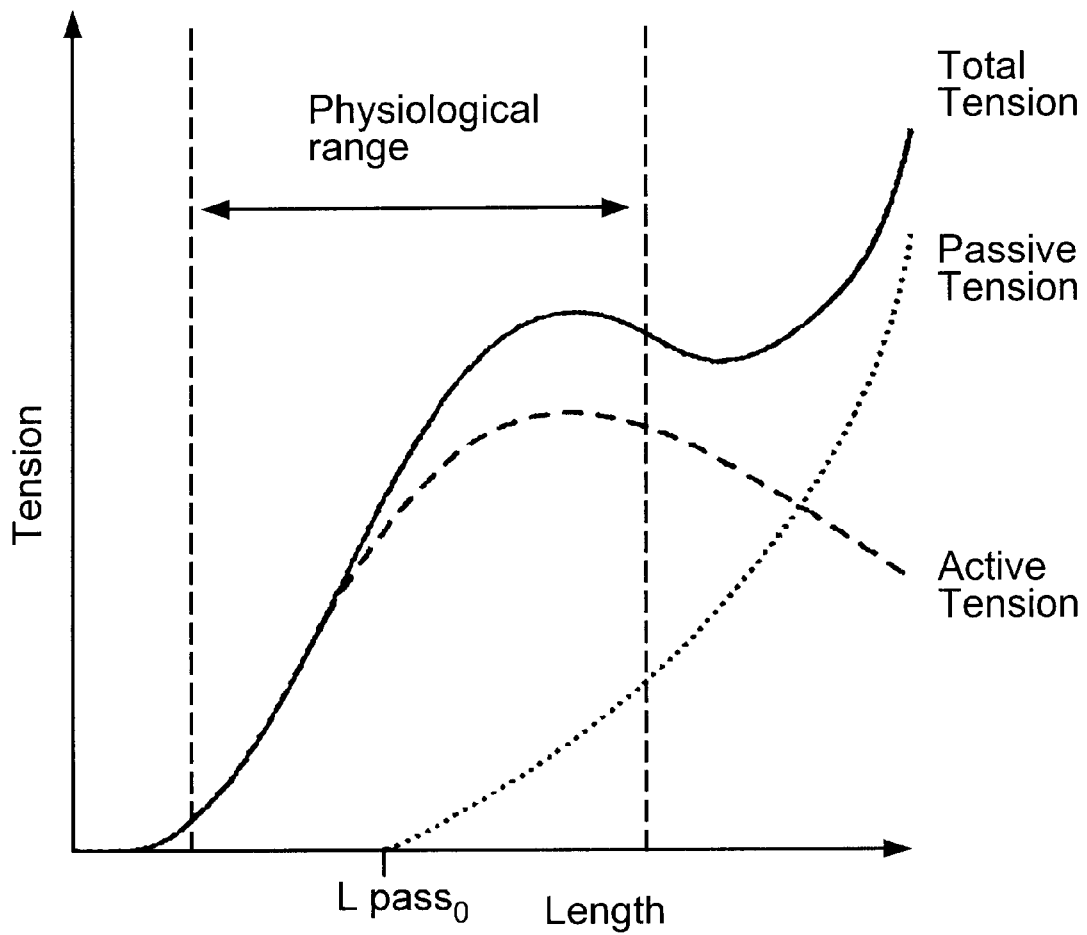
FIG. 1 shows the total muscle tension as the sum of active and passive tensions. (Taken from E. R. Kandel, J. H. Schwartz, and T. M. Jessell. *Principles of Neural Science*, third edition, Elsevier, New York, 1981, p. 552)

The present invention provides a method for quantifying muscle tone and an apparatus that carries out the method.

In general, the device in accordance with the present invention is an automated tone assessment device that non-invasively and properly quantifies tone. Quantification of tone allows a clinician to decide on the nature and degree of intervention to administer. A pre and post-evaluation can also determine the effectiveness of the intervention as well as track the progress of the patient. The system software can easily be modified to output the muscle stiffness of the patient to the clinician in real time. The implications of this are in the operating room where a neuro-surgeuon makes temporary lesions in the brain while monitoring the patient's muscle tone in real time. Once the surgeon finds the proper location in the brain that alleviates the degree of muscle tone with out too much loss in function, he/she can make the lesion permanent.

In an exemplary embodiment the device and method of the present invention are utilized to quantify the forearm muscle tone, in particular, the wrist in a spastic patient. However, it is to be understood that the present method and device are not limited to quantification of forearm muscle tone or to the spastic patient.

When used to quantify muscle tone in the spastic patient, upon determination of the muscle tone, the degree of spasticity that the patient has can be determined, thereby allowing a clinician to decide what form of intervention to take and to what degree. The muscle tone can further be monitored over time to allow the clinician to determine whether the intervention is providing benefits to the patient.

More particularly, the present invention utilizes equation 1 to determine the stiffness, viscosity and inertial parameters.

$$\tau_s(t) = K_H \theta(t) + B_H \dot{\theta}(t) + J_T \ddot{\theta}(t) + \tau_{off} \quad \text{[Eq. 1]}$$

While equation 1 has been used in the past, the methods and devices that were used to apply equation 1 utilized sinusoidal displacements of the ankle or finger joint at various frequencies. Using sinusoidal displacements, as set out above, leads to an indeterminate system, and it is impossible to isolate the stiffness values from the inertia values.

In accordance with the method of the present invention, a desired trajectory that is non-sinusoidal and not a ramp is first determined. The desired trajectory is then input into the device of the present invention, which is an electromechanical system that utilizes a feedback controller to track the desired displacement trajectory.

In accordance with the present method, a desired displacement of the wrist is first determined using the following set of conditions.

(1) The trajectory is 'smooth'. In other words, when perturbing an appendage about its joint of rotation, there should be "no sudden impulsive movements that might synchronize a large number of sensory receptors in an artificial or unphysiological way." (See P. M. H. Rack, H. F. Ross and T. I. H. Brown: *Reflex Response during Sinusoidal Movements of Human Limbs*. Prog. Clin. Neurophysiol., vol. 4, Ed. J. E. Desmedt, pp 216–228, 1978). As used herein, a "smooth discrete trajectory" is mathematically defined as follows:

$\theta_d(t_k)$ is a discrete signal consisting of set of N (1000) points that could be sampled from a continuous, differentiable function, $\theta_d(t)$ for all time t such that:
  a. The sampling frequency (fhz$_{mc}$) of the discrete signal must be near to or greater than or equal to 100 Hz, particularly if the maximum frequency required to represent the discrete signal approaches or exceeds 10 Hz.
  b. In the frequency domain, the maximum frequency needed to represent the desired trajectory must be less than the smaller of one-sixth frequency of the sampling rate of the motor controller, fhz$_{mc}$, or 15 Hz.

(2) At time, t=0, $\theta_d(0)=0$, the motor does not jump rapidly to the initial point.

(3) The trajectory $\theta_d(t)$ is periodic (repeatable) and smooth for all time t>0. In other words $\theta_d(t_{N+1})$ equals $\theta_d(t_1)$.

(4) The trajectory has a finite range of motion with a controllable, defined distribution.

(5) The matrix $\Psi$ has linearly independent columns, which ensures that the matrix $\Psi^T\Psi$ is nonsingular.

Filtered random trajectories are then generated using, for example, MATLAB in the following way. There exist three discrete signals, $r_a(t_k)$, $r_b(t_k)$ and $r_c(t_k)$ in the time domain which correspond to $R_a(\omega)$, $R_b(\omega)$, and $R_c(\omega)$ respectively in the frequency domain. The time between two consecutive points given to the controller is dt$_{mc}$ seconds apart.

(1) A set of N(1000) uniformly distributed numbers is generated from −0.5 to 0.5. The frequency of the motor controller, fhz$_{mc}$, is 128 Hz, so consecutive points are dt$_{mc}$=0.0078 seconds apart in time. This discrete signal is called $r_a(t_k)$.

(2) The discrete Fourier Transform of $r_a(t_k)$ is taken, $R_a(\omega)$ to obtain the magnitude, $|R_a(\omega)|$ and phase, $\phi(R_a(\omega))$ of the signal in the frequency domain.

Figure 2F:
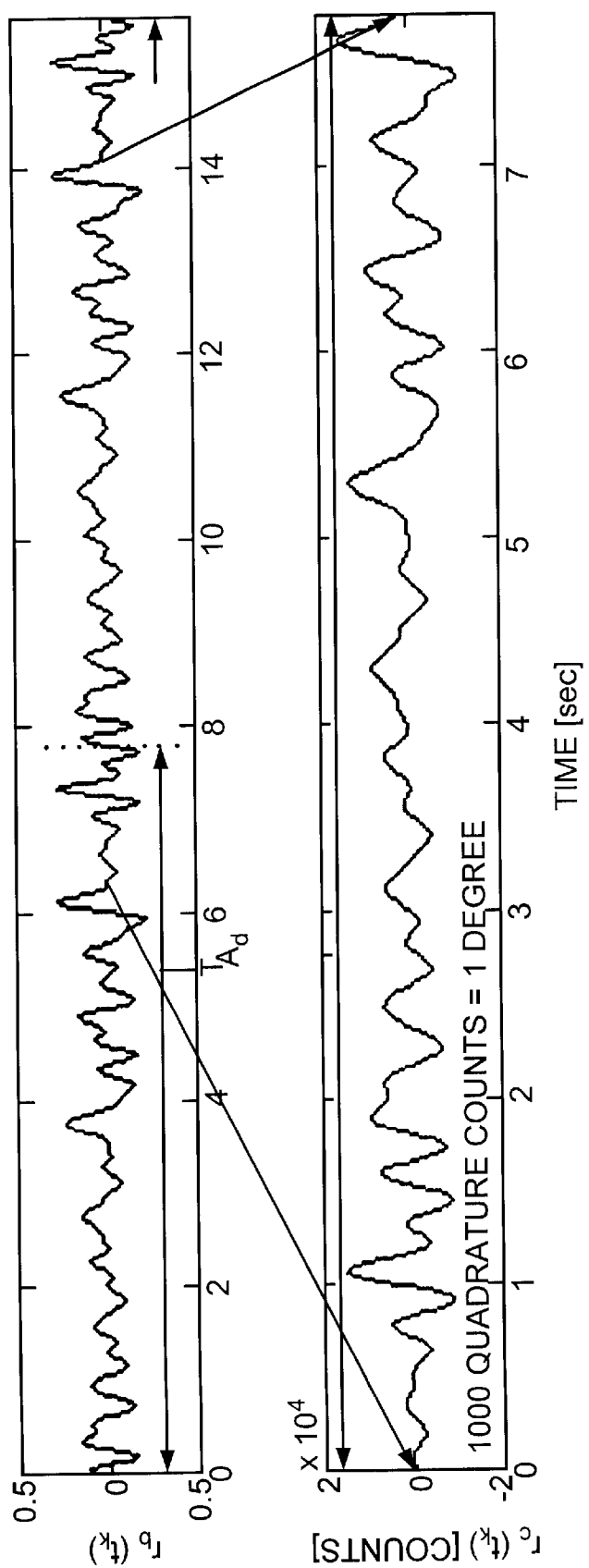
FIG. 2 shows the generation of a smooth filtered random trajectory by limiting the maximum frequency component of a uniformly distributed random number set of 1000 points in the frequency domain. The signal is then taken back to the time domain via the inverse Fourier transform. The filtered random trajectory is selected to start and stop at the origin and finally scaled to have an RMS value of 7000 counts (7 degrees).
Figure 3:
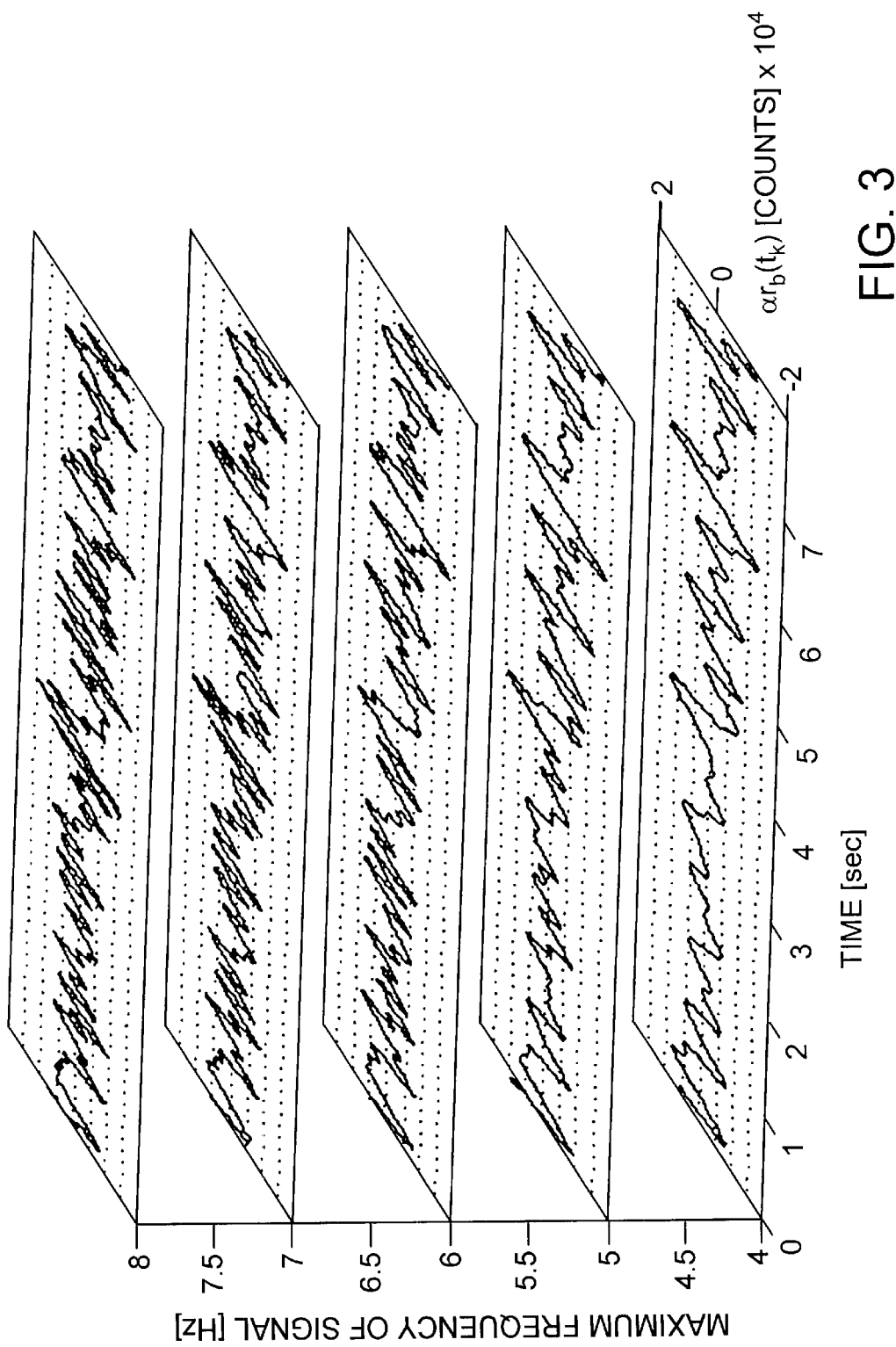
FIG. 3 shows the generation of faster trajectories from the same random number set by increasing the maximum frequency component in the frequency domain in filtering a random number set.
Figure 4A:
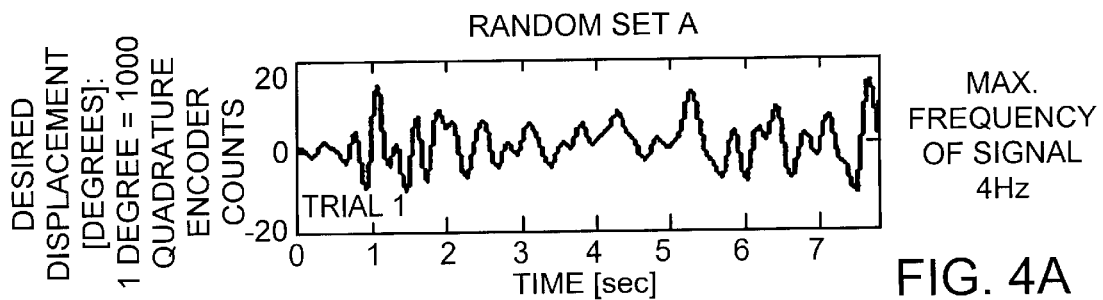
FIG. 4 shows the generation of two sets of filtered random trajectories from two sets of random numbers. Trials 1 and 2 have a maximum frequency component of 4 Hz, trials 3 and 4 have a maximum frequency component of 5 Hz, trials 5 and 6 have a maximum frequency component of 6 Hz, and trials 7 and 8 have a maximum frequency component of 8 Hz. The displacements shown are relative to the bias position or starting angle of the wrist. If the left hand is tested instead of the right, these trajectories are flipped or negated.
Figure 4B:
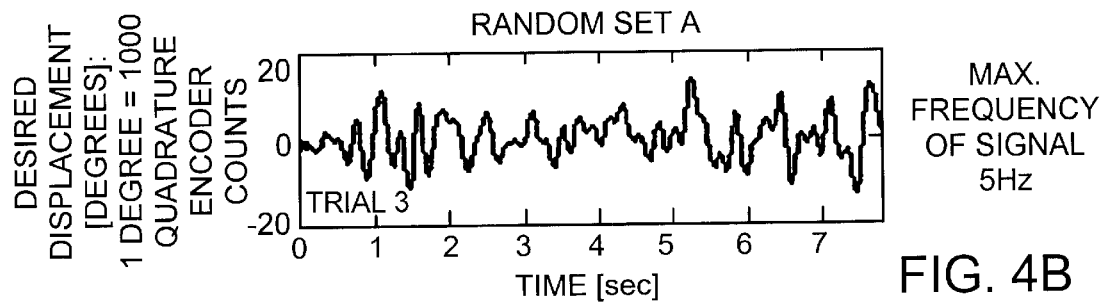
Figure 4C:
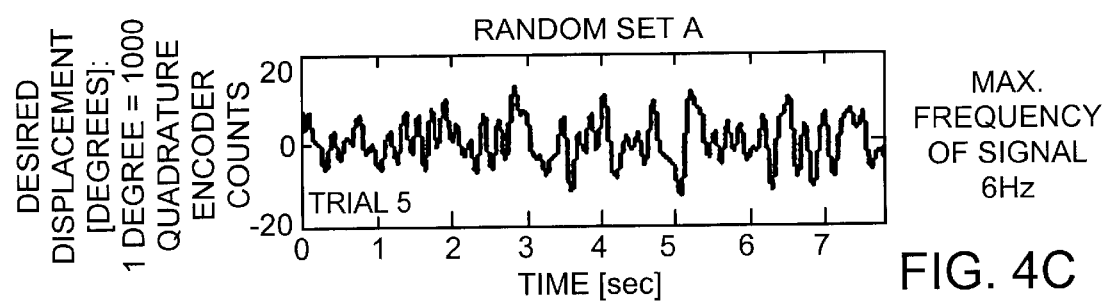
Figure 4D:
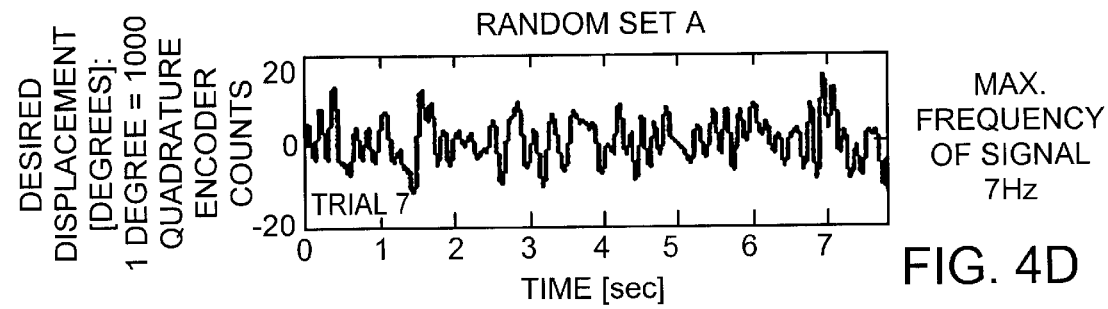
Figure 4E:
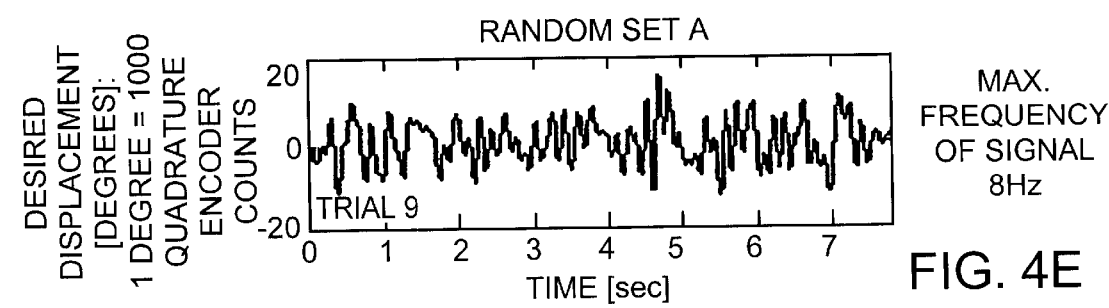
Figure 4F:
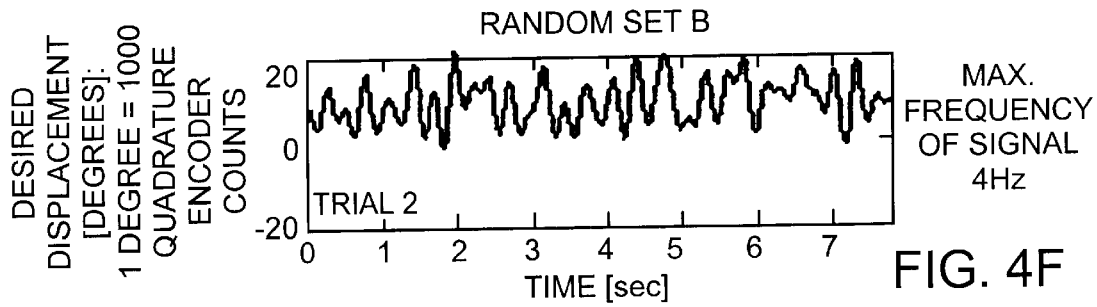
Figure 4G:
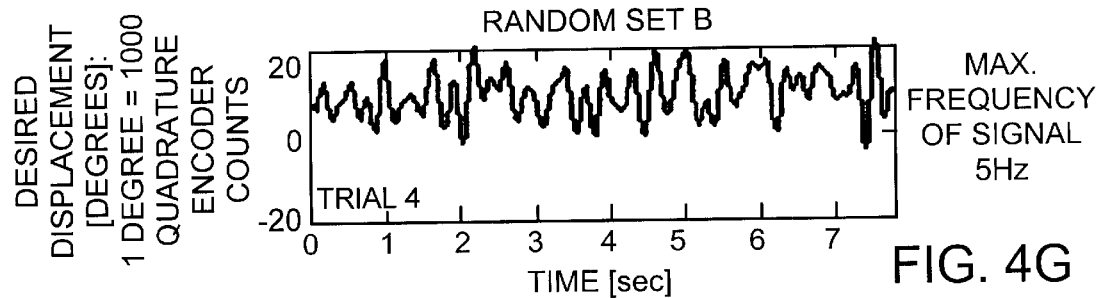
Figure 4H:
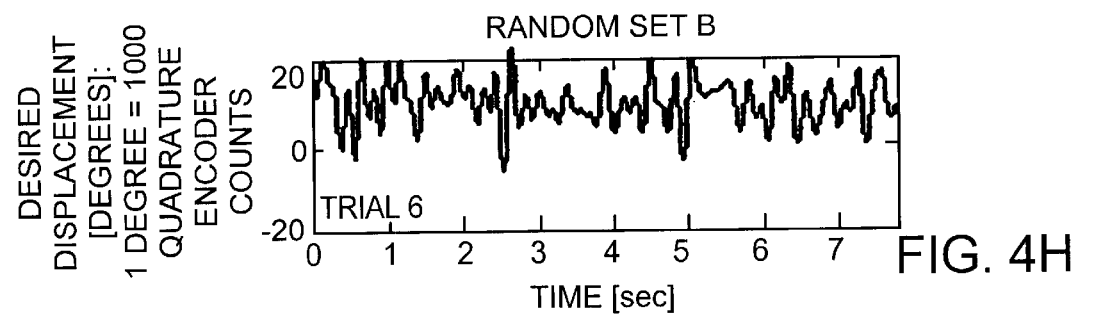
Figure 4I:
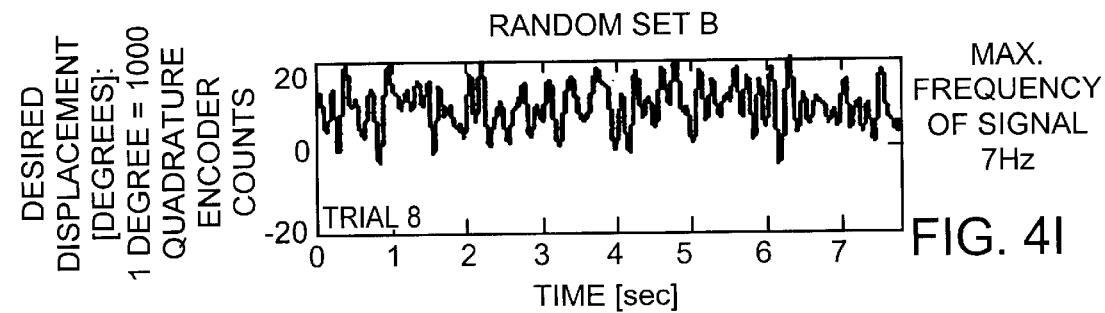
Figure 4J:
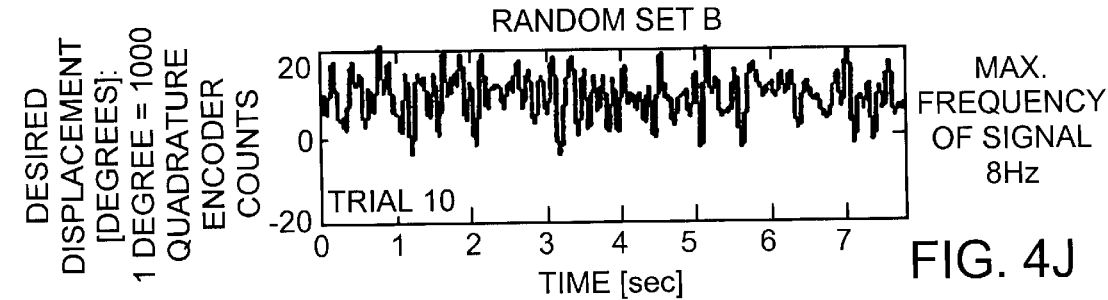

(3) Now, $R_b(\omega)$ is generated. For all $\omega$, $\phi(R_b(\omega))=\phi(R_a(\omega))$. An $\omega_{max}$ is selected such that $|R_b(0)|=0$, for $0<\omega\leq\omega_{max}$, $|R_b(\omega)|=|R_a(\omega)|$, and for all $\omega>\omega_{max}$, $|R_b(\omega)|=0$. In FIG. 2, $\omega_{max}=2\pi*4$ Hz.

(4) The Inverse Fourier Transform of $R_b(\omega)$ is taken to obtain $r_b(t)$. Note that the mean value of $r_b(t_k)=0$.

(5) There is no guarantee that $r_b(0_1)=0$, however, the trajectory does cross $\theta=0$ at several instances in time. The index, min_i is found where $r_b$(tmin_i) has the lowest absolute value which is approximately 0. Note that $r_b(t_k)$ is a continuous periodic function for all time with a period of $T_\theta$=dt$_{mc}$*(N)=7.8125 s.

(6) $r_c(t_k)=\alpha(r_b(t_k+t_{min\_i})-r_b(t_{min\_i}))$. By shifting the signal $r_b(t_k)$ back $t_{min\_i}$ seconds in time, $r_c(0)=0$. $\alpha$ is a scalar number which scales the range of motion of the trajectory. $\alpha$ was selected so that the root mean squared value of $r_c(t_k)$ is 7000/$\sqrt{2}$ counts. Thus, $\alpha$=7000*RMS($r_b(t_k)$)/$\sqrt{2}$ (7) Finally, each data point in $r_c(t_k)$ is rounded to the nearest integer which gives the desired trajectory, $\theta_d(t_k)$. This is done because the encoder (position sensor) and the controller deal with an integer number of digital counts.

The discrete set of finite data points defining the trajectory is then inputted into the controller, and a motor shaft tracks these points at a certain sampling rate. The desired trajectories generated in this fashion satisfy all conditions listed above. Faster desired trajectories can be further generated that cover the same distribution of angular positions from the same random number set. For example, as shown in FIG. 4, two random number sets were used with maximum frequency components of 4, 5, 6, 7, and 8 Hz to give 10 trials.

Generally, the trajectory is determined for testing of the right hand. However, if the left hand is to be tested, these trajectories for the right hand can simply be flipped or negated about the bias position, or relative origin, 0, to ensure symmetry across contralateral limbs.

The device in accordance with the present invention is an electromechanical system that is designed to drive the wrist with the filtered random trajectories described above. Because these trajectories have complex variable position and velocity profiles, an automated feedback controller, or robot, is used which constantly varies the torque, speed and direction of the actuator (motor). The desired trajectory is given as input, and the actuator moves back and fourth tracking the desired trajectory. Thus, design of the system in accordance with the present invention includes a mechanical design, the use of sensors and actuators, feedback control, data acquisition and programming.

Figure 5B:
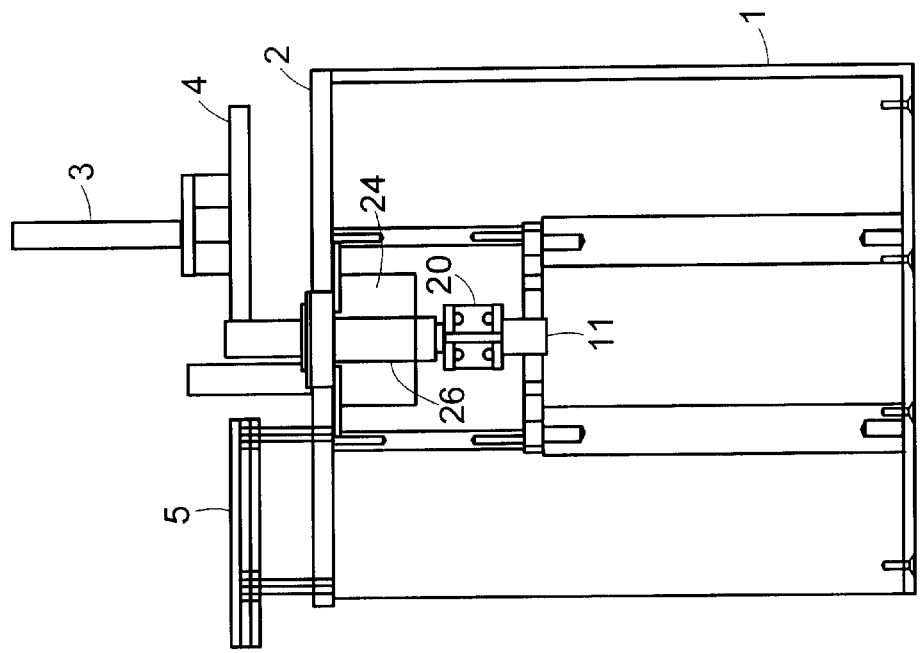
FIG. 5 shows one embodiment of the device in accordance with the present invention.
Figure 5A:
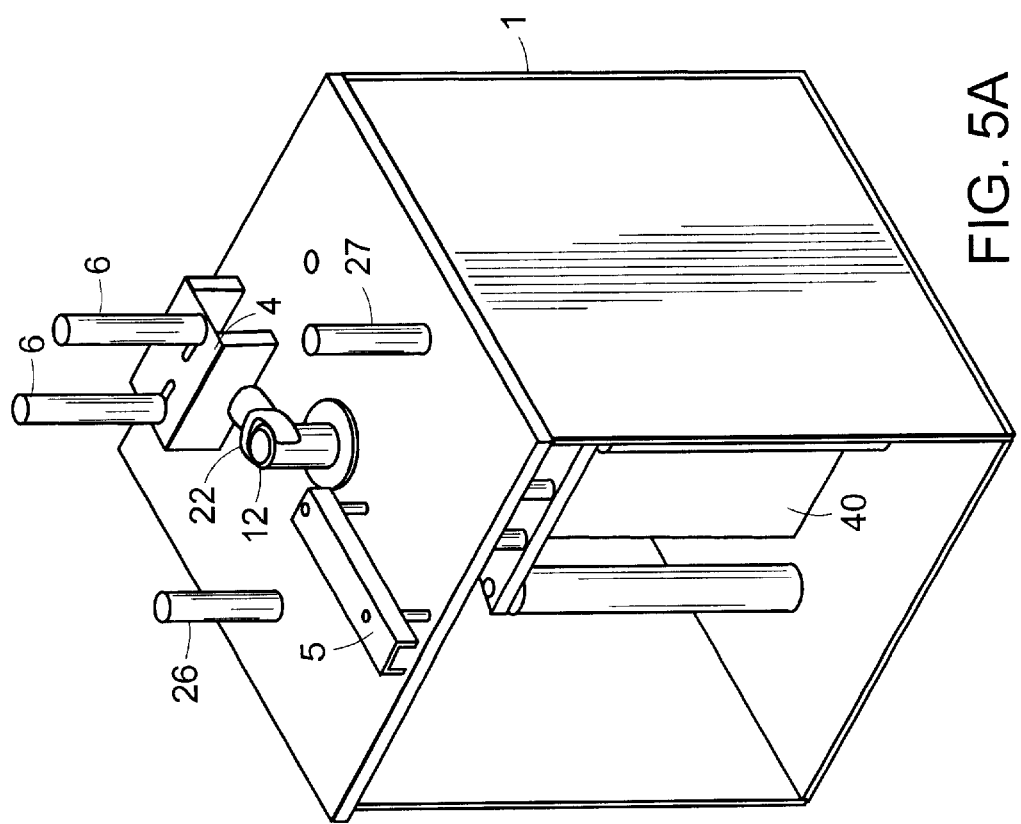

One embodiment of the electromechanical system is shown in FIG. 5. As shown, the device includes a housing 1. The materials used in fabricating the housing are not particularly limited provided they supply the required structural support for holding a patient's arm on the top surface 2 of the housing 1 during testing. One preferred material is a metal such as aluminum. The housing 1 is shown as box-like in shape, however, the shape of the housing 1 is not limited and can come in a variety of shapes. Preferably, the top surface 2 of the housing 1, where the patient's arm rests during testing, is flat.

On the top surface 2 of the housing 1 is a hand securing mechanism 3 where the patent places his hand during the test. The hand securing mechanism 3 is designed such that the patient's hand can be placed sideways within the hand securing mechanism 3 with the palm facing the left (when the right hand is tested) and the thumb facing upwards. To accommodate various sized hands, the hand securing mechanism 3 is preferably adjustable to varying sizes.

Figure 7:
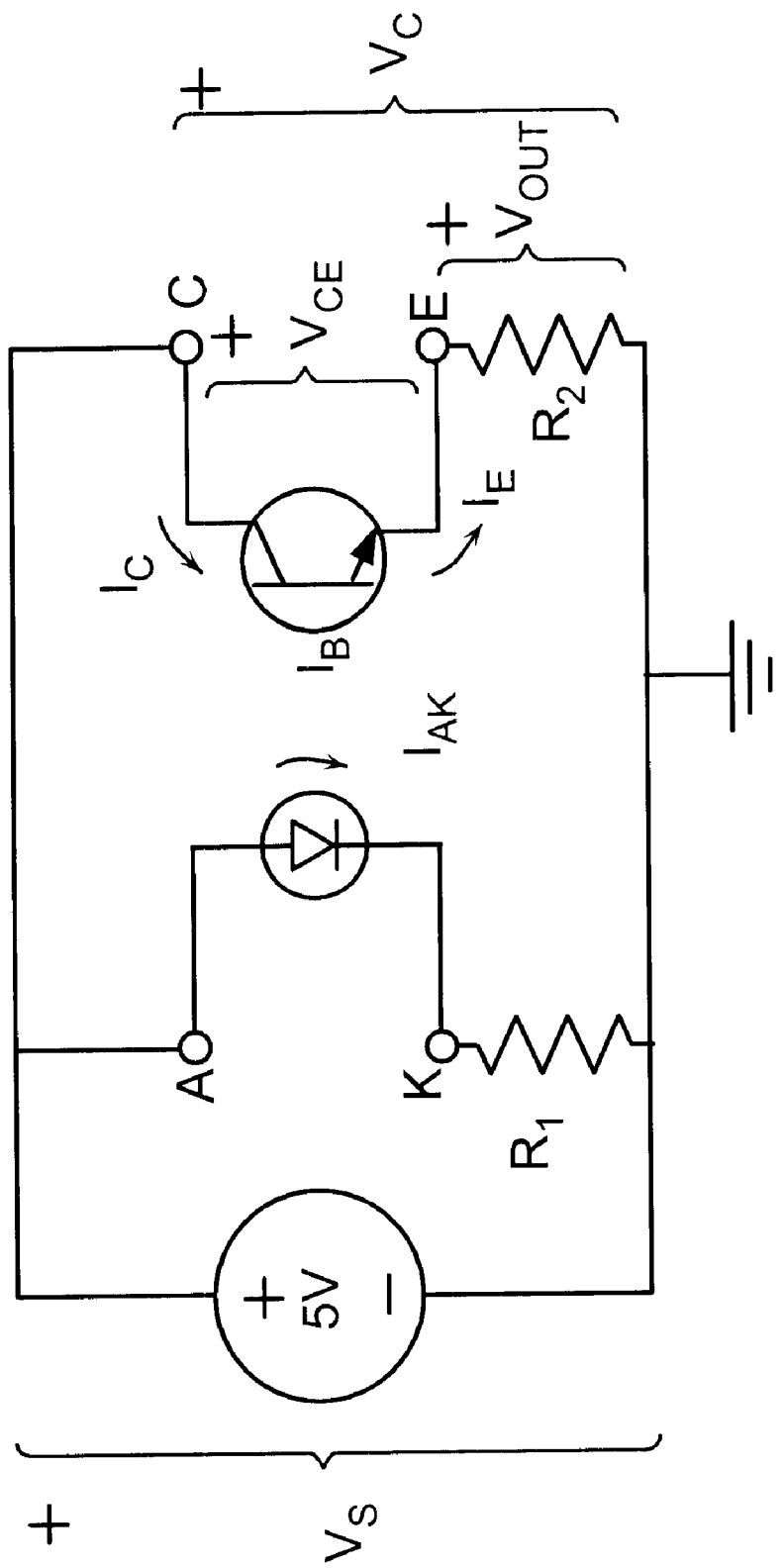
FIG. 7 shows the typical circuitry of an LED/phototransistor pair. When light is transmitted from the LED to the phototransistor $V_{OUT}$ is approximately 5V. When a opaque object blocks the light, $V_{OUT}$ drops to 0V.
Figure 11:
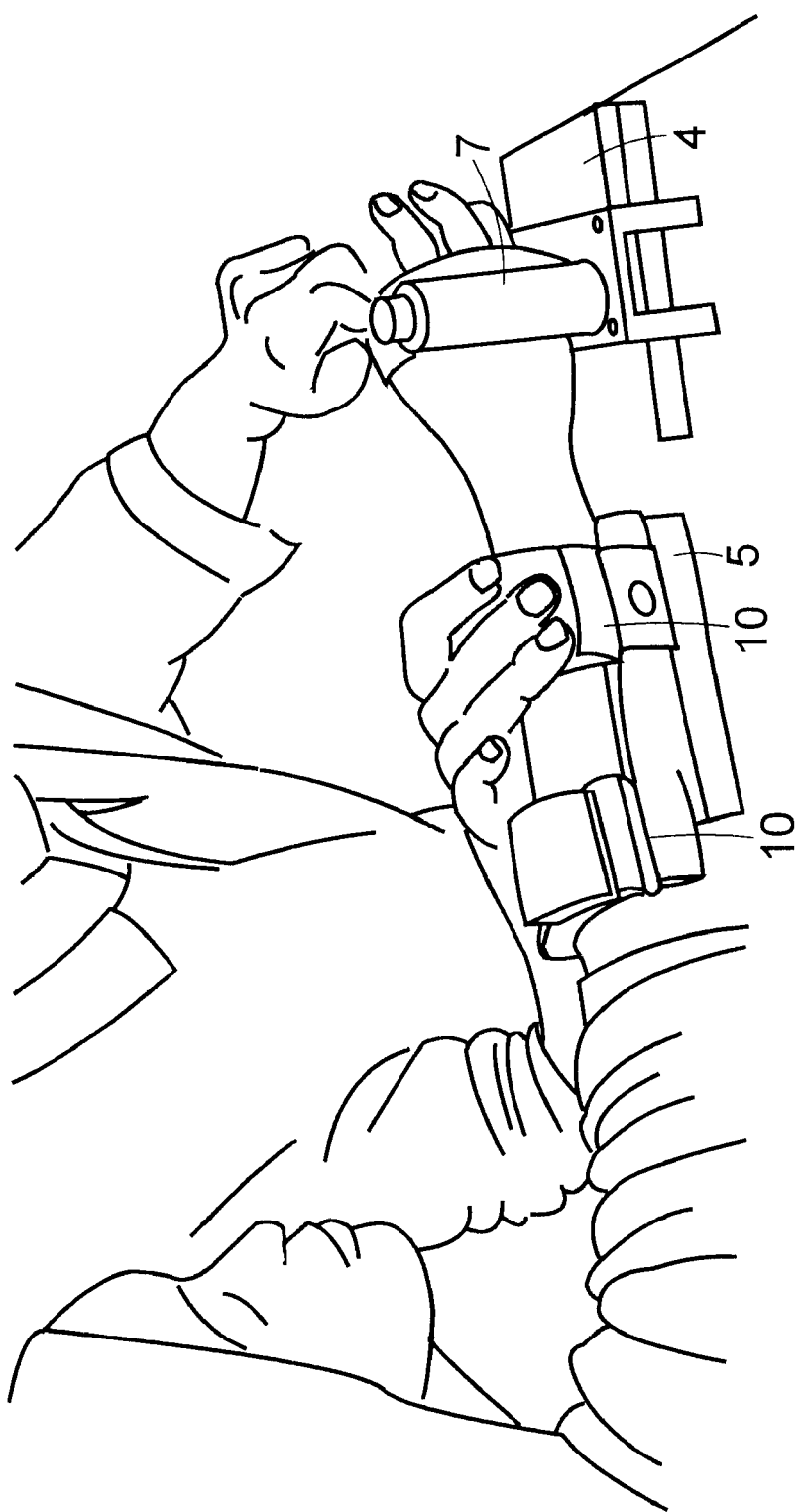
FIG. 11 shows how a patient's arm is properly placed in one embodiment of the device of the present invention.

In one preferred embodiment, as shown in FIG. 5, the hand securing mechanism 3 is formed of two vertical bars 6 that extend upwards from the top surface 2 of the housing 1 so that the patient can place his or her hand between the two bars as shown in FIG. 7. The two vertical bars 6 preferably have padding or cushions 7 on their outer surfaces to provide comfort, as shown in FIG. 11. The two vertical bars 6 may accommodate various sized hands by, for example, slidably attaching the two vertical bars 6 to the housing 1 so that they can be moved inwards and outwards and locked into a desired position. The padding or cushions 7 can also be removable and can come in a variety of thicknesses to provide smaller and larger openings between the two vertical bars 6, thereby accommodating various sized hands. In yet another embodiment, the padding or cushions 7 are compressible and expandable such that the padding or cushions 7 compress or expand as required to hold hands of various sizes in place.

A hand rest 4 and an arm rest 5 may further be mounted on top surface 2 of the housing 1 to assist in providing proper positioning of the arm and hand during testing. Preferably, the arm rest 5 includes an arm securing mechanism 10 such as, for example, one or more Velcro straps, as shown in FIG. 11, to secure the arm in place during testing.

Figure 6:
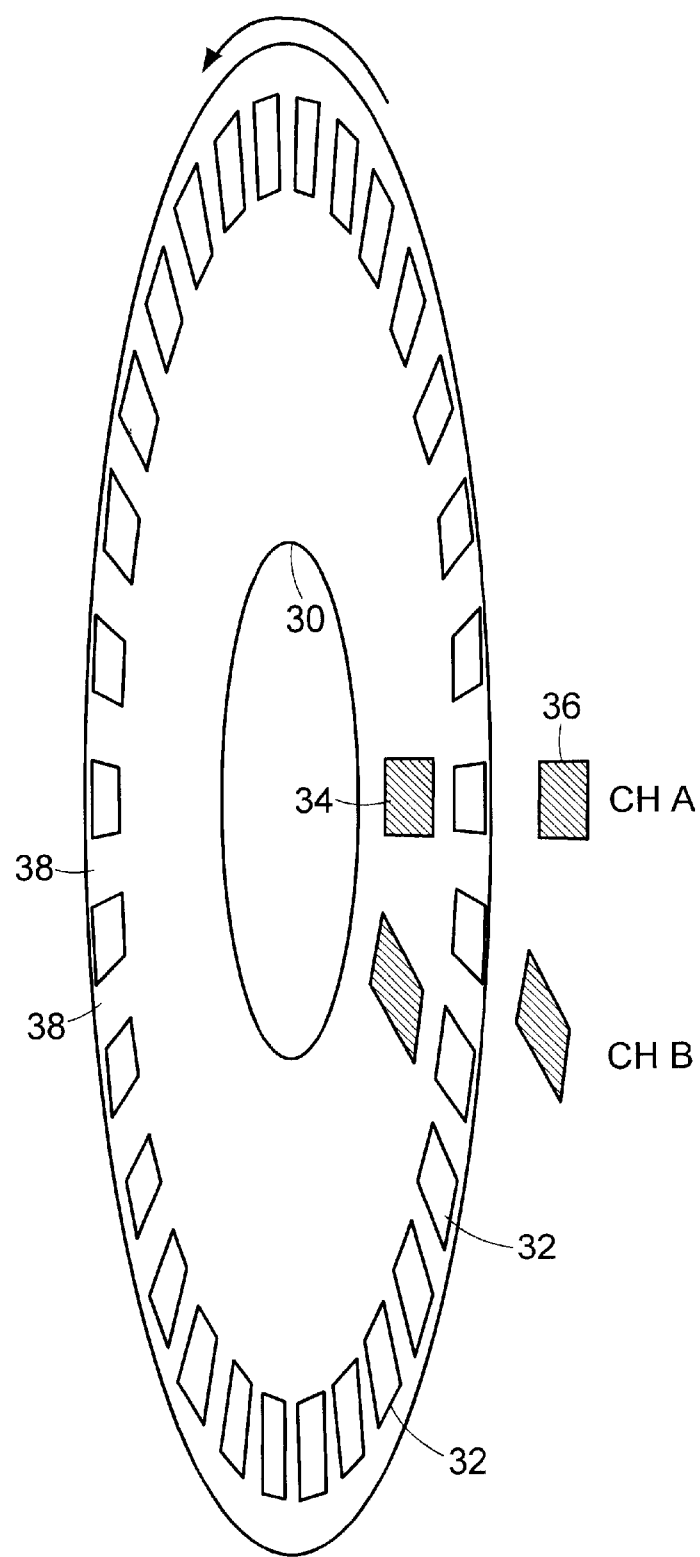

In a preferred embodiment, a motor shaft 11 drives the hand about the wrist joint back and forth to follow the desired trajectories. In this embodiment, a direct drive system is preferably used wherein the hand rest 4 is directly connected to an extension of the motor shaft 11, called the output shaft 12. Preferably, there are no gears in between the motor shaft 11 and the output shaft 12 so that there is no jitteriness or backlash when the motor shaft 11 moves or changes direction. During use, the hand is positioned on the hand rest 4, which may be in the form of a small metal platform as shown in FIG. 6. The hand is secured as it rotates about the wrist joint.

The hand securing mechanism 3, e.g. two vertical bars 6, secure the area of the hand directly proximal to the first joint between the metacarpals and phalanges so that the knuckles lie past the hand securing mechanism 3, as shown in FIG. 11. The hand is secured so that the patient being tested does not grasp the hand securing mechanism 3. In fact, the patient should be completely relaxed so that all muscle contractions are completely involuntary due to the stretch reflex arc. Thus, the patient should not grasp the hand securing mechanism 3 during the test, as there are muscle groups that control flexion/extension of the wrist as well as the fingers.

In a preferred embodiment, the hand rest 4 lies on a sliding forked wrench 22 that is screwed into the output shaft 12. The hand rest 4 is then secured to a position on a sliding track, such that the axis of rotation of the wrist joint lies directly above the axis of rotation of the output shaft 12. During the perturbation of the hand, the remainder of the arm is secured to the arm rest 5 with the arm securing mechanism 10 as set out above. The arm rest 5 is preferably made out of low temperature thermoplastic that is covered with a thin layer of foam for comfort. In a preferred embodiment, the arm rest 5 is on an adjustable track, e.g. a friction screw track, that allows for minor adjustments in the positioning of the arm and hand if necessary.

The arm rest 5 and associated arm securing mechanism 10 hold the arm securely in place with quick setup time and is sized to accommodate various arm sizes. Removable cushions or pads of varying sizes can, for example, be placed in-between the arm rest 4 and the arm to accommodate various sized arms. In one embodiment, a compressible and expandable cushion (not shown) is mounted on the arm rest 5 such that the cushion fits about varying sized arms by compressing or expanding as necessary. Further, the arm rest 5 and arm securing mechanism 10 is preferably adjustable to varying sized arms. For example, in one embodiment, Velcro straps, which can be quickly and easily secured tighter or looser, are used as the arm rest arm securing mechanism 10. In another embodiment, one or more straps having multiple snaps along the length of the straps can be used for varying sized fits. Still further, one or more straps similar to a belt with multiple holes can be used to provide varying sized fits.

A torque transducer 20 (sensor) is placed between the motor shaft 11 and the output shaft 12. The torque transducer 20 may, for example, be placed between the motor shaft 11 and the output shaft via two machined couplings secured with screws. Preferably, a top coupling has a flat surface for a flat end screw to securely hold the output shaft 12 onto the coupling. During fabrication of the device, before the top surface 2 of the housing 1 is put in place, an incremental optical encoder 24 (position sensor) is placed around the output shaft 12 as shown in FIG. 5. After the top surface 2 is secured on top of the housing 1, the inner rotating ring 26 of the encoder 24 is secured to the output shaft 12 with, for example, a clamp adapter ring positioned between the optical encoder 24 and output shaft 12. In a preferred embodiment, the rotating ring 26 is secured to the output shaft 12 via a plurality of hex-screws with the clamp adapter ring in between the inner rotating ring 26 of the optical encoder 24 and the output shaft 12. A rotation of the output shaft 12 corresponds to the same amount of rotation of the code wheel disc of the encoder 24.

The incremental optical encoder 24 is a device that converts motion into a series of digital pulses that can be measured. A preferred incremental optical encoder 24 in accordance with the present invention is shown in FIG. 6 and consists of a disc with a series of equally spaced slits or transparent segments 32 on it. Separating these slits or segments 32 are opaque radial lines 38 of equal arc thickness. On either side of the disk are two LED emitters 34 paired with two phototransistors 36. The typical circuitry of an LED/phototransistor pair is shown in FIG. 7.

Typically the forward voltage drop across the LED, $V_{AK}$ is rated at around 1V at 20 mA. Since $V_S$ is 5V, the resistor, $R_1$ is needed to dissipate 4V. Thus by Ohm's law, $$R_1 = 4V/20\ mA = 200\Omega$$

When there is no opaque object between the emitter and detector, the light from the emitter supplies a base current to the transistor. By Kirchoff's Voltage Law, $$V_C = V_S = 5V$$

The saturated collector emitter voltage, $V_{CE}$ is rated at 0.2V, thus $$V_{out} = 5V - 0.2V = 4.8V$$

If $R_2 = 1M\Omega$, $$I_E = V_{out}/R_2 = 4.8V/1M\Omega = 4.8 \ \mu A$$

By Kirchoff's Current Law, inside the transistor the emitter current is equal to the sum of the base and collector currents, $$I_E = I_C + I_B$$

Also in the transistor, $$I_C = h \ast I_B$$

where h is some positive number. In summary, when there is no opaque object between the LED emitter 34 and the phototransistor 36, there is some finite base current, $I_B$ from the LED emitter 34, and $V_{out}$ has a reading of almost 5V (TTL high). When the opaque radial line blocks the light between the LED emitter 34 and the phototransistor 36, $I_B \approx 0$, and $I_C \approx 0$, thus $V_{out} \approx 0V$. As the disc 30 rotates between the transparent slits 32 and the radial lines 38, the output voltage shifts between TTL high and TTL low respectively, resulting in a square wave output. Typically, the number of square wave cycles (ncypr) generated by an LED/phototransistor pair 34, 36 is equal to the number of radial lines 38 or transparent slits 32 on the disc 30. However if more sophisticated circuitry and interpolation techniques is used, the number of square wave cycles may be greater than the number of radial lines 38 on the disc. The preferred incremental optical encoder used in the present device is the Gurley hollow shaft encoder, which has 11,250 radial lines on the disc and generates 90,000 square wave cycles per revolution.

Figure 8B:
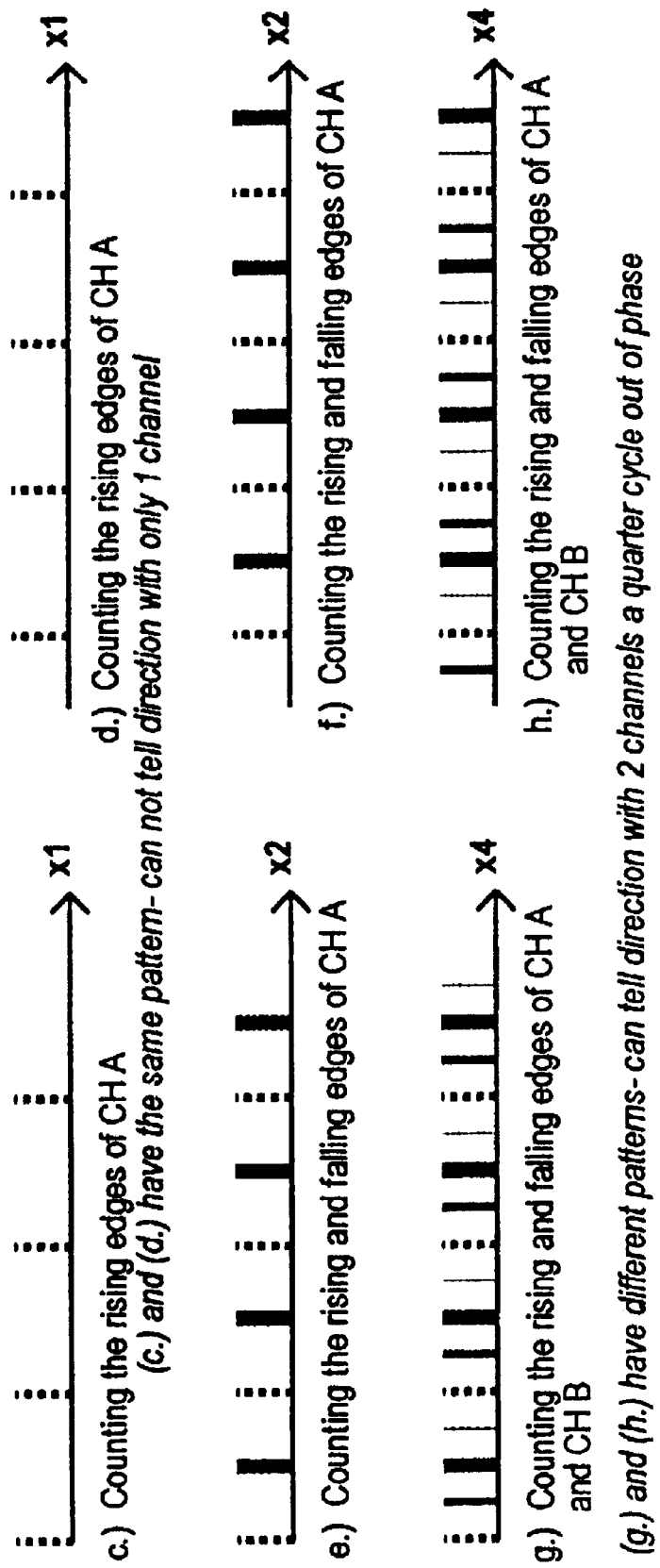
FIG. 8 shows the square wave outputs of two LED/phototransistor channels. Two channels together are able to detect the direction of rotation of the code wheel. Two channels also increase the degree of resolution by 4.

The more radial lines 38 (square wave cycles) that there are on the disc 30, the higher the count resolution. The simplest way to obtain angular position from a pair of LED emitters 34 and phototransistors 36 is to count the number of cycles that go by, either by counting the rising or falling edges of one square wave output (CH A) as depicted in FIG. 8, (c) and (d). In this case, the angular resolution is equal to the number of cycles per revolution [ncypr] counts/rev or [360/ncypr] degrees. As shown in FIG. 8, (e) and (f), both the rising and falling edges of CHA are counted, the resolution can be doubled to [2*ncypr] counts/rev or [720/ncypr] degrees.

If only one channel of square wave output is used, it is impossible to tell the direction of rotation of the disc 30 as the counting pattern of the clockwise and counterclockwise direction are the same (see FIGS. 9(c) and 9(d)). To overcome this problem, an additional LED/phototransistor pair 34, 36 is physically placed around the disk 30 such that it's square wave output (CH B) is a quarter cycle out of phase with that of CH A. Thus, the square wave cycles from both channels are called quadrature signals. When the disk 30 rotates in one direction (i.e. clockwise), CH A leads CH B by a quarter of a cycle, but when the disk 30 rotates in the opposite direction, CH A lags CH B by a quarter of a cycle. Another advantage of using quadrature signals is that the count resolution of the optical encoder 24 can be increased to [4*ncypr] counts/rev by counting the rising and falling edges of both CH A and CH B. This is done using a quadrature decoder chip (for example, the US-Digital PC-6-84-4). As shown in FIG. 8, (g) and 5(h), the count patterns in the clockwise and counterclockwise directions are different—they are reversed. The quadrature decoder converts the signals from CH A and CH B into a direction (up/down pulse) and count pulses, where a count pulse is generated every time the TTL state of either channel changes. Since the Gurley hollow shaft encoder, preferably used in the present device, generates 90,000 cycles per revolution in each channel, after quadrature edge detection, the encoder gives 360,000 counts per revolution, which is an amazing resolution of one thousandth ($10^{-3}$) of a degree.

In the setup of the present invention, the outputs of the optical encoder 24 split and go to both the motion controller for feedback control and to a National Instruments data acquisition card for acquiring data. Theoretically, position information can be obtained by interrogating the motion controller via software, in which case, data acquisition of the position signal is not necessary. However, when the motion controller is interrogated at a high sampling rate, its operation and control of the motor shaft 11 is impeded. The controller software cannot both operate the feedback loop to follow a desired trajectory and output data to the user at 500 Hz.

The optical encoder 24 outputs three additional signals relative to ground, not just A and B. These outputs are the index signals, $\overline{A}$, and $\overline{B}$. Once activated, the optical encoder 24 keeps track of angular position, in counts, relative to the initial angular position where it started counting. The index signal provides an absolute reference so that the absolute position of the hand rest 4 is known in space. In addition to the many equally spaced slits on the disk 30, there is one additional slit that is at a different radial distance away from its center, where the index signal is at TTL 1 only in one absolute position using an additional LED/phototransistor pair 34, 36 as described above. The counter value determined by channels A and B is reset to zero where the TTL value of the index is 1 and, thus, the index serves as an origin in space. Once this position is found, the system knows where the absolute position of the hand rest 4 is in real space.

As used herein, the axis of rotation of the output shaft 12 is defined as pointing upward, so that a counter clockwise rotation is positive change in direction, and a clockwise rotation is negative change in direction. The motion controller however, defines a clockwise rotation as positive, and a counterclockwise rotation as negative.

Preferably, in the device of the present invention, the index signal is not used. Rather, in one preferred embodiment, the reference point used to determine absolute position is the left mechanical stop 26. A right mechanical stop 27 may further be located opposite the left mechanical stop 26. The motor shaft 11 moves counterclockwise at a slow speed until the forked wrench of the hand rest 4 hits the left mechanical stop 26 at which point the motor stops. In this configuration, the mid-axis of the forked wrench is 90 degrees (90940 counts) away from the midline, the counter value with the motion controller is set to −90940 which is −90.940 degrees. Now the counter value reads, and will continue to read, the correct absolute position until the computer that powers the optical encoder 24 is turned off.

Figure 127:
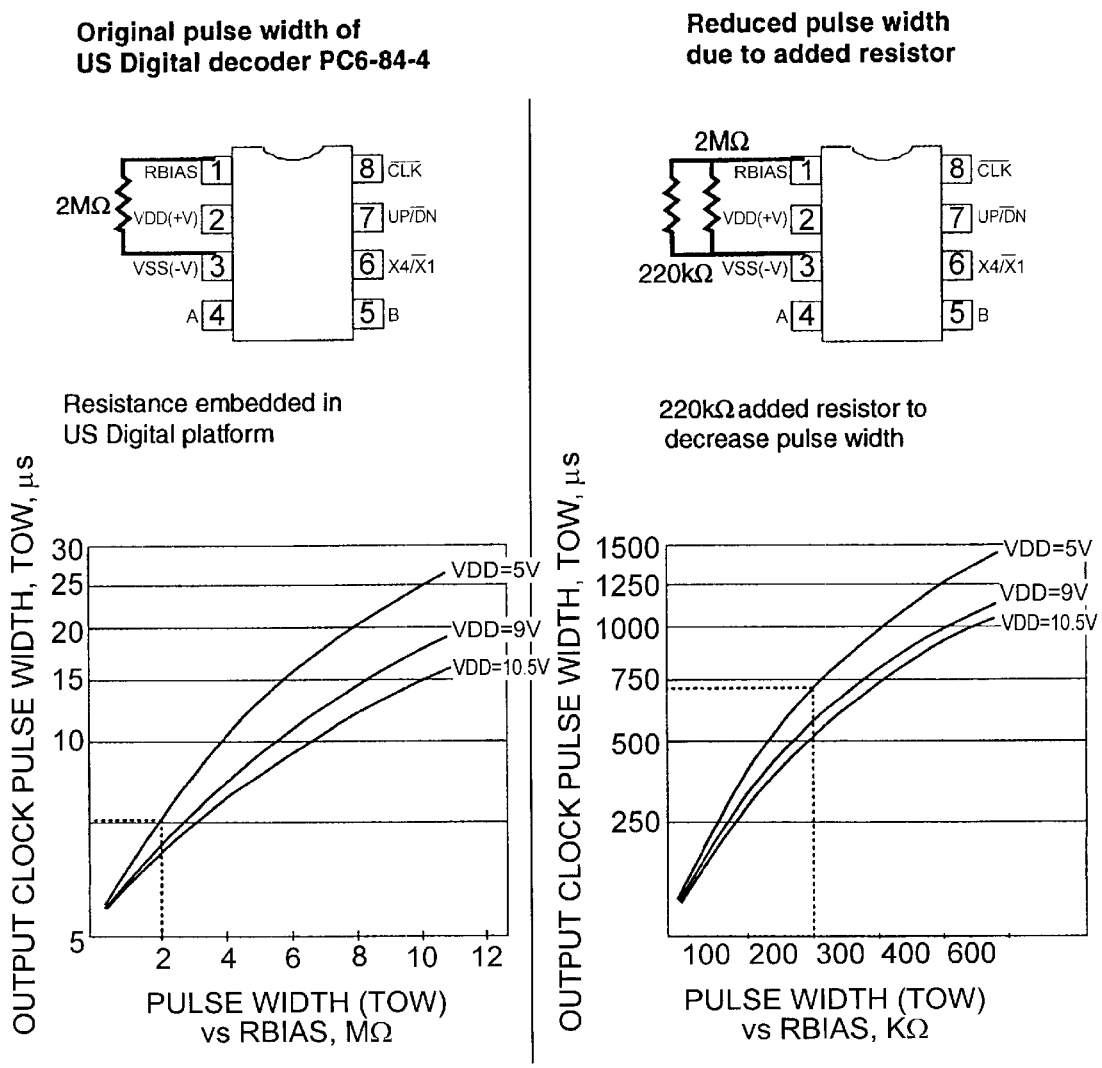
FIG. 127 shows the pulse width of the embedded chip in the US Digital decoder was decreased via the addition of a resistor as shown. This was done because the original pulse width was wide and the optical encoder was skipping counts at high rotational speeds.
Figure 128A:
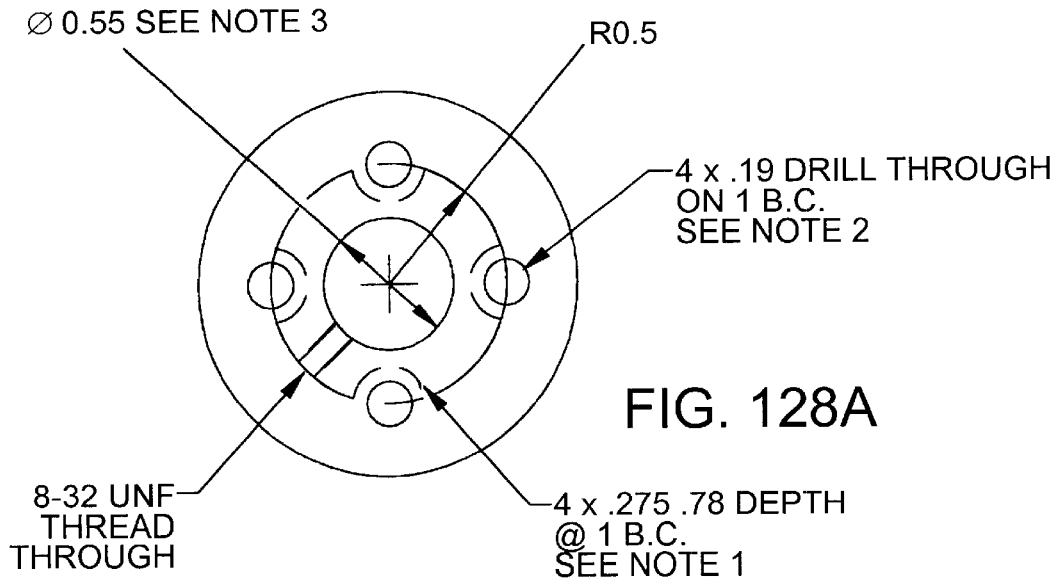
FIG. 128 shows an AutoCAD mechanical design drawing of one embodiment of the motor coupling in accordance with the present invention.
Figure 128B:
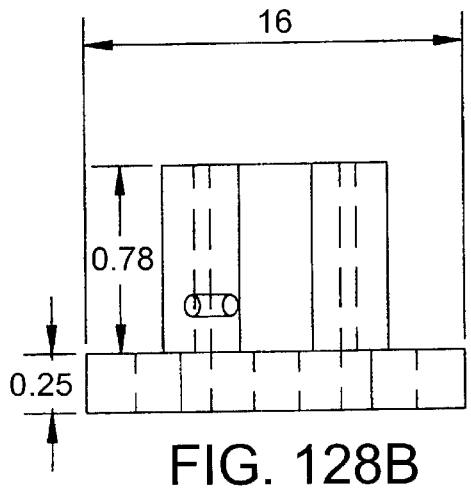
Figure 128C:
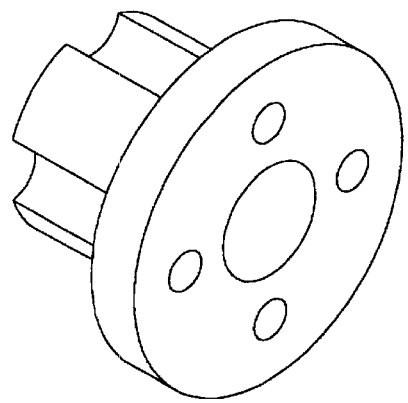
Figure 129A:
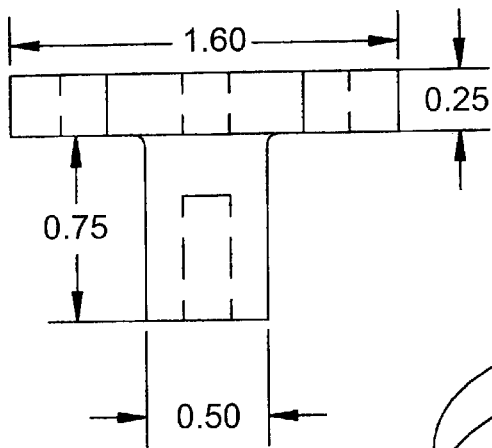
FIG. 129 shows an AutoCAD mechanical design drawing of one embodiment of the shaft coupling in accordance with the present invention.
Figure 129C:
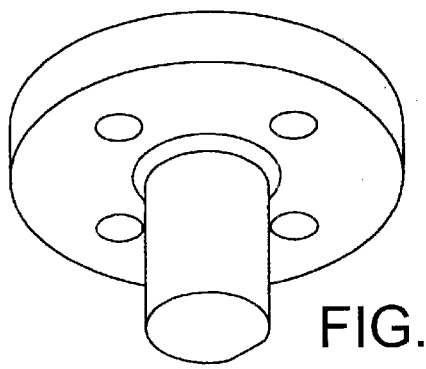
Figure 129B:
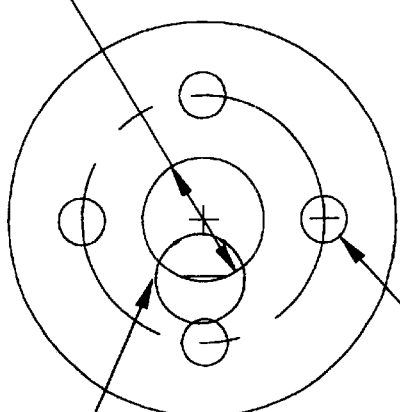
Figures 130A, 130B, 130C, 130D:
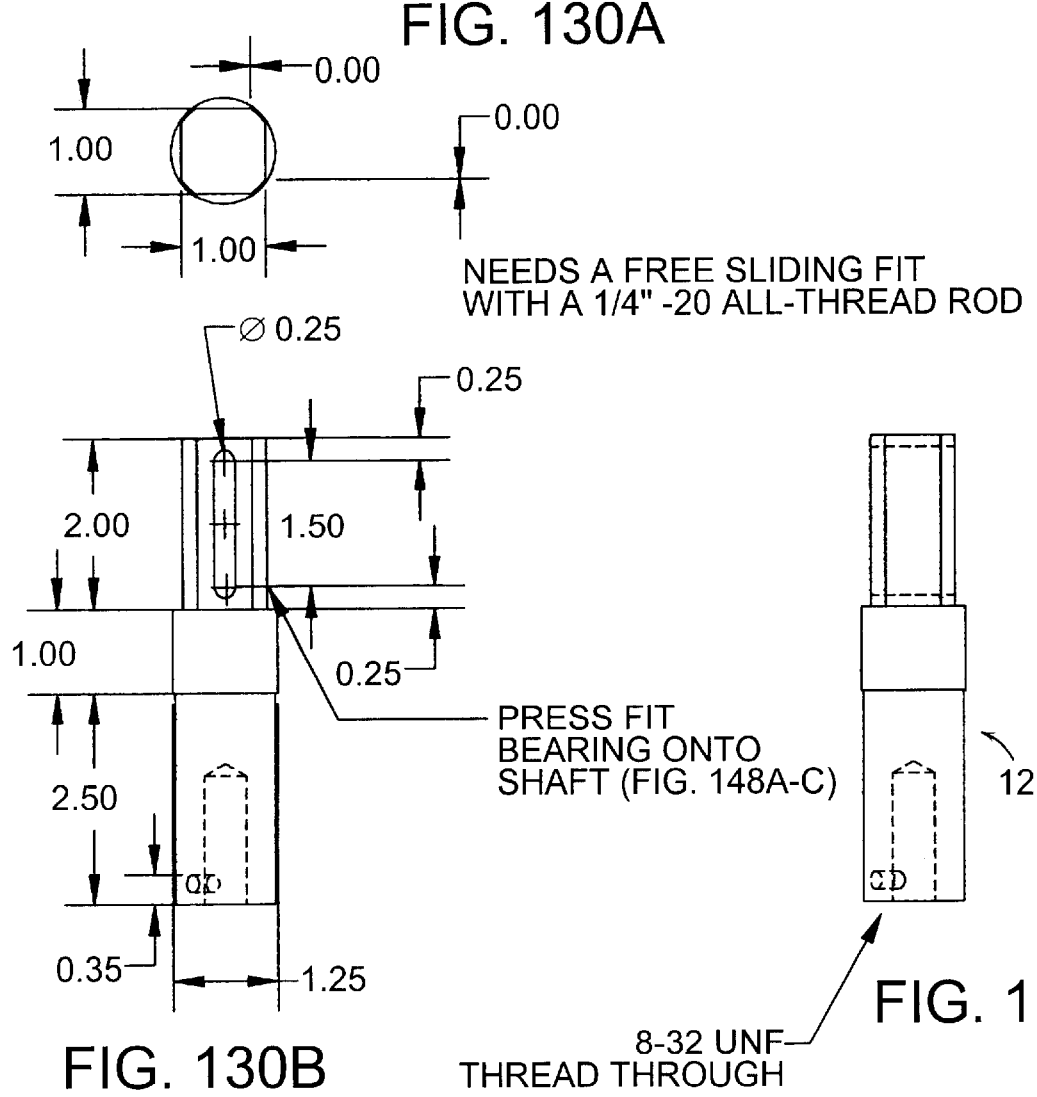
FIG. 130 shows an AutoCAD mechanical design drawing of one embodiment of the output shaft in accordance with the present invention.
Figure 131A:
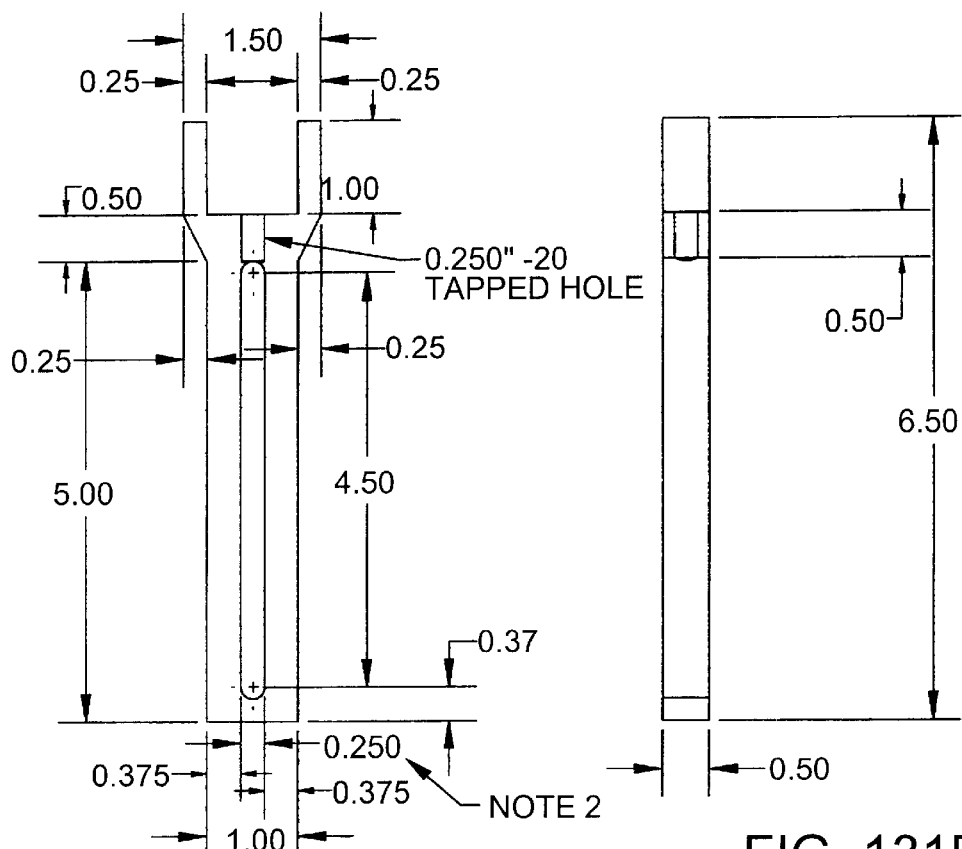
FIG. 131 shows an AutoCAD mechanical design drawing of one embodiment of the forked wrench in accordance with the present invention.
Figure 131C:
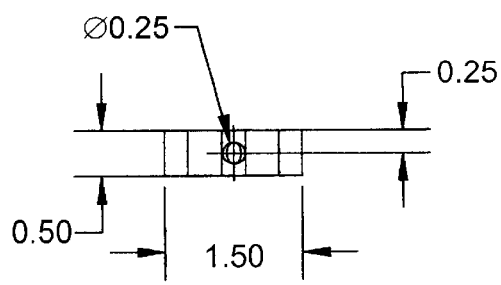
Figure 131D:
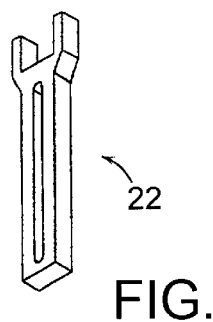
Figure 132B:
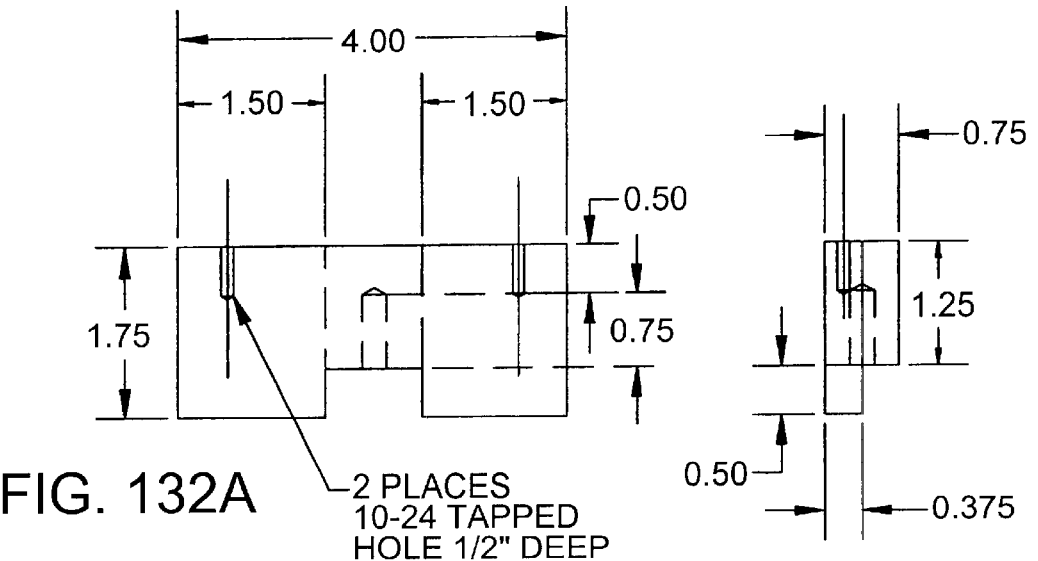
FIG. 132 shows an AutoCAD mechanical design drawing of one embodiment of the hand support in accordance with the present invention.
Figure 132D:
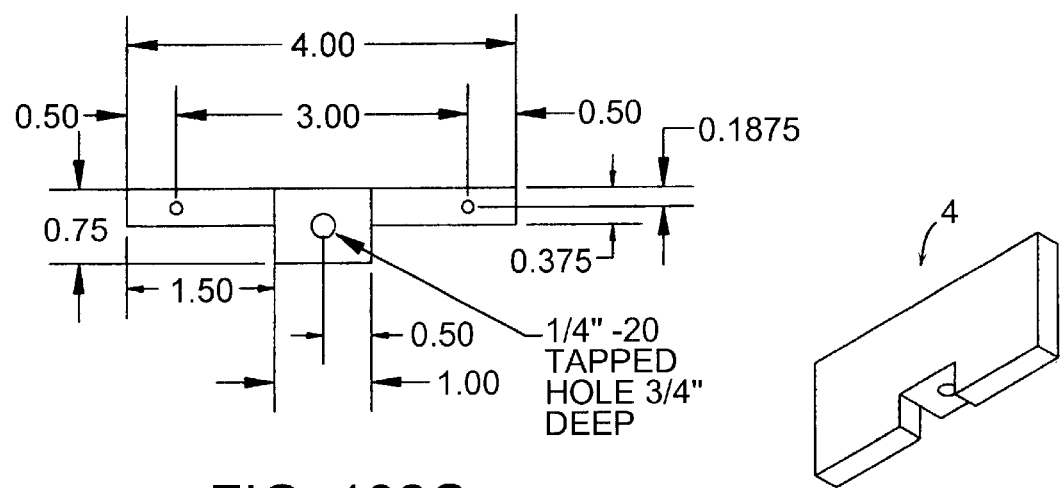
Figure 133A:
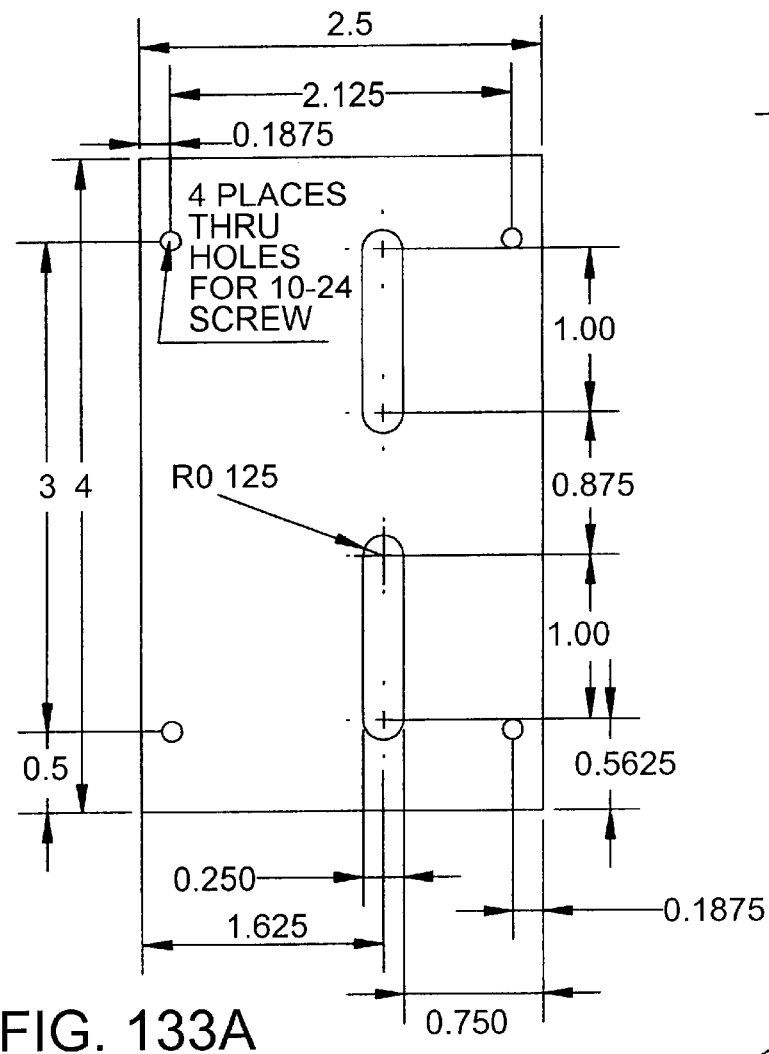
FIG. 133 shows an AutoCAD mechanical design drawing of one embodiment of the hand plate in accordance with the present invention.
Figure 133B:
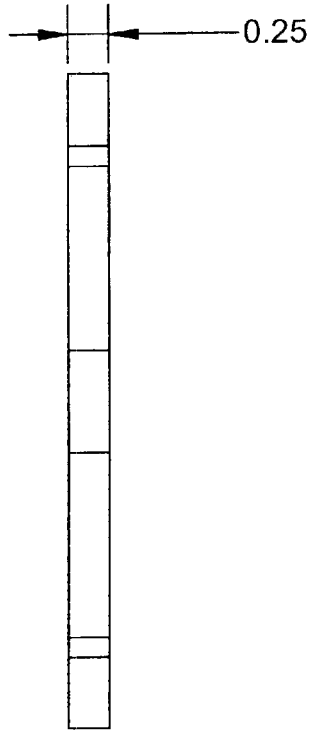
Figure 133C:
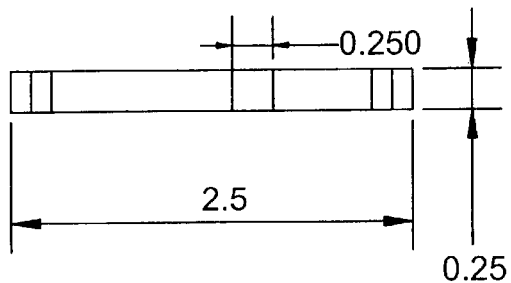
Figure 133D:
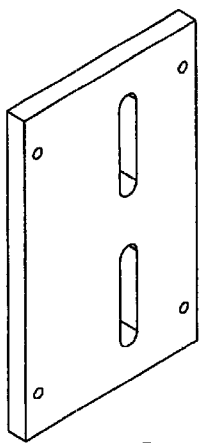
Figure 134A:
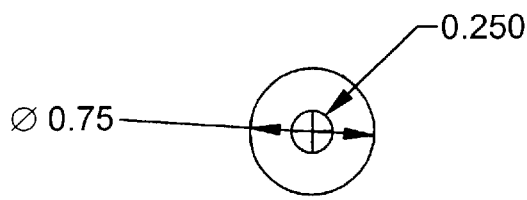
FIG. 134 shows an AutoCAD mechanical design drawing of one embodiment of the poles that secure the hand on the hand plate in accordance with the present invention.
Figure 134C:
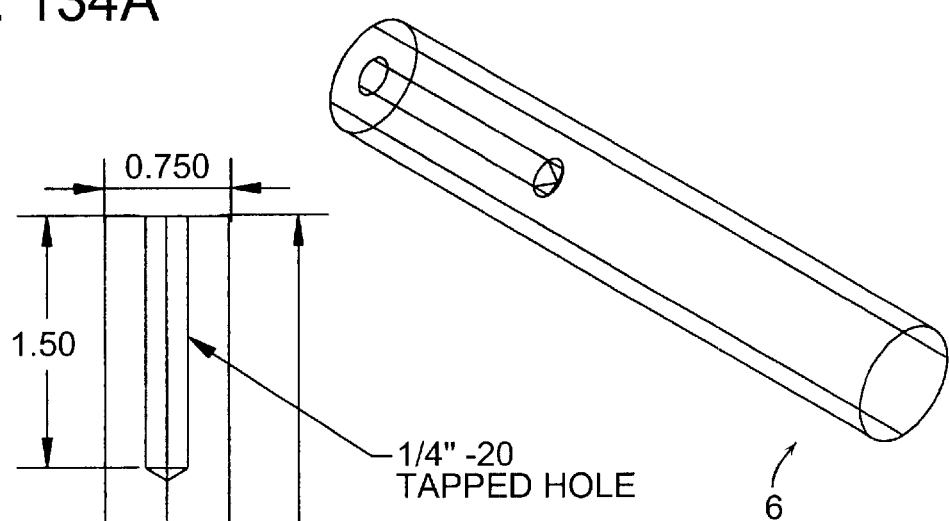
Figure 134B:
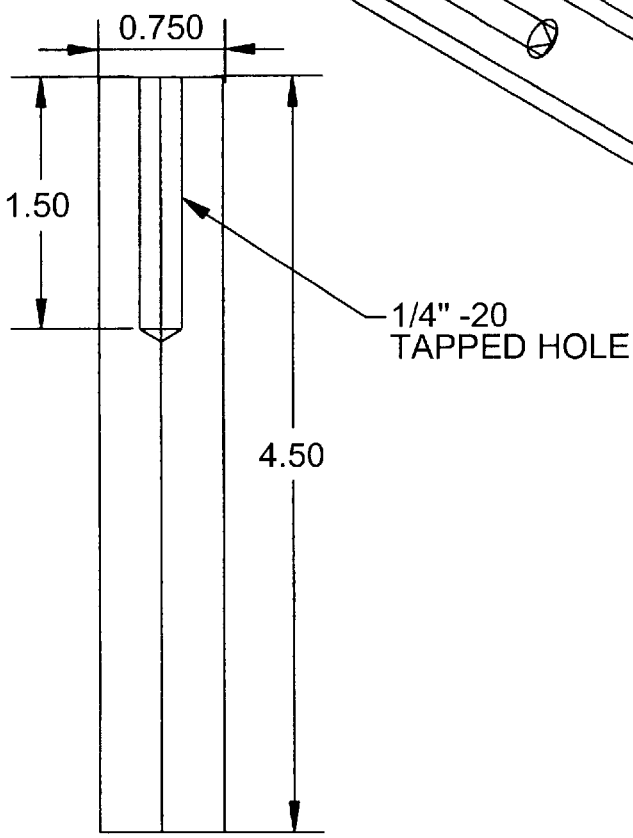
Figure 135A:
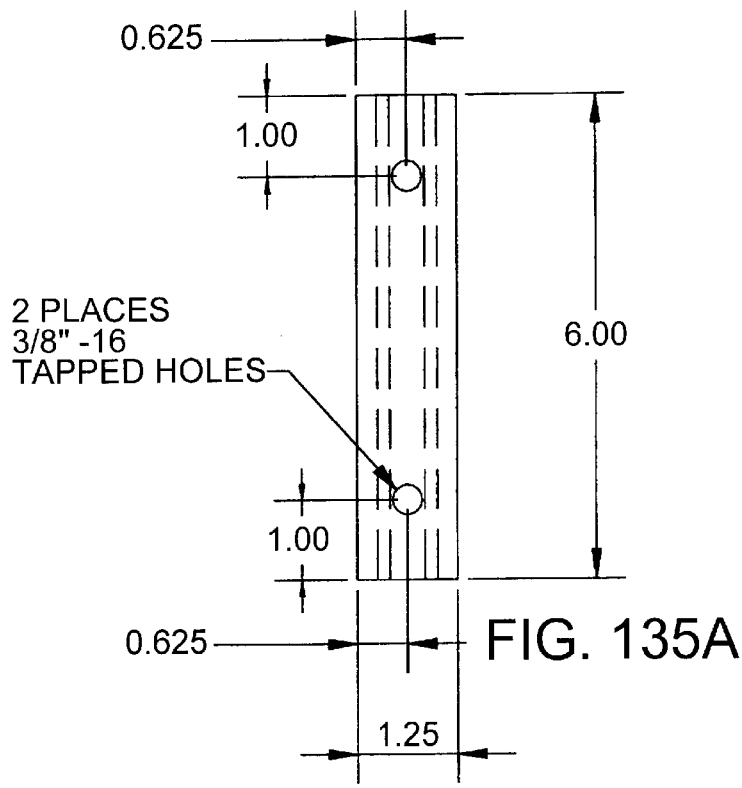
FIG. 135 shows an AutoCAD mechanical design drawing of one embodiment of the arm rest attachment in accordance with the present invention.
Figure 135B:
Figure 135C:
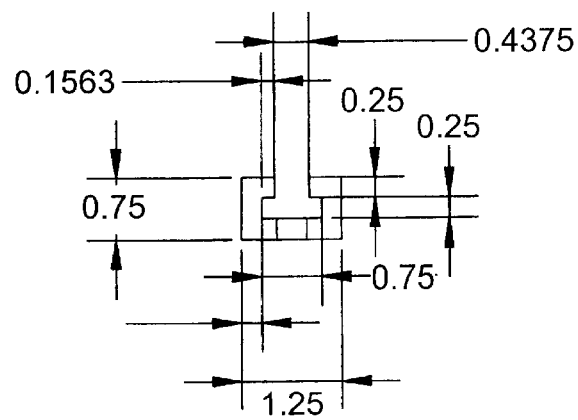
Figure 135D:
Figure 136A:
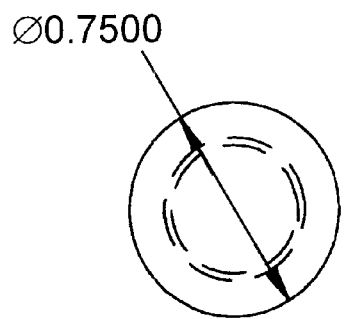
FIG. 136 shows an AutoCAD mechanical design drawing of one embodiment of the Mechanical stop pin in accordance with the present invention.
Figure 136B:
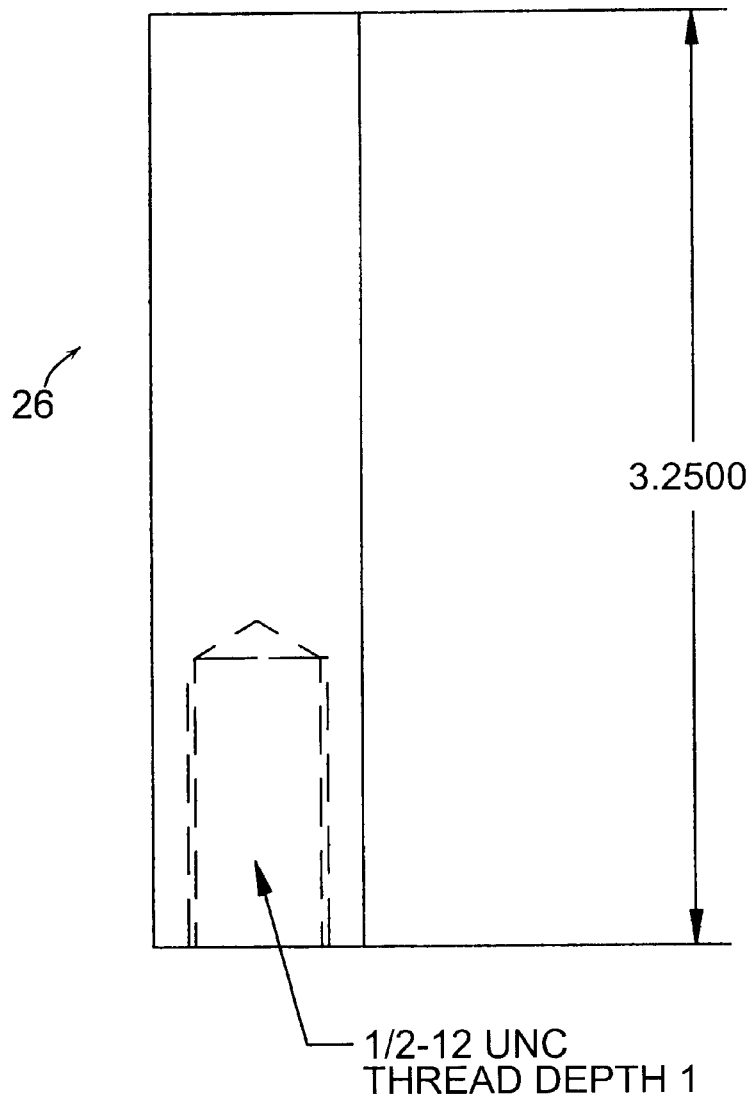
Figures 140A, 140B:
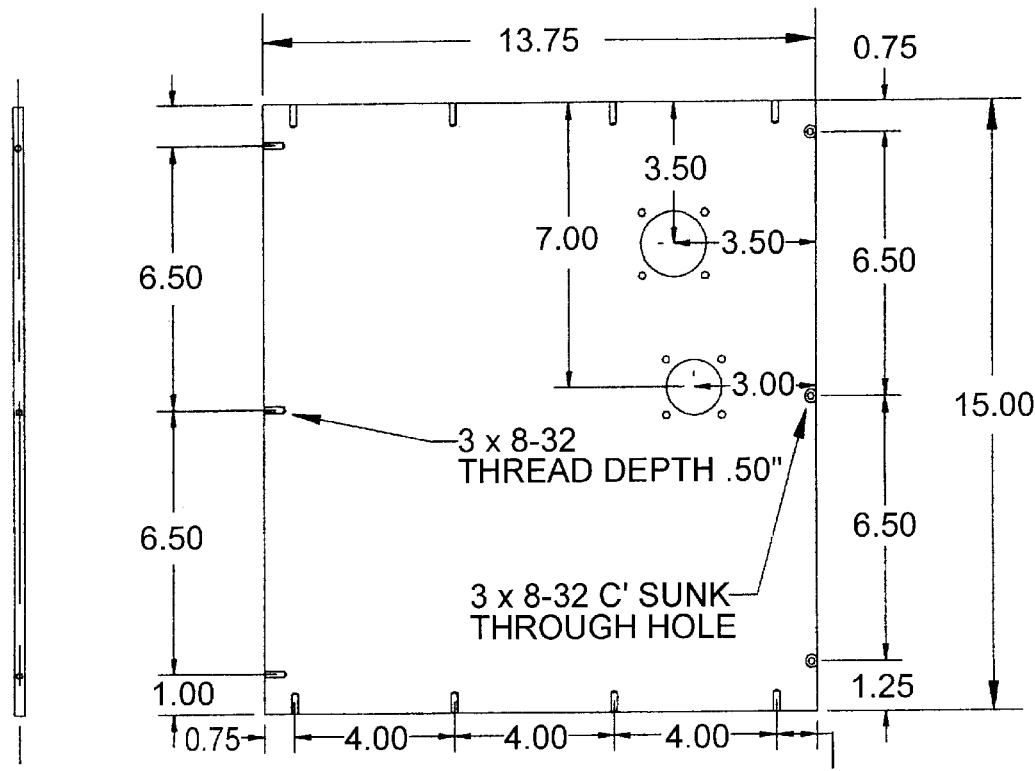
FIG. 140 shows an AutoCAD mechanical design drawing of one embodiment of the left side surface of the housing in accordance with the present invention.
Figure 140C:
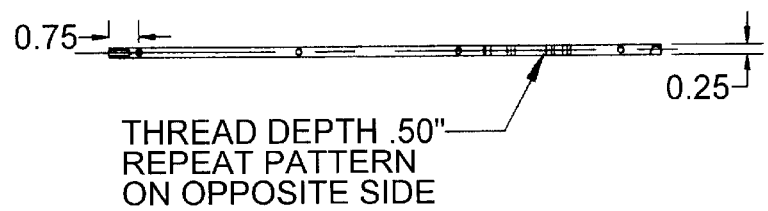
Figure 143A:
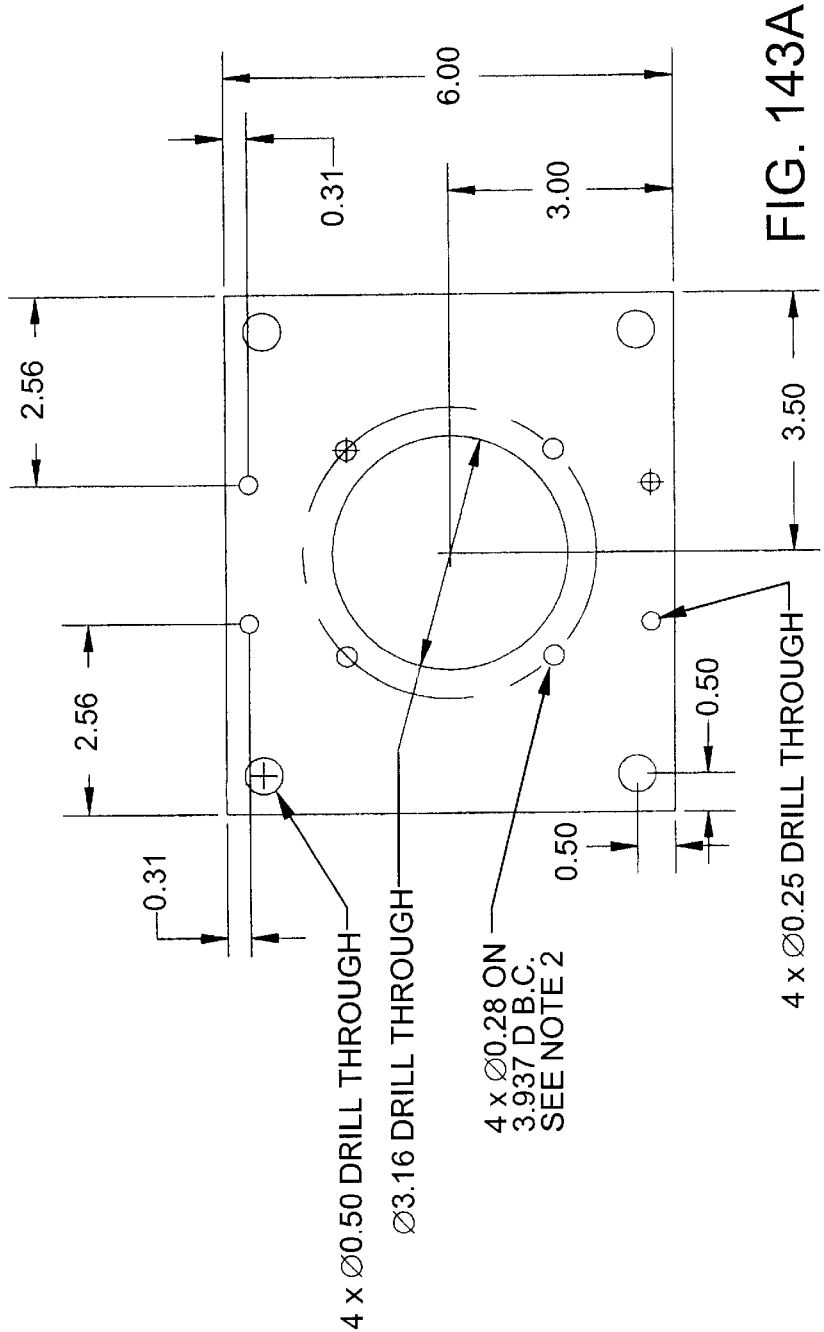
FIG. 143 shows an AutoCAD mechanical design drawing of one embodiment of the motor mounting plate in accordance with the present invention.
Figure 143B:
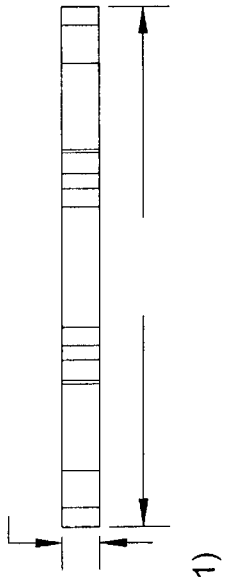
Figure 144A:
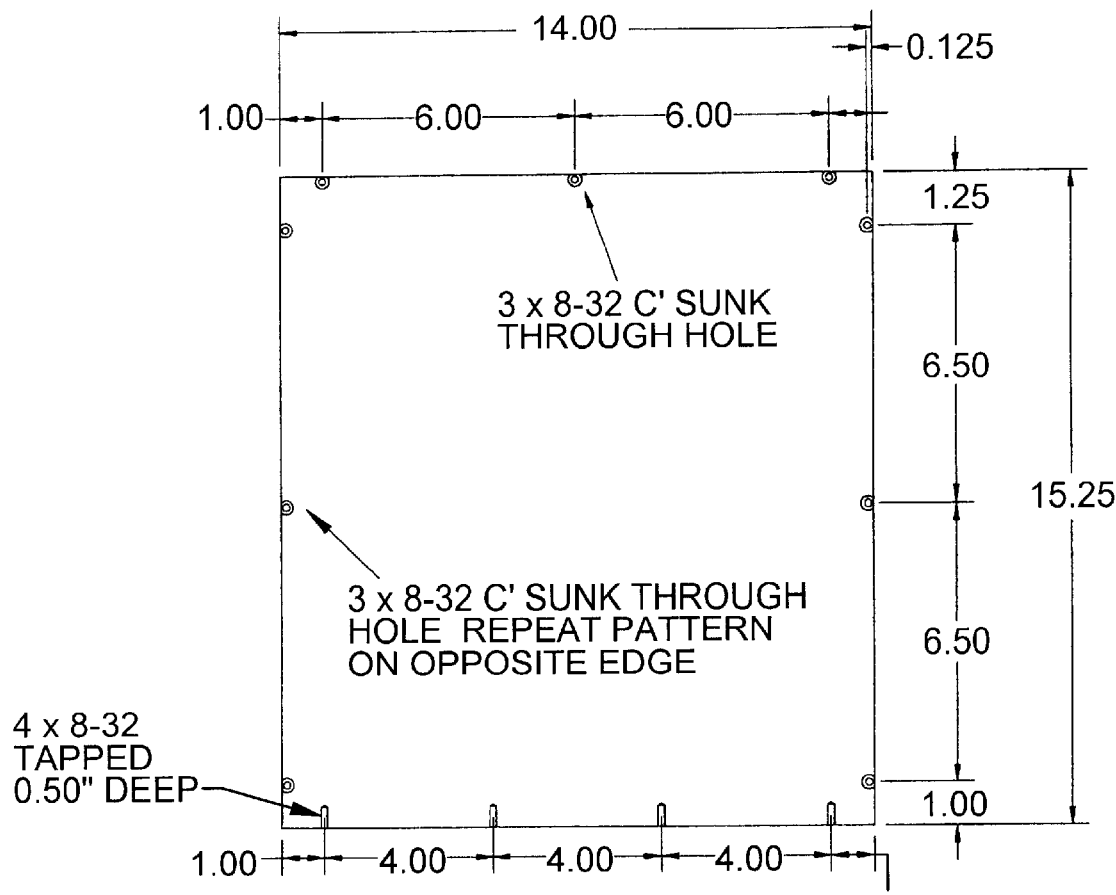
FIG. 144 shows an AutoCAD mechanical design drawing of one embodiment of the front surface of the housing in accordance with the present invention.
Figure 144B:
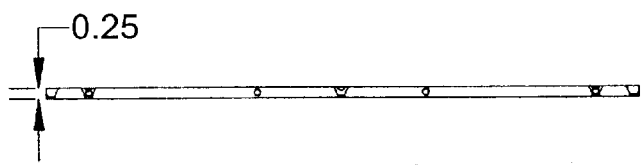
Figure 145A:
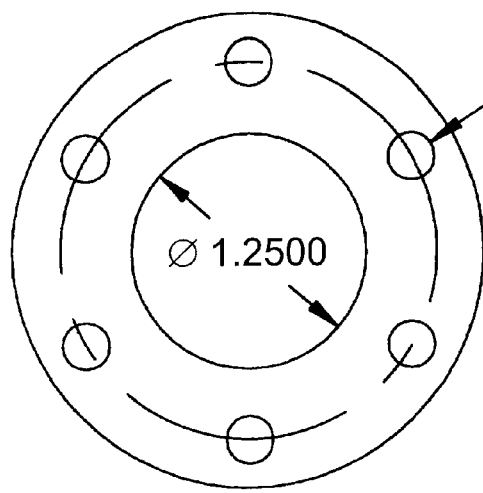
FIG. 145 shows an AutoCAD mechanical design drawing of one embodiment of the bearing on the top surface of the housing in accordance with the present invention.
Figure 145C:
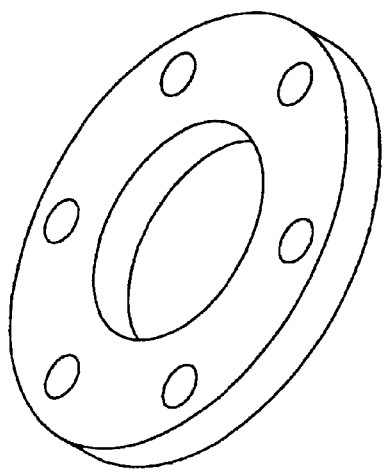
Figure 145B:
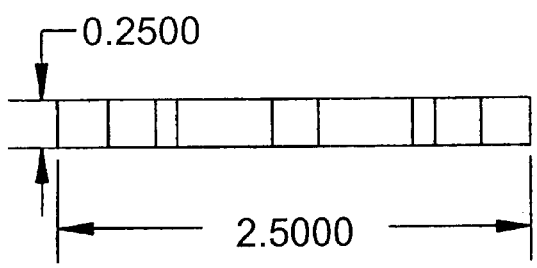
Figure 146A:
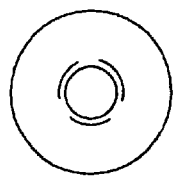
FIG. 146 shows an AutoCAD mechanical design drawing of one embodiment of the motor support column in accordance with the present invention.
Figure 146B:
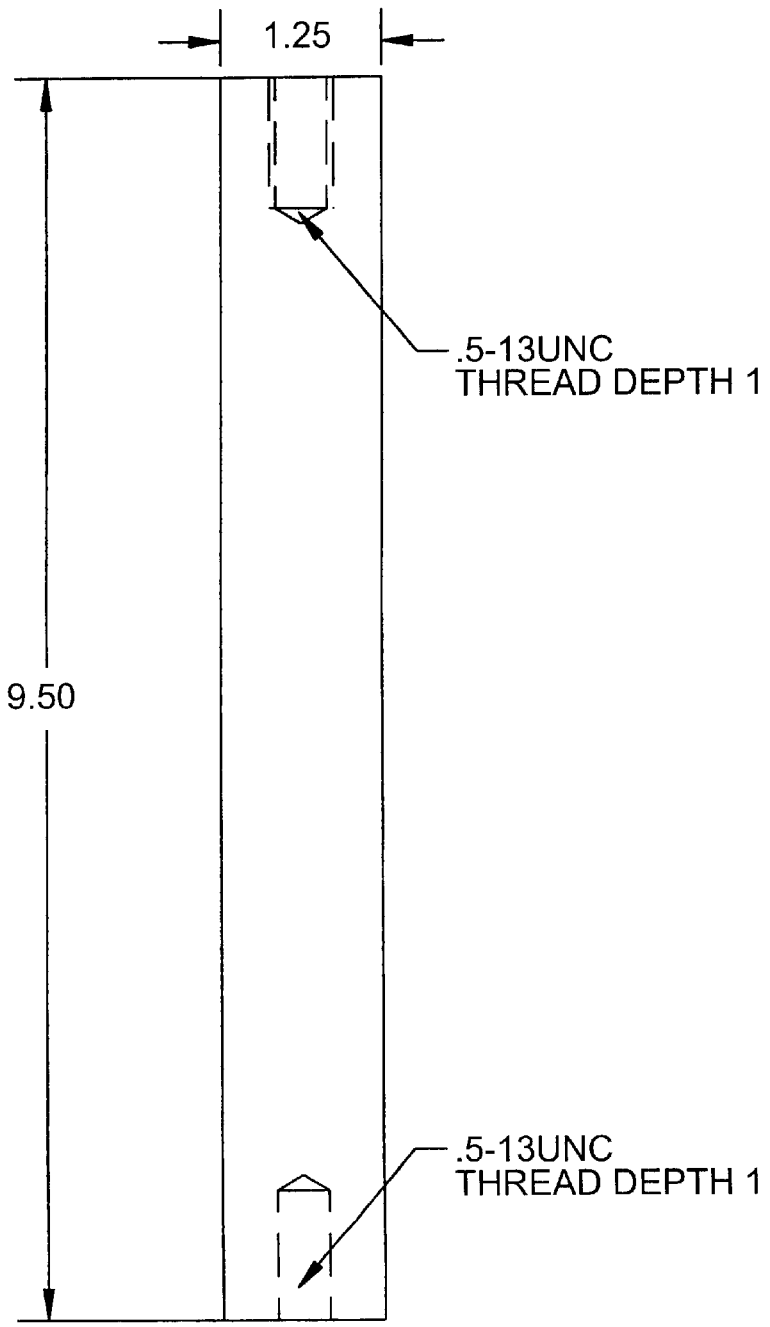
Figures 147A, 147B:
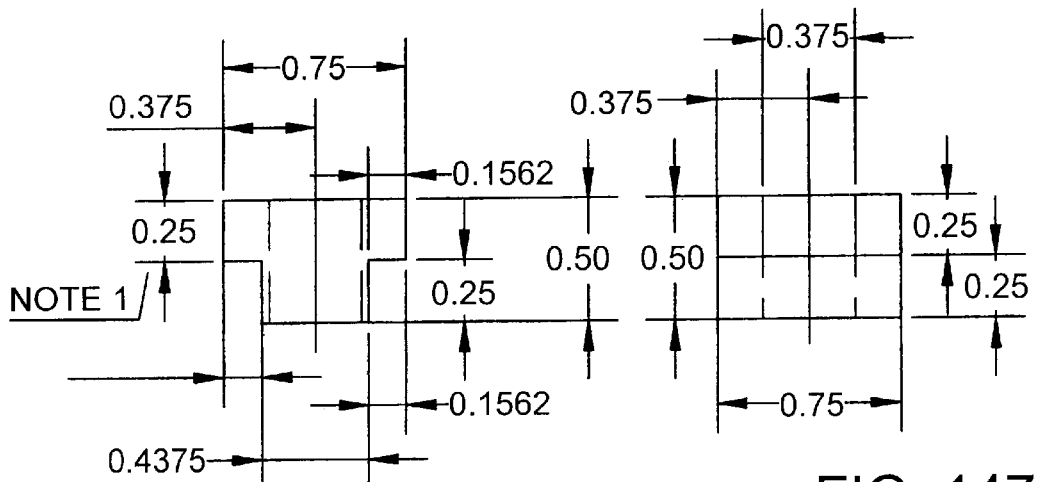
FIG. 147 shows an AutoCAD mechanical design drawing of one embodiment of the armrest slide in accordance with the present invention.
Figure 147C:
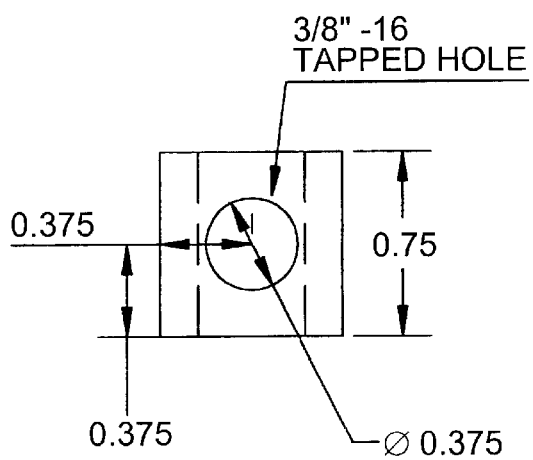
Figure 147D:
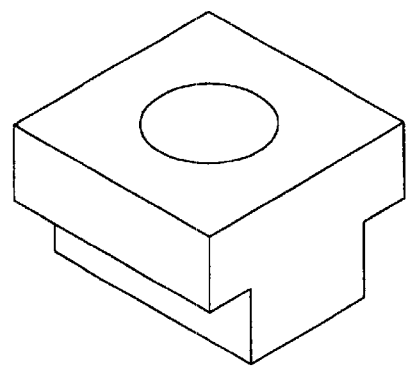
Figure 148A:
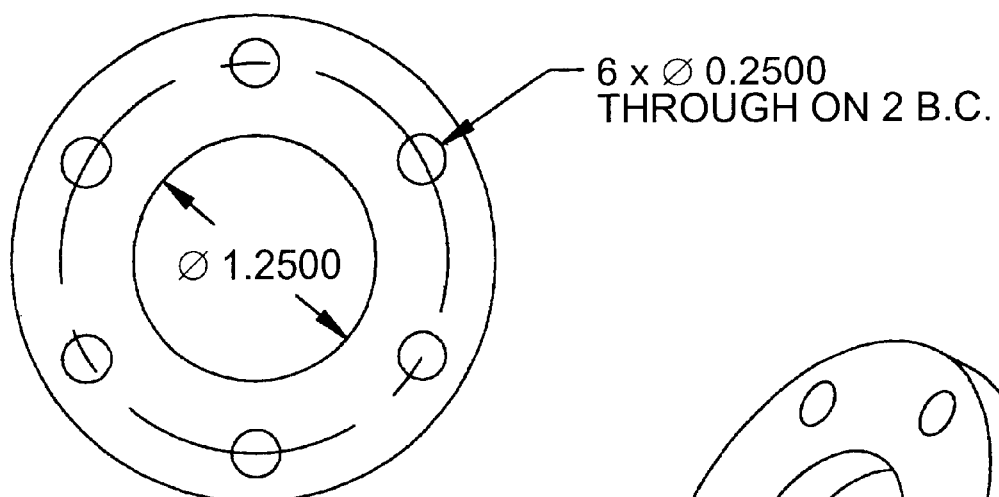
FIG. 148 shows an AutoCAD mechanical design drawing of one embodiment of the bearing clamp ring in accordance with the present invention.
Figure 148C:
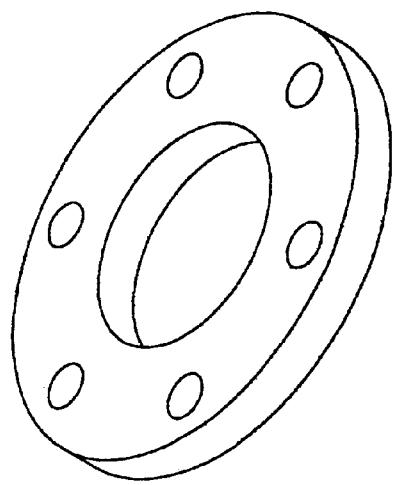
Figure 148B:
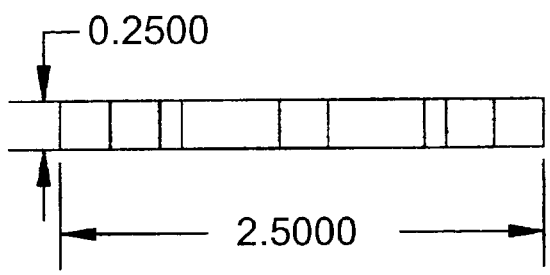
Figure 150A:
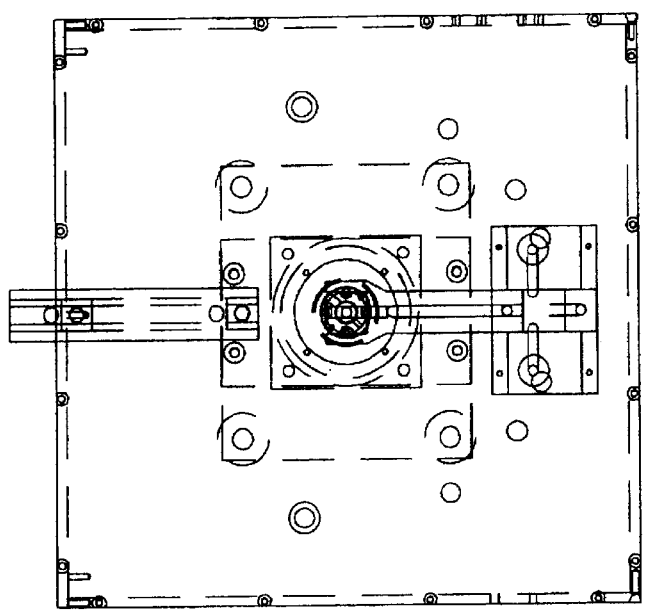
FIG. 150 shows an AutoCAD mechanical design drawing of one embodiment of the complete assembly drawing in accordance with the present invention.
Figure 150B:
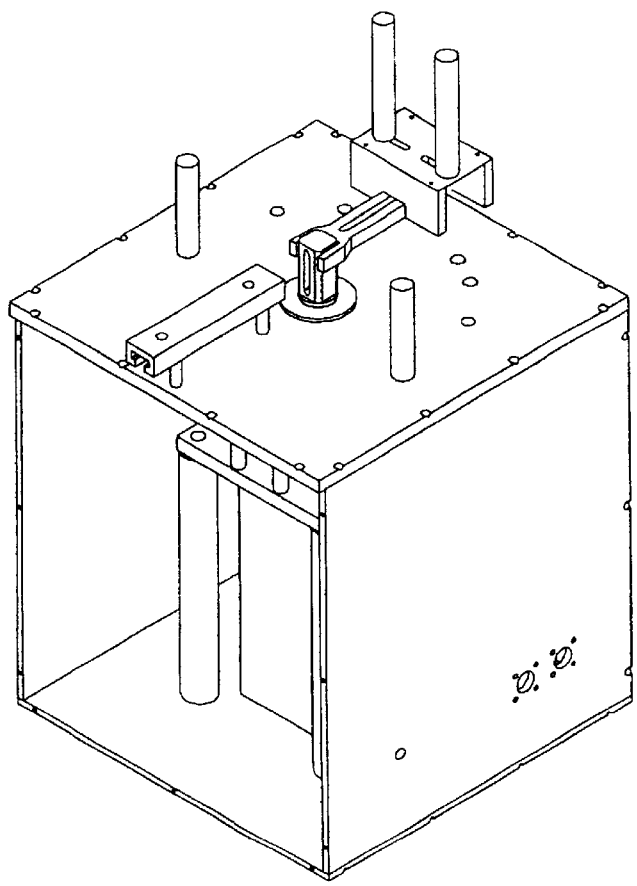
Figure 151:
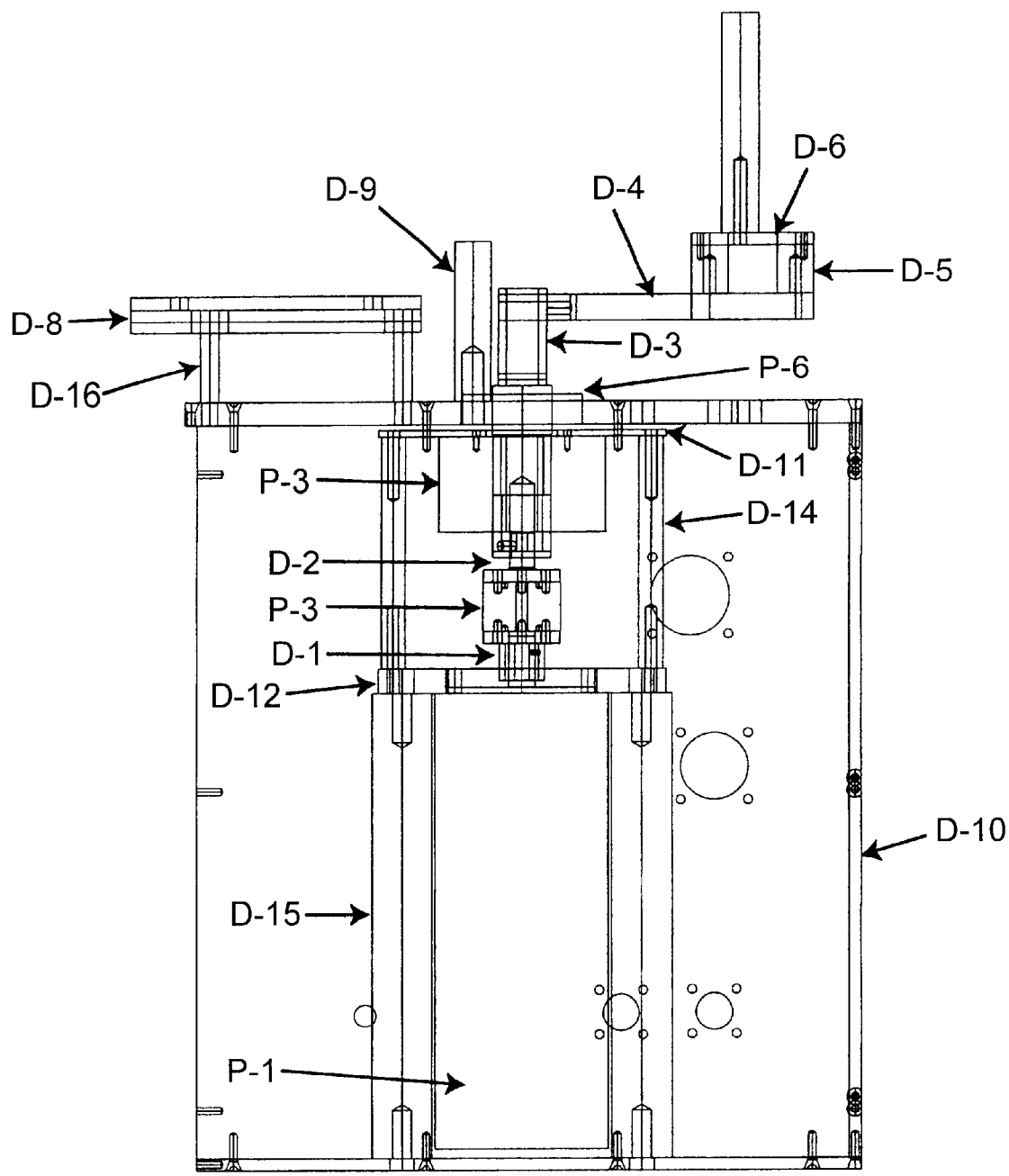
FIG. 151 shows an AutoCAD mechanical design drawing of one embodiment of the labeled parts in accordance with the present invention.

The output pulse width determines the minimum separation between consecutive A and B pulses that can be detected by the decoder chip. If the separation between consecutive A and B pulses is less than the output pulse width of the decoder, then two output pulses overlap and only one count is registered instead of two, resulting in an erroneous position reading. The width of the clock pulse is influenced by the value of the resistor between pins 1 and 3 of the LS7084 quadrature decoder chip embedded in the US-Digital PC-6-84-4 as shown in FIG. 127. In an exemplary embodiment, an added resister across pins 1 and 3 is used to decrease the decoder pulse width to less than 750 ns.

An actuator is a device that converts electromechanical force into motion. This electromechanical force can be explained by Lorentz's Law:

$$\vec{F} = \vec{I} \times \vec{B}$$

When a current in a conductor, $\vec{I}$, is exposed to a magnetic field, $\vec{B}$, a force $\vec{F}$ is produced in the direction perpendicular to both $\vec{I}$ and $\vec{B}$ as described by the right hand rule.

Figure 9:
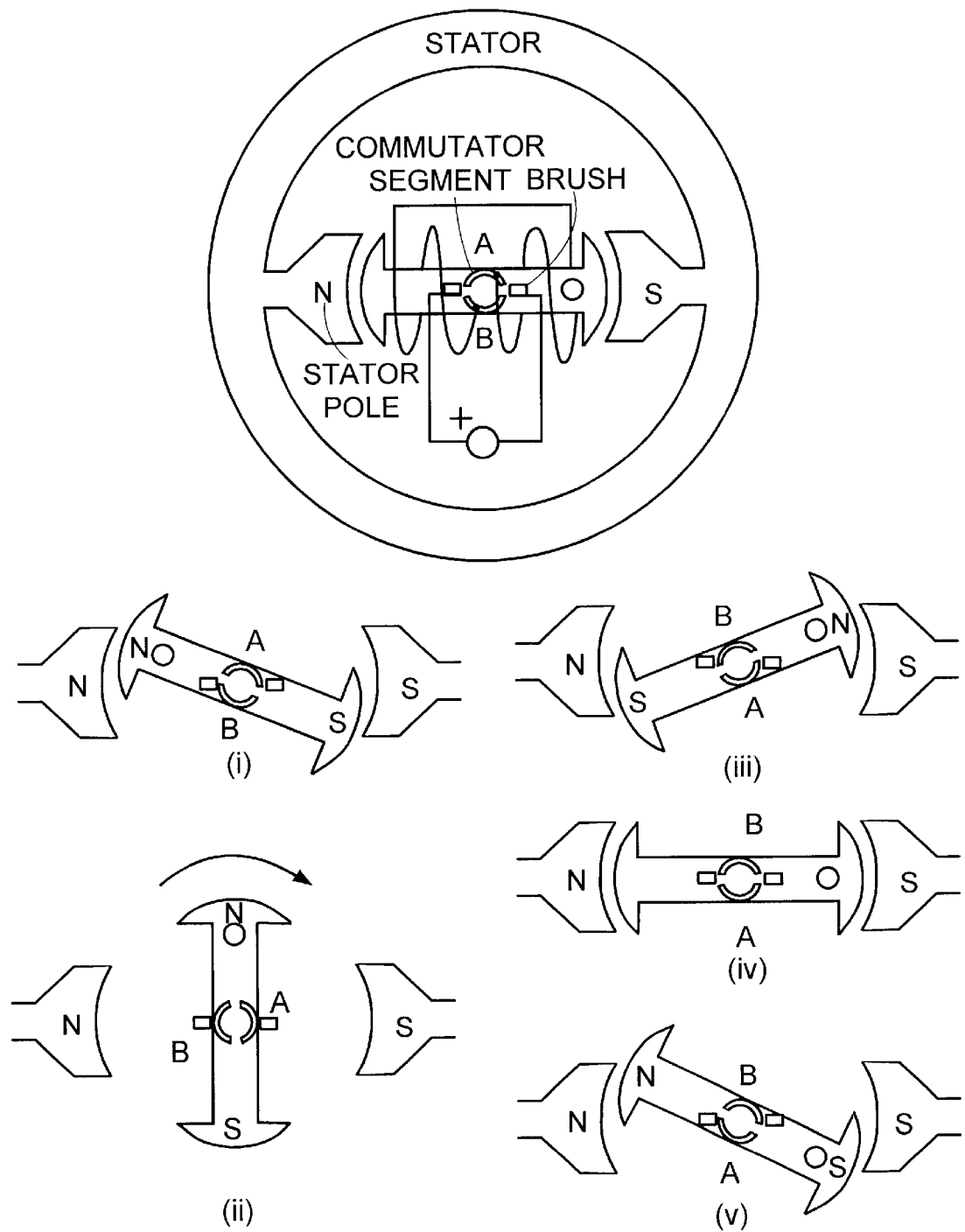
FIG. 9 shows the theory of operation of a simple brushed motor. (Taken from M. B Histand, and D. G. Alciatore, *Introduction to Mechatronics and Measurement Systems*, WCB/McGraw-Hill, Boston, 1999, p. 315).

Since the hand is perturbed about the wrist joint during testing, a motor 40 was used as the actuator for this task. Generally, the stationary outer housing of a motor, the stator, is magnetized either by permanent magnets or by currents flowing through coiled wires wrapped around iron cores. The rotor or rotating shaft is also magnetized either by permanent magnets or winded field coils. The rotor and its windings are collectively known as armature. If the rotor is magnetized via coils, then it has commutator segments where the current is supplied. Brushes provide stationary electrical contact between the power source and the moving commutator and rotor. FIG. 9 shows the theory of operation of a simple two-pole DC motor in view of the long axis of the rotor, wherein "DC" denotes Direct Current. The setup shown consists of a stator that is a permanent magnet and a rotor that is magnetized via coils. In the starting position, (i), the right brush touches commutator segment A and the left brush touches segment B creating a current that flows through the rotor winding. This current magnetizes the rotor into N and S poles as shown. Since like poles repel and opposite poles attract, the rotor rotates in the clockwise direction as shown in (ii) and (iii). In (iv), for a brief instant, the commutators lose contact with the brushes, no current flows through the armature and the rotor is demagnetized. However, the rotor continues to turn clockwise due to momentum. In (v), the commutator contacts switch brushes and the armature current now flows in the opposite direction, so the poles of the rotor are switched. Thus, the motor continues rotating as the armature current constantly switches direction, maintaining torque in the clockwise direction. Like most motors, the motor shown in FIG. 9 is a brush motor. Its stator is a permanent magnet and its rotor armature has a constantly switching current provided by an external current source through the brushes. The brushes of a DC motor have several limitations: brush life, brush residue, maximum speed, and electrical noise. The currents produced in the armature produce a large amount of heat in the rotor that is difficult to dissipate.

The brushless DC motor operates by the same principle as the brush motor except that the rotor consists of a permanent magnet and the stator is magnetized via rotating fields in the stator. It is like a brush motor turned inside out. Indicative of its name, the brushless motor eliminates the need for brushes and commutators. Brushless DC motors are potentially cleaner, faster, more efficient, less noisy, more reliable, produce no sparks and the rotor does not heat up. These motors are also known as permanent magnet motors. Motors that use feedback for a position or trajectory control applications are called servomotors.

Figure 10:
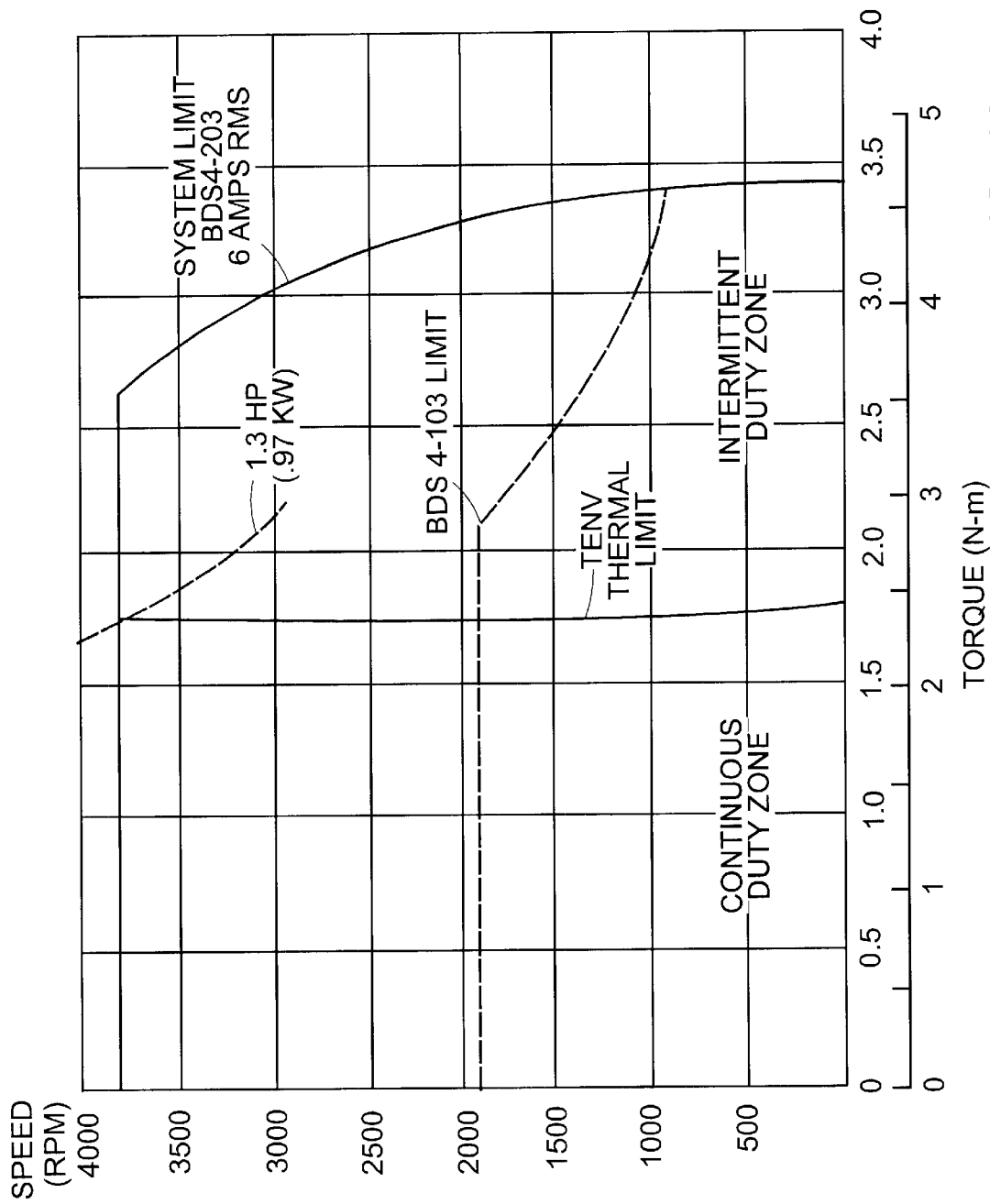
FIG. 10 shows the torque-speed curve of the brushless servomotor (B-202-B-31) used in one embodiment of the present invention.

Preferably, the motor according to the present invention is a brushless DC servomotor, although other types of motors are compatible for use in the present invention. A particularly preferred motor for use in the present invention is the B-202-B-3 1 brushless servomotor from Kollmorgen as its speed range, torque-speed curves and maximum stall torque are acceptable for use in the present invention. The speed torque curve shows the maximum torque the motor can produce at a certain speed using the amplifier of the present invention (see FIG. 10). For the present invention, this is the torque applied by the hand in response to the perturbations given, and, more importantly, the inertias of the hand and the hand rest. As shown in FIG. 10, the maximum possible operating speed of the motor is 3800 RPM. The motor can generate torques up to 3.5 Nm while maintaining a speed fairly close to the maximum value. If the motor is to generate torques above 3.5 N, the maximum speed it can maintain drops very sharply until the motor finally stops moving at the maximum torque of 4.7 Nm. This maximum torque value where the motor shaft is stationary is called the stall torque.

When the load torque on the motor is equal and opposite to the toque produced by the motor while the shaft is stationary, the motor is said to be stalling. This value is limited by the maximum amount of current that the amplifier can supply to the motor. What is considered a fast rotation in most industrial applications is at least an order of magnitude larger than what one would consider a rapid angular joint velocity. In industrial applications, motors may move on the order of $10^3$ RPM. In the present invention, the wrist joint is not expected to be moved to speeds above 25 rads/s or 238 RPM. As shown on the torque-speed curve, the motor can produce close to the maximal stall torque through the entire range of speeds that the present invention is operating at and, thus, the torque-speed relation is not of concern. Rather the concern is that the maximum toque of 4.8 Nm is sufficient for the purpose of the present invention. To determine this, the magnitudes of torques that the motor has to oppose must be analyzed. By Newton's second law, $$\sum \tau = \tau_m + \tau_1 + \tau_f = J_t \ddot{\theta}$$

Rearranging to:

$$\tau_m = J_t \ddot{\theta} - \tau_1 - \tau_f$$

wherein $\tau_m$ is the torque generated by the motor, $\tau_l$ is the load torque applied by the passive and active viscoelastic properties of the muscles and $\tau_f$ is the negligible friction torque of the mechanical apperatus. $J_t$ is the total inertia of the mechanical apperatus (arm rest) $J_m$ plus the inertia of the human hand, $J_l$. The signs of $\tau_l$ and $\tau_f$ are opposite that of $\tau_m$ since they oppose the motor torque and rotation direction, thus:

$$\tau_m = J_t \ddot{\theta} - \tau_1 - \tau_f$$

The majority of the torque that the motor is required to produce is to overcome the total inertia of the system, $J_t$. The inertia of the typical hand was crudely estimated to be around 0.0015 kg m². The inertia of the armrest is around 0.005 kg m². $J_t = J_m + J_f \approx 0.0065$ kg m². Since it is not expected that the wrist joint will be perturbed at accelerations that exceed ±500 rads/s², the maximum torque needed to overcome inertia is $$J_t \ddot{\theta}_{max} = (0.0065 \text{ kgm}^2)(500 \text{ rads/s}^2) = 3.25 \text{ Nm}$$

With the load torque applied in response to the perturbations, the motor selected is sufficient for the present invention because the maximum possible torque that the motor can produce is not expected to be exceeded. Further, based on these specifications, other suitable motors may be readily determined by one of skill in the art. The torque capability of the motor is expressed in terms of the peak stall torque and the continuous stall torque. The peak stall torque is the absolute maximum torque that the motor can produce. This peak torque can only be maintained for a few seconds before the torque settles down to to the continuous stall torque.

The back emf, $V_{emf}$ is an induced voltage by the rotating armature that opposes the applied voltage that is determined by:

$$V_{emf} = K_e \dot{\theta} \text{ or } V_{emf}(s) = K_e(s) \Theta \text{ in the Laplace domain.} \qquad [\text{eq. 8}]$$

$K_e$ is the emf constant of the motor and $\theta$ is the angular velocity of the rotor. If the power supplied to the motor is a voltage source and the voltage supplied at a particular time is $V_m$, then:

$$V_m = L\dot{I}_m + RI_m + V_{emf} = L\dot{I}_m + RI_m + K_e\dot{\theta} \text{ or} \qquad [\text{eq. 9}]$$
$$V_m(s) = (Ls + R)I_m(s) + V_{emf}(s) \text{ in the Laplace domain}$$

$I_m$ is the resulting armature current that can be derived in terms of $V_m$, L and R. L is the inductance, and R is the motor resistance. $\dot{I}$ is the rate of change of the armature current. The torque produced by the motor is proportional to the current supplied to it:

$$\tau_m = K_t I_m$$

or $$T_m(s) = K_t I_m(s)$$

in the Laplace domain [eq. 10]

where $K_t$ is the torque constant of the motor.

Equation 10 can be rewritten as:

$$\tau_m + \tau_1 = B_m \dot{\theta} + J_t \ddot{\theta} \text{ or } T_m(s) + T_1(s) = \qquad [\text{eq. 11}]$$
$$(B_m s + J_t s^2) \Theta(s) \text{ in the Laplace domain.}$$

The amplifier is the variable power supply to the motor. It amplifies the command voltage from the controller into either a voltage or a current to the motor 40. The input to the amplifier is the command voltage given by the Galil motion controller. There are three modes of operation of an amplifier: voltage source mode, current source mode, and velocity loop mode, all of which are described below:

Voltage Source Mode: In this mode, the output to the motor is a voltage, $V_m$, that is some unitless gain, $K_V$, times the command voltage, $V_{cmd}$.

$$V_m = K_V V_{cmd} \qquad [\text{eq. 12}]$$

The resulting armature current can be derived from equation 9. The result is quite cumbersome since equation 9 is a first order differential equation in terms of $I_m$ and also depends on the time varying velocity and the back emf constant, as well as the impedance and resistance of the motor. The resulting motor toque, $\tau_m$ is simply proportional to the current $I_m$ by the torque constant. It is not easy to derive the torque output of the motor given the amplifier output of $V_m$ because of the complexity of equation 9. The transfer function that is the ratio of motor position to voltage command $V_{cmd}$ is:

$$\frac{\Theta(s)}{V_{cmd}(s)} = \frac{K_V K_t}{J_t L s^3 + (B_m L_m + J_t R_m)s^2 + (B_m R_m + K_t K_e)} \qquad [\text{eq. 13}]$$

Current Source Mode: The relationship between the motor voltage, $V_m$ and motor torque, $\tau_m$ is a complicated differential equation with respect to many variables. In current source mode, advantage can be taken of the simple linear relationship between the motor current and torque output as described by the torque constant, $K_t$ as shown in equation 10. Here the amplifier takes the command voltage, $V_{cmd}$ from the Galil controller and amplifies it to the current $I_m$ the gain $K_a$:

$$I_m = K_a V_{cmd} \qquad [\text{eq. 14}]$$

The units of $K_a$ are [Amps*RMS/Volt]. Here, the transfer function between the motor position and voltage command is:

$$\frac{\Theta(s)}{V_{cmd}(s)} = \frac{K_a K_t}{J_t s^2 + B_m s} \qquad [\text{eq. 15}]$$

Velocity Loop Mode: The velocity loop mode is the same as the current mode with an added feedback component. A tachometer that senses velocity converts the velocity into a voltage by the gain, $K_u$, and sends it back to the amplifier. The units of $K_u$ are [V*s/count]. In this mode the transfer function between the motor position and command voltage is:

$$\frac{\Theta(s)}{V_{cmd}(s)} = \frac{K_a K_t}{J_t s^2 + B_m s + K_u K_a K_t} \qquad [\text{eq. 16}]$$

Figure 12:
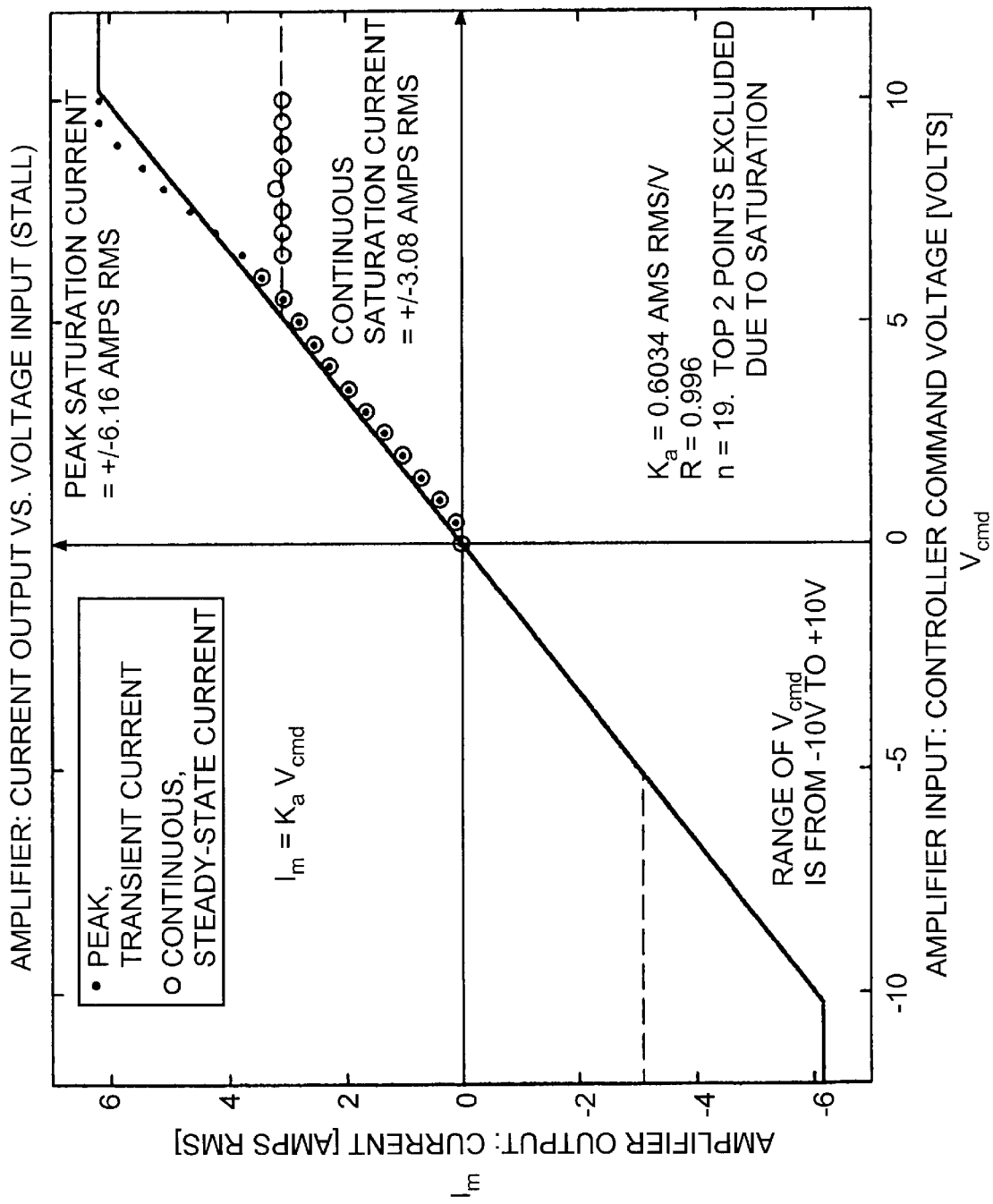
FIG. 12 shows the proportional relationship between the input voltage and the output current of the amplifier. The constant of proportionality, or amplifier gain, was experimentally adjusted so that the maximum range of voltage (+/−10 V) would correspond to the maximum possible current output as listed in the manufacturer specification sheet (+/−6 Amps).

A preferred amplifier for use in the present invention is the Kollmorgen BDS4-1033-0101-202B2, which matches the desired motor characteristics. In an illustrative embodiment, the amplifier is set up in the current mode. This mode makes the analysis of the control system fairly simple. The preferred power supply used for the amplifier is the PSR4/5-112-0102, which can supply a peak current to the above-described motor of about 6 Amps RMS, that lasts for around 2 seconds, and a maximum continuous current of about 3 Amps RMS, as shown by the dashed line in FIG. 12.

After setting up the system, prior to operating the motor 40, the gain of the amplifier and other adjustments are set via tuning pots located on the chassis of the amplifier. The command scale pot is used to adjust the velocity loop gain, $K_u$. However, since the velocity loop is disabled, this is not necessary. Pin 18 on Connector C1 of the amplifier is used to monitor the current output relative to common (pin 17). The output is a voltage proportional to the current output where 1V =0.75 Amps RMS. This feature is used to monitor the current supplied by the amplifier. The balance pot is used to make sure that when 0V is commanded from the Galil controller, the current output of the amplifier is 0 Amps RMS and the motor produces no torque. Equation 14 above is really of the form:

$$I_m = K_a V_{cmd} + \alpha \qquad [\text{eq. 14}]$$

where $\alpha$ is the offset current that is adjustable with the balance pot. With the motor enabled, the input to the amplifier, $V_{cmd}$ is set to 0V and the balance pot is rotated such that $I_m$ read 0 Amps to ensure no offset current. The current limit pot is turned all the way clockwise to maximize the maximum amount of current that the amplifier can supply (up to ±6 Amps RMS). The most important adjustment is the stability or gain adjustment. This determines the magnitude of $K_a$. This adjustable amplifier gain is set experimentally so that the maximum possible value of $V_{cmd}$ (10 V) would correspond to the maximum current limit (approximately 6A) of the amplifier to take advantage of the full range of currents. Thus, the stability pot is adjusted so that value of $K_a$ is set to 0.6 Amps RMS/V.

An experiment was conducted where the voltage output from the Galil controller was set from 0V to 10V at 0.5V increments. To measure the torque output of the motor, $\tau_m$, the motor shaft was kept stationary using the mechanical stops. In this state, $$\dot{\theta} = 0 \text{ and } \ddot{\theta} = 0$$

and $$\tau_m = -\tau_m \text{ from equation 11.}$$

This torque was measured with the torque transducer. The motor torque and amplifier current was measured at each command voltage to produce the plots shown in FIG. 12.

Figure 13:
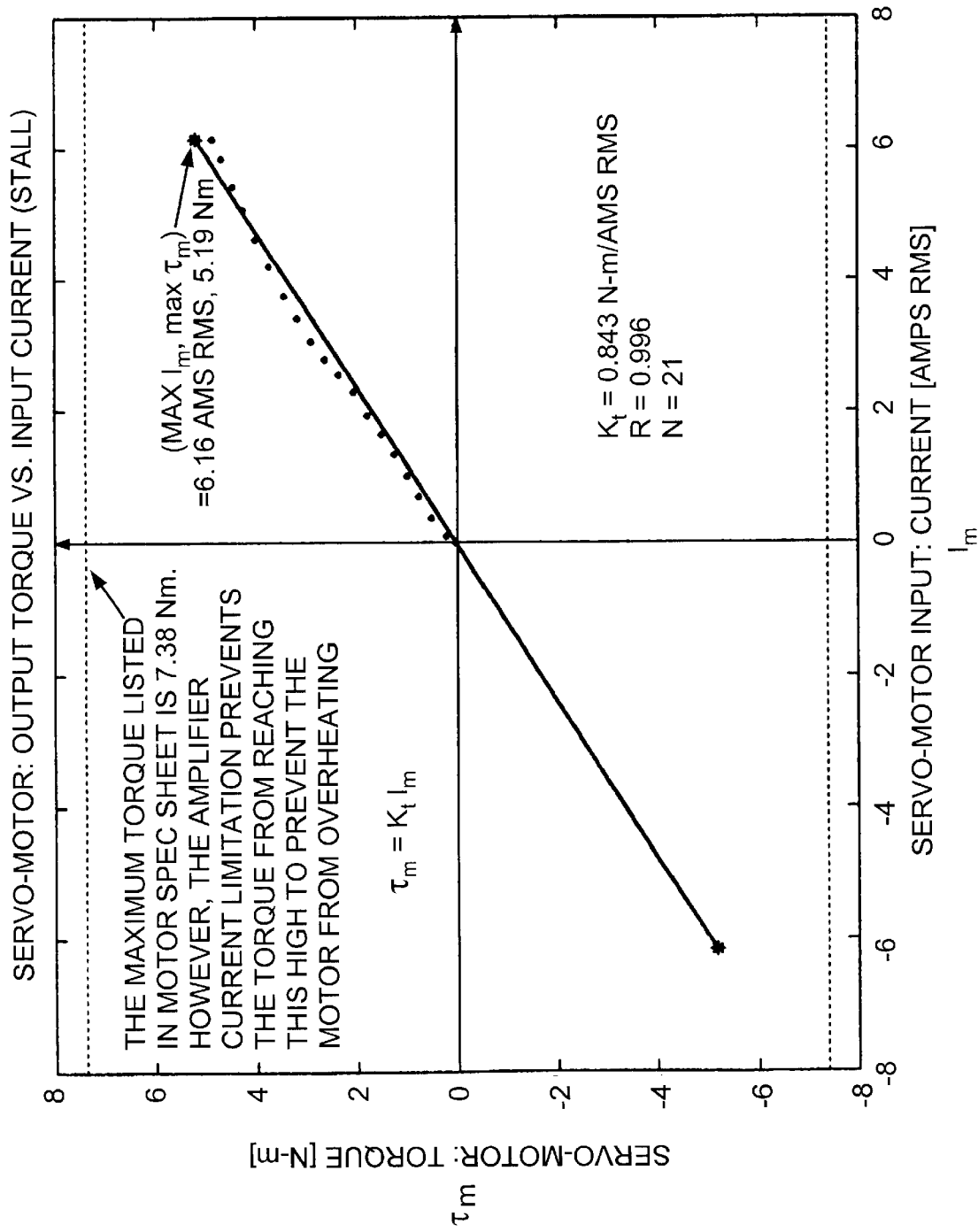
FIG. 13 shows the proportional relationship between the input current and the torque output of the servomotor. The constant of proportionality, or torque constant was experimentally determined.
Figure 14:
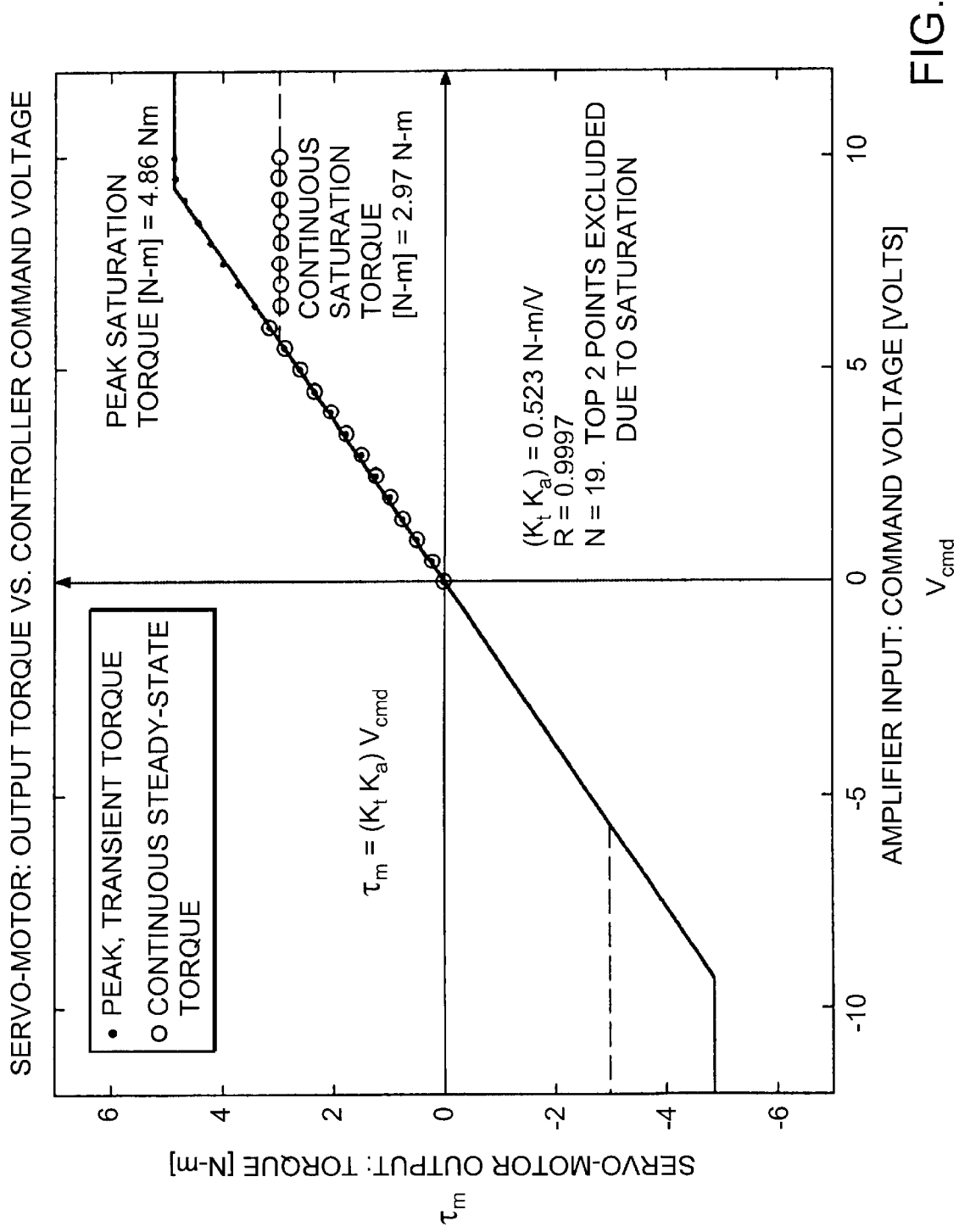
FIG. 14 shows the proportional relationship between the input voltage to the amplifier and the torque output of the servomotor. The constant of proportionality between the two is the product of the torque constant and the amplifier gain.

For each command voltage, the correspontind amplifier currents and motor torques were plotted against each other and $K_t$ was determined by a linear fit through the origin as shown in FIG. 13.

The maximum torque the motor can produce is limited by the maximum current supplied by the amplifier as defined by equation 10. Thus the peak transient torque the motor can produce is 4.86 Nm, which lasts for about 2 seconds before it drops to about 3 Nm.

The controller is the brain of the feedback system, which consists of hardware and software. It controls the command voltage, $V_{cmd}$ that is sent to the amplifier that controls the output torque of the motor shaft since $\tau_m = K_t K_a V_{cmd}$ and $K_a$ and $K_t$ are known constants. The controller has two inputs at any given discrete time instant, $t_i$: the desired position of the motor shaft, $\theta_d(t_k)$ and the actual position of the motor shaft, $\theta(t_i)$. The encoder 24 gives the actual position of the motor shaft 11 with a resolution accuracy of 0.001 degrees, as there are 360,000 counts in one revolution of the motor shaft 11. The controller deals with positions in [counts] since that is the digital output of the encoder/decoder. The command voltage it sends to the amplifier is some function of the position error, $\theta_e$ where:

$$\theta_e(t_i) = \theta_d(t_i) - \theta(t_i)$$

The desired trajectory, $\theta(t_k)$ is given as a set of digital points $dt_{mc}$ seconds apart. This is the period of one cycle of the feed back loop. A new command voltage is sent to the amplifier every $dt_{mc}$ seconds. Thus the frequency of the desired trajectory fed into the controller in Hz is $$fhz_{mc} = \frac{1}{dt_{mc}}$$

The points in the desired trajectory are either generated offline or online. If they are generated offline, the exact points of the trajectory have to predetermined and fed into the controller as an array. This is what is done, for example, when the desired trajectories are the filtered random trajectories that are generated with MATLAB. Since the desired trajectory is periodic, only one period of the trajectory needs to be inputted to the controller. If the points in the desired trajectory are dependent on some output state such as torque or continuously change with time, then they have to be generated online within the loop. When the desired trajectory is a sinusoid, each point of the desired trajectory is generated online based on the time elapsed from the start and the user defined amplitude and frequency. If the points are to be generated within the loop, then everything from sensing the necessary output states to computing the next desired position or torque has to take place in less that $dt_{mc}$ seconds. This is done so the sampling frequency of the controller is maintained at 128 Hz, otherwise the frequency of the controller needs to be decreased to increase the amount of time per loop. At substantially low sampling frequencies, the trajectory will become "choppy" and will not be smooth as defined earlier.

Preferred components of the controller selected for the present invention can be obtained from Galil Motion Control. Several high-level motion controllers can be considered. Preferably, the controllers can be interfaced and, thus, controlled by LabVIEW software, which is the preferred code used in the present device. Preferably, the device is entirely automated and, thus, intervention of the user is minimal as he/she only gives certain desired inputs such is file identifier and the desired trajectories for the device to follow. The components of the Galil controller include the following:

the DMC-1410 single-axis motion controller for the ISA bus.

the ICM-1460 interconnect module.

the WSDK-32 Servo Design Kit for Windows 95,98 the Setup-32 software for Windows 95,98 a 37 pin connector cable from the DMC-1410 to the ICM-1460

The controller uses a high level code, which is attached hereto as Appendix A. Of course, controllers having similar components and that function as required by the present invention could also be used.

Figure 15:
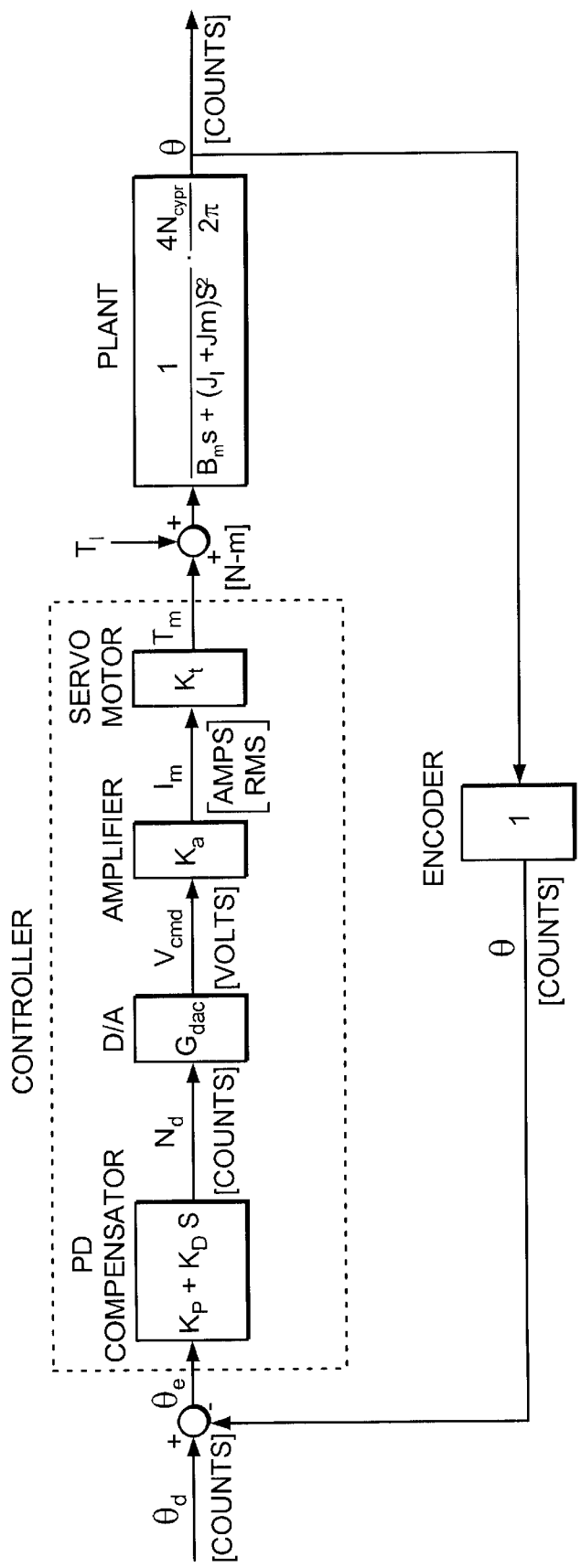
FIG. 15 is a block diagram showing components of the PD closed loop control system used to follow the desired trajectories in accordance with one embodiment of the present invention.

FIG. 15 shows one preferred embodiment of a block diagram of components of the PD closed loop control system used to follow the desired trajectories.

As shown in FIG. 15, a PD Compensator is utilized. A preferred PD Compensator for use with the present invention has the following specifications:

Manufacturer: Galil Motion Control

Input: position error, $\theta_e$ [counts]

Output: digital number, $N_d$ from −32767 to 32767

Description: motion control software downloaded to PLC takes desired trajectory input and feedback from encoder to control motor output.

Transfer Function:

$$\frac{N_d}{\theta_e} = (K_P + K_D S)$$

Constants: $K_P$=0.75 (chosen) $K_D$=0.1563 s$^{-1}$ (chosen)

Further shown in FIG. 15 is a Digital to Analog converter (D/A). A preferred D/A for use with the present invention has the following specifications:

Manufacturer: Galil Motion Control

Input: digital number, $N_d$ from −32767 to 32767.

Output: command voltage, $V_{cmd}$ from −10 V to 10 V.

Description: converts the digital number from −32767 to 32767 to an analog voltage output from −10 V to 10 V.

Transfer Function:

$$\frac{V_{cmd}}{\theta_e} = G_{dac}$$

Constants: $G_{dac}$=20/65535 (fixed, set by PWM & hardware)

Further shown in FIG. 15 is an amplifier. A preferred amplifier for use with the present invention has the following specifications:

Manufacturer: Kollmorgen Industrial Drives

Input: command voltage, $V_{cmd}$ from −10 V to 10 V.

Output: motor armature current, $i_m$, from −6.16 Amps RMS to 6.16 Amps RMS.

Description: produces a current proportional to the input voltage. The adjustable amplifier gain was set experimentally so that the maximum possible value of $V_{cmd}$ would correspond to the maximum current limit of the amplifier to take advantage of the full range of currents.

Transfer Function:

$$\frac{I_m}{V_{cmd}} = K_a$$

Constants: $K_a$=0.603 Amps RMS/V (experimentally set)

Further shown in FIG. 15 is a servo motor. A preferred servo motor for use with the present invention has the following specifications:

Manufacturer: Kollmorgen Industrial Drives

Input: motor armature current, $i_m$, from −6.16 Amps RMS to 6.16 Amps RMS.

Output: torque produced by motor from −5.19 Nm to 5.19 Nm.

Description: produces a torque proportional to the input current.

Transfer Function:

$$\frac{T_m}{I_m} = K_t$$

Constants: $K_t$=0.843 Nm/Amps RMS (fixed, experimentally determined)

Further shown in FIG. 15 is a plant. A preferred plant for use with the present invention has the following specifications:

Input: motor torque, $T_m$ plus external load torque, $T_l$ applied by human [Nm].

Output: actual motor shaft position, θ [counts].

Description: the resulting motor shaft position is determined by the input torques, combined viscosities and inertia of the motor shaft, all mechanical loads attached to the motor shaft including the arm rest $B_m$ and $J_m$. The position is also affected by the inertia of the hand, $J_l$ if attached.

Transfer Function:

$$\frac{\theta}{(T_l + T_m)} = \frac{1}{B_m s + (J_l + J_m)s^2} \cdot \frac{4N_{cypr}}{2\pi}$$

Note: all units in the control system are expressed in SI units except for the angular positions which are not in radians but in counts. ($4N_{cypr}$ counts=$2\pi$ radians)

Constants:

$B_m$=0.003 Nm s/rad experimentally determined, $J_m$≈0.0048 kg m². The exact value slightly varies depending on the position of the armrest on the sliding bar.

$J_l$≈0.0023 kg m². The exact value varies depending on the mass distribution, and geometry of the hand of the subject being tested.

$N_{cypr}$=90,000. This is the number of square wave cycles per revolution of the incremental encoder. With quadrature edge detection, there are $4N_{cypr}$ counts per revolution.

The entire closed loop PD system preferably has the following specifications:

Input: desired motor shaft positions (trajectory), $\theta_d$ [counts].

Output: actual motor shaft position, θ [counts].

Description: the system implemented is a Linear Time Invariant second order model of the system.

Transfer Function:

$$\frac{\theta}{\theta_d} = \frac{(K_D G_{dac} K_a K_t)s + K_P G_{dac} K_a K_t}{\frac{(J_l + J_m)\pi}{2N_{cypr}} s^2 + \left(K_D G_{dac} K_a K_t + \frac{B_m \pi}{2N_{cypr}}\right)s + K_P G_{dac} K_a K_t}$$

$$= \frac{24.256s + 465.705}{0.1239s^2 + 24.308s + 465.705}$$

It is important that the system characteristic equation or denominator of R(s), gives poles at:

$$\frac{-\left(K_D G_{dac} K_a K_t + \frac{B_m \pi}{2N_{cypr}}\right) \pm \sqrt{\left(K_D G_{dac} K_a K_t + \frac{B_m \pi}{2N_{cypr}}\right)^2 - \frac{2\pi(J_l + J_m)(K_P G_{dac} K_a K_t)}{N_{cypr}}}}{\frac{(J_l + J_m)\pi}{N_{cypr}}} -$$

87.56 and −10.73 after substitution and simplification. Since the roots have negative real parts, it can be said that the linear time-invariant system is bounded-input, bounded-output and asymptotically stable. The fact that roots are unequal and have no imaginary parts says that the system is overdamped (ζ>1). In fact, for the inertia constants used above, ζ=1.6. For smaller inertias, ζ increases slightly and for larger hand inertias, ζ decreases slightly.

Figure 16A:
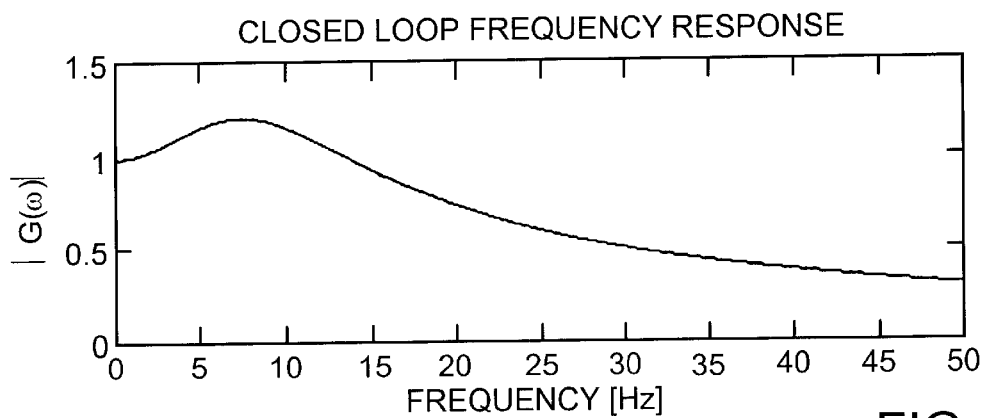
FIG. 16 shows a typical analytical frequency response and step response of the entire closed loop system shown in FIG. 15.
Figure 16B:
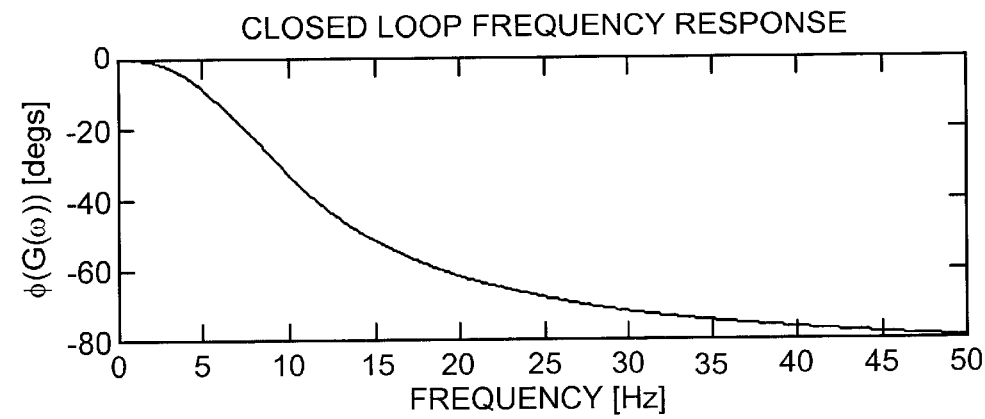
Figure 16C:
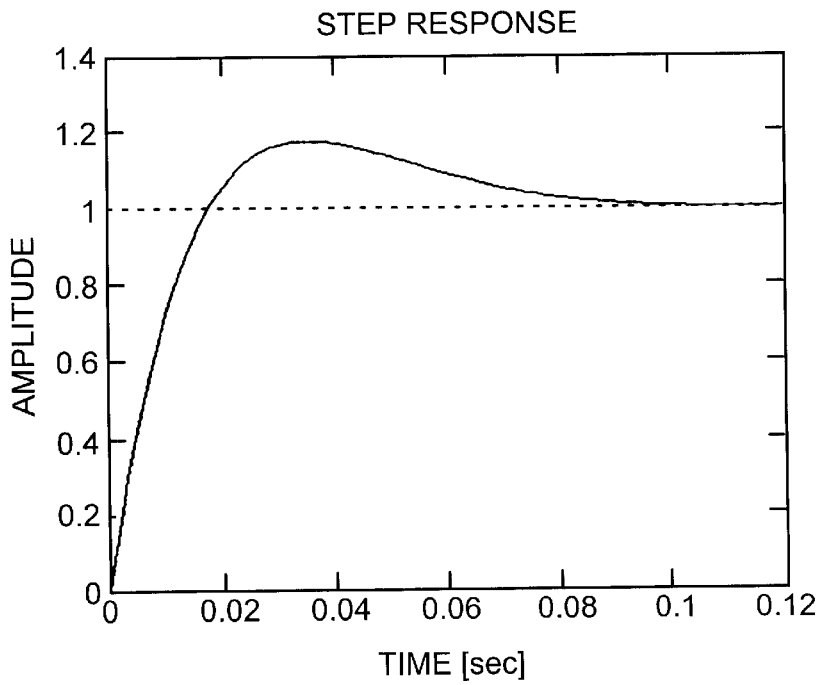

Using typical values for constants $J_m$, and $J_l$ shown above and substituting jω for s, the analytical magnitude and phase of the frequency response is shown in FIG. 16. The analytical step response is also shown in FIG. 16.

The tuning parameters, $K_p$ and $K_d$, are chosen so that the system will have a fast response time without making them too large. The torque saturates when small position and velocity error gives rise to a large digital output $N_d$ and a command voltage, $V_{cmd}$ close to +/−10V. Preferably, from 0 to 8 Hz, the magnitude of frequency remains close to 1. The actual trajectory of the shaft was checked for all types of desired trajectories both analytically using the MATLAB function mypid.m (see Appendix A) as well as experimentally by measuring the actual output position of the shaft.

A preferred test setup and procedure in accordance with the present invention is as follows. The patient being tested with the device of the present invention is preferably seated in front of the device. Two surface electrodes are placed on the patient's arm to monitor activity of the flexors and extensors. The ground electrode is placed on an inactive or neutral site. After the absolute position of the motor shaft is calibrated, the seat is adjusted such that the patent's left or right arm can be placed in the arm rest 5. At this point, the patient's elbow is preferably at about 145 to 160 degrees. The patient's hand is placed on the hand rest 4 in the neutral supination/pronation position such that his or her knuckles are slightly passed between the padded vertical bars 6. The vertical bars 7 are moved closer together and tightened such that the hand is comfortably secured in place. The hand rest 4 is then slid forward or backward so that the wrist joint is lined up with the motor shaft 11. Now the subject is simply told to relax and not to resist the robot's movement as the robot moves to the initial bias position and follows the desired trajectories as described above. The robot automatically cycles through the desired trajectories (trials 1–10) while collecting torque, position and EMG data. If an additional test is to be performed in a different bias position, the patient's arm is preferably removed from the apparatus for 2 or 3 minutes before the procedure is repeated at the new initial bias position.

The bias position is the absolute initial angular position of the wrist joint that the motor shaft 11 moves to before each perturbation trajectory or trial is carried out. A bias position of 0 degrees corresponds to the neutral flexion/extension position. It is also the median angular position of the trajectory. The user selects the bias or initial position, and the motor shaft 11 automatically moves to that position before the desired trajectory is carried out. In testing control subjects, selecting a 0-degree bias position is not a problem as control subjects have a wide range of motion. Almost all patients with spasticity and others with neurological problems, however, have a limited range of motion. Their resting position is in a hyper-flexed position and it is painful or impossible for them to extend their hand beyond the 0-degree absolute position due to the contracted state of the flexor muscles. Due to this constraint, subjects in the patient population were tested in the 30 degree flexed position. Control subjects were tested at both 0 and 30 degree flexed bias position. Since the left or right arm may be tested, the four possible combinations of bias positions are shown in FIG. 17.

For more detailed instructions about the procedure, please refer to the user's manual attached hereto as Appendix B.

Next, the raw data is taken and transformed into the torque offset, elastic stiffness, viscosity and inertia parameters described above and represented by the variables $\tau_{off}$, $K_H$, $C_H$, and $I_T$ respectively. $\tau_{off}$ is the offset torque, $K_H$ is the combined angular elastic stiffness of all the muscles acting on the wrist joint, $C_H$ is the combined angular viscosity of all the muscles acting on the wrist joint, and $I_T$ is the moment of inertia of the moving hand as well as the moving mechanical parts of the apparatus (hand rest).

Data obtained from subject JF (a 28 year old, male control subject) is identified as experiment DMJF. In this experiment, the 10 trial random trajectories were run on the right hand at a bias of 0 degrees. The entire data analysis procedure will be described from obtaining the raw data until the computation of impendence parameters in equation 1.

As mentioned above, for each perturbation trajectory given, five measurements are collected and stored using LabVIEW and a National instrument PCI-E series data acquisition board at 500 Hz. A reading from each sensor is synchronously collected every 2 ms. These raw data points are stored as an n×5 array in ASCII format. Data is collected for 20 seconds (n=10,000) per trial. The first data column is just a timestamp of when data from each sensor is collected (i.e. 0 ms, 2 ms, 4 ms . . . ). The second data column is a set of integer counts from the encoder 24, which make up the angular position signal of the motor shaft 11 and the wrist joint. The third data column is a list of torque readings from the torque transducer in Nm. The fourth and fifth data columns are flexor and extensor EMG readings respectively, in mV. Since each experiment consists of ten filtered random trajectories, there are ten arrays of raw data stored as DMJFI1t1, DMJFI1t2, . . . , DMJFI1t10.

The raw signals of each of the 10 trials in experiment DMJF are shown in FIGS. 18–27.

In one preferred embodiment, the device utilizes a filter. One preferred filter is a Savitsky-Golay filter (Savitsky & Golay, Press et. al: *Numerical Recipes*). A filter can provide a number of advantages. The discretization of position gives a finite resolution of position based on the resolution of the encoder. In the present invention, this resolution is 0.001 degrees. Filtering enables displacement positions to fall between these increments. Since the resolution is very high, this is particularly important when using low-resolution encoders, with a low ncypr. Further, filters can assist in the timing of data acquisition. Still further, filters are useful in obtaining smooth first and higher order derivatives of a discrete signal. A crude method to obtain the derivative (slope or tangent) at a point in a discrete signal is to take the difference between neighboring points and then divide it by the sampling period. This is based on the assumption that the two neighboring points are sufficiently close enough such that the points in between lie on a straight-line between the two. Sharp discontinuities in the derivative signal are observed using this technique. As in most smooth signals, the present displacement signal between any two points is actually a curve. Thus, the filter utilizes a better technique to obtain derivatives by fitting a polynomial through a window of neighboring points. The Savitsky-Golay filter, for example, is a smoothing filter that is useful when determining derivatives such as velocity and acceleration offline when the raw displacement signal has already been collected and stored. This smoothing technique fits a polynomial to a moving window of data using least squares fitting. Derivatives, as well as the function value, can be determined at the center point of each window. Since the coefficients of the fitted polynomial are linear in the data values, the filter coefficients can be pre-computed. The filter coefficients are then convoluted with the raw digital signal to obtain the actual smoothed version of the raw waveform as well as well as its derivatives at each center point.

The Savitsky-Golay algorithm operates as follows with the following variables:

$d_{raw}$: the column vector of actual displacement data points

N: total number of points in the raw digital displacement signal (rads)

ord: the order of the polynomial.

wins: the number of equally spaced points to be fit by the polynomial, the size of the window. This number is always odd.

$y_i$: a sub vector of $d_{raw}$ of length wins with i being the index of the center point.

hw=(wins−1)/2: half width of the window.

The matrix X of dimension wins by (ord+1) is taken as $$X_{winsXord+1} = \begin{vmatrix} -hw^0 & -hw^1 & \cdots & -hw^{ord-1} & -hw^{ord} \\ -(hw-1)^0 & -(hw-1)^1 & \cdots & -(hw-1)^{ord-1} & -(hw-1)^{ord} \\ \vdots & \vdots & \vdots & \vdots & \vdots \\ 0 & 0 & 0 & 0 & 0 \\ (hw-1)^0 & (hw-1)^1 & \cdots & (hw-1)^{ord-1} & (hw-1)^{ord} \\ -hw^0 & -hw^1 & \cdots & -hw^{ord-1} & -hw^{ord} \end{vmatrix}$$

The sum of the squared error, S, is minimized between the elements of $y_i$ and $y_j$, an estimate of $y_i$:

$$y_j = X*F*y_i$$

where F is a (ord+1) by wins matrix. The sum of the squared errors can be written as:

$$S = (y_j - y_i)^{T} * (y_j - y_i) = (y_i - X*F*y_i)^{T}(y_i - X*F*y_i)$$

A matrix F is evaluated such that the least possible sum-squared error, S, is obtained. To do this, the derivative of S is set with respect to F to 0, dS/dF=0. This yields the pseudo-inverse solution, $$F = (X^T*X)^{-1}*X^T$$

The columns of F are then reversed and the $k^{th}$ derivative is then given by k! multiplied with the $(k+1)^{th}$ row of F divided by $(dt\_daq)^k$ convolved with the raw displacement data. Before applying the Savitsky-Golay filter, the encoder count signal is converted into radians. Since the resolution of the encoder gives us 1000 counts for a degree of angle, the raw encoder count signal is multiplied by $$\frac{\pi}{180000}$$

to give the raw displacement data in radians in the column vector, rawrads. In equation form, the $i^{th}$ element of the $k^{th}$ derivative using the Savitsky-Golay filter is given as:

$$\frac{d^k(rawrads)}{dt^k}(i) = \left(\frac{1}{dt\_daq^k}\right)*k!*\sum_{j=-hw}^{hw}(rawrads_i * F_{k+1,i+1-j})$$

A third order polynomial (ords=3) is used with a window size of 21 points. Thus, F is a 4 by 21 matrix. From the equation above, the $i^{th}$ element of the filtered displacement signal is given as:

$$disp(i) = \sum_{j=-10}^{10}(rawrads_i * F_{1,i+1-j})$$

the velocity signal is given as:

$$vel(i) = \frac{d(rawrads)}{dt}(i) = \left(\frac{1}{0.002}\right)*\sum_{j=-10}^{10}(rawrads_i * F_{2,i+1-j})$$

and the acceleration signal is given as:

$$acc(i) = \frac{d^2(rawrads)}{dt^2}(i) = \left(\frac{1}{4*10^{-6}}\right)*2*\sum_{j=-10}^{10}(rawrads_i * F_{3,i+1-j}).$$

Figure 28:
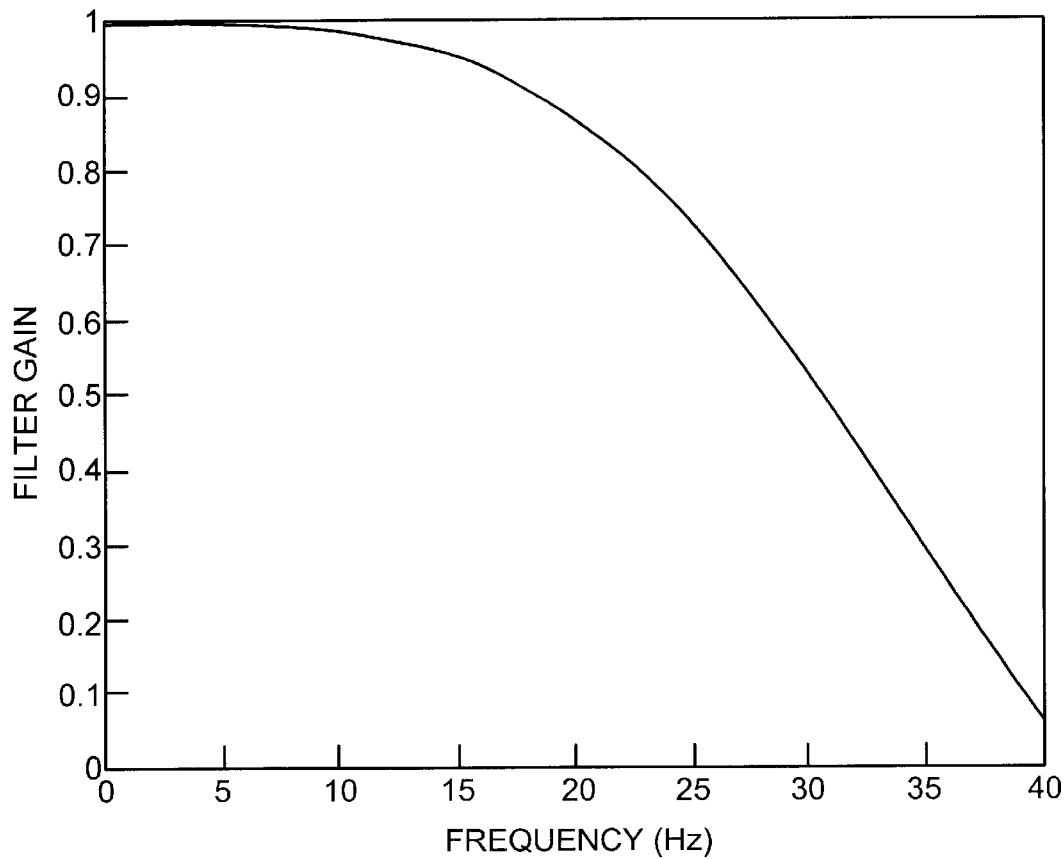
FIG. 28 shows the frequency response of the Savitsky-Golay filter used on the encoder counts.

Since the units of the elements in the raw rads vector are in rads or radians, elements in the displacement, velocity, and acceleration array are in rads, rads/s, and rads/s$^2$ respectively. The beginning and the end of each vector are truncated by a number of points equal to the half width of the window. The frequency response of the Savitsky-Golay filter using a third order polynomial with a window size of 21 points (0.04 s) in the frequency domain can be seen using the freqz MATLAB function which shows the Z-transform digital filter frequency response as follows:
>>sav=sav_golay(3,21);
>>[h,f]=freqz(sav(1,:),1);
>>plot(f*500/(2*pi),abs(h),'k');

This produces the frequency response plot shown in FIG. 28. There is no phase lag since the window is symmetric with respect to the point at which the polynomial is evaluated (center point).

Unlike digital signals, such as that from the encoder 24, analog signals from torque transducers have high frequency noise components that do not give a true representation of the actual torque exerted. Low pass digital filters are often used offline to attenuate the high frequencies in the torque signal. A zero lag 8$^{th}$ order digital Butterworth filter can be used to greatly attenuate these high frequencies.

In MATLAB, [b,a]=butter(n,Wn) designs an order n low-pass digital Butterworth filter with cutoff frequency Wn. It returns the filter coefficients of length n+1 in row vectors b and a, with coefficients in descending powers of z:

$$H(z) = \frac{B(z)}{A(z)} = \frac{b(1)+b(2)z^{-1}+\ldots+b(n+1)z^{-n}}{1+a(2)z^{-1}+\ldots+a(n+1)z^{-n}}$$

The cutoff frequency is that frequency where the magnitude response of the filter is $\sqrt{1/2}$. For example, for MATLAB's butter function, the cutoff frequency, Wn must be a number between 0 and 1, where 1 corresponds to half the sampling frequency (the Nyquist frequency). A preferred embodiment of the present invention uses a Wn of 0.075, which corresponds to a cutoff frequency of 18.75 Hz (see getstatesgbw.m in Appendix A). Normally, Butterworth filters have a phase response where there is a lag between the filtered and the raw signal as a function of frequency of the raw signal. In other words the filtered torque signal is nonlinearly shifted in time with respect to the original signal as a function of frequency. Thus, the filtered torque signal also lags behind the encoder signal. These phase lags are particularly significant in high order filters. This lag is problematic because it is important for the torque waveform to be synchronized with the position velocity and acceleration waveforms in order to evaluate the parameters in the viscoelastic model described herein. However, the filtfilt function in MATLAB is prefereably used. y=filtfilt(b,a,x) performs zero-phase digital filtering by processing the input data in both the forward and reverse directions.

After filtering in the forward direction, the filtered sequence is reversed and it runs it back through the filter. The resulting sequence has precisely zero-phase distortion and double the filter order (A. V. Oppenheim, and R. W. Schafer. *Discrete-Time Signal Processing*. Englewood Cliffs, N.J.: Prentice Hall, 1989. Pgs. 311–312).

Stiffness, viscosity, and inertial parameters are obtained from position and torque signals obtained from the optical encoder and torque transducer. Velocity and acceleration signals are also required, as shown in equation 1. These signals are derived inherently from the position signal via the Savitsky-Golay filter described above. Filtering of the flexor and extensor EMG signals is not crucial since these signals are not necessary for post processing. However, monitoring live EMG information can be used to monitor possible voluntary contractions. Ideally the muscle should be fully relaxed before perturbing the wrist, since spasticity is being measured, which is an involuntary reflex. Thus, the EMG information can be used live to ensure proper integrity of the data collected. Since flexor and extensor EMG activity is monitored, the EMG data can also be collected and stored. Post processing on EMG signals can be useful to answer more basic questions, such as the investigating reflex delay times from the onset of single or repetitive muscle perturbations to muscle contraction. Thus, the total time it takes for the entire reflex loop can be measured. Researchers have shown that two separate response times can be measured, one due to spinal pathways to the spinal cord and back, and one due to supra-spinal pathways which involve upper motor neurons from the brain (See J. C. Houk: *Participation of Reflex Mechanisms and Reaction-Time Processes in the Compensatory Adjustments to Mechanical Disturbances. Cerebral Motor Control in Man: Long Loop mechanisms.* Prog. clin. Neurophysiol., vol 4, Ed. J. E. Desmedt, pp 193–215, Krager Basel, 1978; W. G. Tafton, P. Bawa, I. C. Bruce, R. G. Lee: *Long Loop Reflexes in Monkeys: An Interpretative Base for Human Reflexes. Cerebral Motor Control in Man: Long Loop mechanisms.* Prog. clin. Neurophysiol., vol 4, Ed. J. E. Desmedt, pp 229–245, Krager Basel, 1978). Naturally, the supra-spinal response occurs after the spinal response.

EMG signals are extremely noisy, particularly if surface electrodes are used. EMG signals measured with surface electrodes are influenced by hair, oil, lotions and dead skin. The actual action potentials sent to the muscles are internally amplified by 1000, typically resulting in a signal from 0 to ±5 V. Preferably, internal to the Delsys 2-channel EMG unit is a 20–450 Hz band pass filter. Once the data is collected through the data acquisition board and stored, further filtering is then performed offline in MATLAB as follows.

First a moving root-mean-square (RMS) window is applied to the raw output of the EMG signal where the size of the window is 15 points or 28 milliseconds. Thus, the $k^{th}$ sample point is of the RMS EMG signal is equal to $$EMG_{RMS}(k) = \sqrt{\frac{1}{15} \sum_{i=k-7}^{k+7} (EMG_{RAW}(k))^2}$$

After the RMS EMG signal is obtained, it is passed through a low pass butterworth filter as applied to the torque signal. The result gives the final filtered EMG signal. The cutoff frequency used in this butterworth filter is 37.5 Hz.

Figure 29:
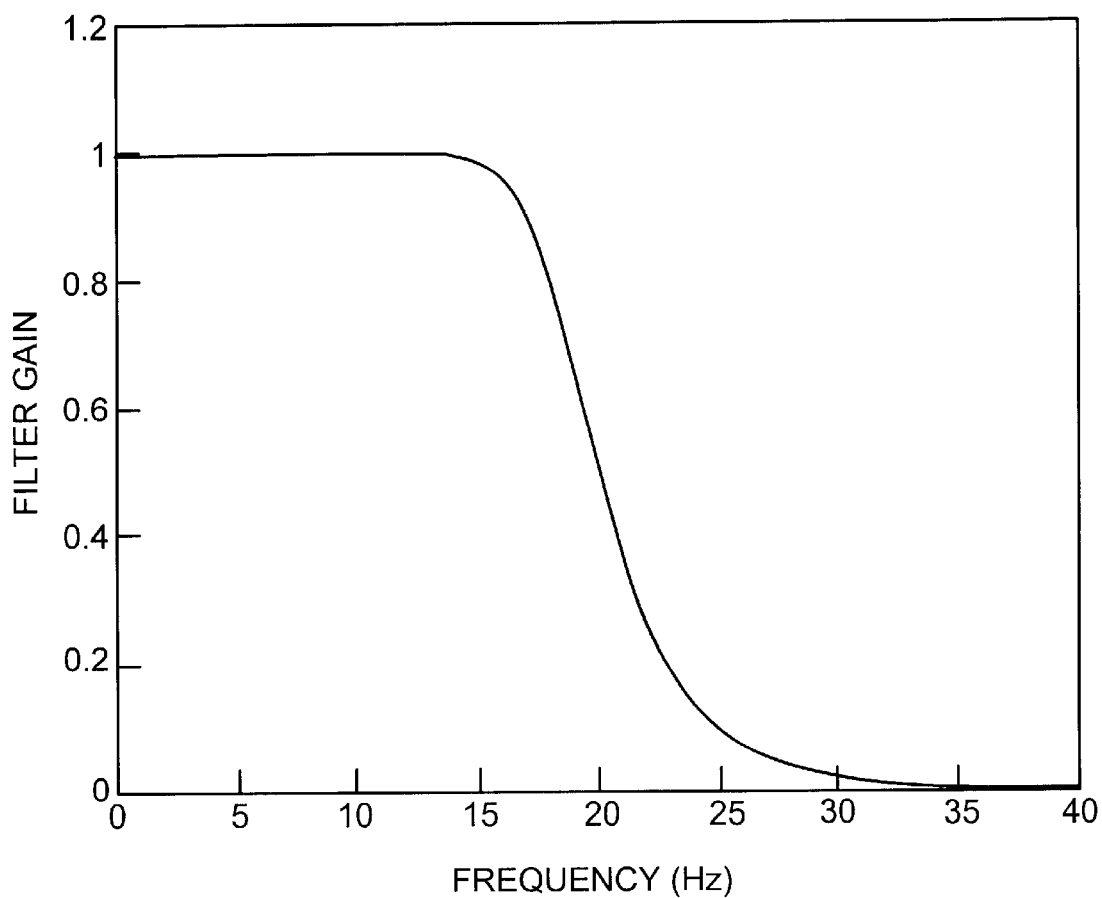
FIG. 29 shows the frequency response of the butterworth filter used on the torque signal.
Figure 40A:
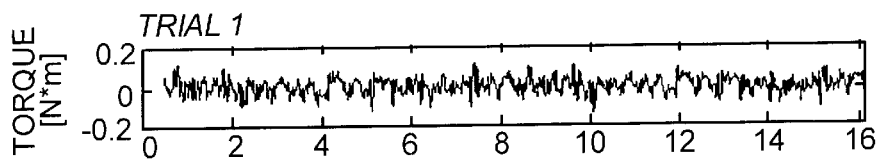
FIG. 40 shows the amount of residual torque when using one set of time invariant parameters, $\tau_{off}$, $\tilde{K}_H$, $\tilde{B}_H$, and $\tilde{J}_T$ over the entire data set in each trial in experiment DMJF.
Figure 40B:
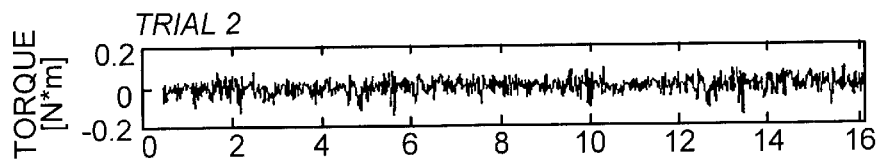
Figure 40C:
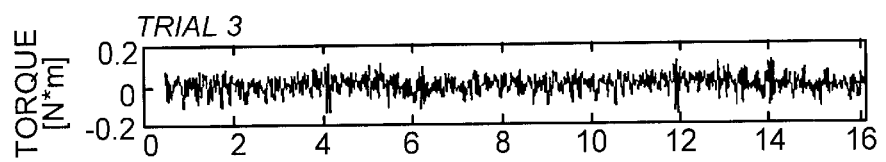
Figure 40D:
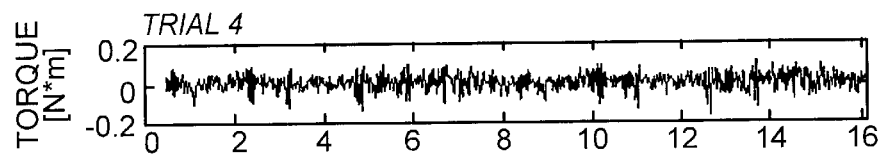
Figure 40E:
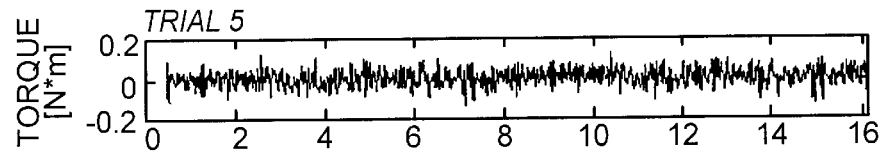
Figure 40F:
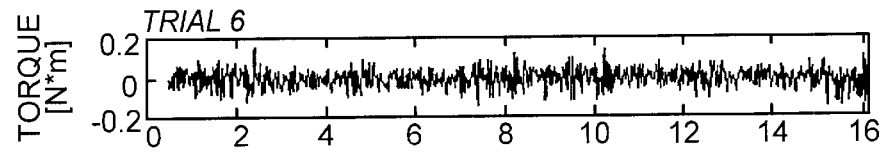
Figure 40G:
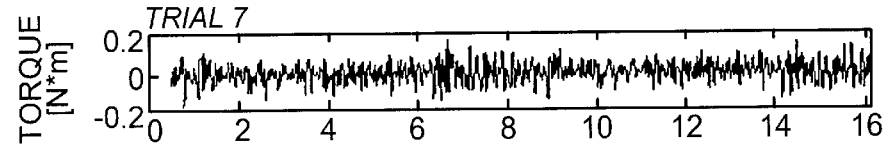
Figure 40H:
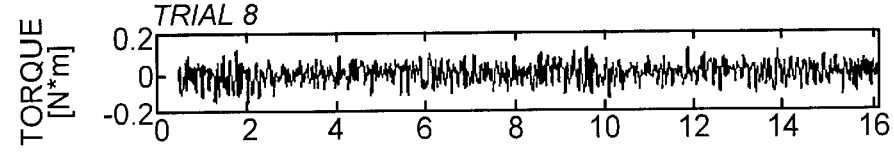
Figure 40I:
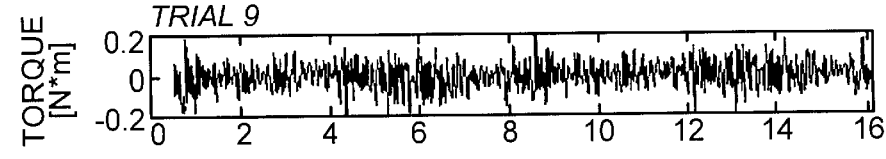
Figure 40J:
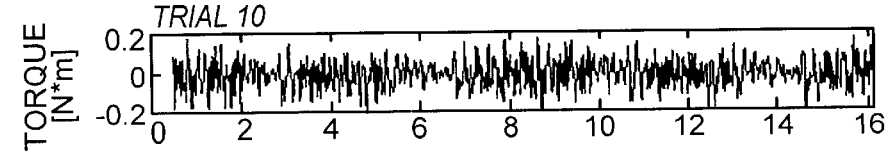

The displacement, velocity and acceleration signals using the Savitsky-Golay filter on the encoder signal for each of the 10 trials are shown in FIGS. 30–29. The filtered torque and EMG signals are also shown. Filtered data obtained from two cycles or periods of each random displacement signal are used for further processing.

Now all the proper state measurements $$(\tau_s(t_i), \theta(t_i), \dot{\theta}(t_i), \text{ and } \ddot{\theta}(t_i))$$

are known after the signal processing described above, and the data can now be fit to the model of the present invention:

$$\tau_S(t_i) = \tau_{off} + K_H * \theta(t_i) + B_H * \dot{\theta}(t_i) + J_T * \ddot{\theta}(t_i)$$

where $\tau_S$ is the filtered torque signal from the transducer. $K_H$ and $B_H$ are the angular stiffness and viscosity of the combined flexor and extensor muscle groups that act on the wrist joint. $J_T$ is the combined inertia of oscillating appendage, $J_H$, and the rotating components of the apparatus, $J_A$. $J_T = J_H + J_A$. $\tau_{off}$, the offset torque is equal to $-K_H * \theta_{RP}$ as described above. $\theta$ is the angular displacement of the system.

$$\dot{\theta} \text{ and } \ddot{\theta}$$

are velocity and acceleration, respectively which are the first and second derivatives of displacement. The data was fit using a linear least squares fit pseudo-inverse (See A. Bjorck, *Numerical Methods for Least Squares Problems*, SIAM, Philadelphia, 1996; H. Anton, C. Rorres, *Elementary Linear Algebra*, Applications version, sixth edition, Wiley & Sons, New York, 1991), as follows. For a set of discrete samples, the following matrices are constructed:

$$Ts = \begin{vmatrix} \tau_S(t_1) \\ \tau_S(t_2) \\ \tau_S(t_3) \\ \vdots \\ \tau_S(t_n) \end{vmatrix}_{n \times 1} \text{ and } \Psi = \begin{vmatrix} 1 & \theta(t_1) & \dot{\theta}(t_1) & \ddot{\theta}(t_1) \\ 1 & \theta(t_2) & \dot{\theta}(t_2) & \ddot{\theta}(t_2) \\ 1 & \theta(t_3) & \dot{\theta}(t_3) & \ddot{\theta}(t_3) \\ \vdots & \vdots & \vdots & \vdots \\ 1 & \theta(t_n) & \dot{\theta}(t_n) & \ddot{\theta}(t_n) \end{vmatrix}_{n \times 4}$$

It is possible to obtain the set of three parameters, $$\tilde{N} = \begin{vmatrix} \tilde{\tau}_{off} \\ \tilde{K}_H \\ \tilde{B}_H \\ \tilde{J}_T \end{vmatrix}_{4 \times 1}$$

that best fits the present model in equation 1:

$$\tau_S(t_i) = \tau_{off} + K_H * \theta(t_i) + B_H * \dot{\theta}(t_i) + J_T * \ddot{\theta}(t_i)$$

using the pseudo-inverse which minimizes the sum squared error, a positive scalar value. In matrix equation form the sum-squared error can be written as:

$$SSE = (\hat{O}_S - \emptyset * \tilde{N})^T * (\hat{O}_S - \emptyset * \tilde{N})$$

The matrix P that minimizes SSE is evaluated as:

$$\tilde{N} = pinv(\emptyset) * \hat{O}_S = (\emptyset^T * \emptyset)^{-1} * \emptyset^T * \hat{O}_S \quad [\text{eq. 15}]$$

First the pseudo-inverse is performed to obtain one set of parameters utilizing all data over 2 whole periods (15.625 s or n=7815) that construct one large $\hat{O}_S$ (7815×1) vector of torque measurements and one large $\emptyset$ (7815×4) state matrix. Let us denote the four evaluated parameters as $\tau_{off}$, $\tilde{K}_H$, $\tilde{B}_H$, and $\tilde{J}_T$. These evaluated parameters for the experiment DMJF whose data is shown below.

TABLE 2

The use of overall data in each trial to obtain one set of best-fit parameters for each trial for experiment DMJF.

| Trial | $\tilde{\tau}_{off}$ Torque Offset [N * m] | $\tilde{K}_H$ Stiffness [N * m/rad] | $\tilde{B}_H$ Viscosity [N * m * s/rad] | $\tilde{J}_T$ Total Inertia [kg * m²] |
|---|---|---|---|---|
| 1 | −0.03667 | 0.76224 | 0.05009 | 0.00687 |
| 2 | −0.03744 | 0.76663 | 0.04372 | 0.00673 |
| 3 | −0.03740 | 0.81638 | 0.04503 | 0.00682 |
| 4 | −0.04743 | 0.89976 | 0.04170 | 0.00701 |
| 5 | −0.04922 | 0.83478 | 0.04355 | 0.00701 |
| 6 | −0.05149 | 0.88837 | 0.04229 | 0.00707 |
| 7 | −0.06263 | 0.92421 | 0.04594 | 0.00720 |
| 8 | −0.06939 | 0.89970 | 0.04502 | 0.00715 |
| 9 | −0.06859 | 0.94812 | 0.05022 | 0.00730 |
| 10 | −0.07785 | 1.01639 | 0.05268 | 0.00737 |
| Average | −0.05381 | 0.87566 | 0.04603 | 0.00705 |
| Standard dev. | 0.01496 | 0.08074 | 0.00372 | 0.00021 |

To determine whether the model used in the present invention to obtain overall parameters for each trial is a reasonable one, the residual torque, $\tau_R$ is plotted. The residual torque is the amount of torque that is unaccounted for by the model and for a particular time sample. In equation form, it is defined as:

$$\tau_R(t_i) = \tau_s(t_i) - \left[\tilde{\tau}_{off} + \tilde{K}_H * \theta(t_i) + \tilde{B}_H * \dot{\theta}(t_i) + \tilde{J}_T * \ddot{\theta}(t_i)\right]$$

From the residual torque plots in FIG. 40, it is shown that the amount of measured torque, $\tilde{o}_S(t_i)$ that is not accounted by the model (the residual, $\tau_R(t)$) is only about 4% on average. This demonstrates that the present model described by equation 1 fits to the data well, even when estimating only one set of parameters, $\tilde{\tau}_{off}$, $\tilde{K}_H$, $\tilde{B}_H$ and $\tilde{J}_T$ over the entire data set in each trial. If, however the residuals are large, this would indicate that the equation of the present model is inadequate, or that a single set of time invariant, four parameters applied to the state data $$\left(\theta(t), \dot{\theta}(t), \text{ and } \ddot{\theta}(t)\right)$$

over the whole trial is insufficient to describe the torque output. In other words, if the residual is large using only one set of time invariant parameters, the model may be good, but the impedance parameters of torque offset, stiffness and viscosity may be changing in time, within a given trial. To estimate how the impedance parameters change within a given trial, rather than have a single $T_S$, $P_S$ and $\Psi$ matrix over the whole trial as shown above, multiple $T_S$, $P_S$ and $\Psi$ matrices can be used by applying a smaller, one second moving window (501 samples) over the data as follows. First it is assumed that the total inertia does not change within each trial. This is a reasonable assumption since the distribution of mass of the moving parts about the center of the motor shaft does not change and the subject's hand is secured in place with the vertical bars 6. For each trial, $\tilde{J}_T$ is used, which is evaluated above as the total inertia of the system. It is possible for the other three parameters to change within a trial. For a particular point in time, these now time varying parameters are denoted with subscripts as $\tau_{off}(t_i)$, $K_H(t_i)$, $B_H(t_i)$. Using these time varying parameters and subtracting the torque due to inertia results in a slightly modified equation of the model:

$$\tau_S(t_i) - J_T * \ddot{\theta}(t_i) = \tau_{off}(t_i) + K_H * \theta(t_i) + B_H * \dot{\theta}(t_i)$$

The torque data set with out the contribution of inertia is now fit as follows: The data is fit using a linear least squares fit pseudo-inverse similar to above, but this is performed multiple times, once for each window as follows:

$$T_{si} - \tilde{J}_T * \ddot{\Theta}_i = \begin{vmatrix} \tau_s(t_{i-250}) - \tilde{J}_T * \ddot{\theta}(t_{i-250}) \\ \vdots \\ \tau_s(t_i) - \tilde{J}_T * \ddot{\theta}(t_i) \\ \vdots \\ \tau_s(t_{i+250}) - \tilde{J}_T * \ddot{\theta}(t_{i+250}) \end{vmatrix}_{501 \times 1} \text{ and}$$

$$\Psi_i = \begin{vmatrix} 1 & \theta(t_{i-250}) & \dot{\theta}(t_{i-250}) \\ \vdots & \vdots & \vdots \\ 1 & \theta(t_i) & \dot{\theta}(t_i) \\ \vdots & \vdots & \vdots \\ 1 & \theta(t_{i+250}) & \dot{\theta}(t_{i+250}) \end{vmatrix}_{501 \times 3}$$

where i goes form 251 to 8064 that cover two periods of the random trajectory or 15.63 seconds). For each i, the matrices $$\left[T_{si} - \tilde{J}_T * \ddot{\Theta}_i\right]$$

and $\emptyset_i$ are obtained and $P_i$ is computed for each i as follows:

$$\tilde{N}_i = \begin{vmatrix} \hat{\tau}_{OFF}(t_i) \\ \hat{K}_H(t_i) \\ \hat{B}_H(t_i) \end{vmatrix}_{3 \times 1}$$

where $P_i$ is calculated similar to P above as follows:

$$\tilde{N}_i = pinv(\emptyset_i) * \hat{O}_{S_i} = (\emptyset_i^T * \emptyset_i)^{-1} * \emptyset_i^T * \hat{O}_{S_i}$$

Figures 41D, 41E, 41F:
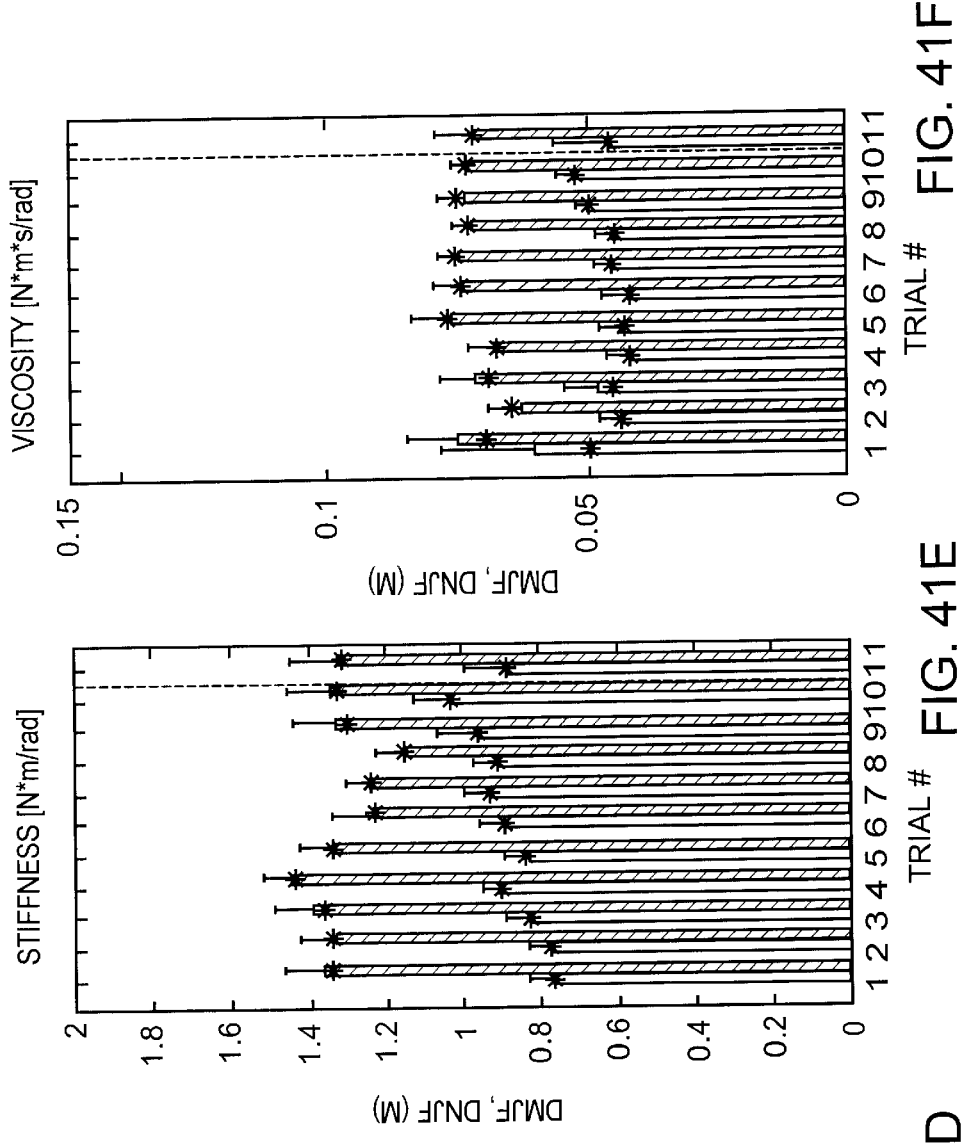
FIG. 41 shows the results for control adult subject JF. JF's right arm was tested at a bias of both 0 degrees and 30 degrees flexion at each of the ten filtered, random trajectories.
Figures 42G, 42H, 42I:
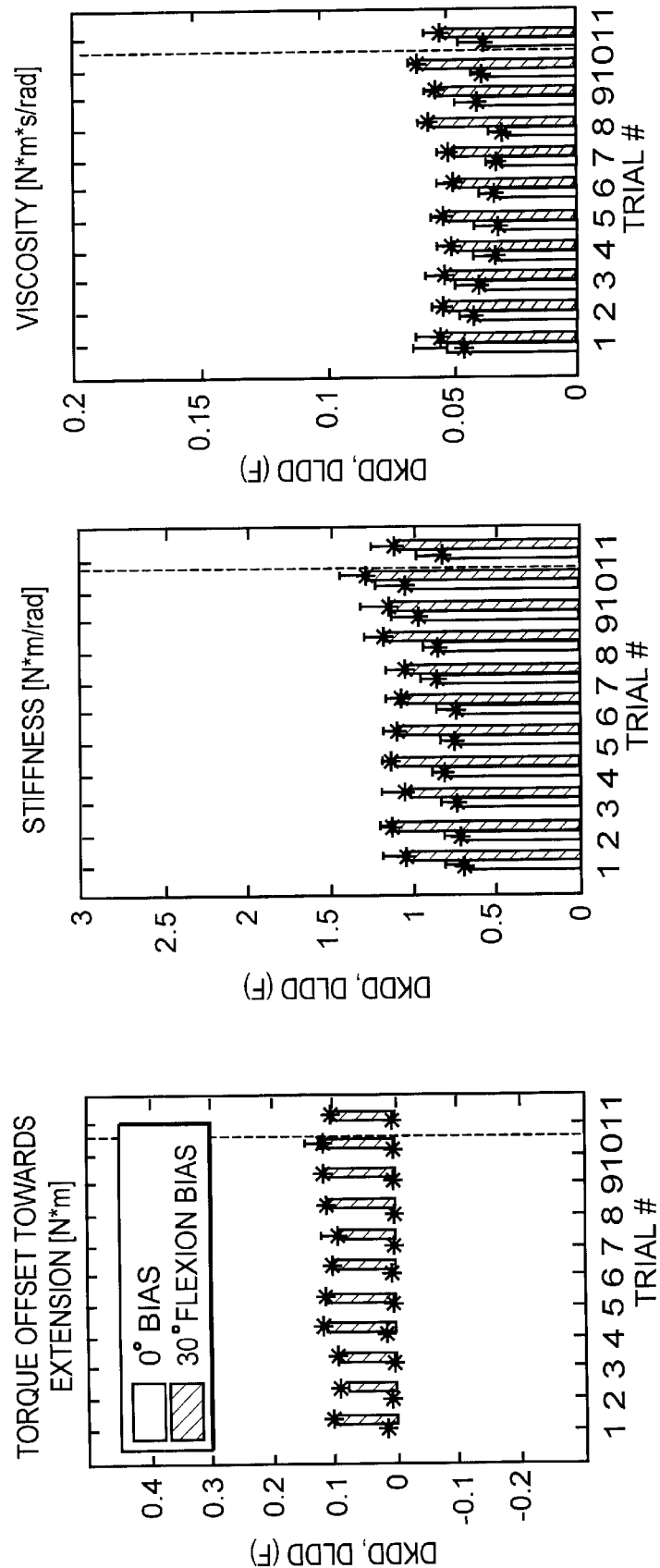
FIG. 42 shows results for control adult subjects PW, JM, and DD. One arm was tested at a bias of both 0 degrees and 30 degrees flexion at each of the ten filtered, random trajectories.
Figures 43D, 43E, 43F:
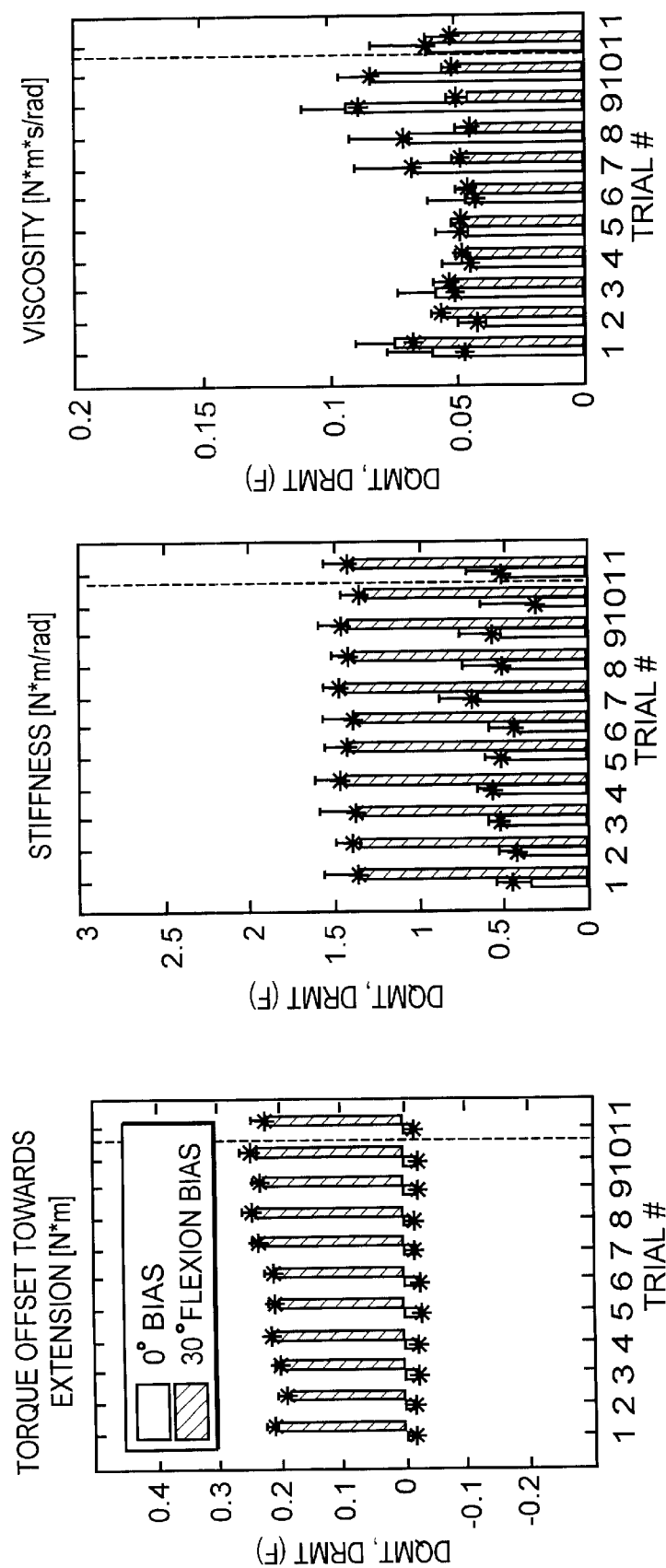
FIG. 43 shows results for control adult subjects JF, MT, and RP. One arm was tested at a bias of both 0 degrees and 30 degrees flexion at each of the ten filtered, random trajectories.
Figures 43G, 43H, 43I:
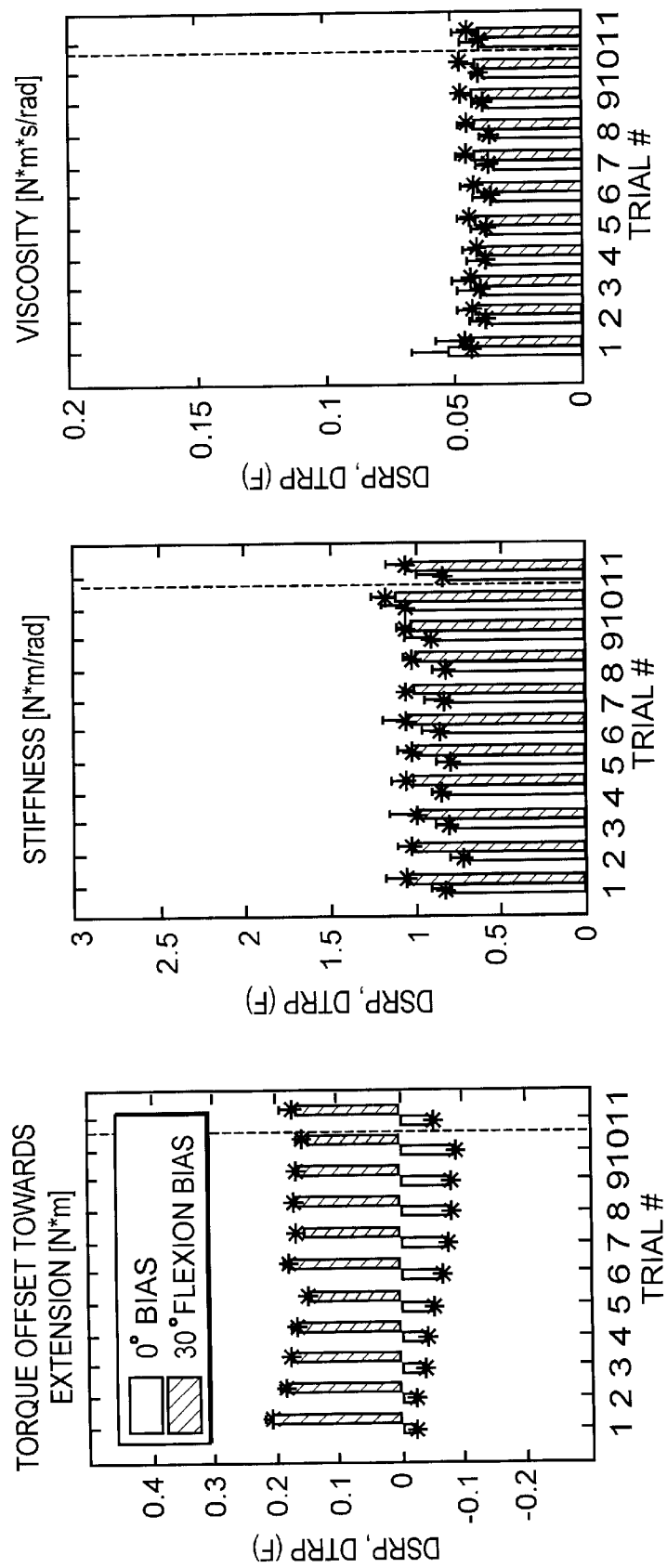
Figure 44A:
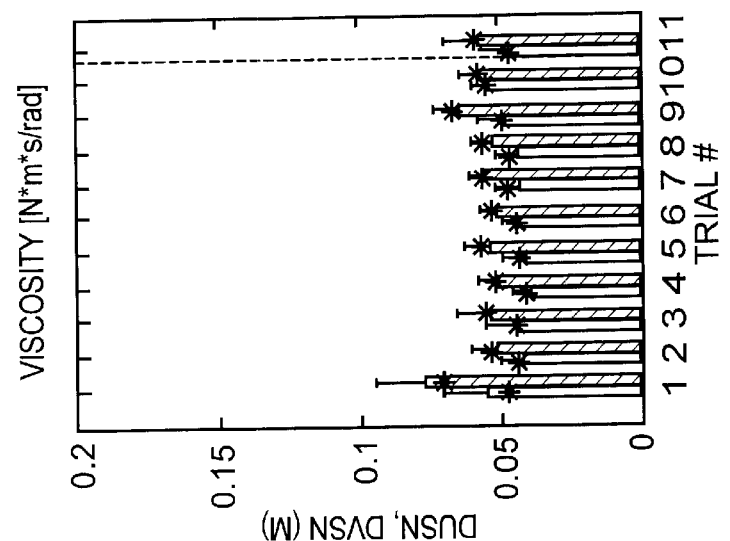
FIG. 44 shows results for control adult subjects SN, JC, and SB. One arm was tested at a bias of both 0 degrees and 30 degrees flexion at each of the ten filtered, random trajectories.
Figure 44B:
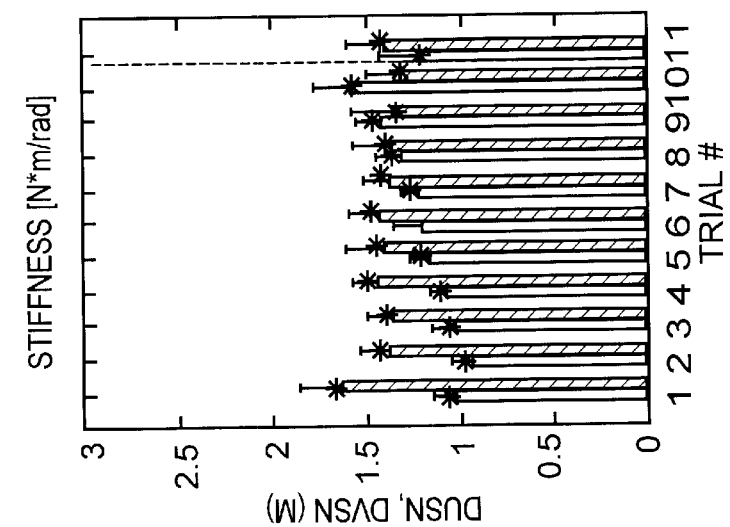
Figure 44C:
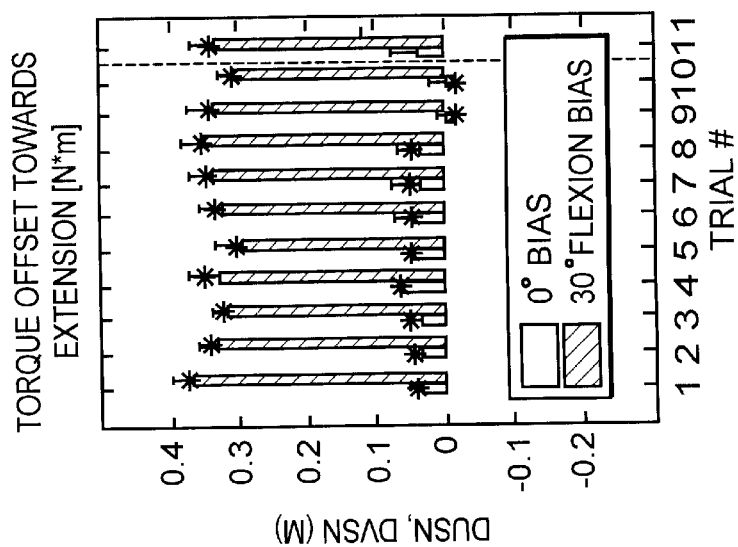
Figures 44D, 44E, 44F:
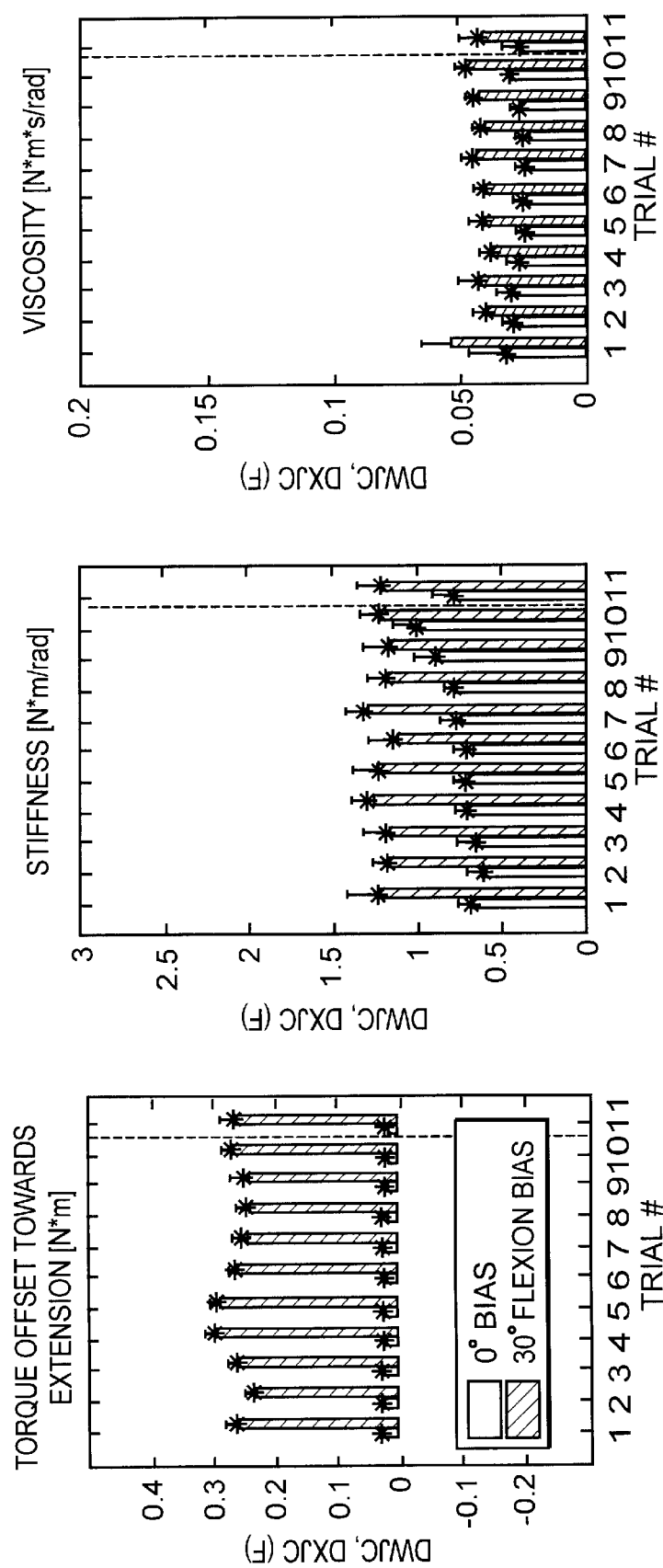
Figures 44G, 44H, 44I:
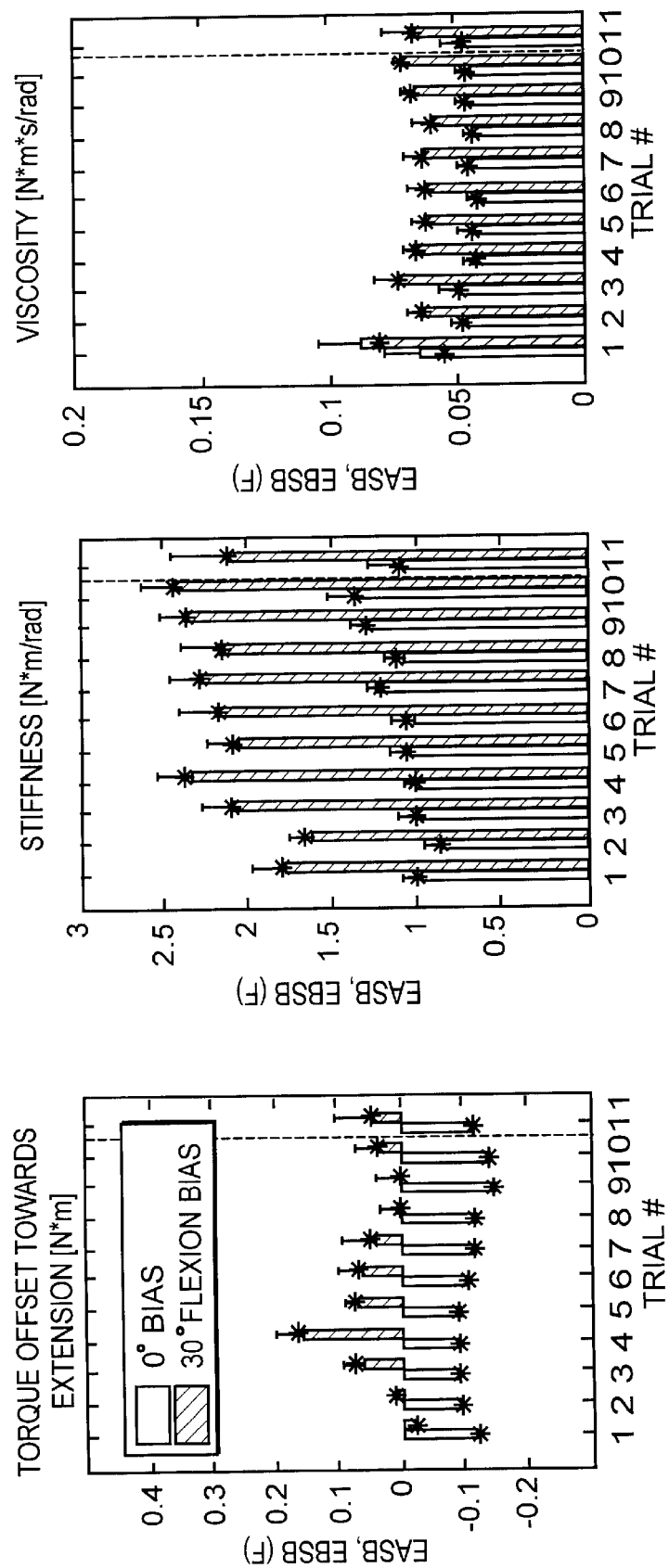
Figure 45C:
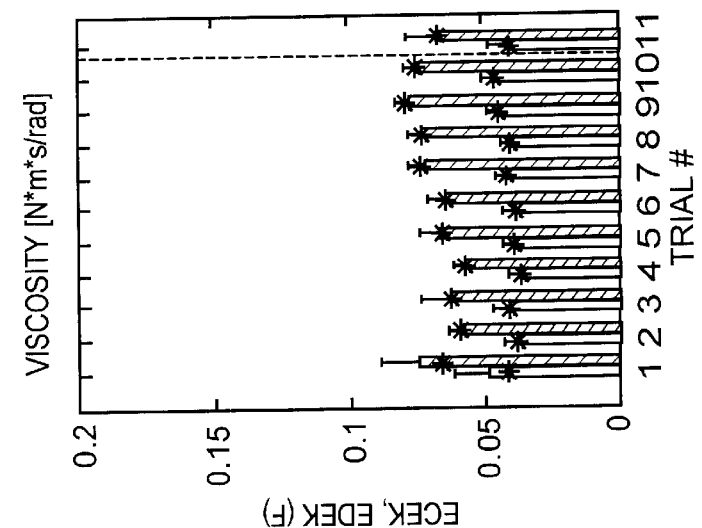
FIG. 45 shows results for control adult subjects EK, SW, and JH. One arm was tested at a bias of both 0 degrees and 30 degrees flexion at each of the ten filtered, random trajectories.
Figure 45B:
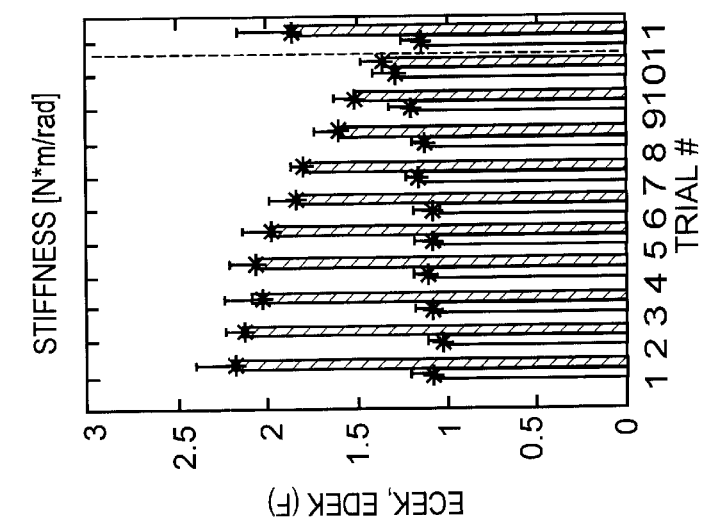
Figure 45A:
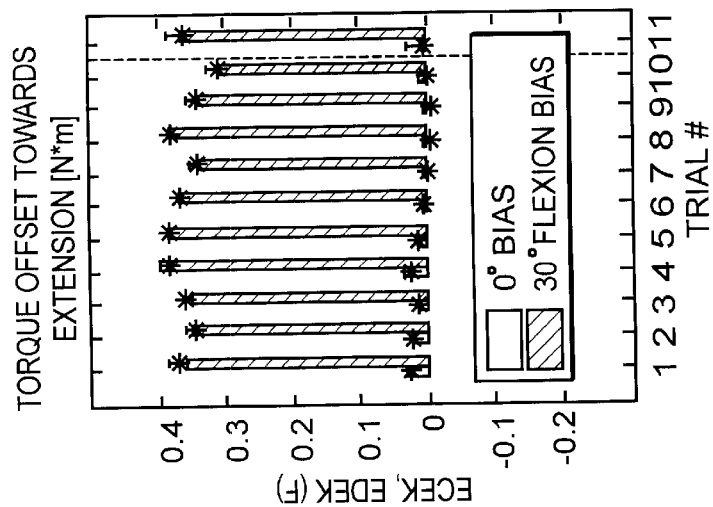
Figures 45D, 45E, 45F:
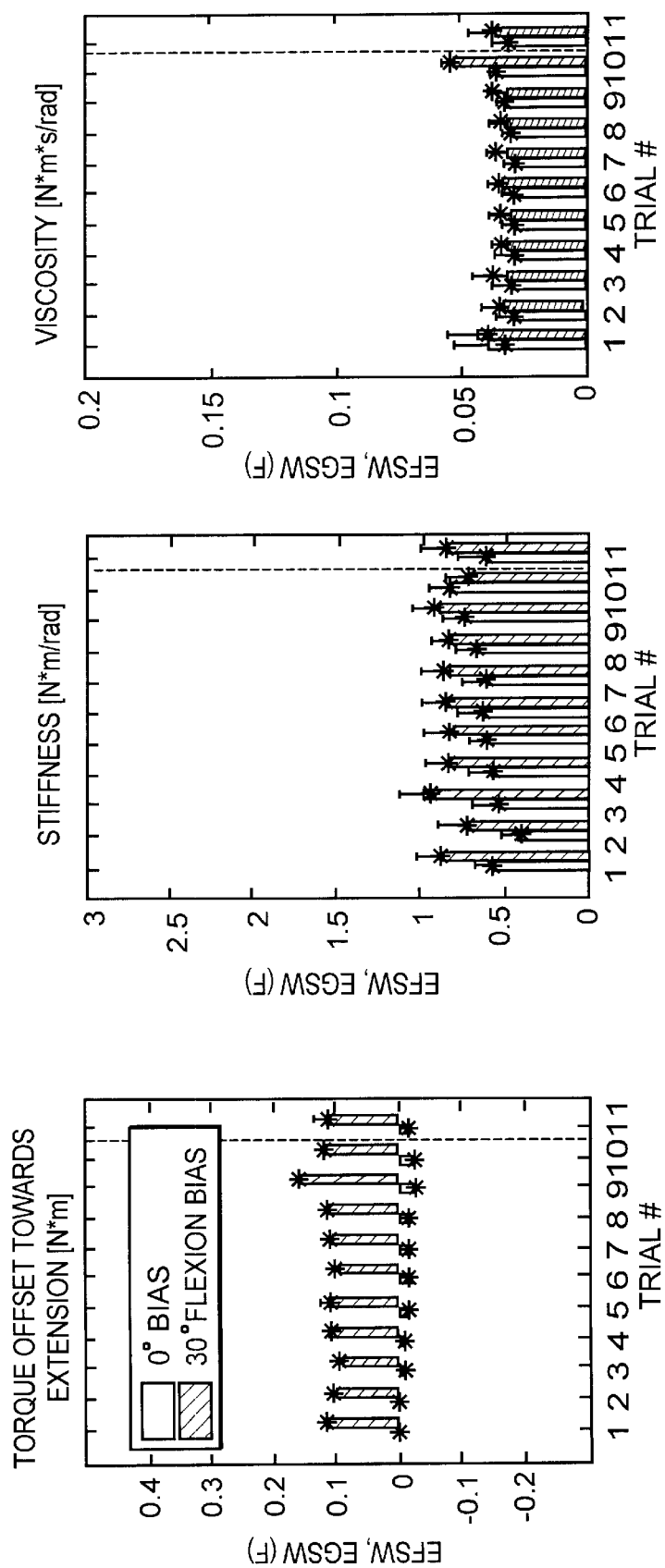
Figures 45G, 45H, 45I:
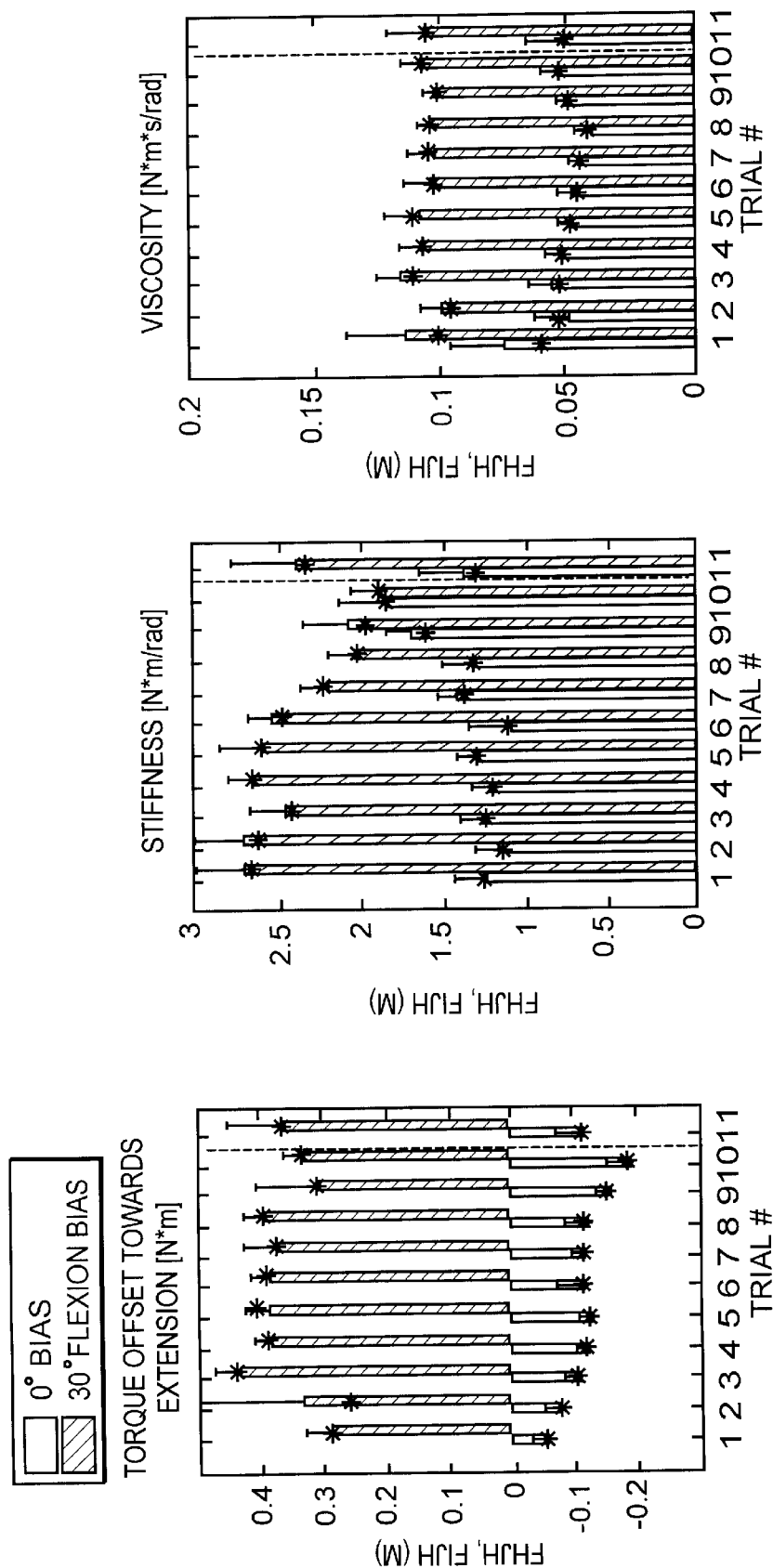
Figures 46A, 46B, 46C:
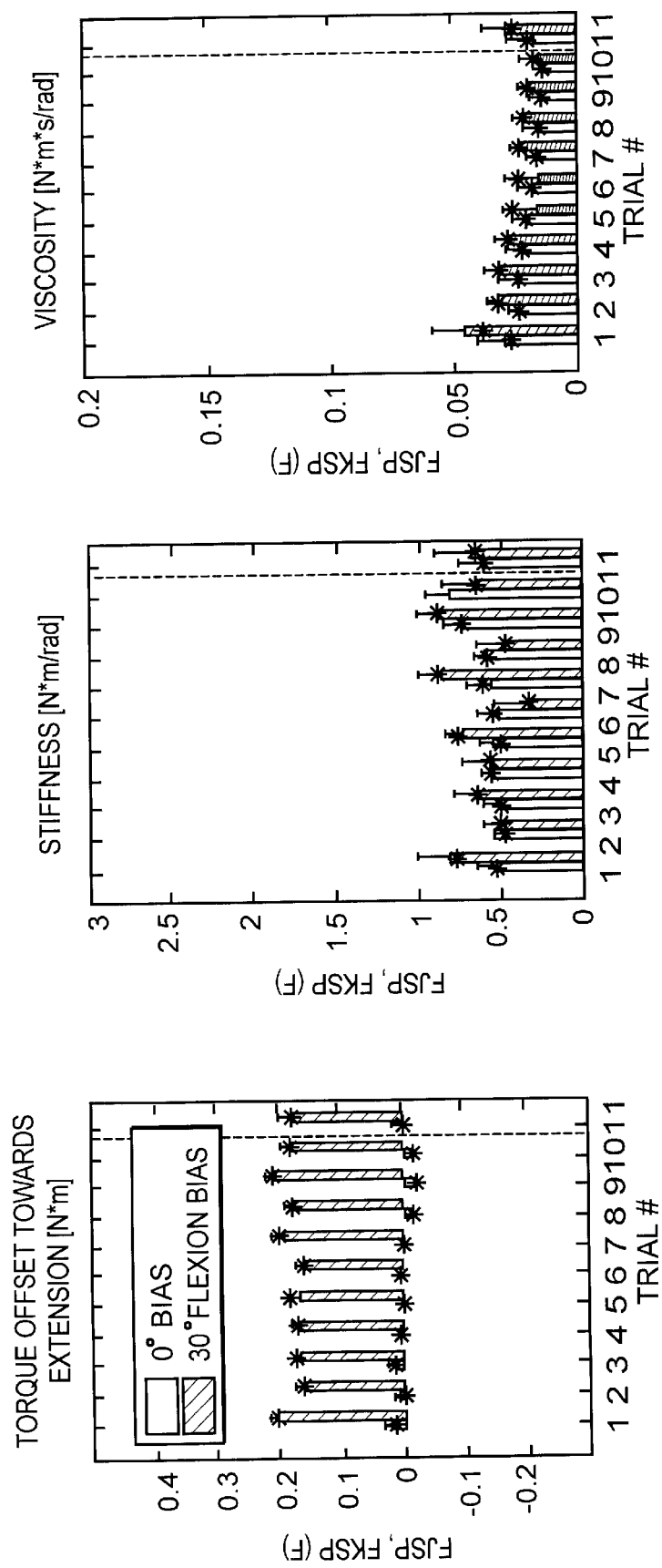
FIG. 46 shows results for control adult subjects SP, VG, and NM. One arm was tested at a bias of both 0 degrees and 30 degrees flexion at each of the ten filtered, random trajectories.
Figure 46F:
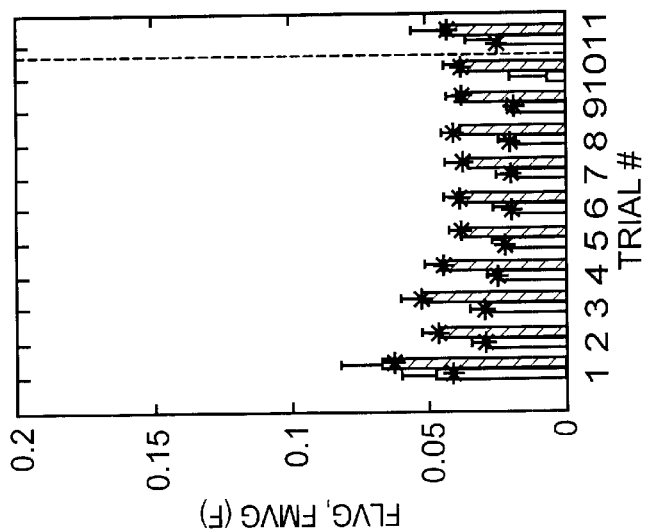
Figure 46E:
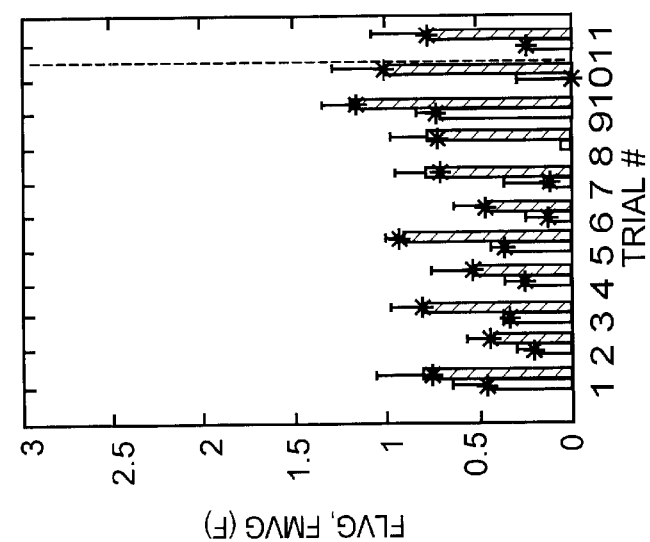
Figure 46D:
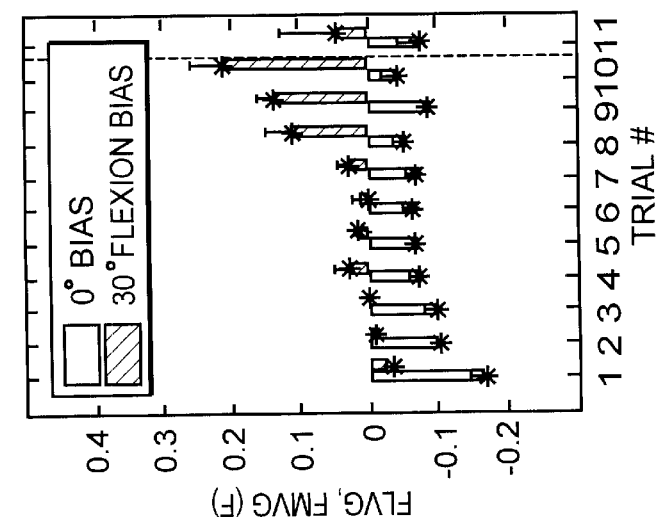
Figure 46I:
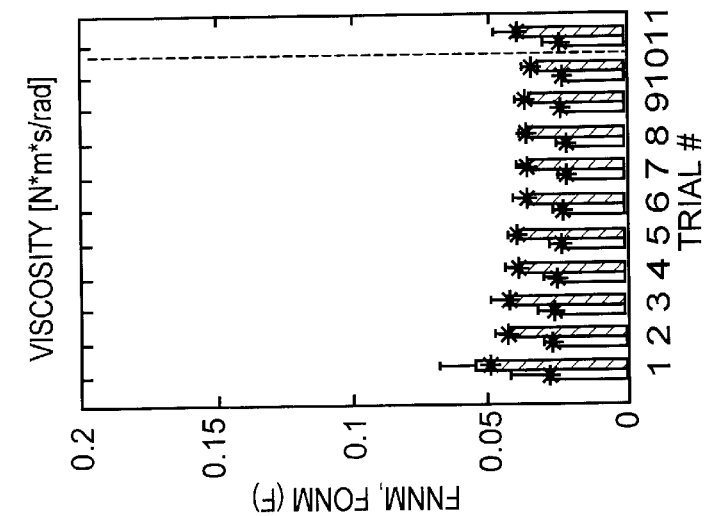
Figure 46H:
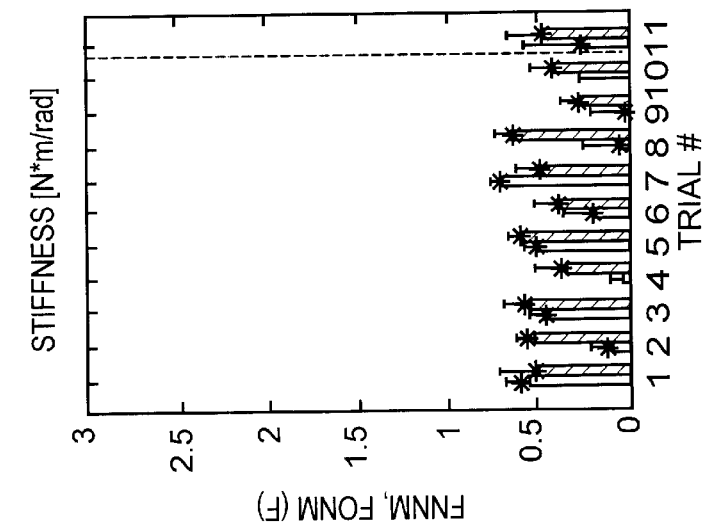
Figure 46G:
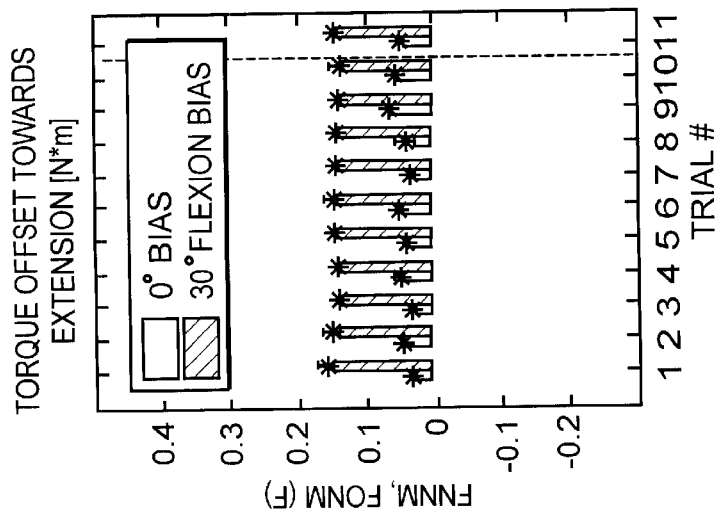
Figure 47C:
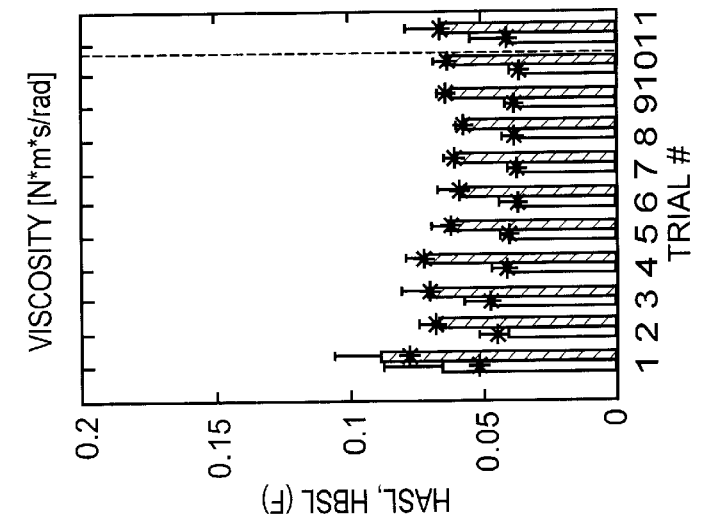
FIG. 47 shows results for control adult subjects SL, SR, and HH. One arm was tested at a bias of both 0 degrees and 30 degrees flexion at each of the ten filtered, random trajectories.
Figure 47B:
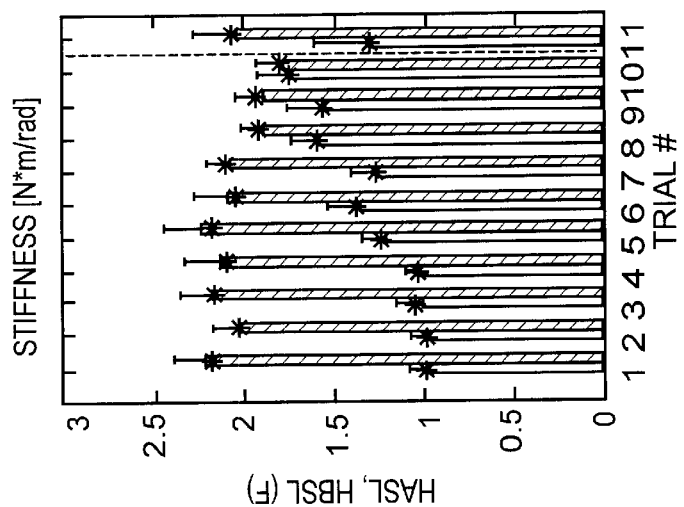
Figure 47A:
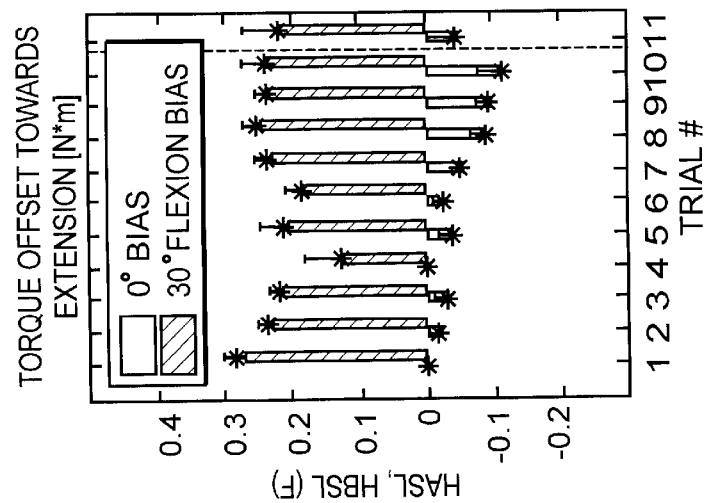
Figure 47F:
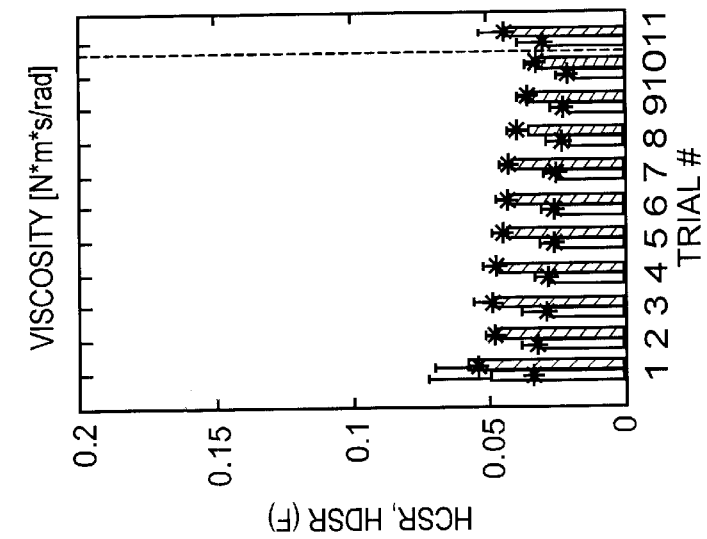
Figure 47E:
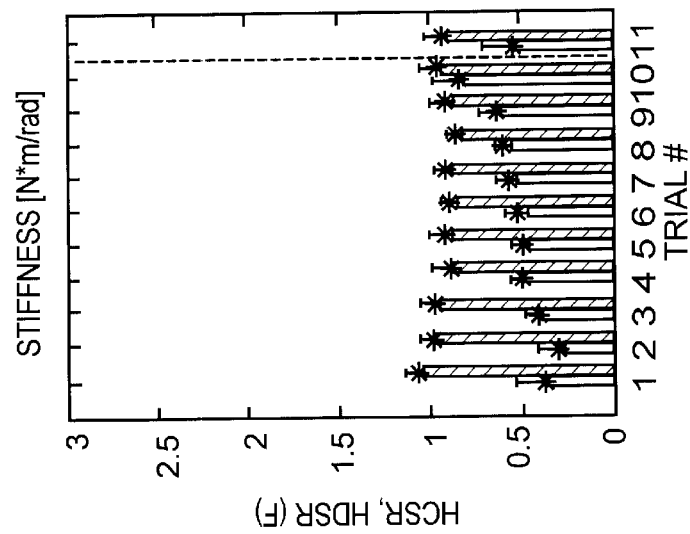
Figure 47D:
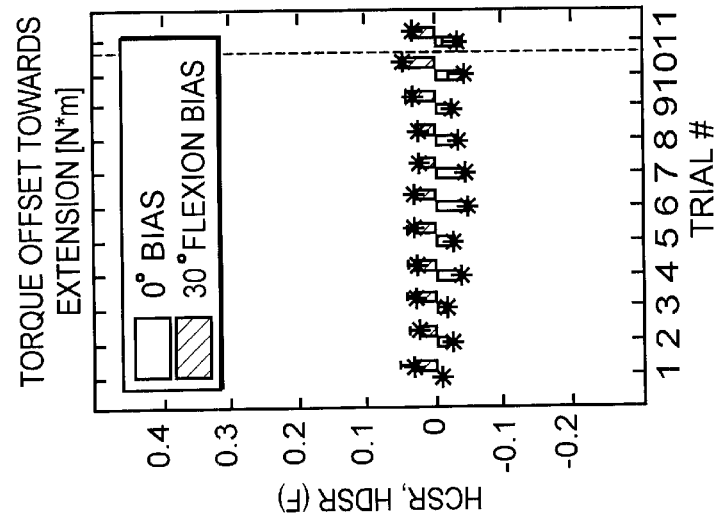
Figure 47I:
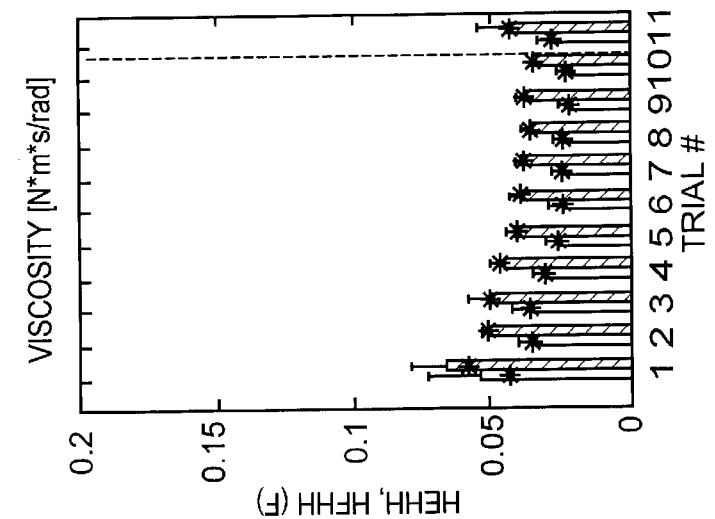
Figure 47H:
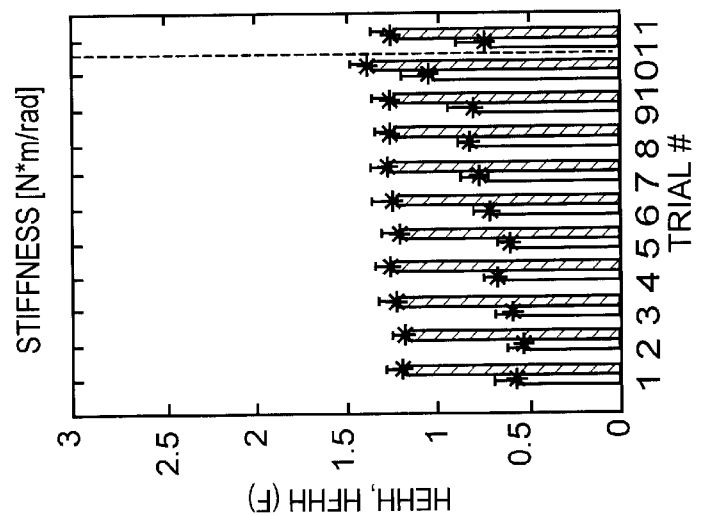
Figure 47G:
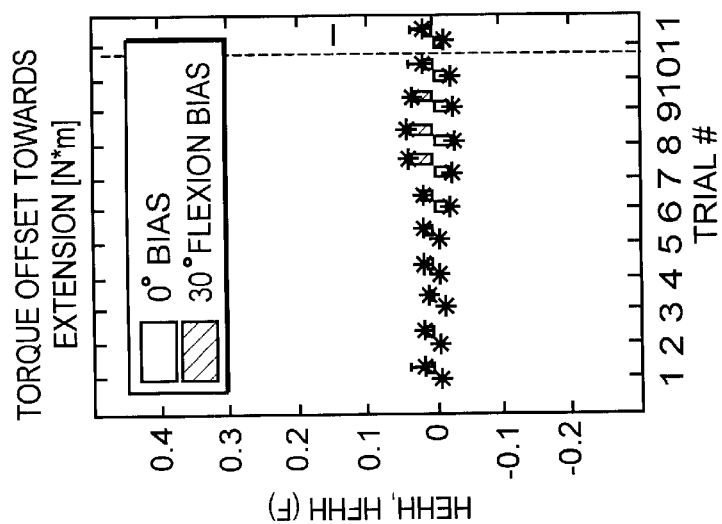
Figure 48C:
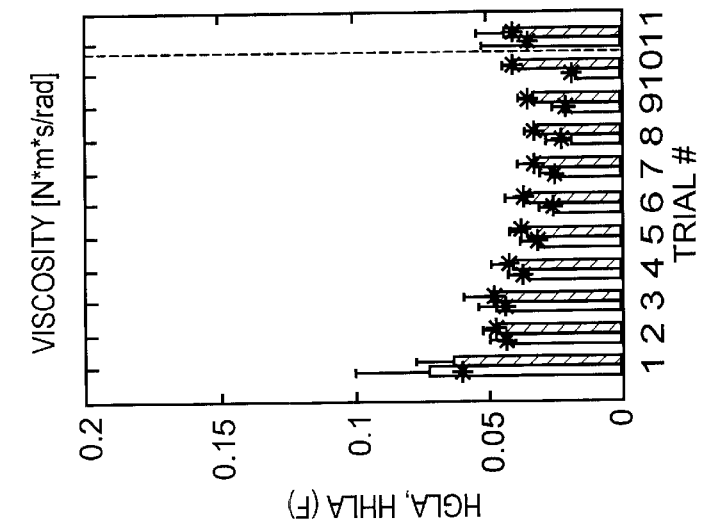
FIG. 48 shows results for control adult subjects LA, CS, and SD. One arm was tested at a bias of both 0 degrees and 30 degrees flexion at each of the ten filtered, random trajectories.
Figure 48B:
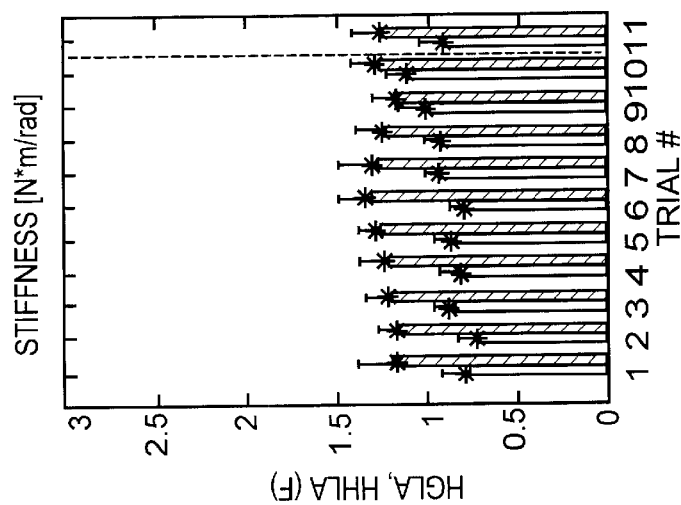
Figure 48A:
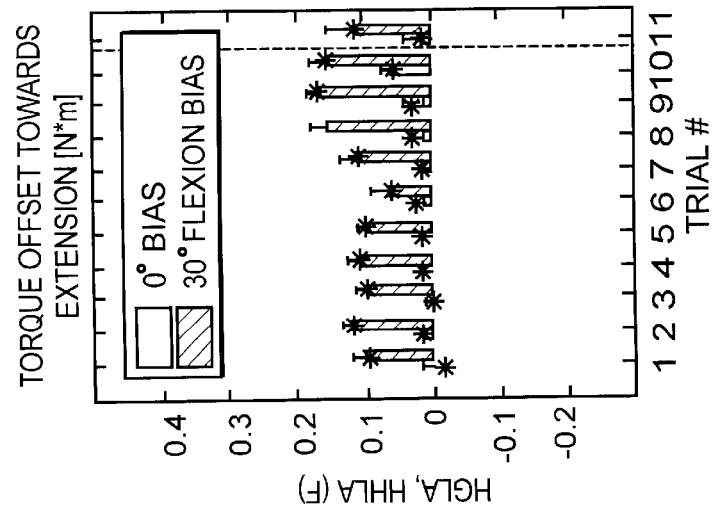
Figure 48F:
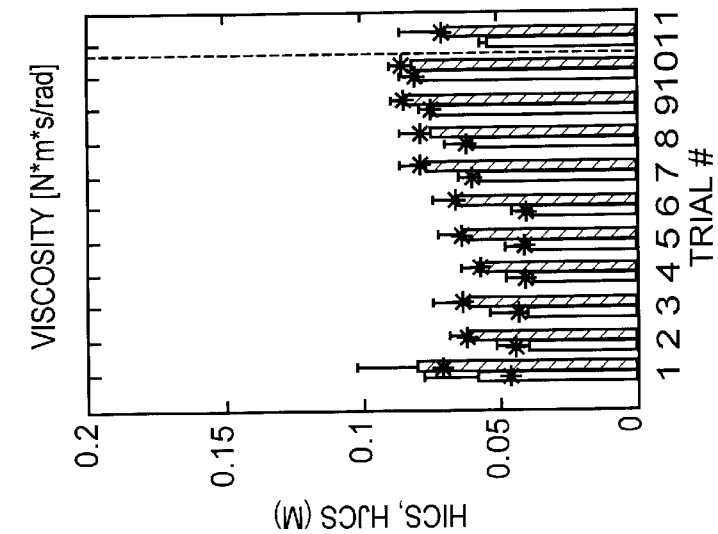
Figure 48E:
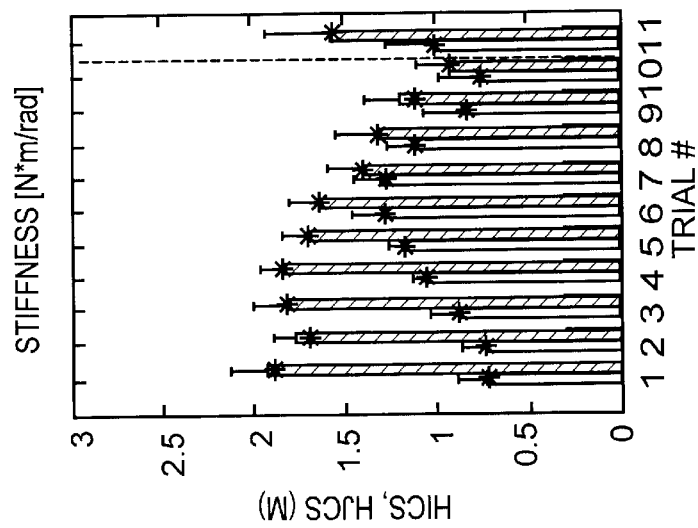
Figure 48D:
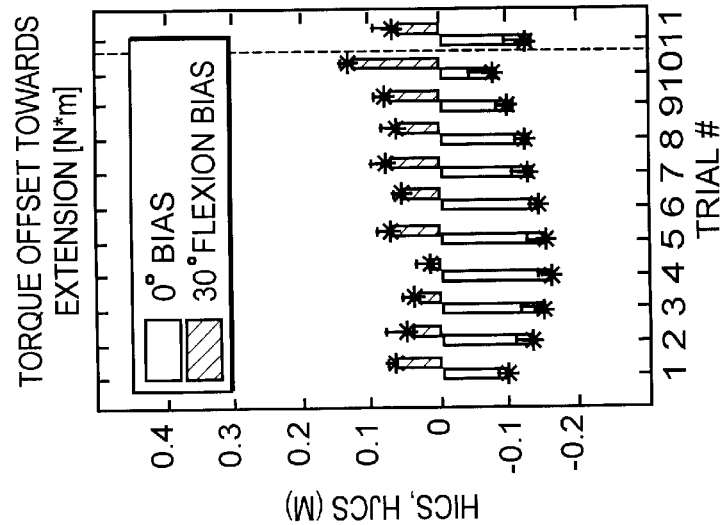
Figure 48I:
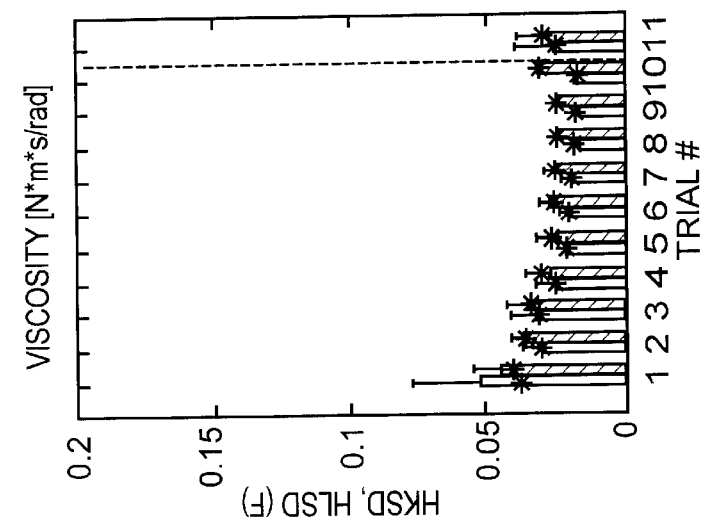
Figure 48H:
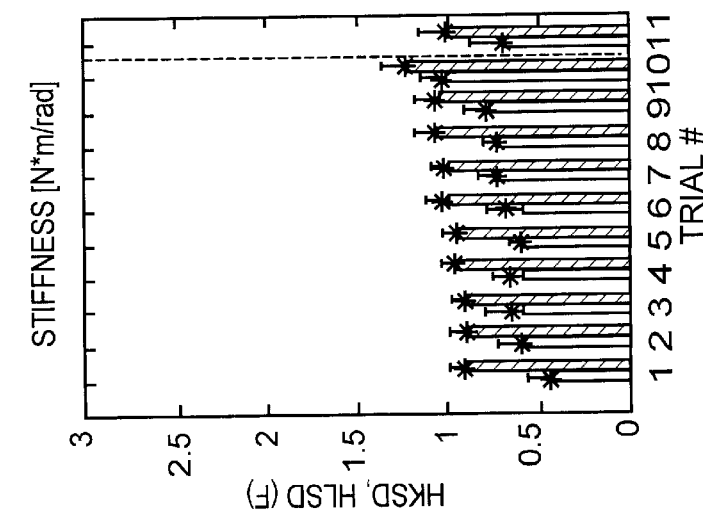
Figure 48G:
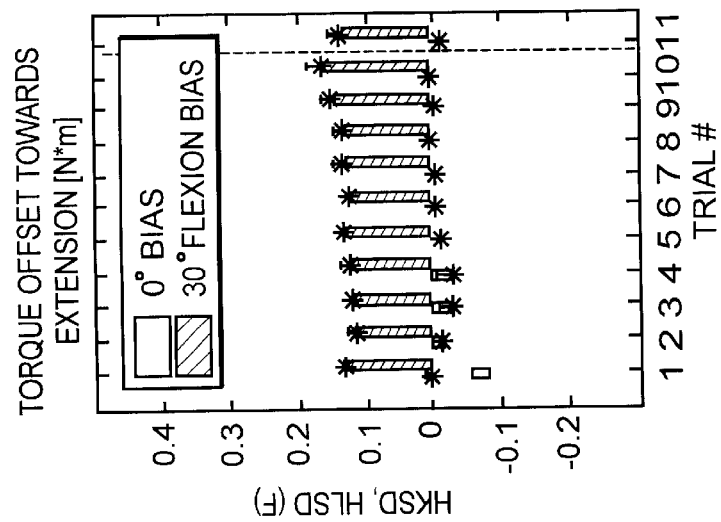
Figures 49A, 49B, 49C:
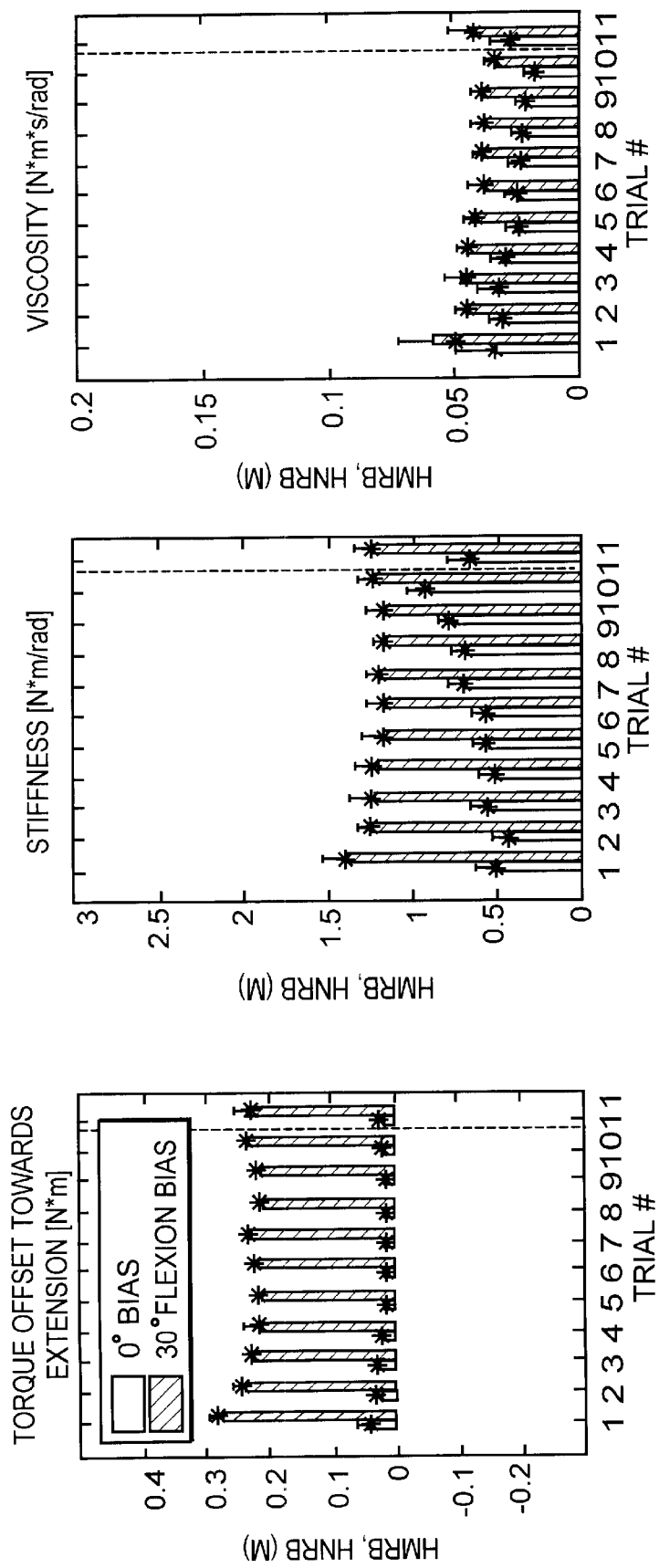
FIG. 49 shows results for control adult subjects RB, LA, and HC. One arm was tested at a bias of both 0 degrees and 30 degrees flexion at each of the ten filtered, random trajectories.
Figure 49F:
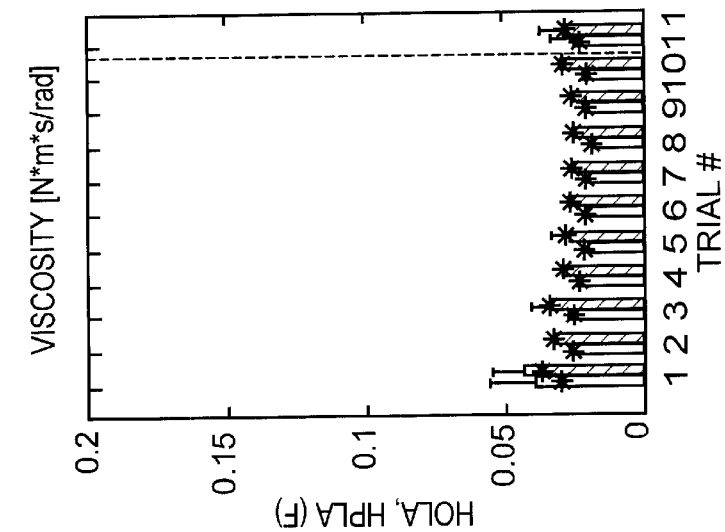
Figure 49E:
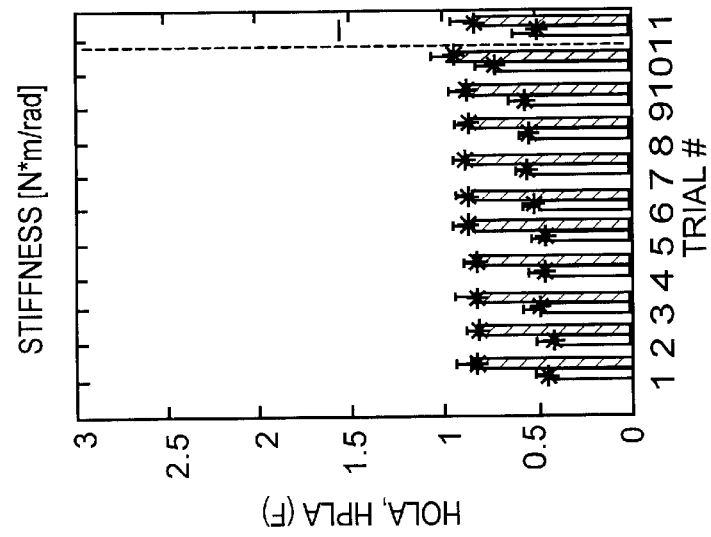
Figure 49D:
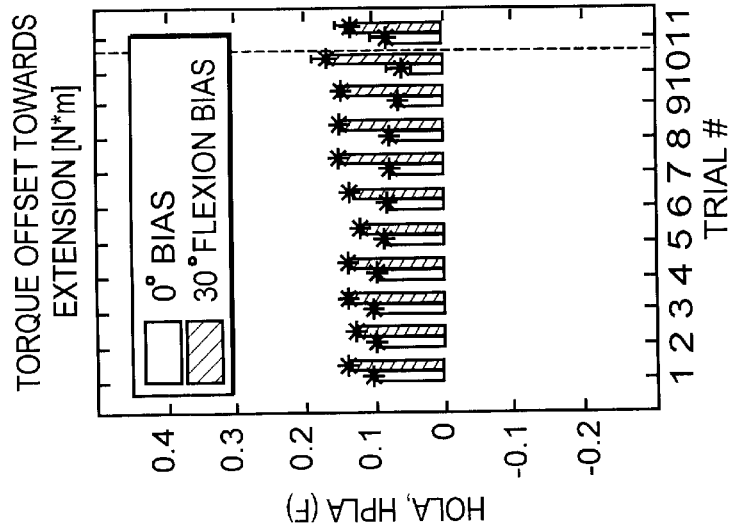
Figure 49I:
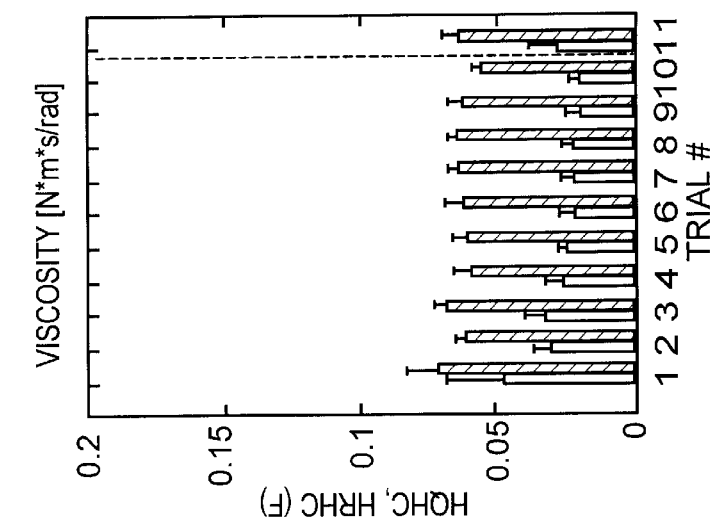
Figure 49H:
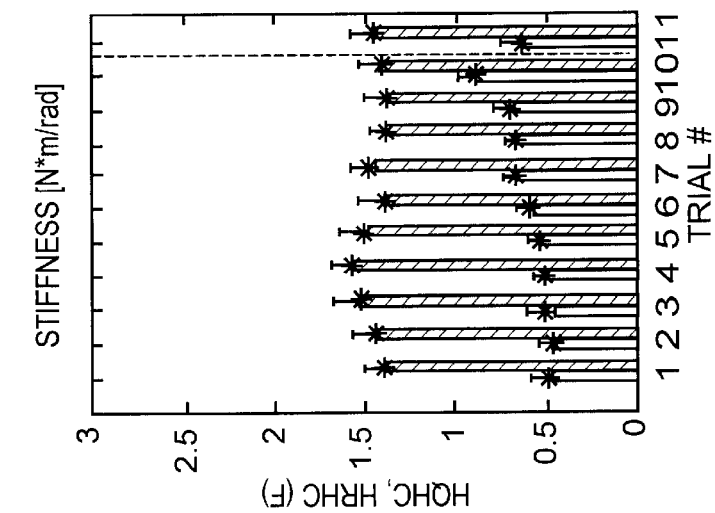
Figure 49G:
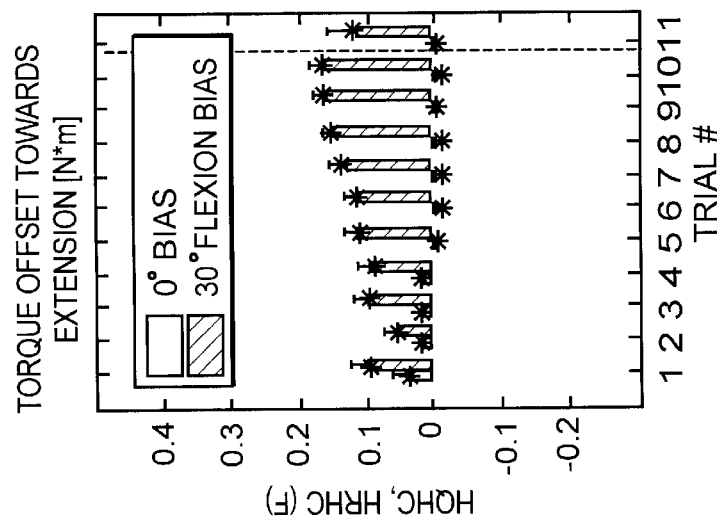
Figure 50C:
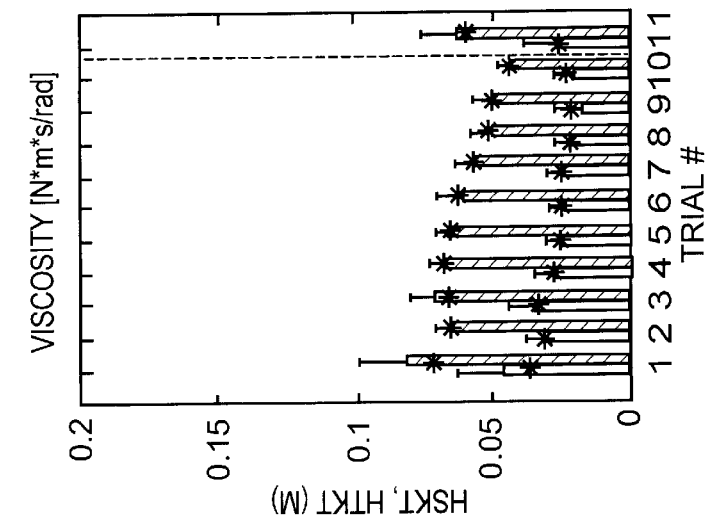
FIG. 50 shows results for control adult subjects KT, WZ, and MH. One arm was tested at a bias of both 0 degrees and 30 degrees flexion at each of the ten filtered, random trajectories.
Figure 50B:
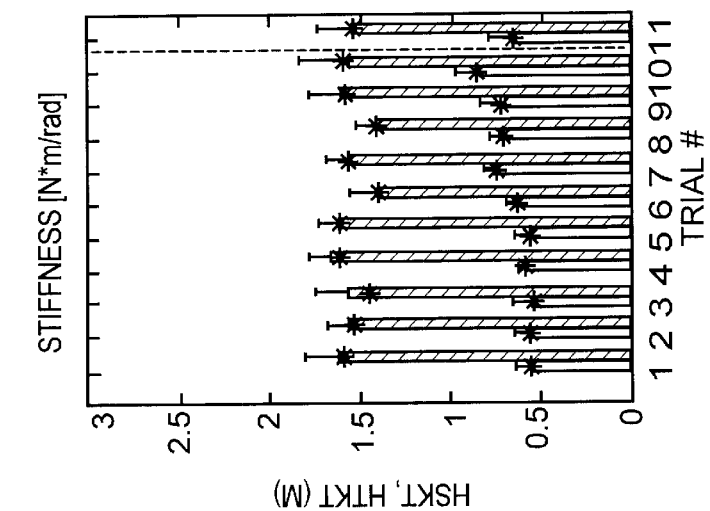
Figure 50A:
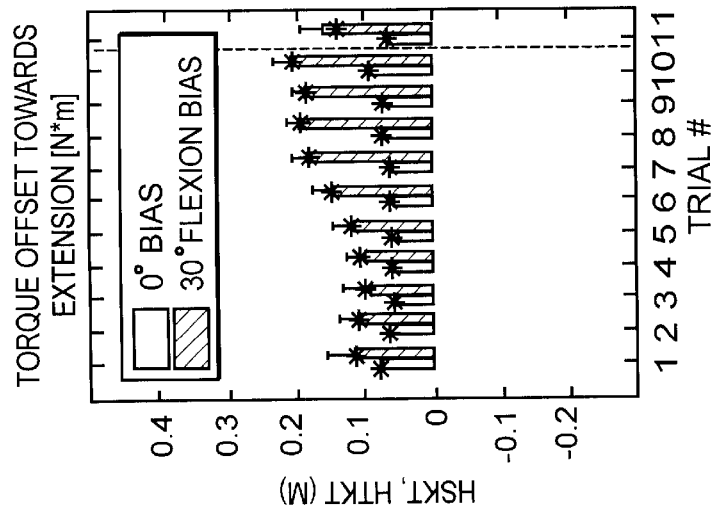
Figure 50I:
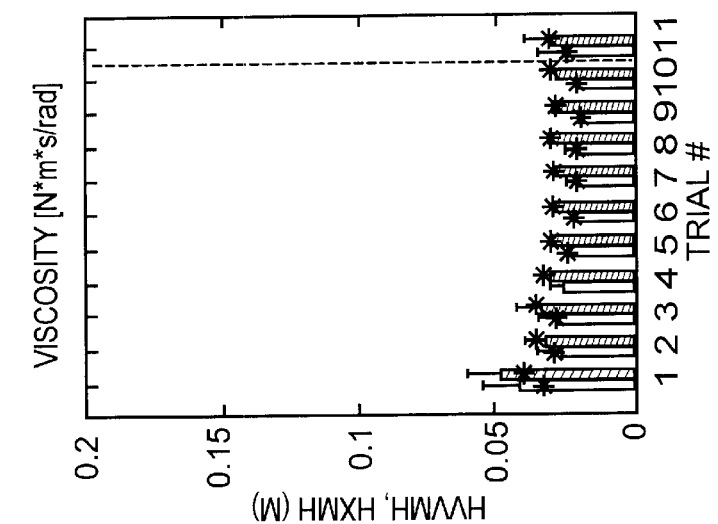
Figure 50H:
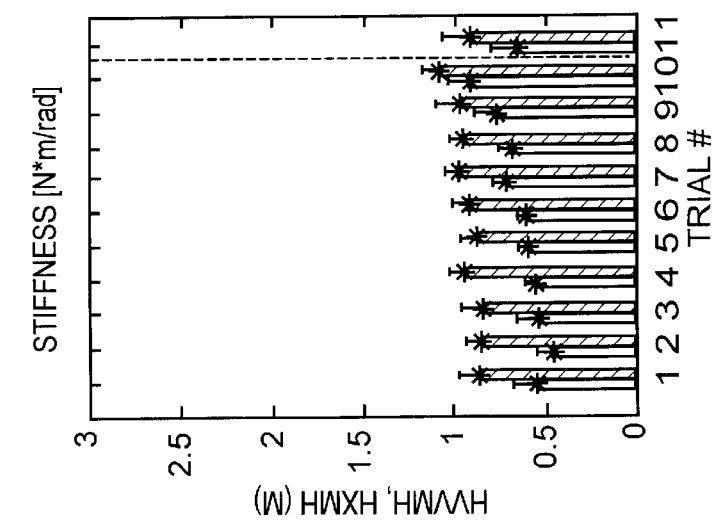
Figure 50G:
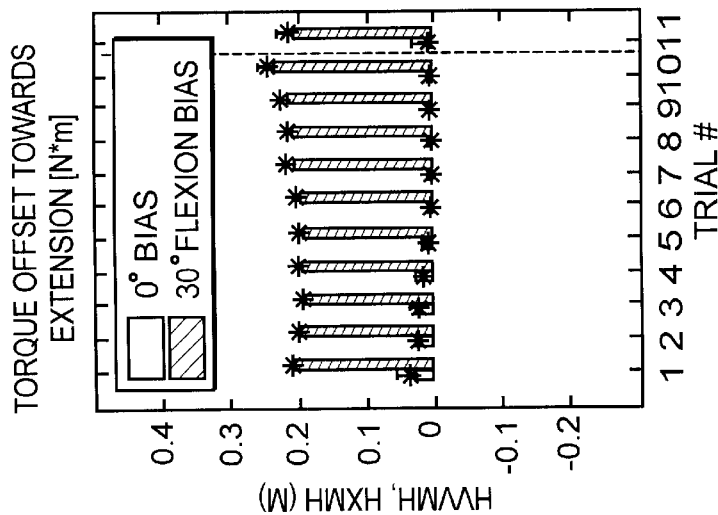
Figures 51D, 51E, 51F:
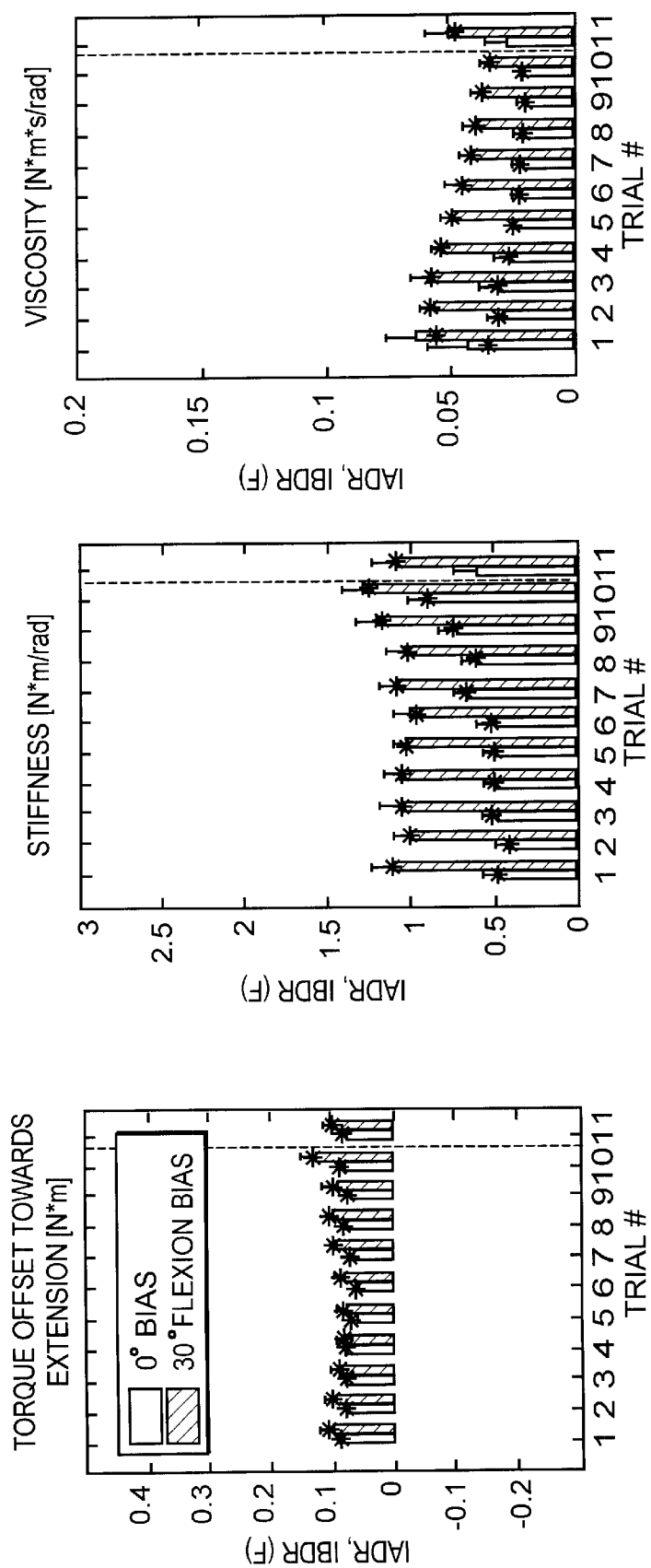
FIG. 51 shows results for control adult subjects LH, DR, and RW. One arm was tested at a bias of both 0 degrees and 30 degrees flexion at each of the ten filtered, random trajectories.
Figure 51I:
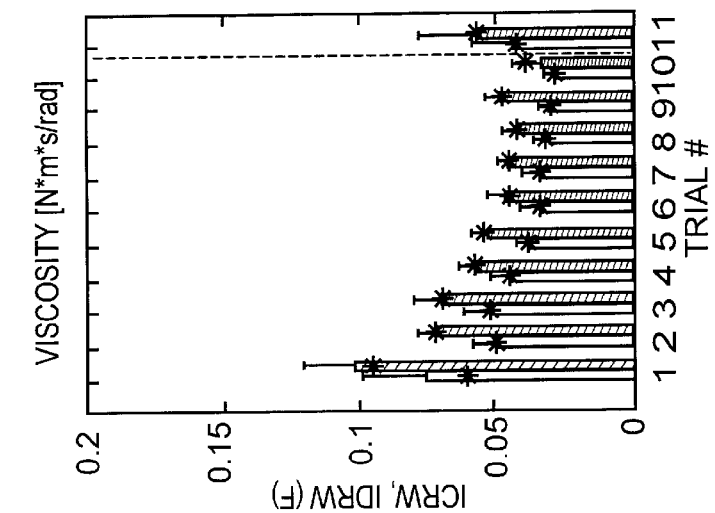
Figure 51H:
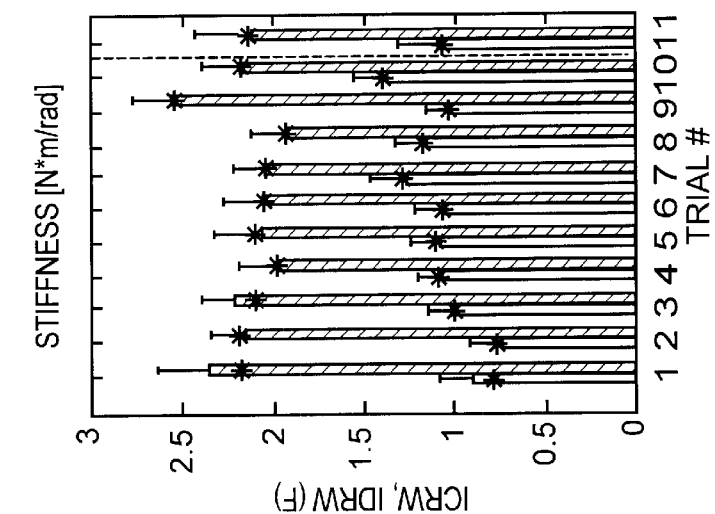
Figure 51G:
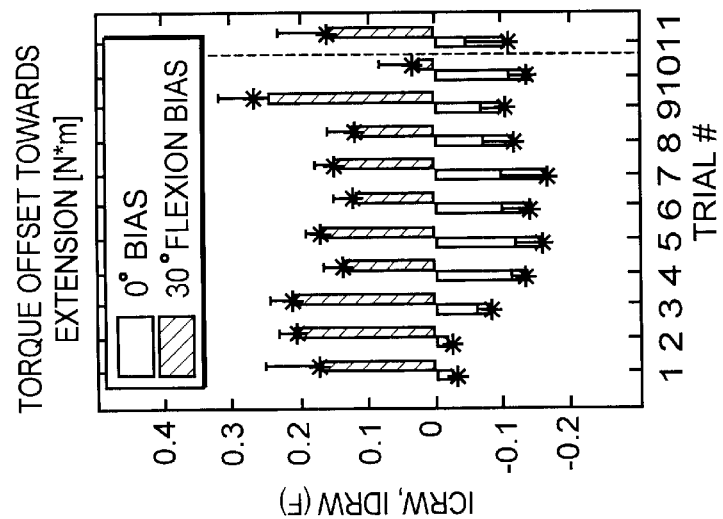
Figures 52A, 52B, 52C:
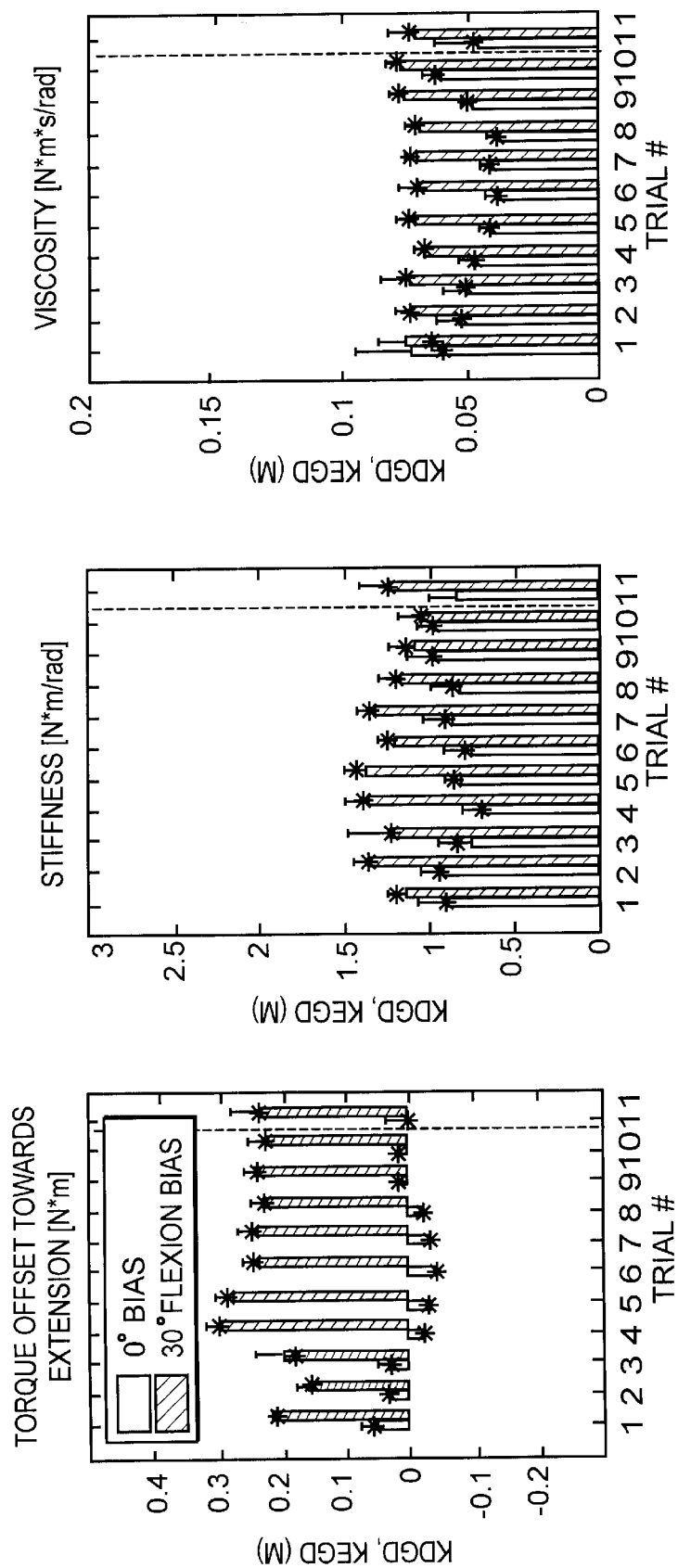
FIG. 52 shows results for control adult subject GD. One arm was tested at a bias of both 0 degrees and 30 degrees flexion at each of the ten filtered, random trajectories.

Since I goes from 251 to 8064, there are 7813 $\hat{\tau}_{off}$, $\hat{K}_H$, and $\hat{B}_H$ values per trial. The mean and variance or standard deviation of these values for each trial is determined. If the standard deviation of these values: std$\{\hat{\tau}_{off}(t_i)\}$, std$\{\hat{K}_H(t_i)\}$, and std$\{\hat{B}_H(t_i)\}$ are small, this indicates that the stiffness and viscosity of the subject's flexors and extensors remain fairy constant within each trial and the torque residuals of the time invariant model would be small as shown in FIG. 40. Note also that the mean of the time-variant impedance parameters values (denoted with the x̂) should be very close to the evaluated time-invariant parameters (denoted with the x̃), that is:

mean$\{\hat{\tau}_{off}(t_i)\} \approx \tilde{\tau}_{off}$;

mean$\{\hat{K}_H(t_i)\} \approx \tilde{K}_H$; and mean$\{\hat{B}_H(t_i)\} \approx \tilde{B}_H$;

This is shown in FIG. 41.

The first row of bar plots in FIG. 41 show the results for the torque offset, stifffiess, and viscosity parameters obtained for each of the ten trials in experiment DMJF. The asterisk '*' plots the values of $\tilde{\tau}_{off}$, $\tilde{K}_H$, and $\tilde{B}_H$ where one set of best-fit parameters over the whole trial as described above. The location of the tip of each bar graph represents mean$\{\hat{\tau}_{off}(t_i)\}$, mean$\{\hat{K}_H(t_i)\}$, and mean$\{\hat{B}_H(t_i)\}$ where a set of $\tau_{\textit{off}}$, $\hat{K}_H$, and $\hat{B}_H$ is obtained for each moving window of 501 data samples as described above. The height of the error bar indicates the standard deviation of these values, std$\{\tau_{\textit{off}}(t_i)\}$ std$\{\hat{K}_H(t_i)\}$, and std$\{\hat{B}_H(t_i)\}$.

The eleventh bar shows a summary of all ten trials. The asterisk on the eleventh bar shows the average of the ten $\tau_{\textit{off}}$, $\tilde{K}_H$, or $\tilde{B}_H$ values, or in equation form:

$$\frac{1}{10}\sum_{k=1}^{10}(\tilde{\tau}_{\textit{off}} \text{ for trial } k), \frac{1}{10}\sum_{k=1}^{10}(\tilde{K}_H \text{ for trial } k), \text{ and}$$

$$\frac{1}{10}\sum_{k=1}^{10}(\tilde{B}_H \text{ for trial } k)$$

The location of the tip of the eleventh bar is the average of the height of the ten bar graphs, or in equation form:

$$\frac{1}{10}\sum_{k=1}^{10}(mean\{\hat{\tau}_{\textit{off}}\} \text{ for trial } k), \frac{1}{10}\sum_{k=1}^{10}(mean\{\tilde{K}_H\} \text{ for trial } k),$$

$$\text{and } \frac{1}{10}\sum_{k=1}^{10}(mean\{\hat{B}_H\} \text{ for trial } k)$$

As mentioned earlier, there are 7813 $\hat{\tau}_{\textit{off}}$, $\hat{K}_H$, and $\hat{B}_H$ values per trial. If all ten trials are grouped together, then there are 78130 $\hat{\tau}_{\textit{off}}$, $\hat{K}_H$, and $\hat{B}_H$ values. The height of the error bar of the eleventh bar plot is the standard deviation of all 78130 values.

Experiment DMJF was performed on the right arm of a control adult subject tested at a bias of 0 degrees. Each control subject was also tested at a bias position of degrees flexion. The bottom row of graphs in FIG. 41 shows the results of parameters for two sets of experiments, DMJF, and DNJF, as labeled on the left of the graphs. The 'M' in the parentheses, indicates that the subject JF is a male. The bar graphs for experiment DMJF are plotted in white (bias of 0 degrees) and bar graphs for experiment DNJF are plotted in grey (bias of 30 degrees flexion) as indicated by the legend.

The results of subject JF show that the stiffness values when tested at a bias of 30 degrees are markedly higher than when tested at a bias of 0 degrees in all ten trials. The average $\tilde{K}_H$ across all ten trials are 0.876 N*m/rad and 1.30 N*m/rad at a bias of 0 and 30 degrees respectively. The asterisks on the eleventh bars show these values. Thus, the cumulative stiffness of all the muscles acting on the wrist joint is 48% higher at a bias of 30 degrees flexion.

Similarly, the viscosity values are markedly higher when tested at a bias of 30 degrees flexion than at a bias of 0 degrees for all ten trials. The average $\tilde{C}_H$ across all ten trials are 0.0460 N*m*s/rad and 0.0714 N*m*s/rad at a bias of 0 and 30 degrees respectively and the cumulative stiffness of all the muscles acting on the wrist joint is 55% higher at a bias of 30 degrees flexion.

The resulting torque offsets, $\tau_{\textit{off}}$ tell us something very interesting. The first noticeable thing about these values is not only that they are different in magnitude but also opposite in sign. $\tau_{\textit{off}}$ is an important variable that tells us the angular position the hand prefers to be relative to the selected bias position or origin, $\theta_0$. If the bias position was chosen to be the resting position of the wrist joint, then in the equation below $\theta_{RP}=0$, $$\tau_{\textit{off}}=-K_H*\theta_{RP}$$

and ideally, $\tau_{\textit{off}}$ would be 0 Nm. For a given angular stiffness, the further the bias position is selected from the preferred resting position of the wrist joint, the greater the torque offset, $\tau_{\textit{off}}$ will be. The preferred resting position of the wrist joint is determined by the relative passive stiffness of flexor muscle group to the extensor muscle group. It should also be noted that $\tau_{OFF}$ is also dependent on the stiffness $K_H$. Since the active stiffness of muscles are influenced when they are perturbed, $\tau_{OFF}$ is influenced by these wrist perturbations or oscillations. If, however, the bias position is very close to the resting position of the wristjoint, $\tau_{\textit{off}}$ will be very close to 0 Nm regardless of the magnitude of $K_H$ since $\theta_{RP}\approx 0$. A positive torque offset indicates that this contribution of torque is applied in the clockwise direction by the subject's arm and a negative torque offset indicates that this contribution of toque is applied in the counter clockwise direction. This information is important when interpreting the sign of $\tau$off. The subject JF's right arm was tested in experiments DMJF and DNJF. As shown in the plots in FIG. 41, when tested at a bias of 0 degrees, the torque offset values are very slightly negative. The mean overall torque offset, $\tau_{\textit{off}}$ for all ten trials shown by the asterisk on the eleventh bar is equal to −0.0538 Nm at a bias of 0 degrees, and the contribution of torque by $\tau_{\textit{off}}$ is in the counter clockwise direction. At a bias of 30 degrees flexion, this value is equal to 0.110 Nm and the contribution of torque by $\tau_{\textit{off}}$ in this case is in the clockwise direction. This means that there is less resistance in the wrist flexors at a bias of 0 than of 30 degrees flexion and the resting position of the hand of the control subject is close to the neutral flexion-extension position. The magnitude of these numbers is small as compared to the torque offset values in the spastic population as will be shown. It is important to note that if contra-lateral left arm of the subject was tested instead, then the sign of $\tau_{\textit{off}}$ is expected to switch by virtue of symmetry. Thus, in order to compare the left hand to the right hand, if the left hand of a subject is tested, then the sign of $\tau_{\textit{off}}$ is switched. Hence, the sign of $\tau_{\textit{off}}$ no longer represents clockwise or counterclockwise torque. Rather, a positive torque offset indicates that the contribution of $\tau_{\textit{off}}$ is in the direction towards the extension direction of the hand being tested relative to the selected bias position. Conversely, a negative torque offset indicates that the contribution of $\tau_{\textit{off}}$ is in the direction towards the flexion direction of the hand being tested relative to the selected bias position.

Now, the results of each individual control adult will be shown. Either the left or right hand of 31 control adults was tested, at a bias position of both 0 and 30 degrees flexion. 10 of the subjects were male and 21 were female. The average age of control subjects tested was 31.29, the youngest was 18 years of age and the eldest was 60 years of age. The plots of the results for each individual subject are shown in FIGS. 42–52. All graphs that are plots of results of the same variable are plotted on the same scale so that visual comparisons can be made.

Figures 53A, 53B, 53C:
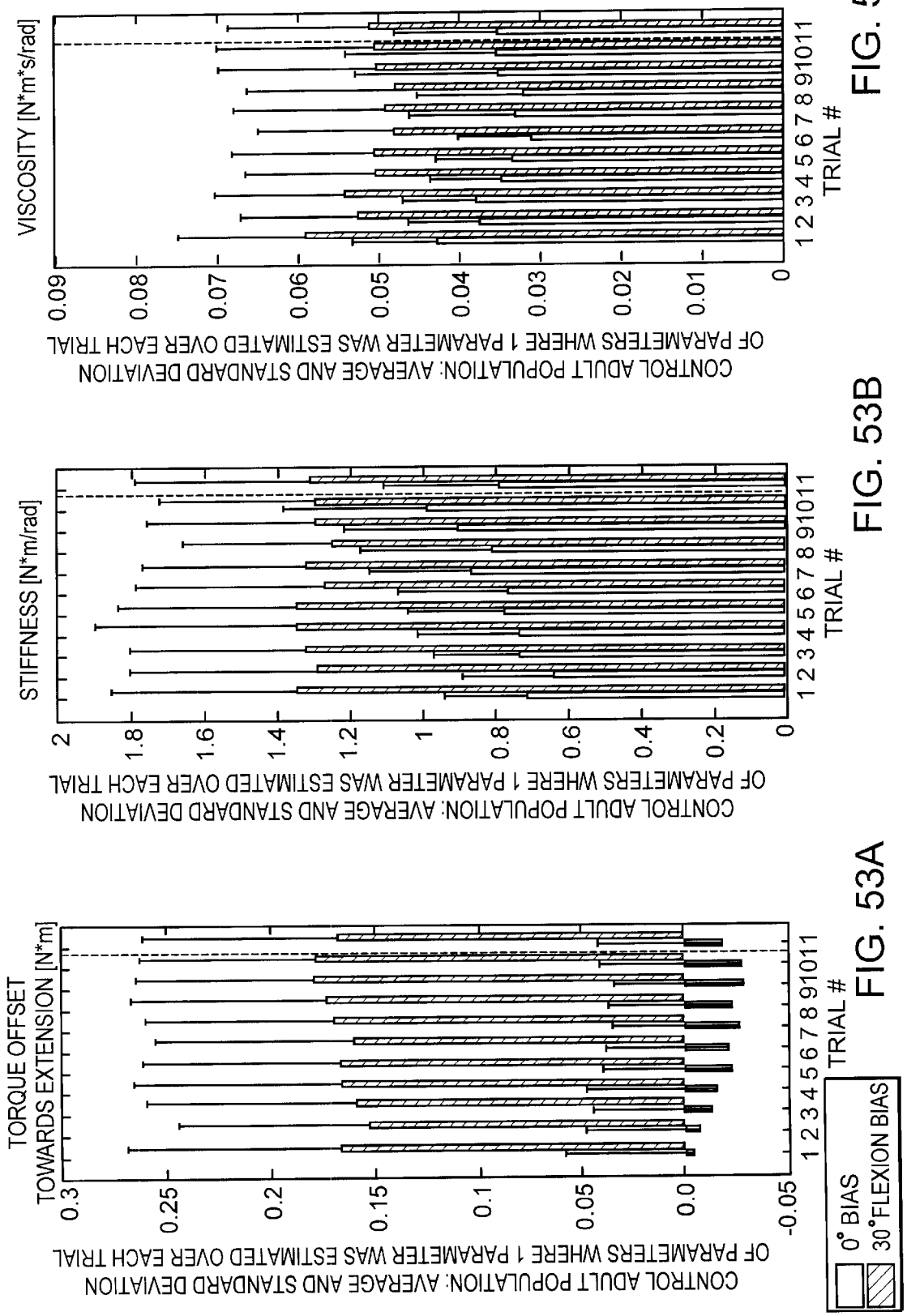
FIG. 53 shows the average $\tau_{off}$, $\tilde{K}_H$ and $\tilde{B}_H$ values across all control adults for each trail. The eleventh bar shows the overall average and standard deviation across all control adults, across all ten trials.
Figure 54C:
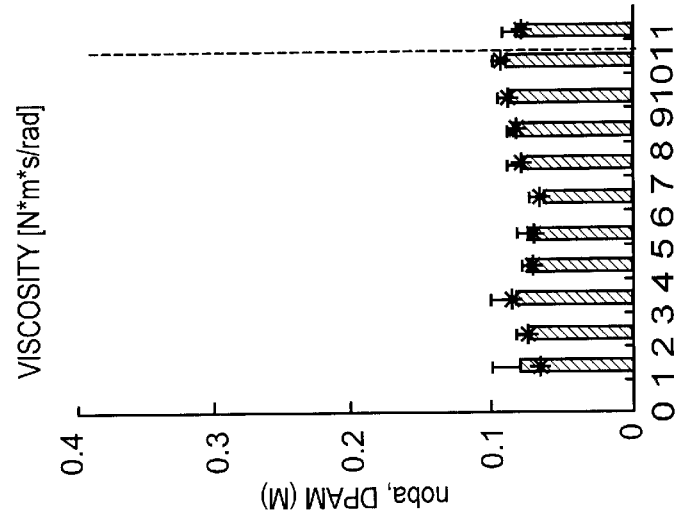
FIG. 54 shows the results for adult subjects with hemiplegic spasticity: AM, JS, and SH. The affected and unaffected arms were tested at a bias of 30 degrees flexion at each of the ten filtered, random trajectories.
Figure 54B:
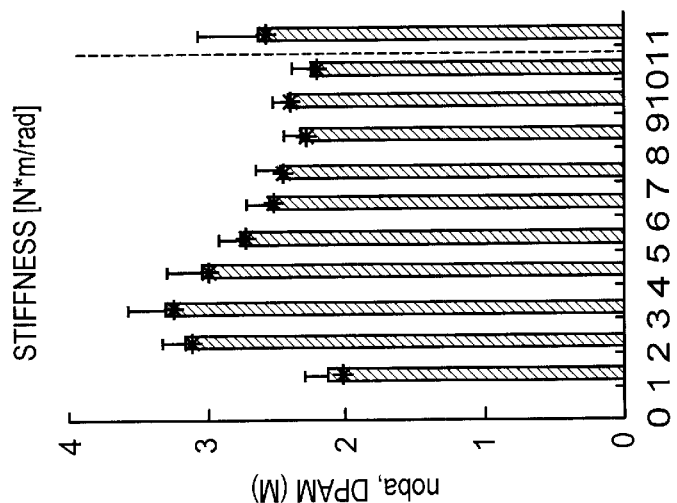
Figure 54A:
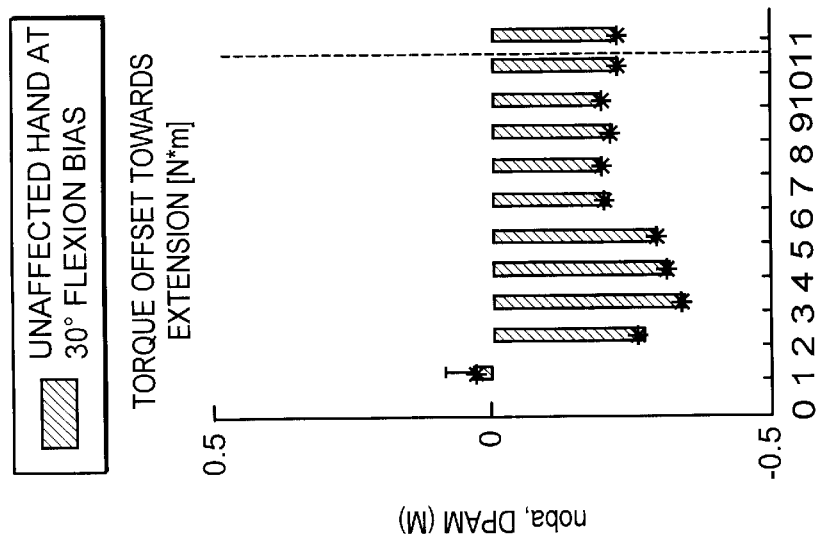
Figure 54F:
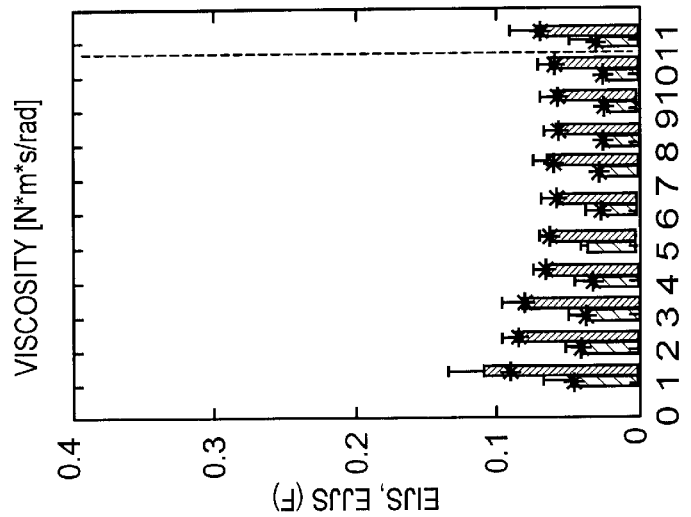
Figure 54E:
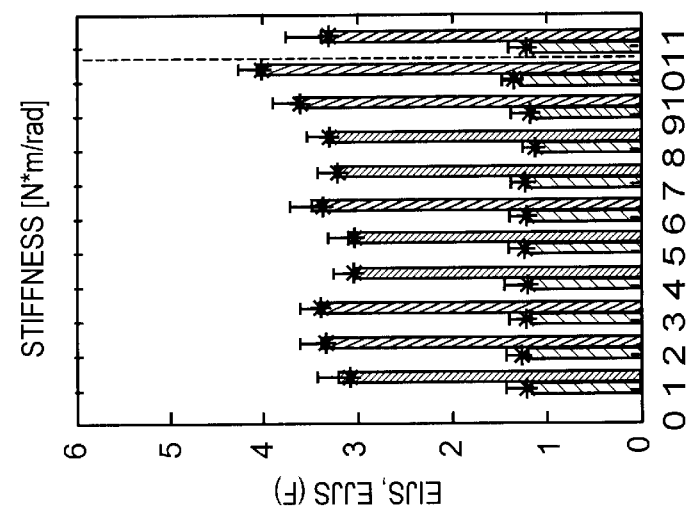
Figure 54D:
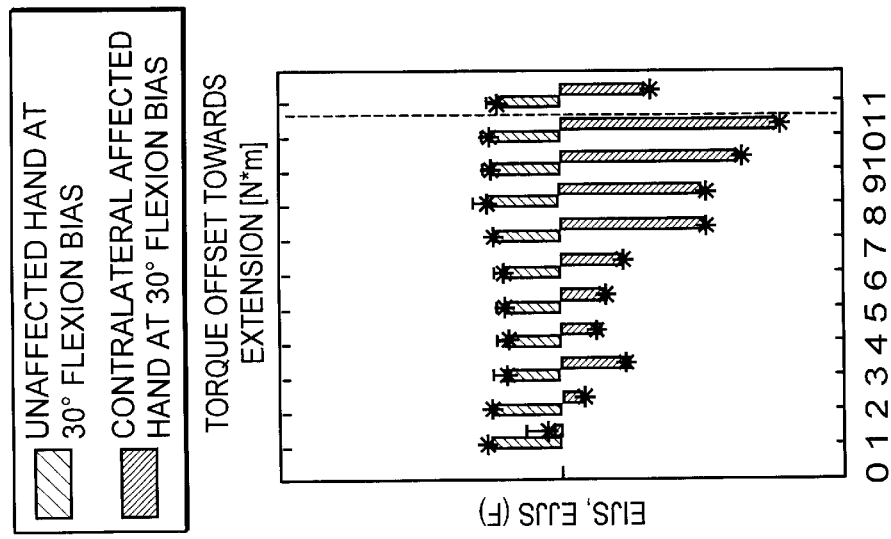
Figures 54G, 54H, 54I:
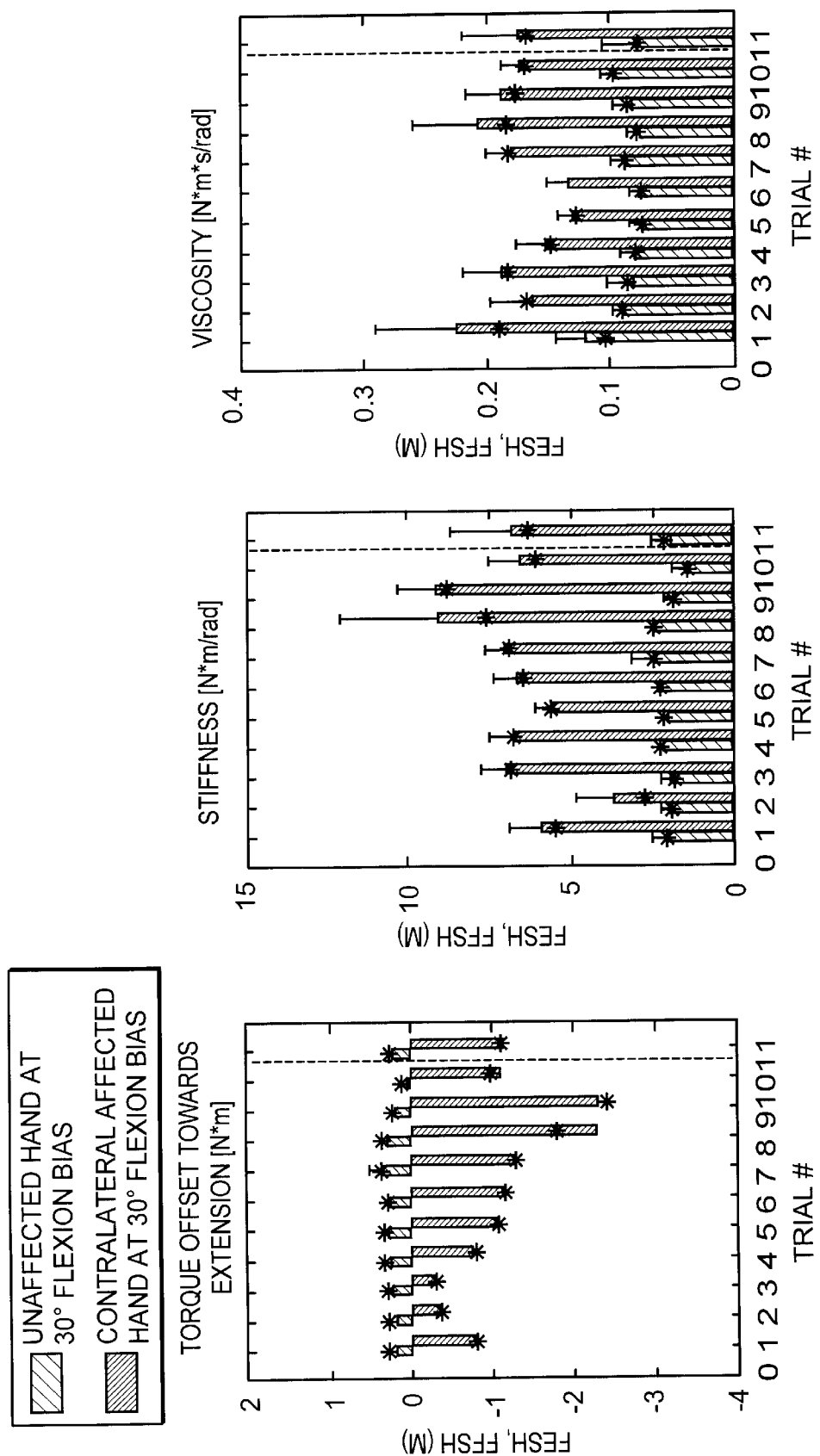

As shown in FIGS. 42–52, when looking at the average of $\tau_{\textit{off}}$, $\tilde{K}_H$ and $\tilde{B}_H$ over all ten trials for each experiment (denoted by the asterisk over the eleventh bar labeled trial 11), the following conclusions can be made. At a bias position of 0, the magnitude of $\tau$offacross all ten trials, for all 31 subjects is negligible, some being positive in value, some negative. This indicates that the resting position of a control subject's hand is very close to the neutral flexion/extension where muscles acting on the wrist exhibit the least amount of tension. At a bias of 30 degrees the torque-offset values are significantly higher and positive in sign. This indicates that the hand exhibits more elastic tension at this bias position. The positive sign indicates that the hand prefers to be at the neutral 0 degree bias position. All 31 subjects had a higher stiffness at a 30 degree flexion bias than at a 0 degree bias. 30 subjects had a higher mean viscosity value at a 30 degree flexion bias than at a 0 degree bias. Only 1 subject (MT) had a lower mean viscosity value at a 30 degree flexion bias than at a 0 degree bias. The average and standard deviation (denoted by the height of the error bars) of $\tau_{off}$, $\tilde{K}_H$ and $\tilde{B}_H$ values across all control adults for each trail are shown in FIG. 53. The eleventh bar shows the overall average and standard deviation across all control adults, across all ten trials.

Null-hypothesis significance tests can be used to quantitatively test how significant these different observations are between testing at the bias of 30 degrees flexion versus the bias of 0 degrees. For each experiment, the mean $\tau_{off}$, $\tilde{K}_H$, and $\tilde{B}_H$ are taken over the ten trials and these parameters are separated into two groups according to bias position. Thus, there are 31 mean$\{\tau_{off}\}$, mean$\{\tilde{K}_H\}$, and mean$\{\tilde{B}_H\}$ parameters for each of the two bias positions. The null hypotheses test indicates that the mean torque offsets, mean stiffnesses and mean viscosities are not significantly higher at a bias of 30 degrees than they are at a bias of 0 in control subjects. From the null hypothesis test, the p-value is obtained, wherein the p-value is the probability of observing the given result by chance given that the null hypothesis is true. Small values of p cast doubt on the validity of the null hypothesis. The probability of the null hypothesis stating that the average torque offset values are higher at 0 than at 30 degrees is true is $p=9.2*10^{-4}$ The probability of the null hypothesis stating that the average stiffness values are higher at 0 than at 30 degrees is true is $p=2*10^{-5}$ The probability of the null hypothesis stating that the average viscosity values are higher at 0 than at 30 degrees is true is $p=4.2*10^{-5}$. Since a resulting p-value of $5*10^{-3}$ is considered to be very significant, there is no question that the increase in all three parameters $\tau_{off}$, $\tilde{K}_H$, and $\tilde{B}_H$ is extremely significant when testing at a bias position of 30 degrees flexion rather than 0 in the control adult subject population.

Table 3 below shows the average and standard deviation of $\tau_{off}$, $\tilde{K}_H$ and $\tilde{B}_H$ values across all ten trials across all control adult subjects which are indicated by the height of the $11^{th}$ bars shown in FIG. 53. Table 4 shows the range of average $\tau_{off}$, $\tilde{K}_H$ and $\tilde{B}_H$ values across all ten trials in the control adult group.

TABLE 3

| Bias position | $\tilde{\tau}_{off}$ [N * m]: Torque offset towards extension | $\tilde{K}_H$ [N * m/rad]: Stiffness | $\tilde{B}_H$ [N * m * s/rad]: Viscosity |
|---|---|---|---|
| 0 degrees | −0.0189 ± 0.0609 | 0.789 ± 0.309 | 0.0353 ± 0.0127 |
| 30 degrees flexion | 0.1667 ± 0.0936 | 1.305 ± 0.480 | 0.0512 ± 0.0175 |

TABLE 4

| Bias position | $\tilde{\tau}_{off}$ [N * m]: Torque offset towards extension | $\tilde{K}_H$ [N * m/rad]: Stiffness | $\tilde{B}_H$ [N * m * s/rad]: Viscosity |
|---|---|---|---|
| 0 degrees | −0.123 to 0.089 | 0.233 to 1.347 | 0.021 to 0.059 |
| 30 degrees flexion | 0.0241 to 0.361 | 0.482 to 2.345 | 0.0274 to 0.105 |

An additional observation from FIG. 53 is that when testing at a bias of 0 degrees, the elastic stiffness increases from trial 1 to trial 10. As stated previously, trials 1 and 2 have a maximum frequency component of 4 Hz, trials 3 and 4 have a maximum frequency component of 5 Hz, trials 5 and 6 have a maximum frequency component of 6 Hz, and trials 7 and 8 have a maximum frequency component of 8 Hz. One hypothesis that can explain this observation is that because velocities of the perturbations increase with trial number, the primary afferents of the muscle spindle sense these greater rates of muscle stretch in turn activating the stretch reflex causing muscles to contract and become stiffer. Thus, the hypothesis says that the combined active stiffness of the muscles acting on the wrist may be increasing with trial number. An observed increase in EMG activity at the greater trial numbers supports this hypothesis. This trend, however, is not shown at the bias of 30. This is likely because extensor muscles are already active in all 10 trials as they are stretched to a length further from the neutral position.

Many subjects with spasticity cannot be tested at a neutral bias position of 0 degrees as they have difficulty extending their wrist joint to that position. The resting configuration of the hand of someone with spasticity is in the hyper-flexed position due to hyperactivity of the flexor muscle group. Four adult patients with hemiplegic spasticity were tested, AM, JS, SH, and BY, 3 males and 1 female. A hemiplegic patient is one where one side of his or her body is affected by spasticity whereas the contra-lateral side is practically unaffected or less affected. Because the contra-lateral arm is unaffected or less affected, it can serve as a control to the spastic arm when testing a patient with hemiplegic spasticity. JS is a patient with Parkinson's disease, SH suffers from traumatic brain injury due to a motorcycle accident, and BY is a patient who severely lost function of his left hand after a stroke. AM's affected arm was tested at a bias of 30 degrees flexion. For subjects JS, SH, and BY the affected arms and unaffected contra-lateral arms were tested, both at a bias of 30 degrees. The results of these experiments are shown in FIGS. 54 and 55. Unlike the figures showing results of the control subjects, all plots are not on the same scale due to the large range in values. The white bar graphs show results for the unaffected arm and the grey bar graphs show results for the contra-lateral affected arm. Both arms were tested at a bias of 30 degrees flexion.

Looking at the average of $\tau_{off}$, $\tilde{K}_H$ and $\tilde{B}_H$ over all ten trials for each experiment denoted by the asterisk over the eleventh bar labeled trial 11, the following conclusions can be made. In the experiment with the unaffected hand at the bias of 30 degrees flexion, the average $\tau_{off}$ across all ten trials are comparable to what is seen in control subjects when tested at the same bias. As in the control subjects, the torque offset values are positive indicating that the unaffected hand prefers to be at the neutral 0 degree bias position as in the control subjects. However, when testing the affected, spastic side at the 30-degree bias, the $\tau_{off}$ values are negative in sign and greater in magnitude. This indicates that the preferred resting position of the subject's spastic wrist joint is at a flexed position even greater than 30 degrees, as the hand is pushing towards an even further flexed position. This phenomenon is what is called hyper-flexion. This observation of increase in magnitude and change in sign in the average $\tau_{off}$ across the ten trials when testing the affected hand versus the unaffected hand is significant (p=0.0177). All 3 subjects tested on both arms have a higher average stiffness (mean of $\tilde{K}_H$ across the ten trials) in their spastic arm as compared to their contra-lateral arm (p=0.0743). When comparing the average stiffness between contralateral arms, in subjects JS, and SH, the difference is large. Also, in general, the average viscosity, $\tilde{B}_H$, across the ten trials is greater in the affected hand when compared to the unaffected hand, but the difference seen in viscosity values is not as great as the difference seen in the stiffness values (p=0.199). Here, the difference between the affected spastic arm is compared with the unaffected contra lateral arm within the spastic group.

Figures 56A, 56B, 56C:
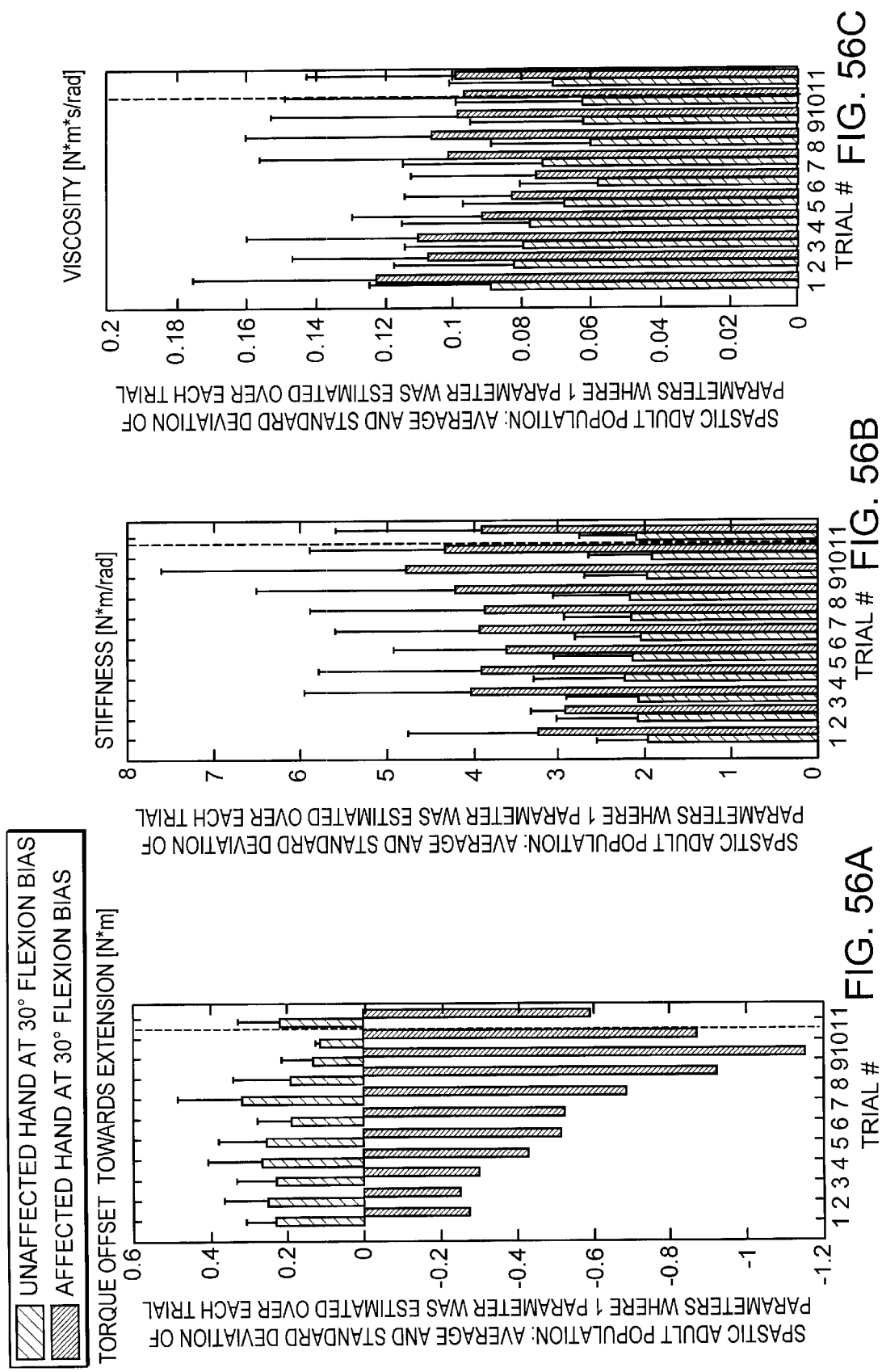
FIG. 56 shows the average $\tau_{off}$, $\tilde{K}_H$ and $\tilde{B}_H$ values across all adults with hemiplegic spasticity for each trail. The eleventh bar shows the overall average and standard deviation across all adults with spasticity, across all ten trials.
Figure 57A:
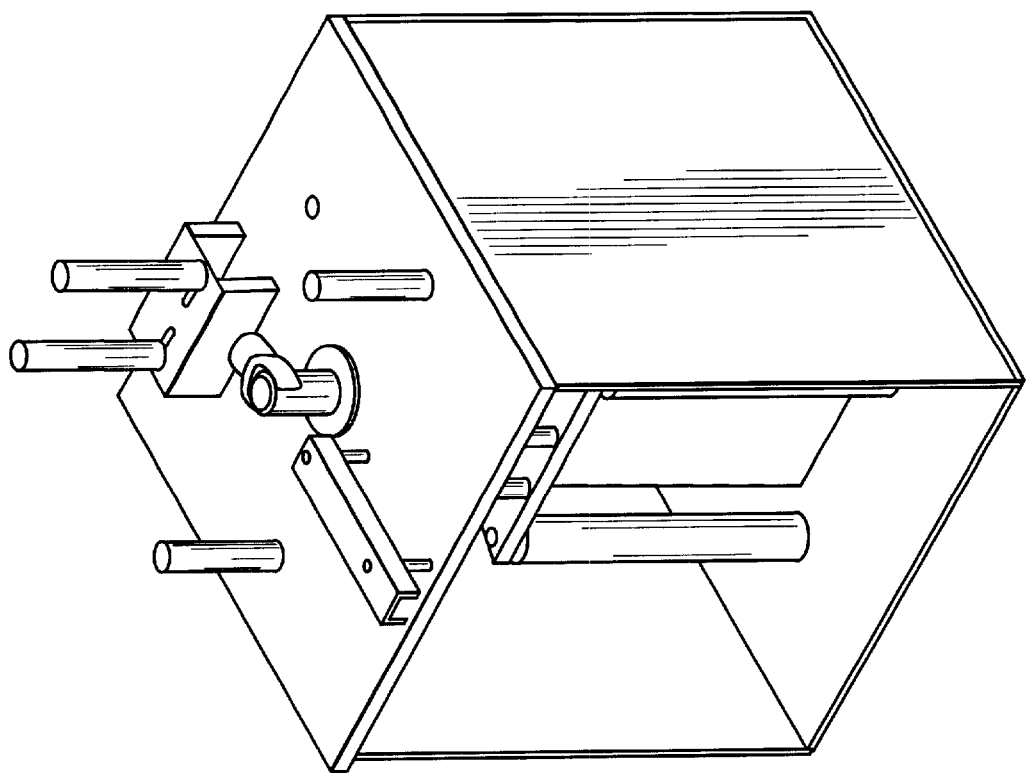
FIGS. 57–124 show block diagrams of code used in accordance with one embodiment of the present invention.
Figure 57B:
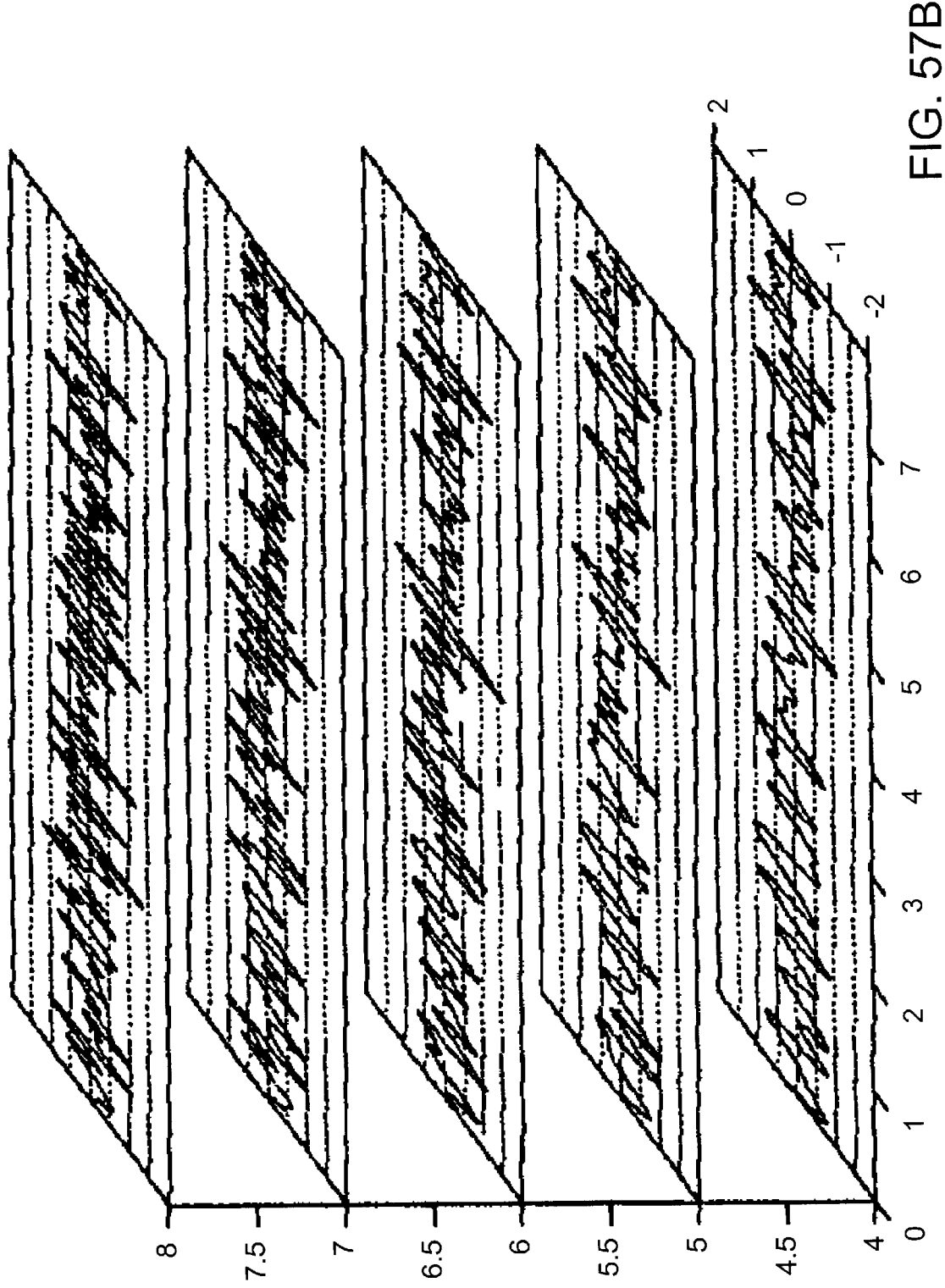
Figure 58:
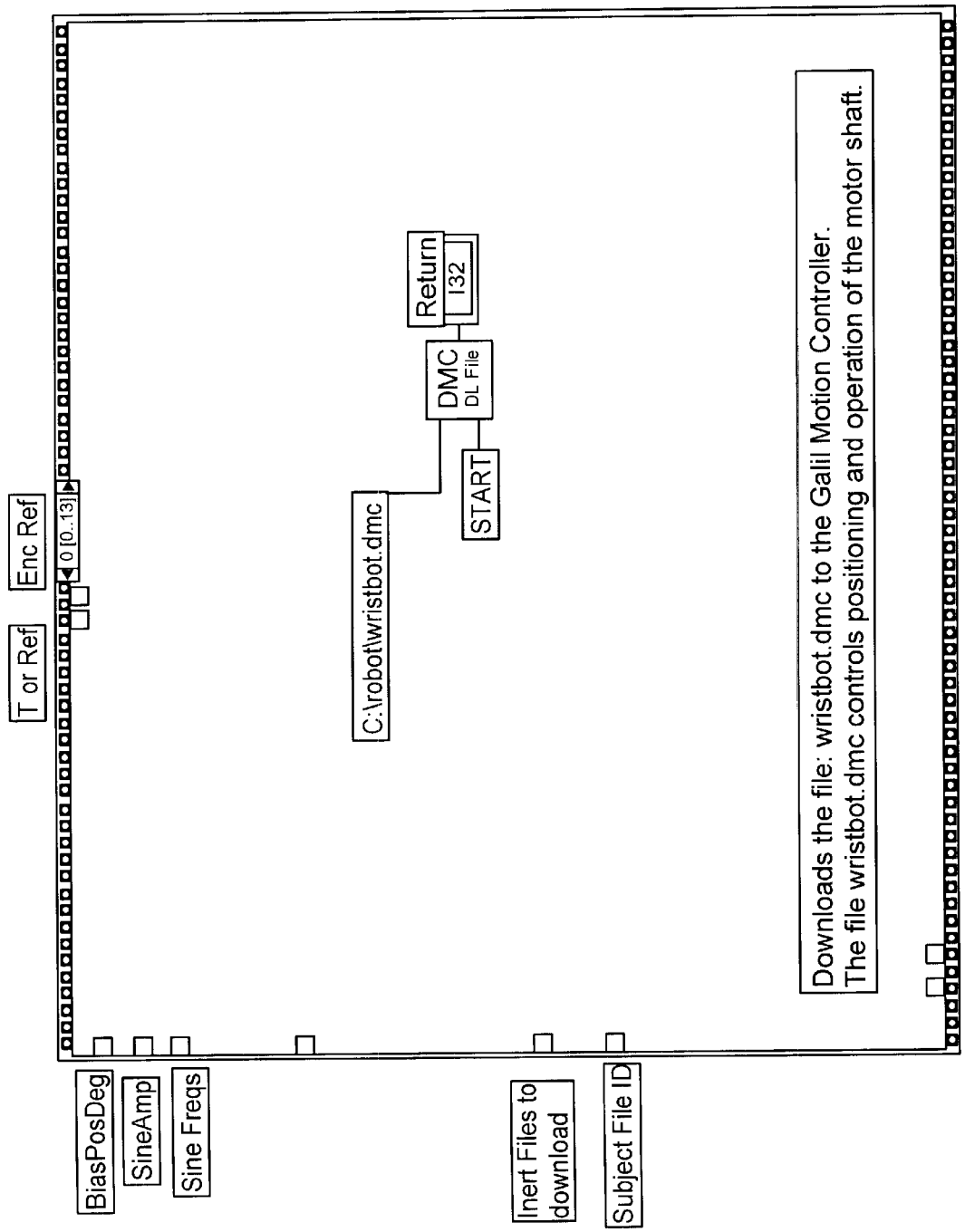
Figure 59:
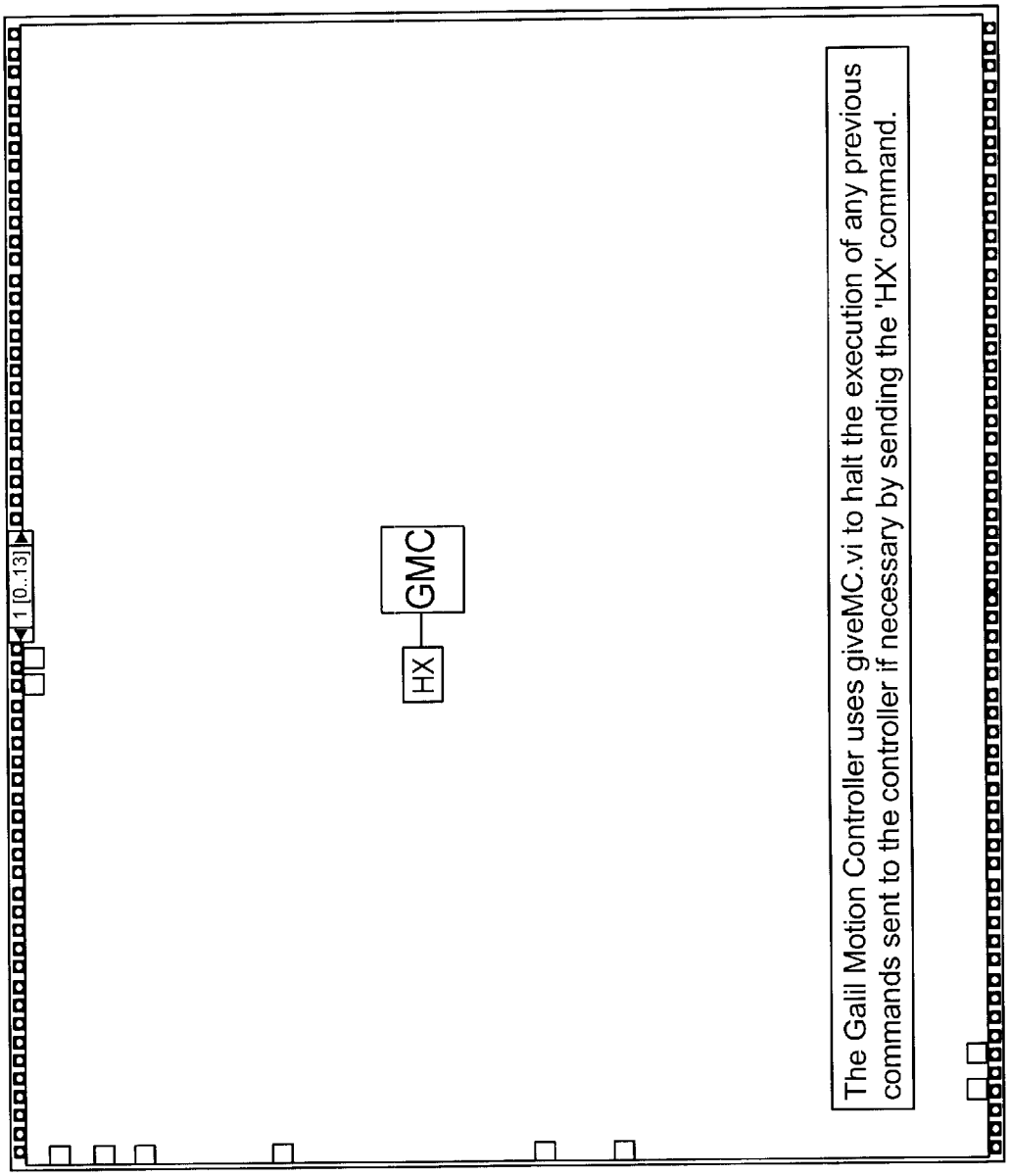
Figure 60:
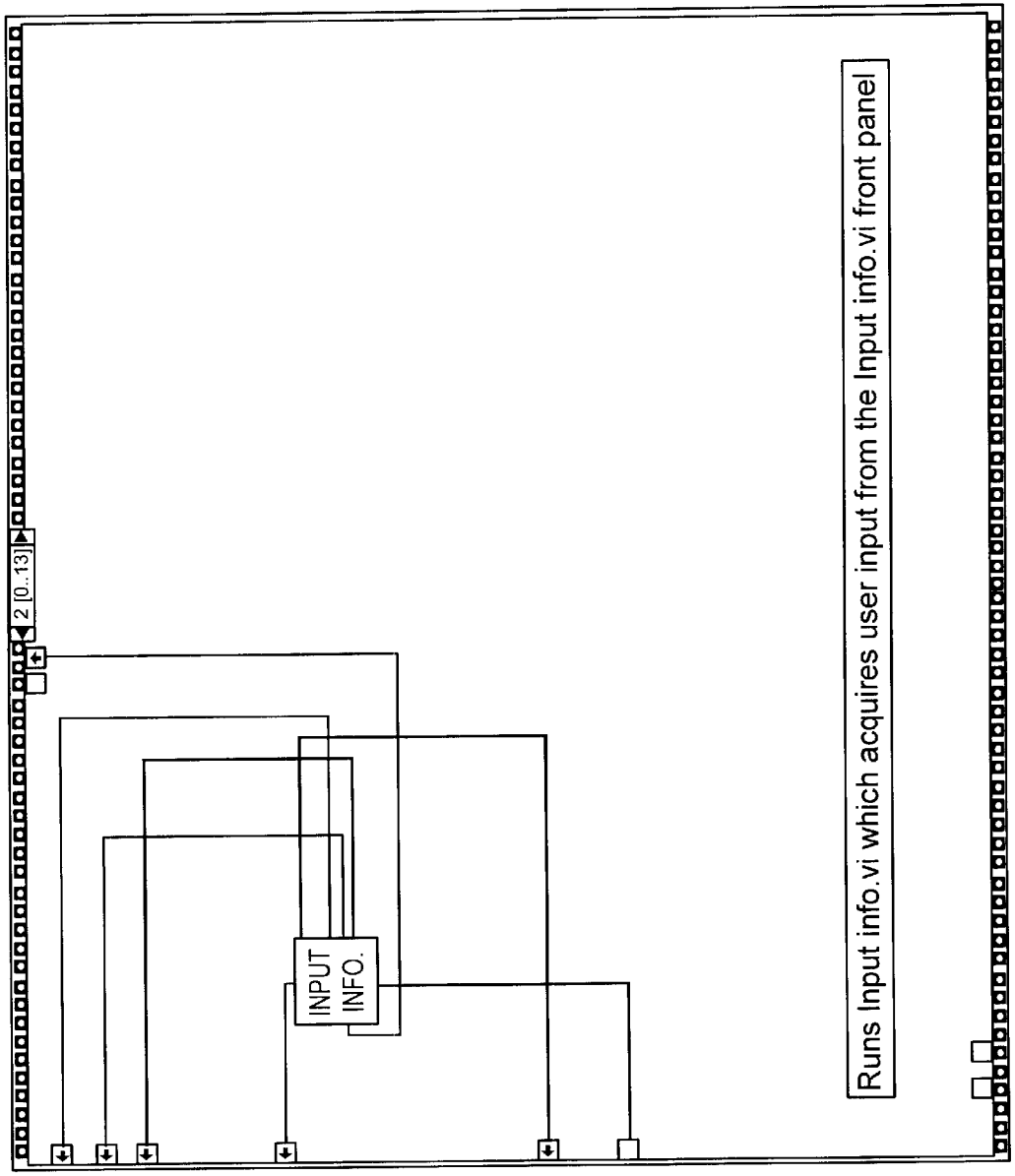
Figure 61:
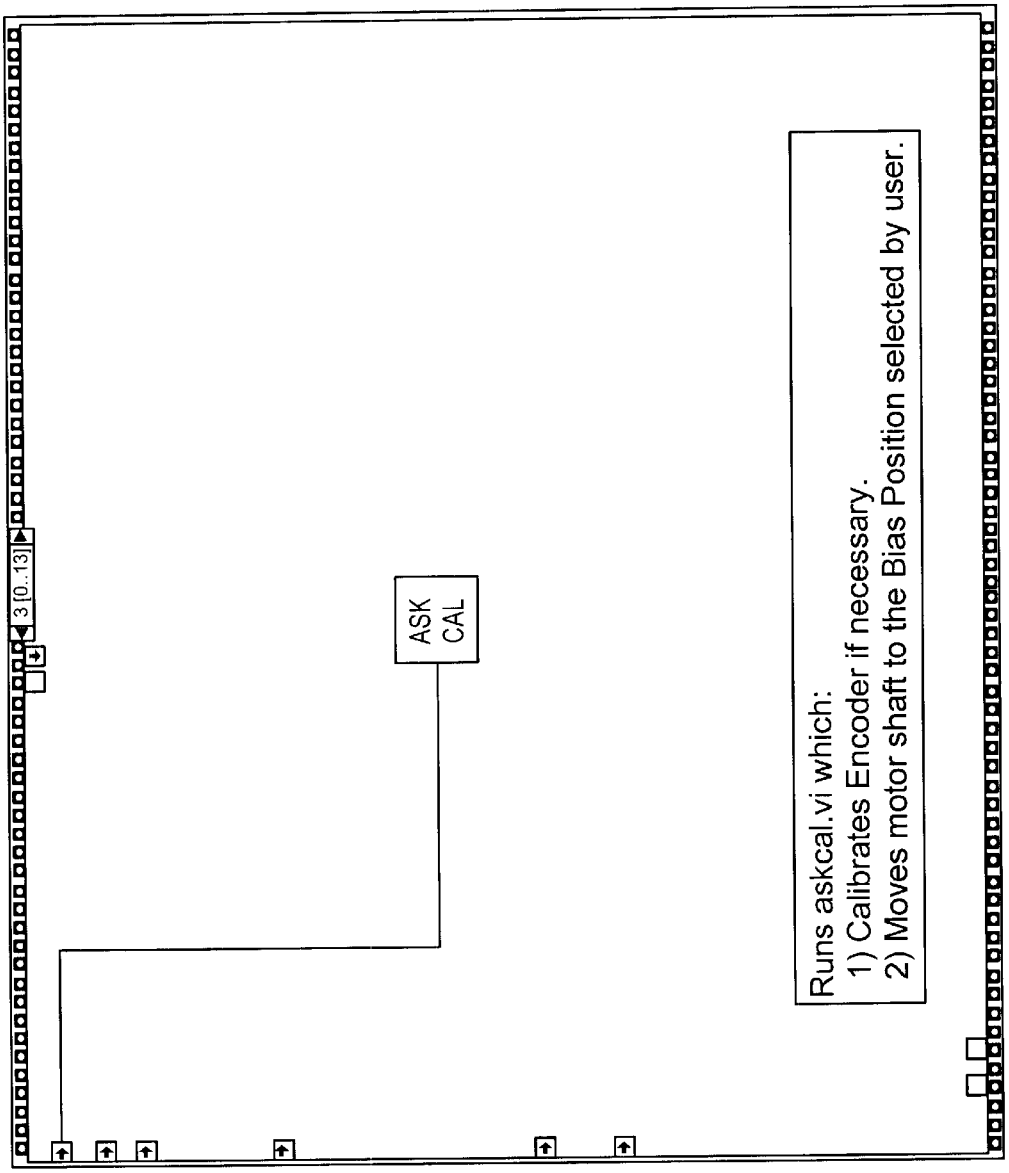
Figure 62:
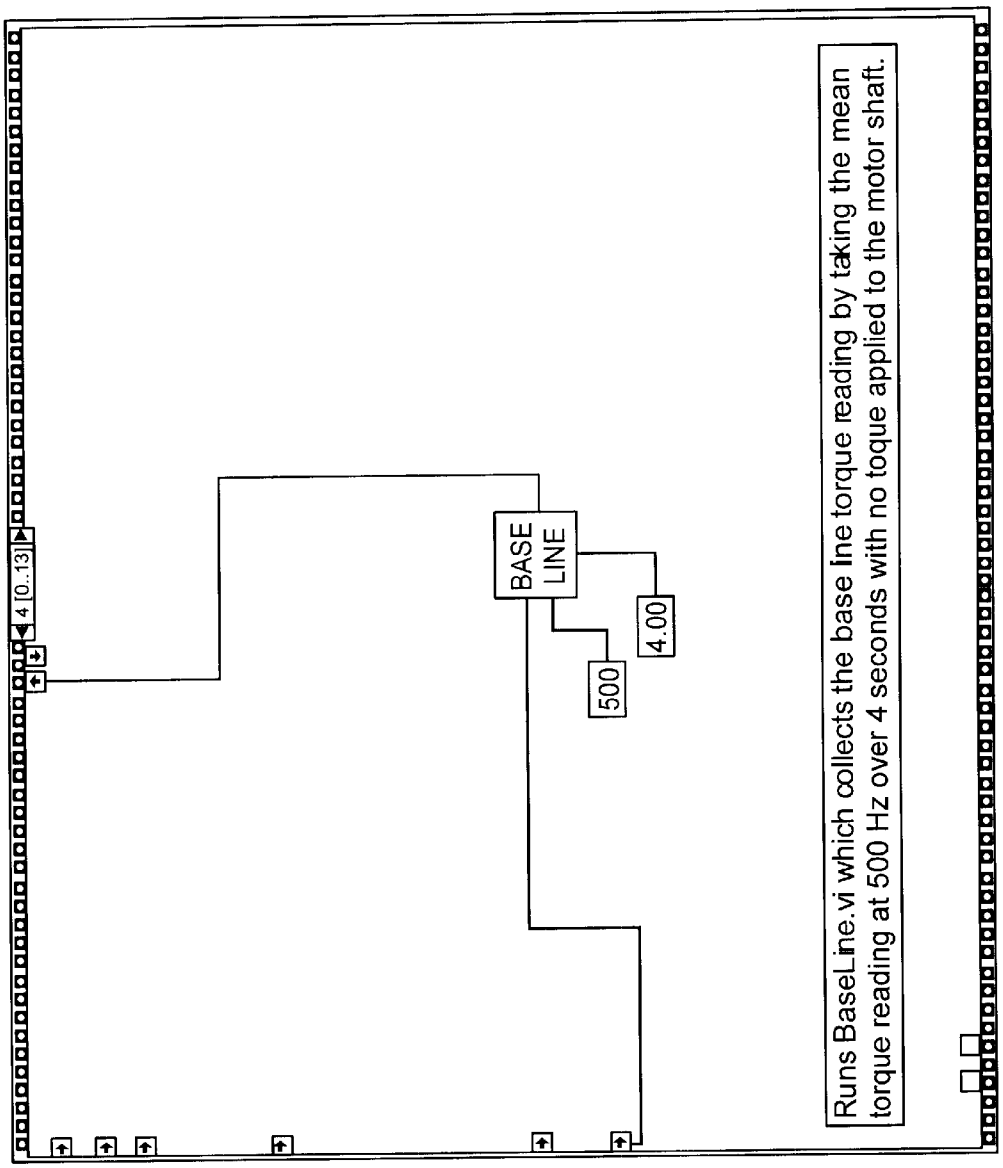
Figure 63:
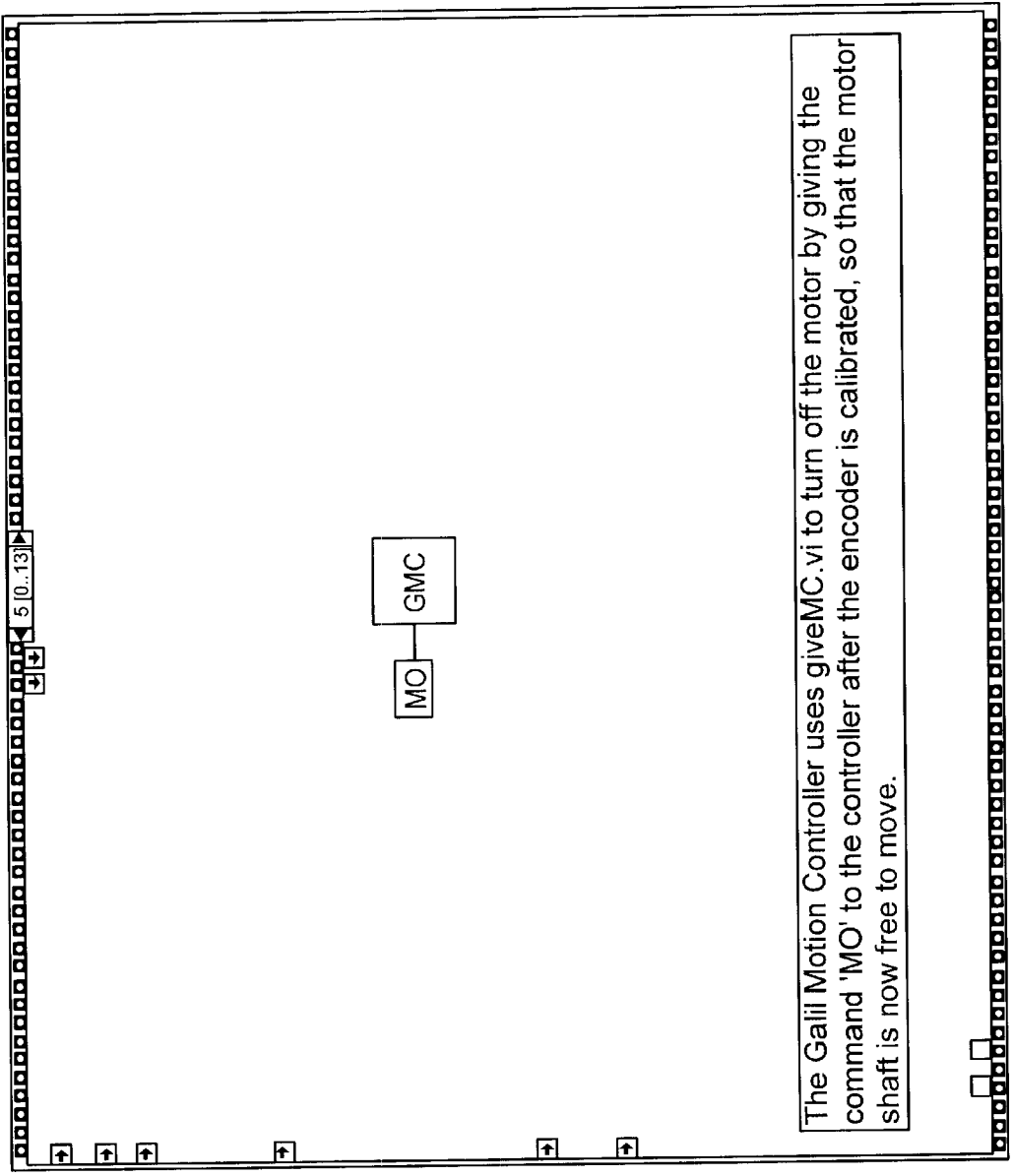
Figure 64:
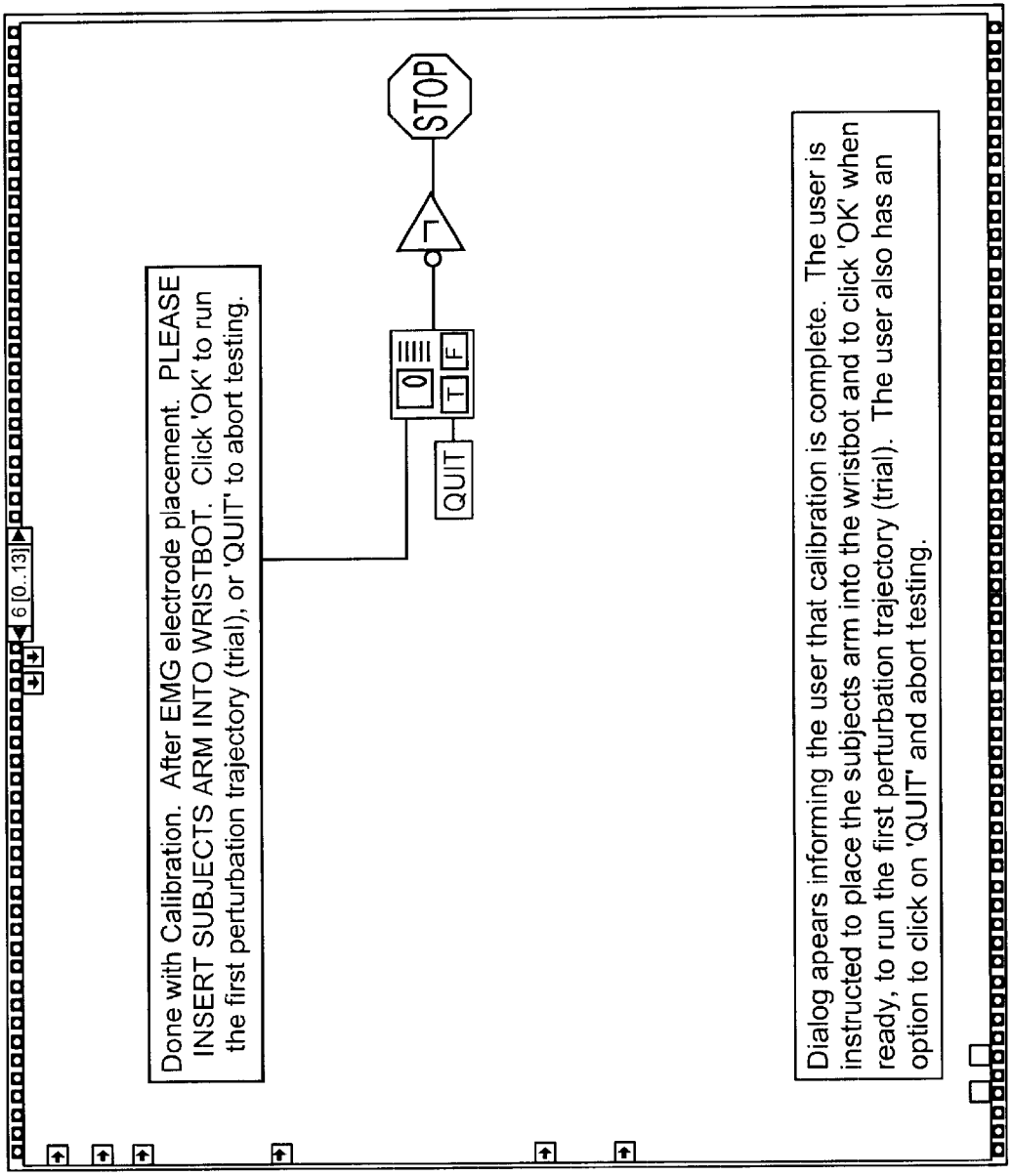
Figure 65:
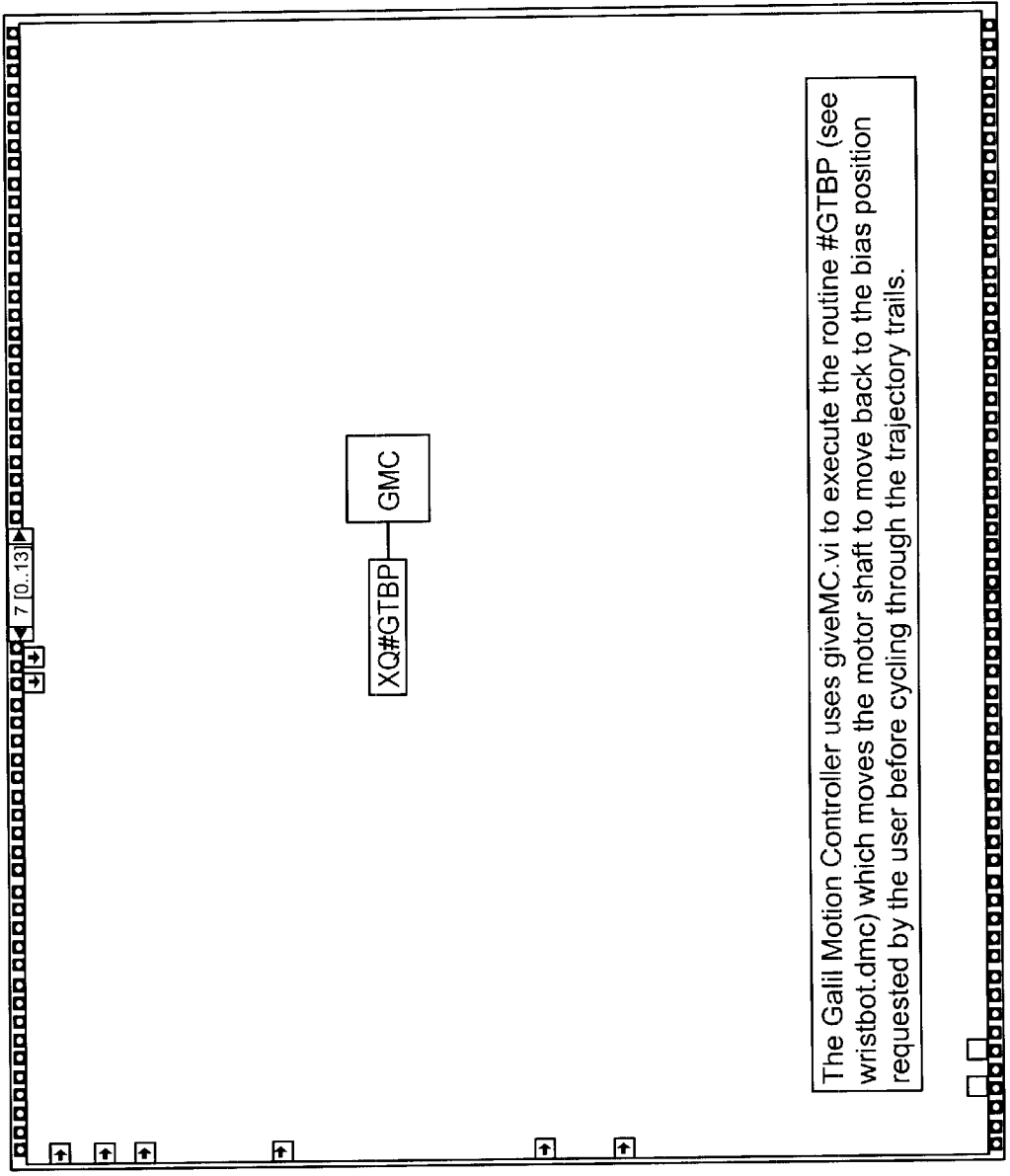
Figure 66:
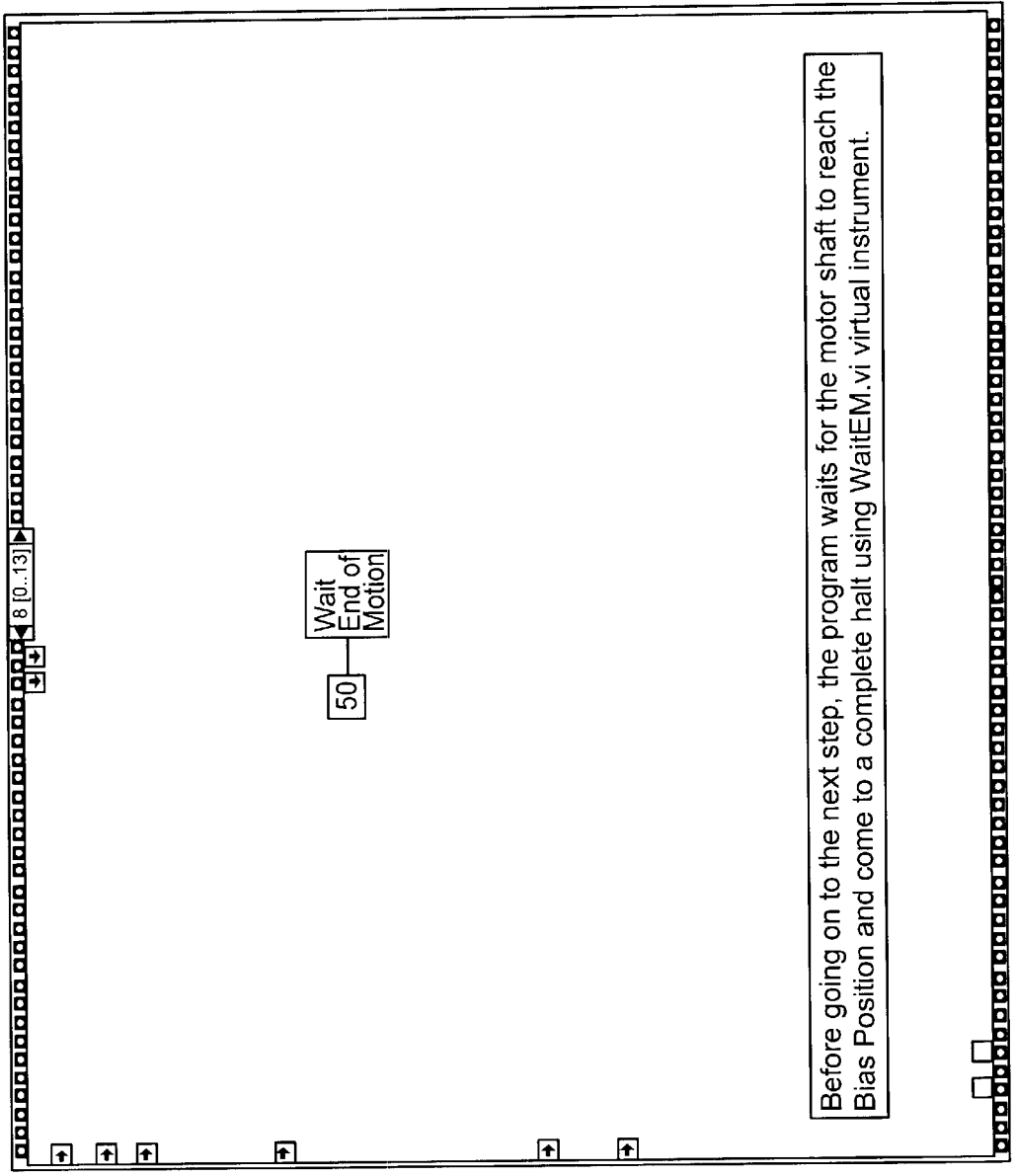
Figure 67:
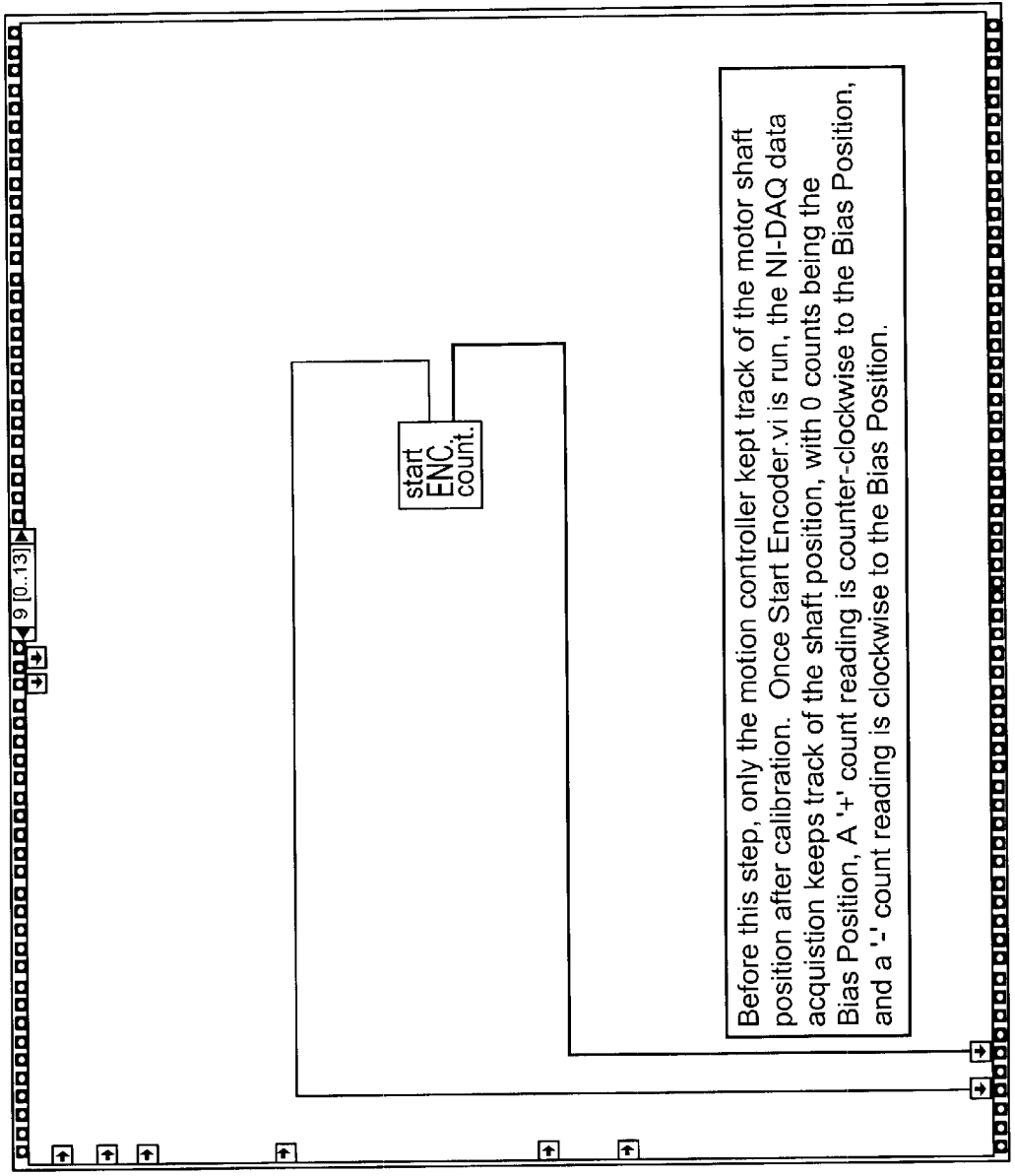
Figure 68:
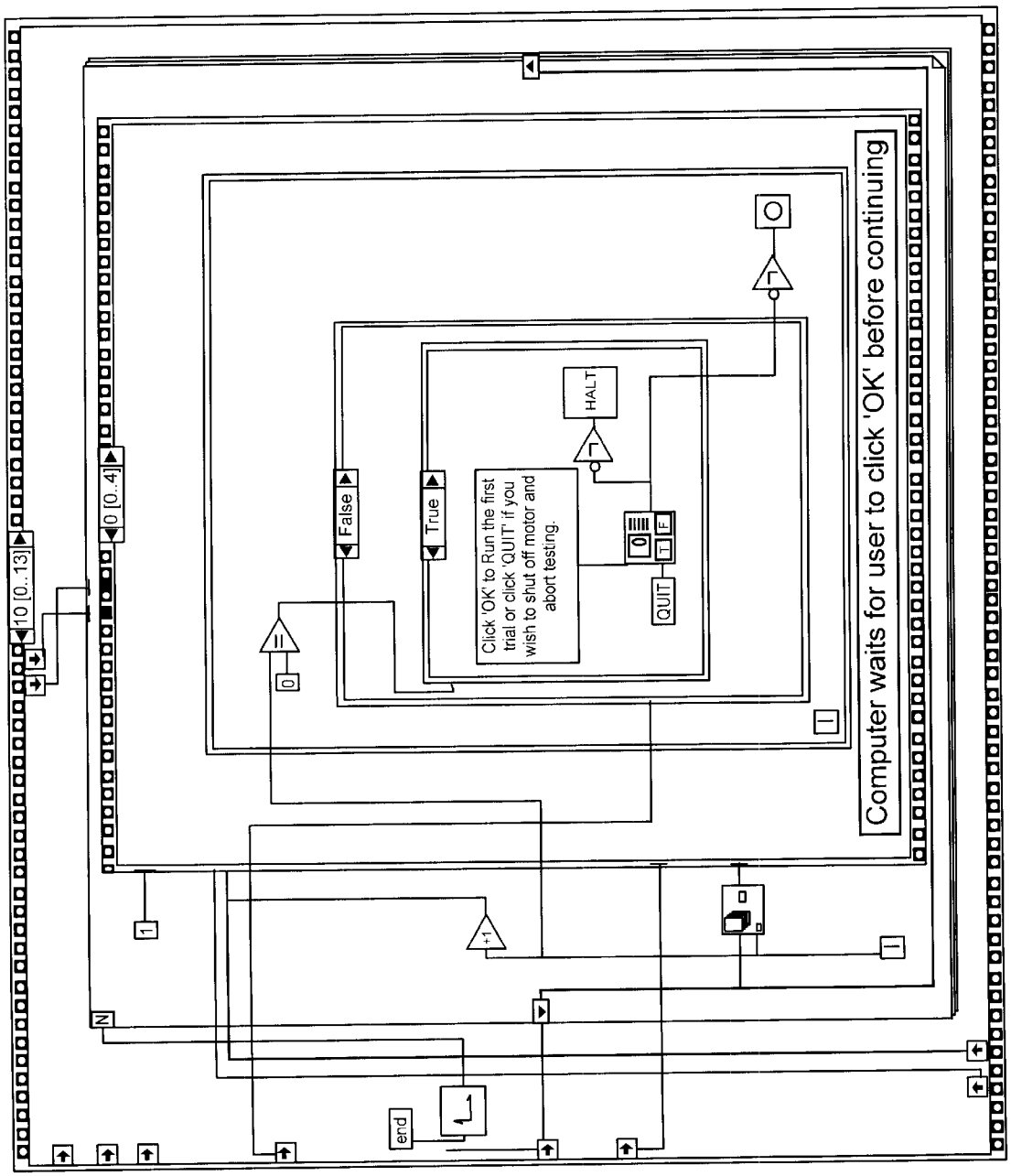
Figure 69:
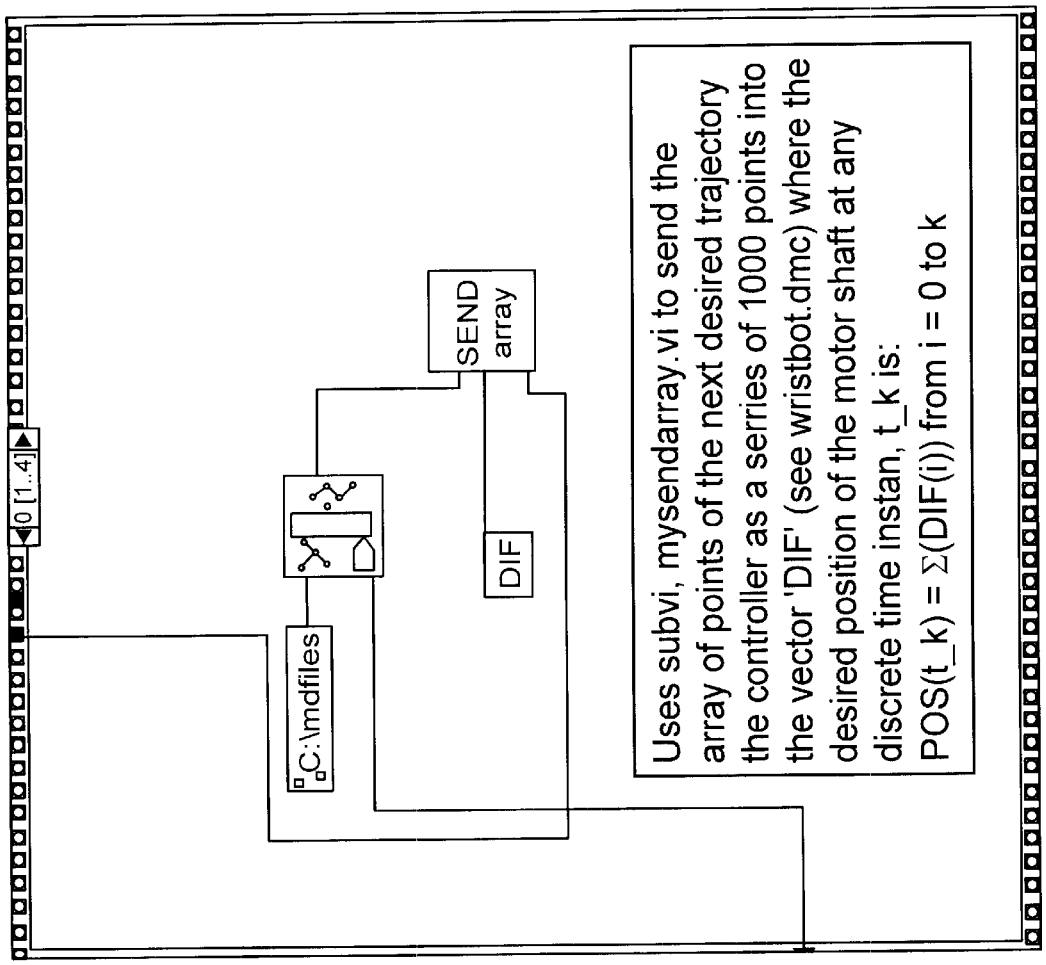
Figure 70:
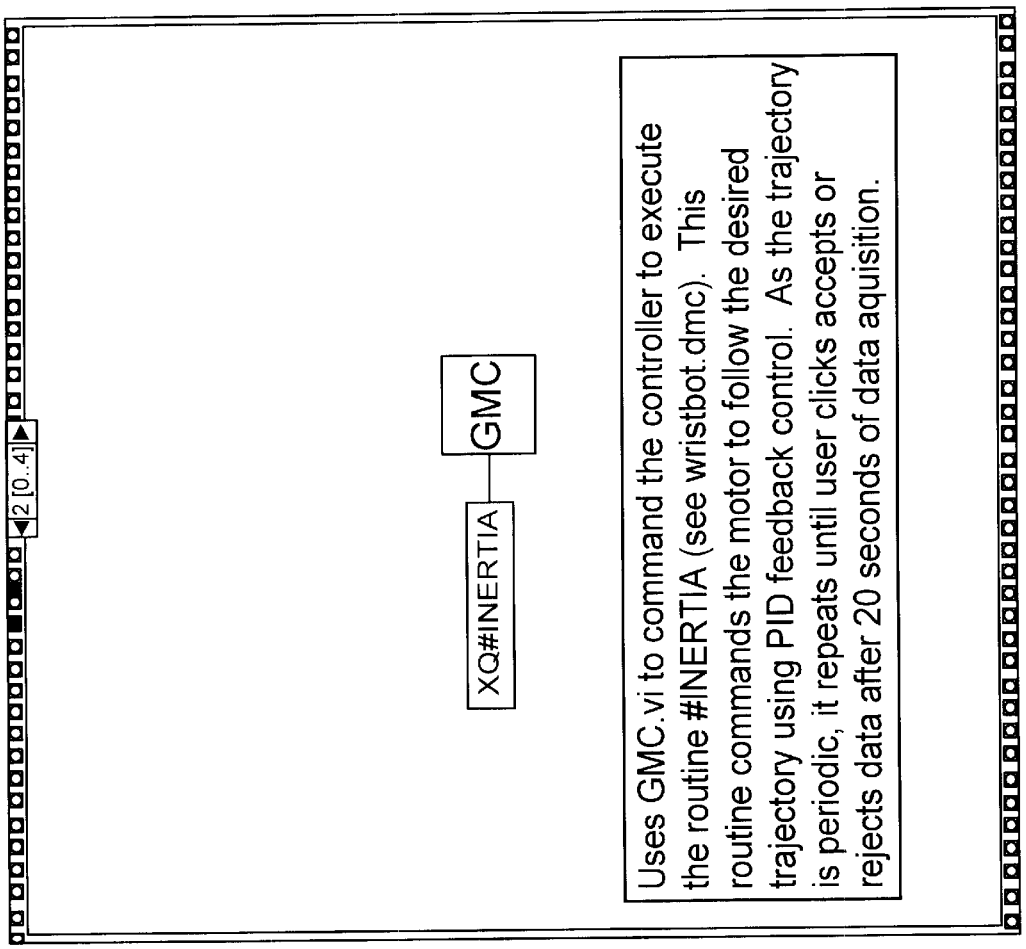
Figure 71:
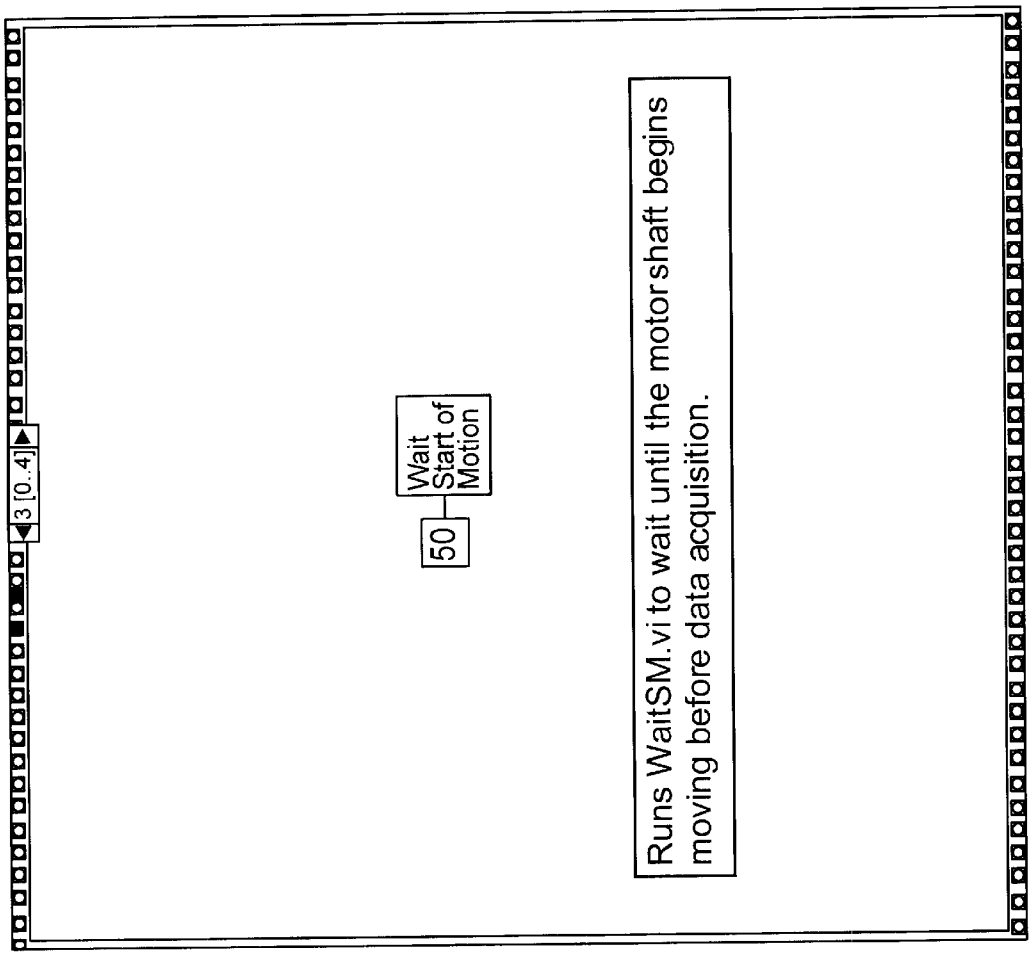
Figure 72:
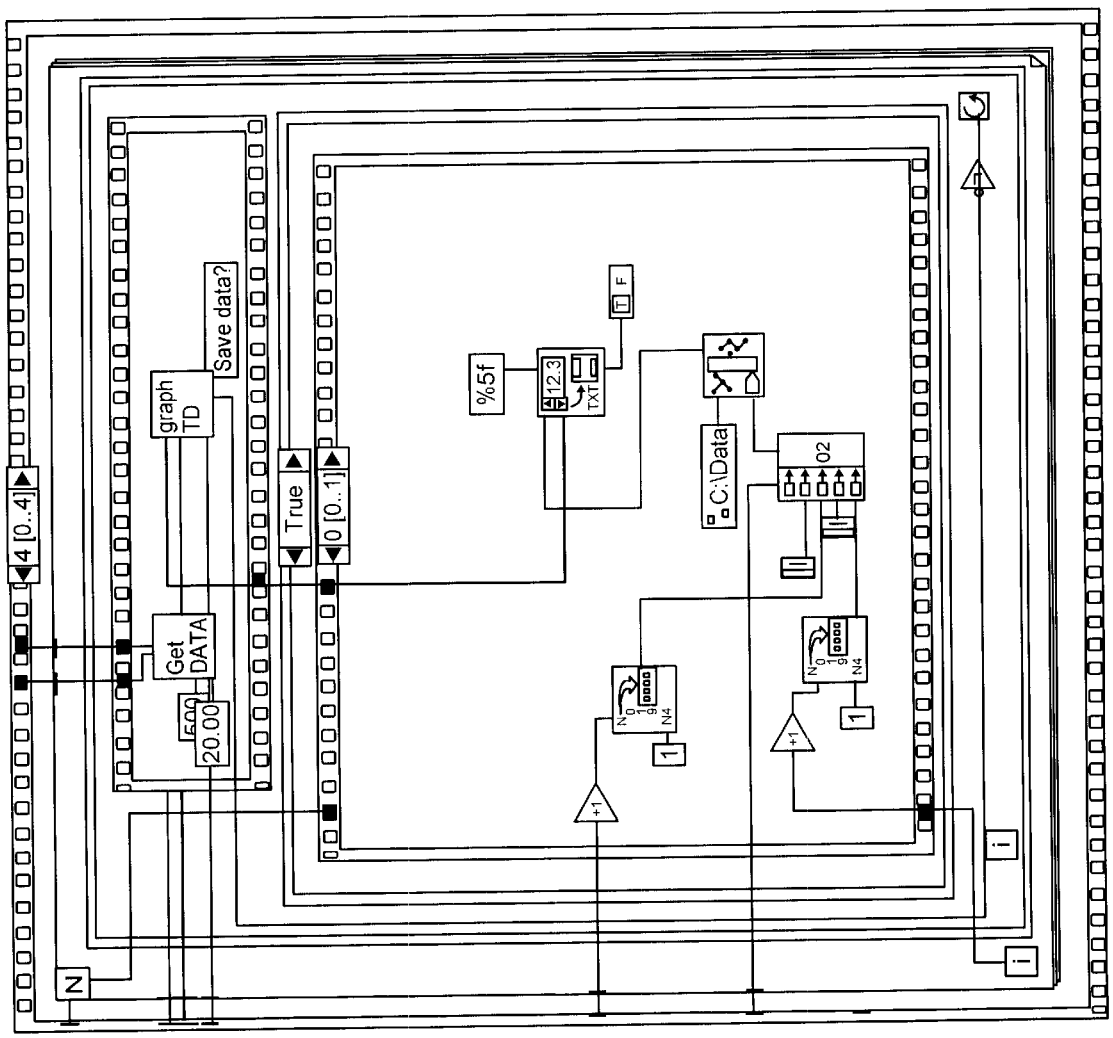
Figure 74:
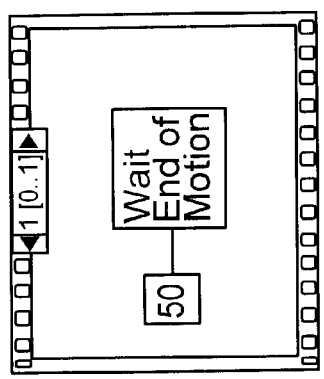
Figure 73:
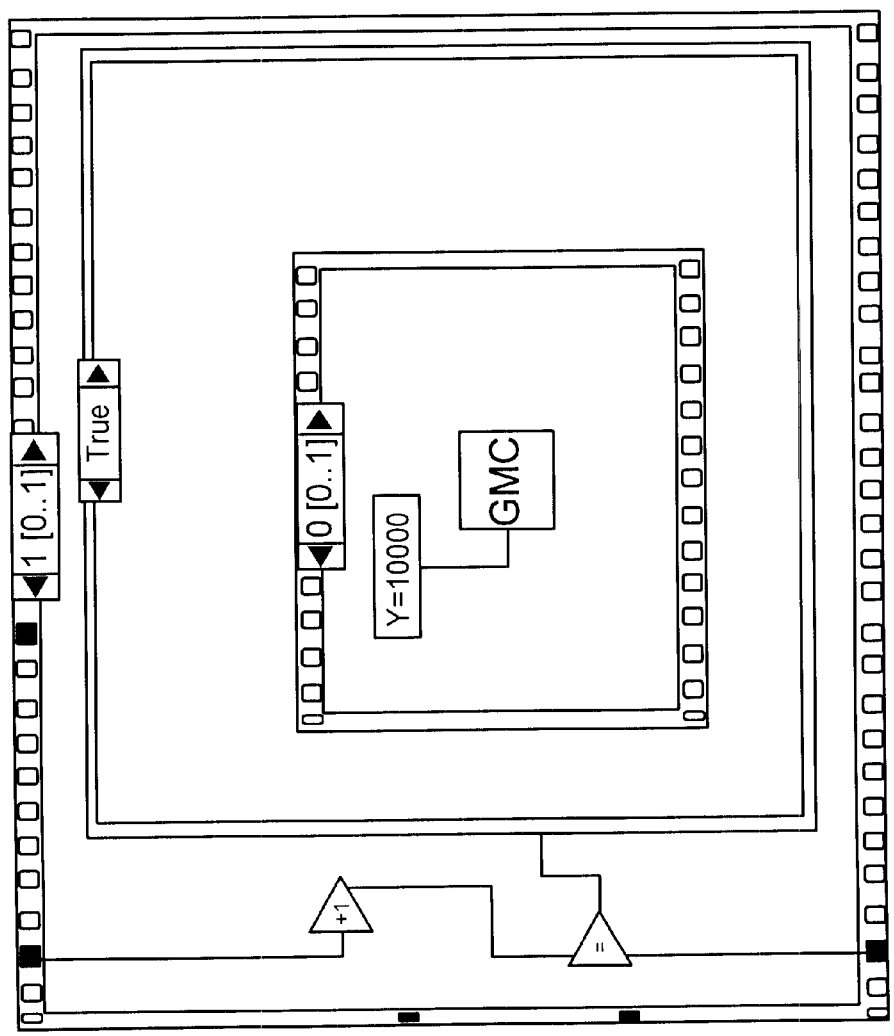
Figure 75:
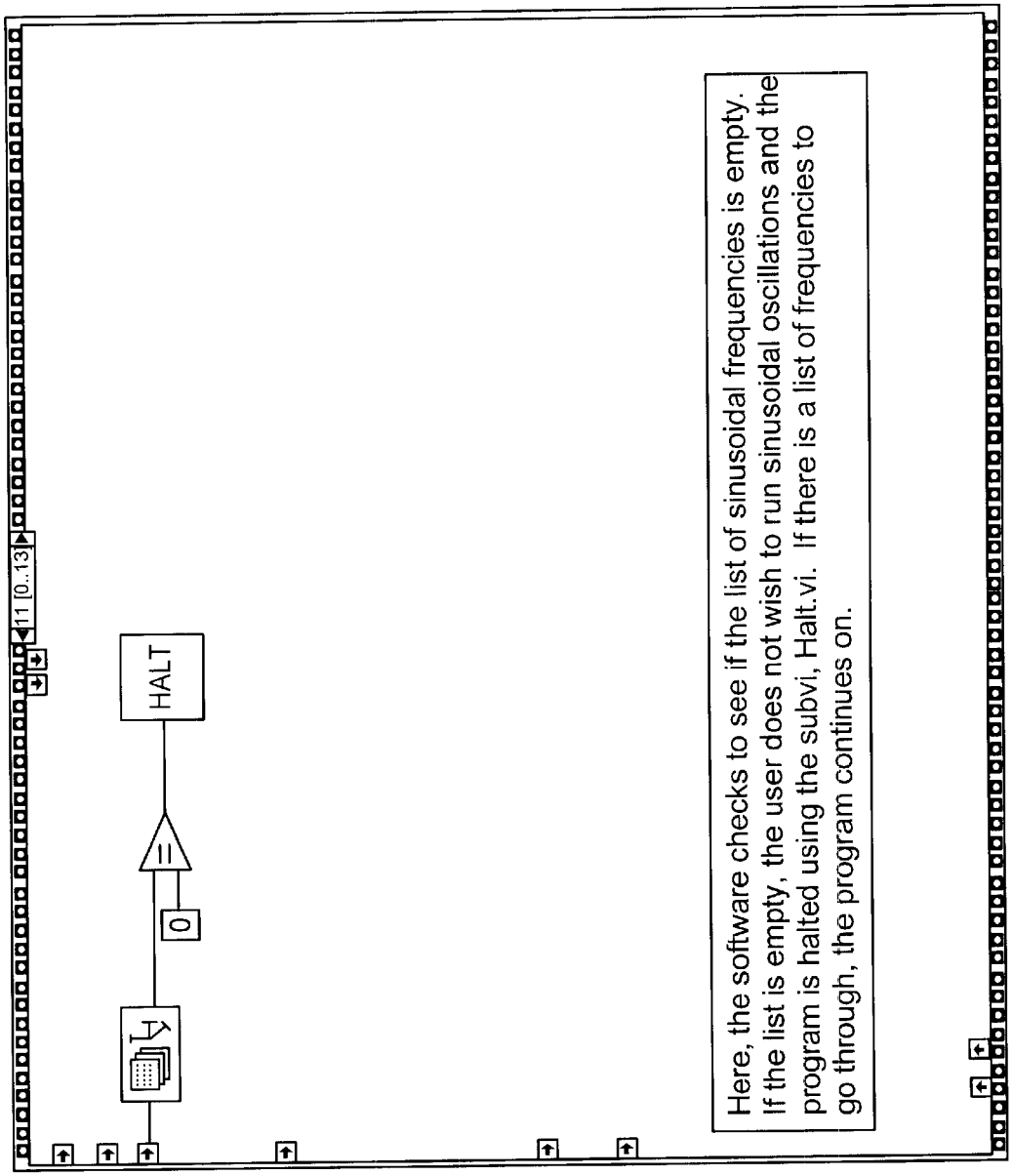
Figure 76:
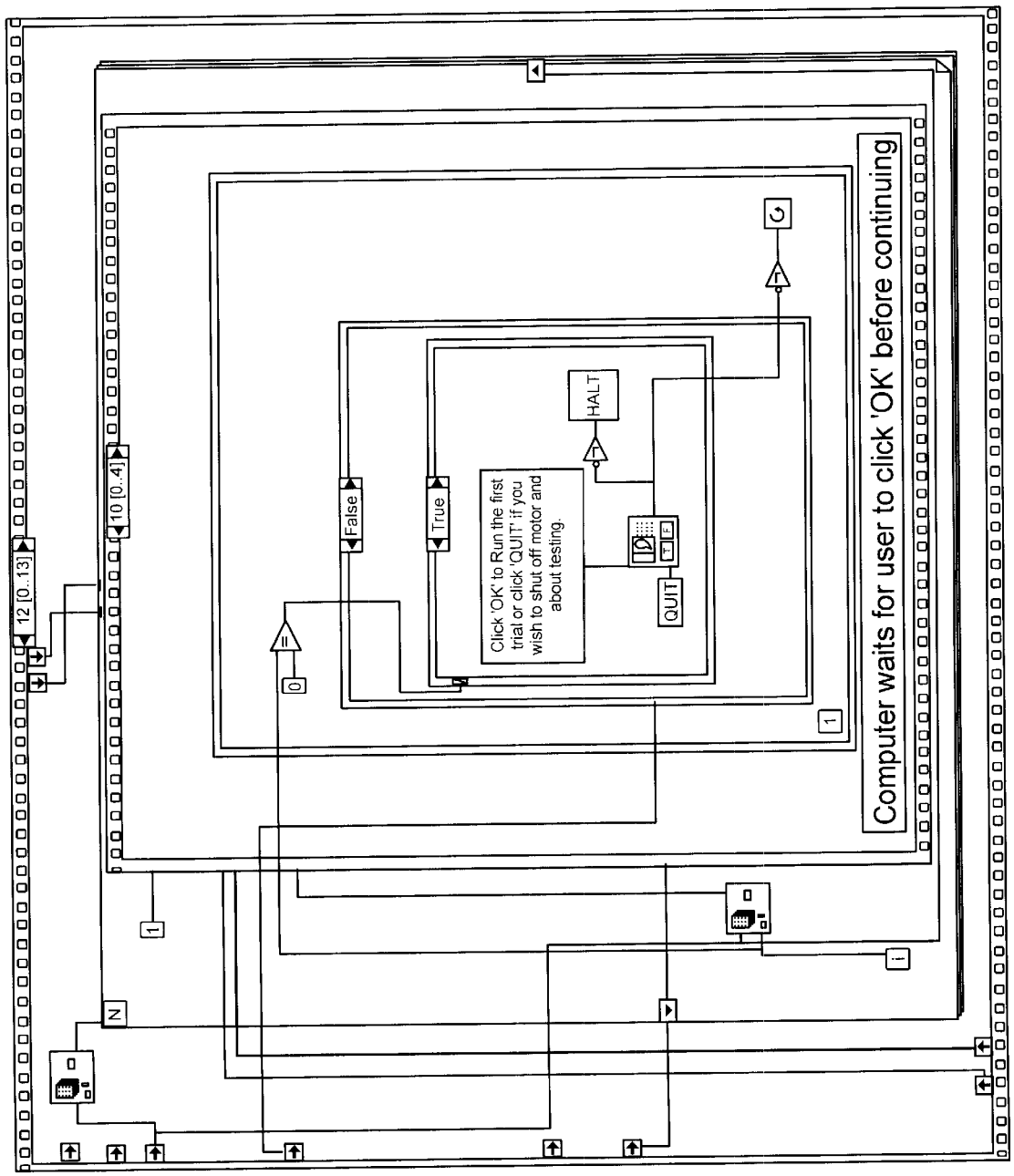
Figure 78:
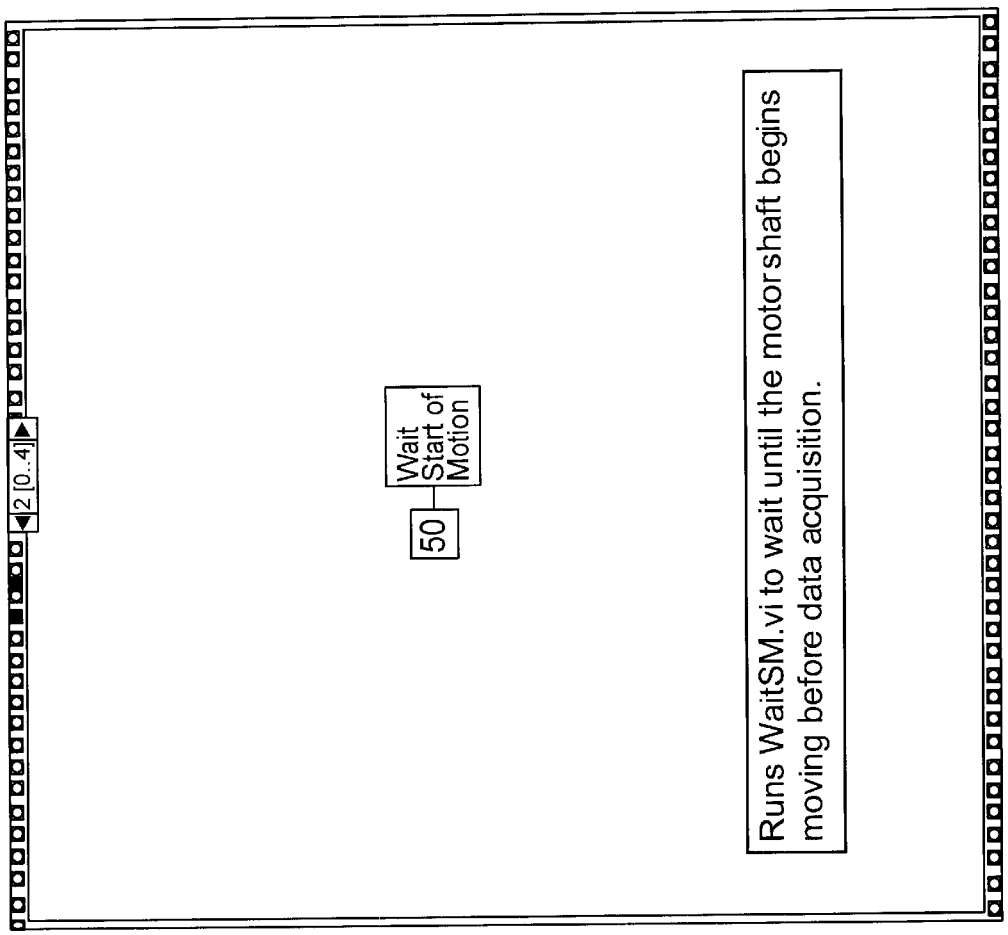
Figure 77:
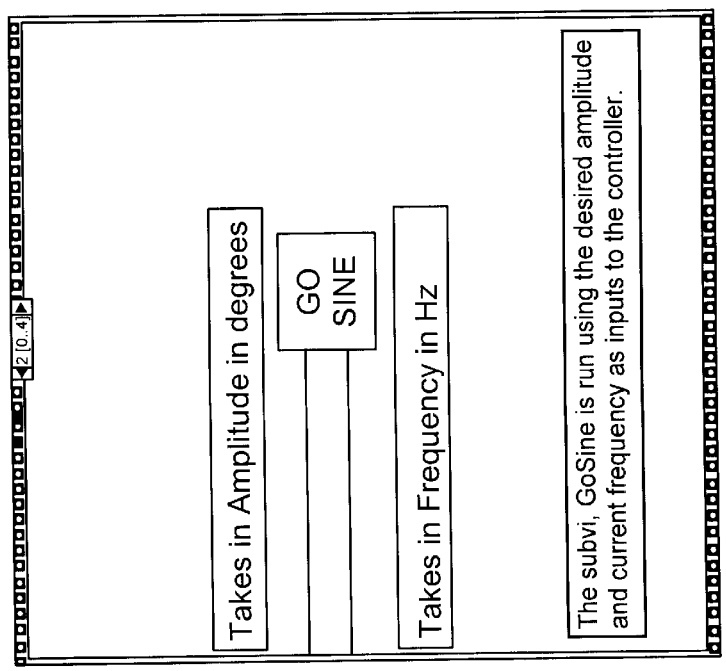
Figure 79:
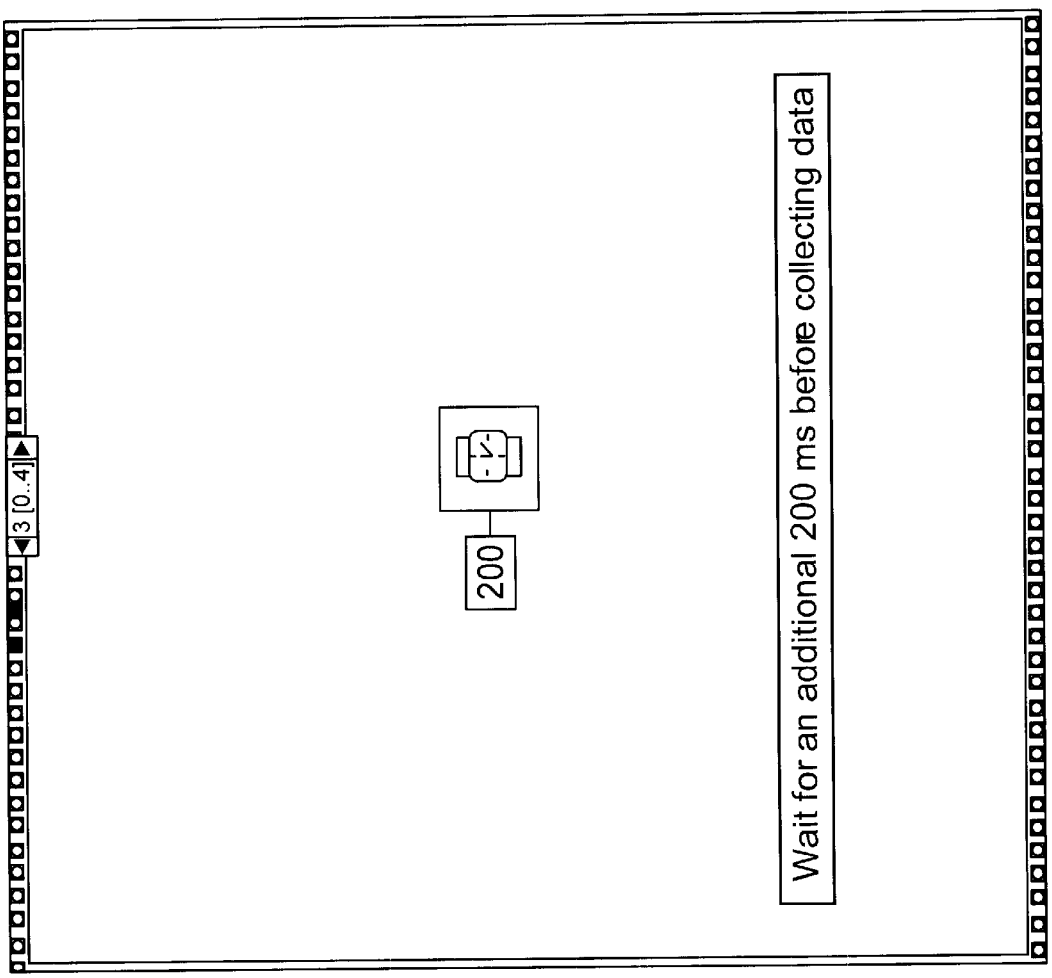
Figure 80:
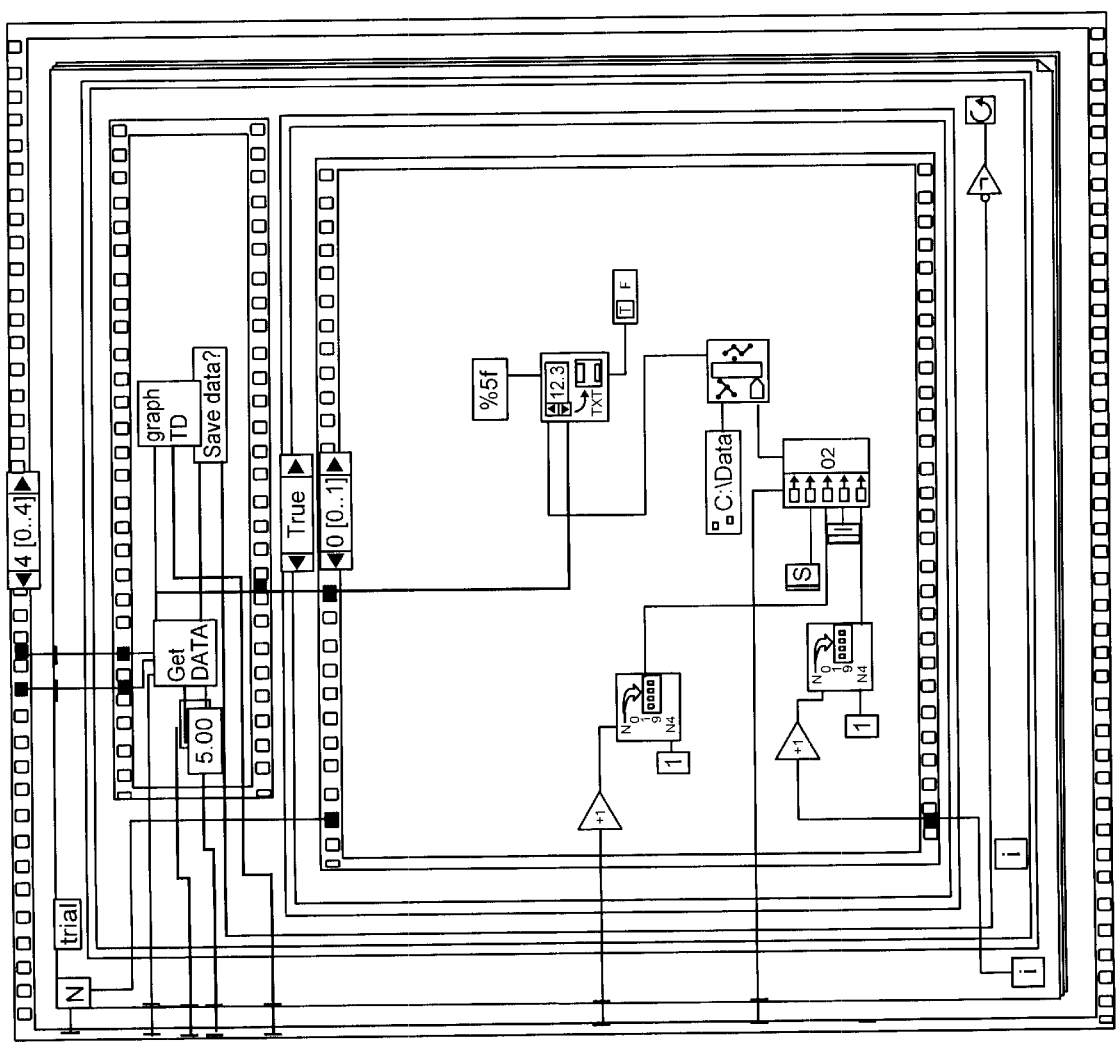
Figure 82:
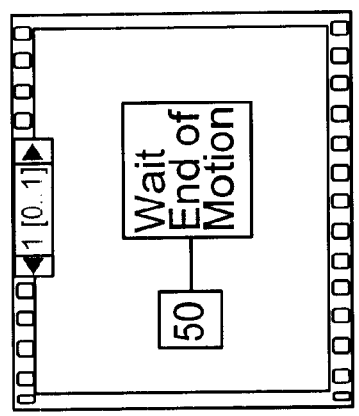
Figure 81:
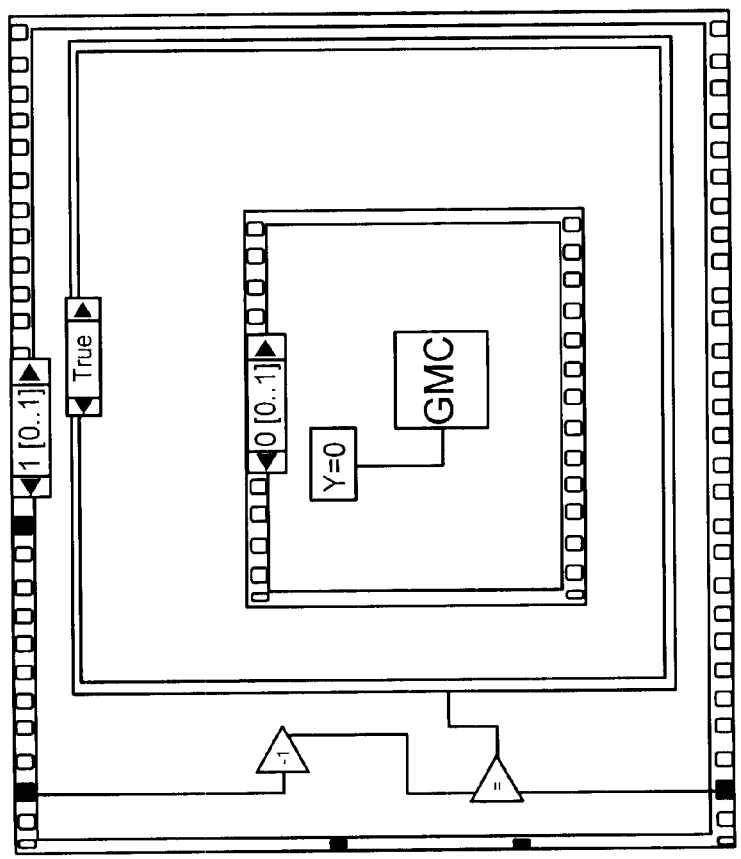
Figure 83:
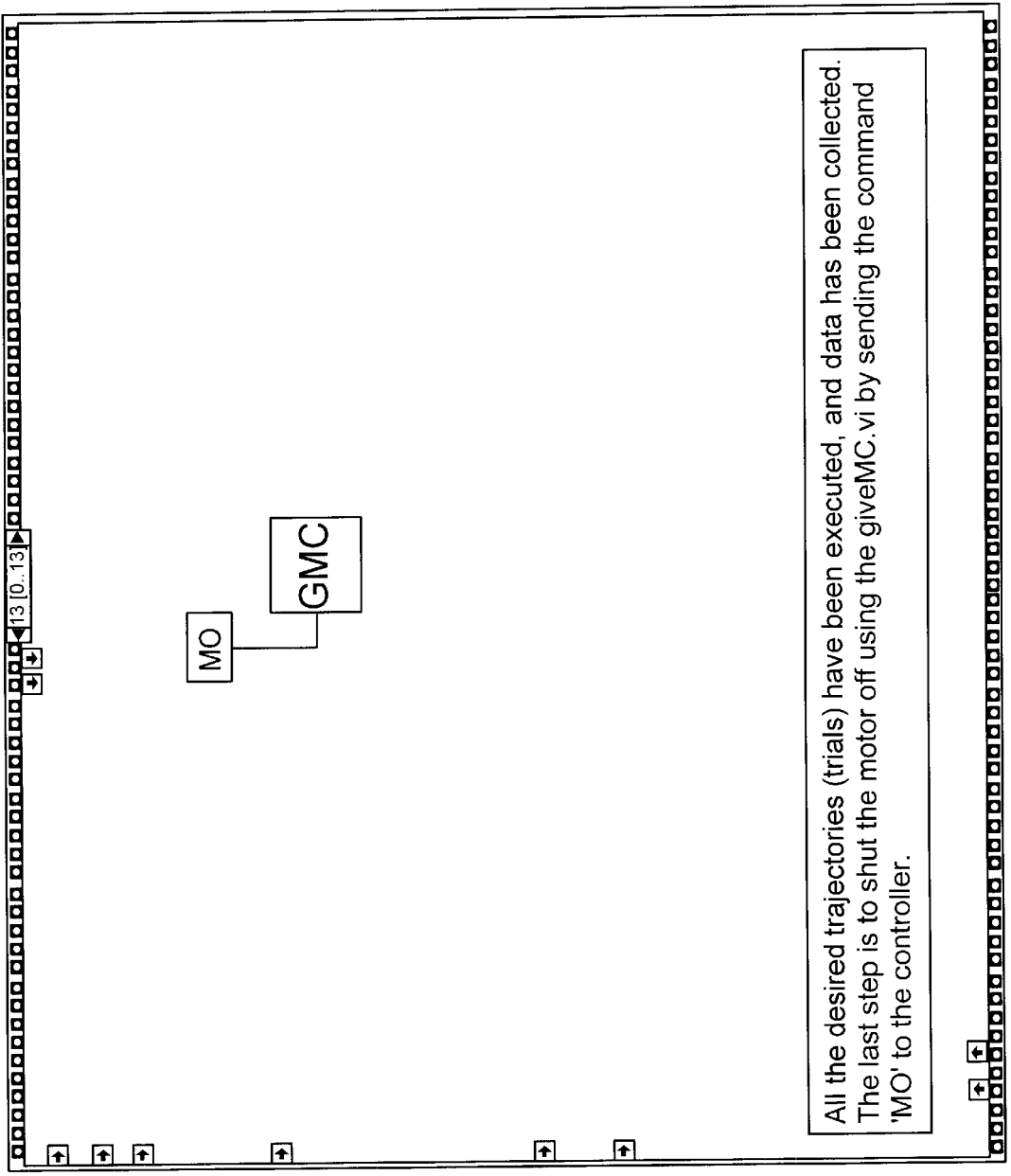
Figure 85:
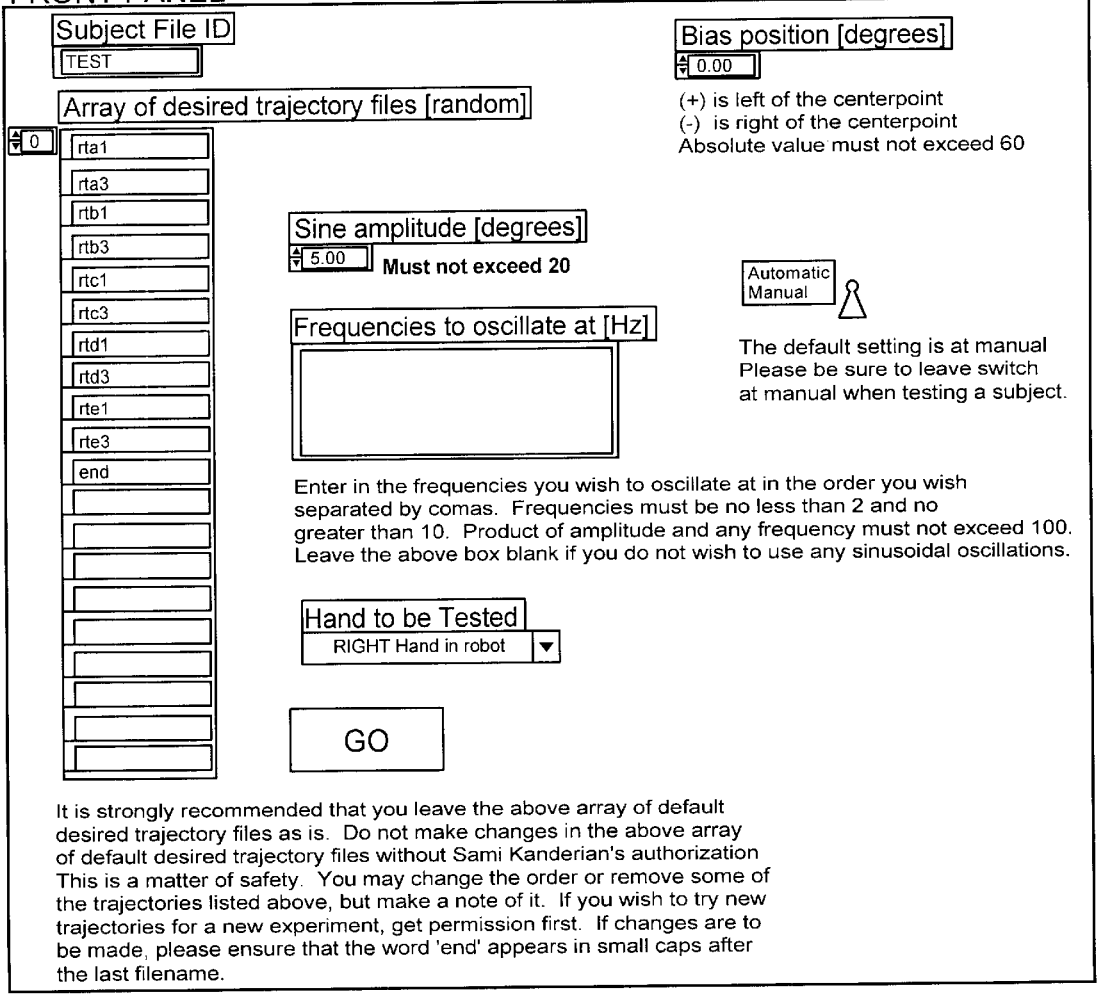
Figure 86:
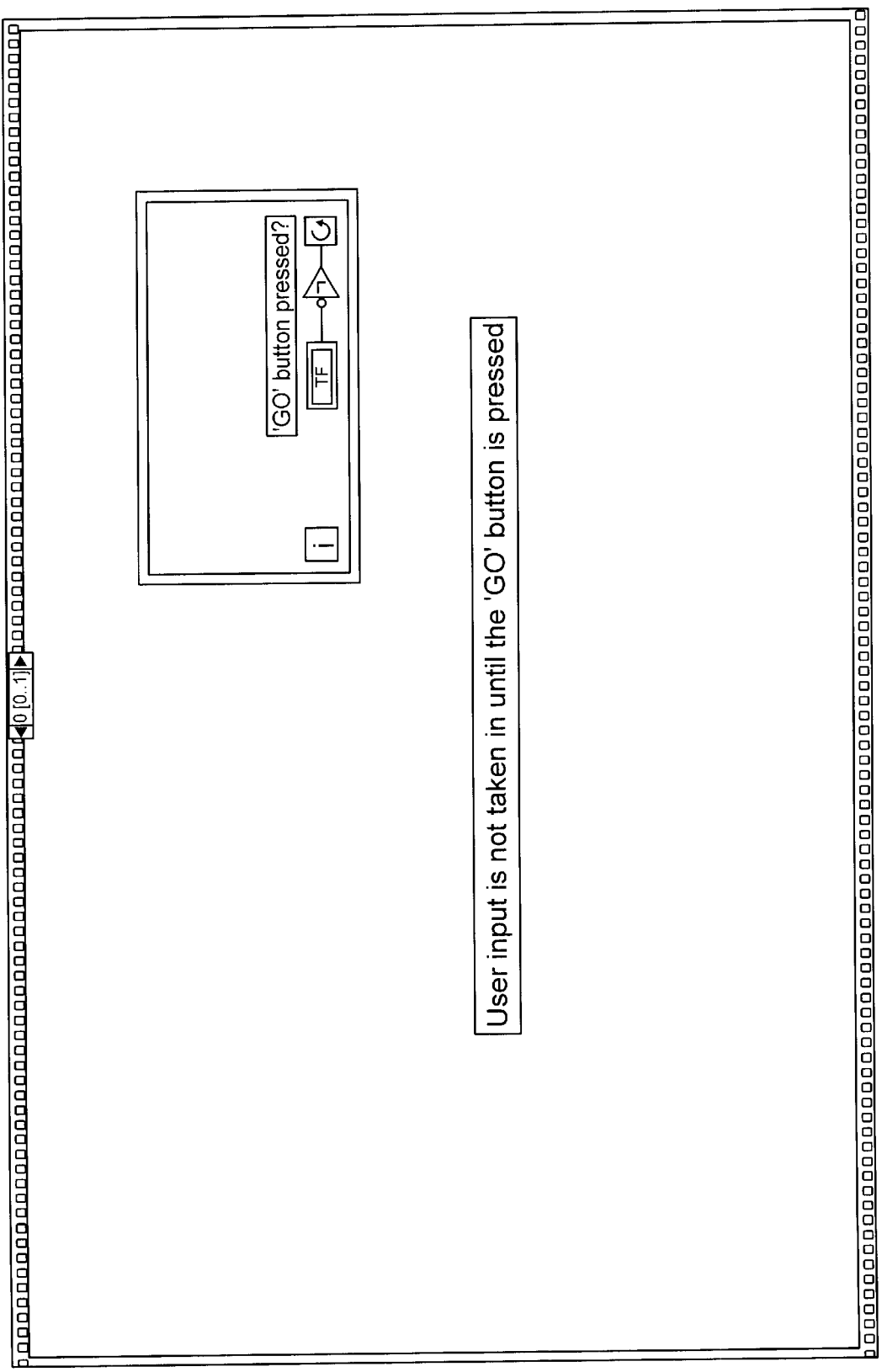
Figure 87:
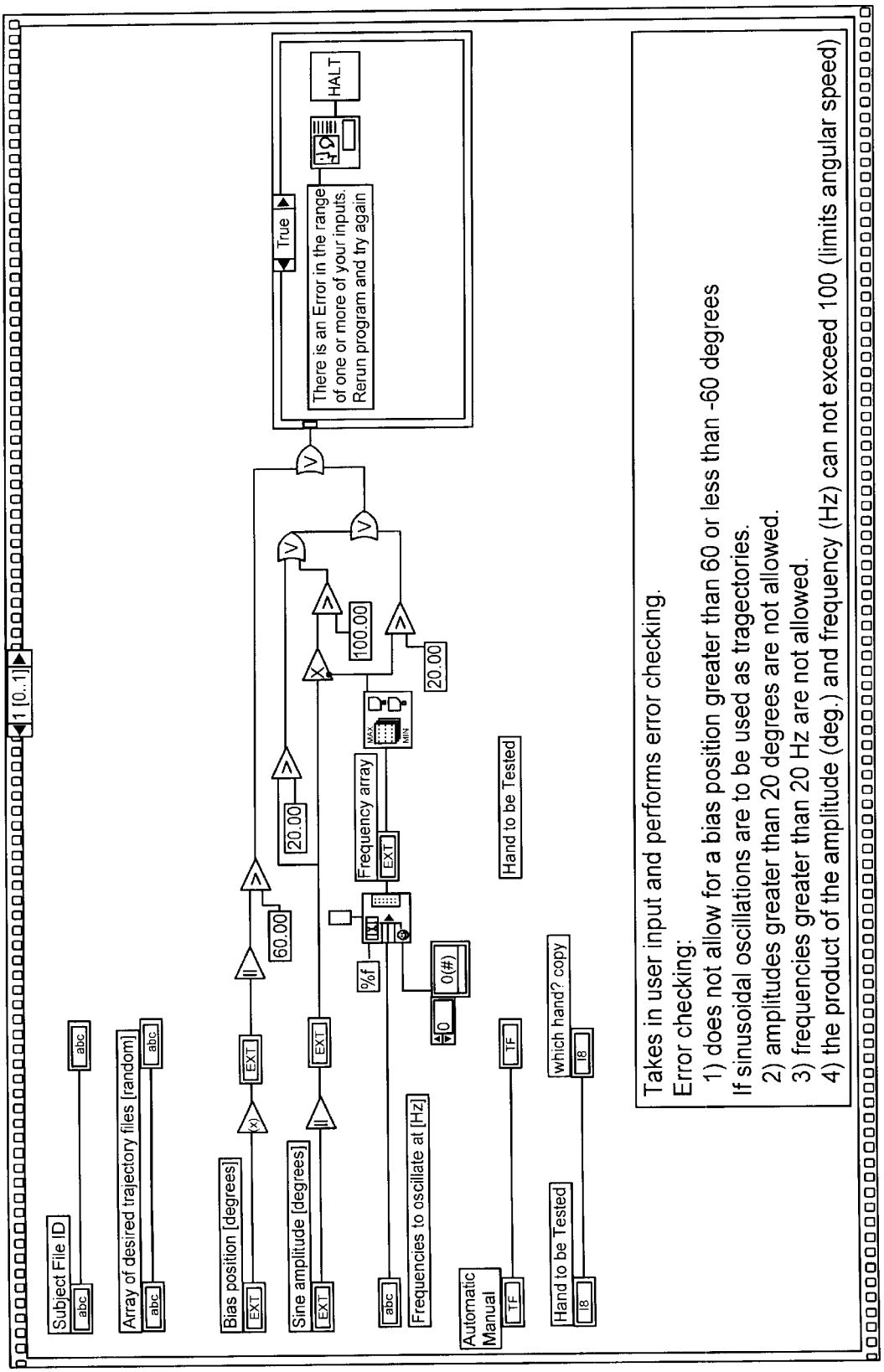
Figure 88:
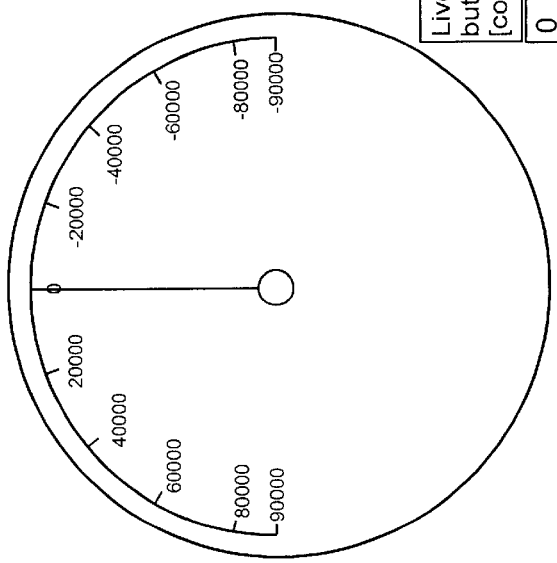
Figure 89:
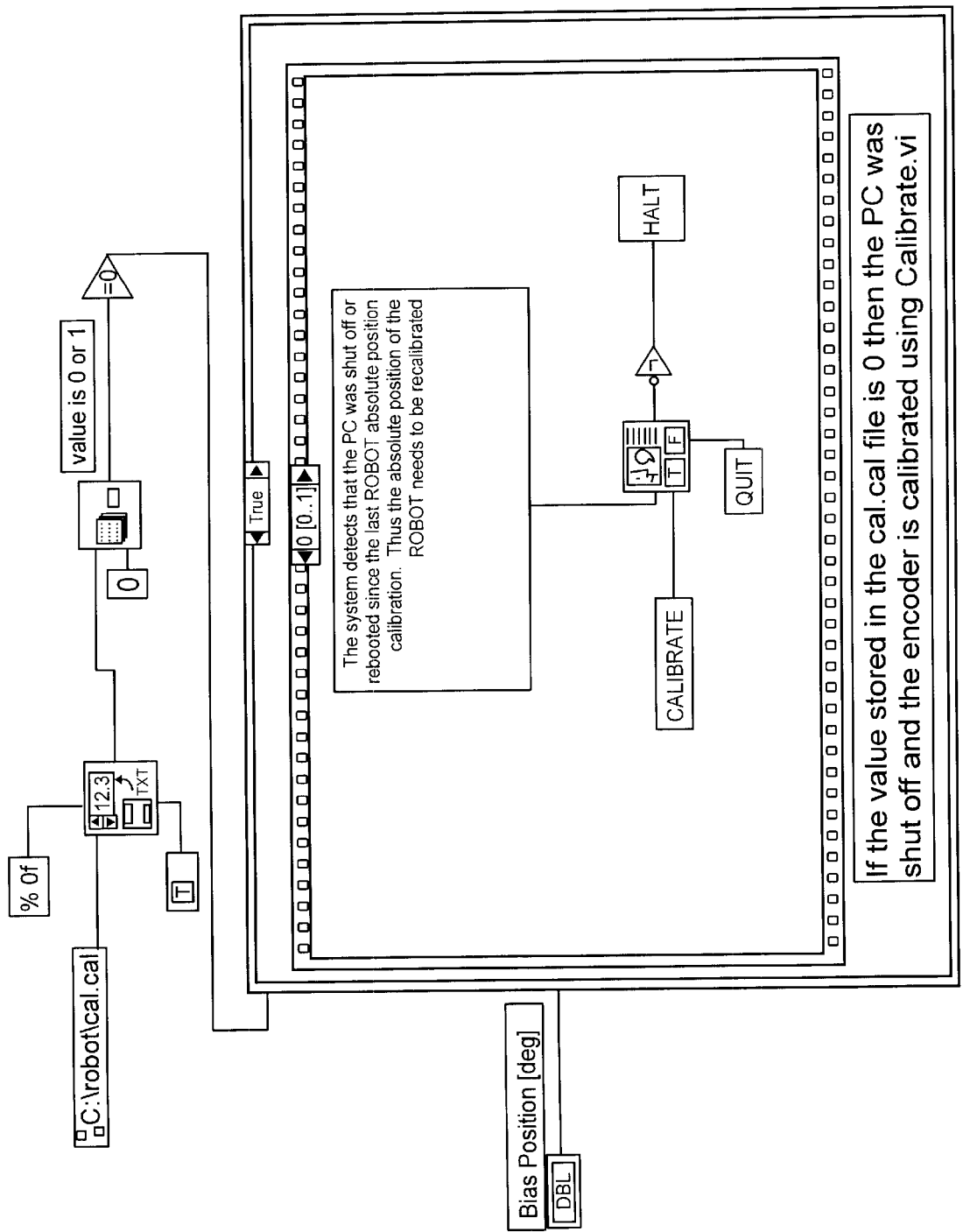
Figure 90:
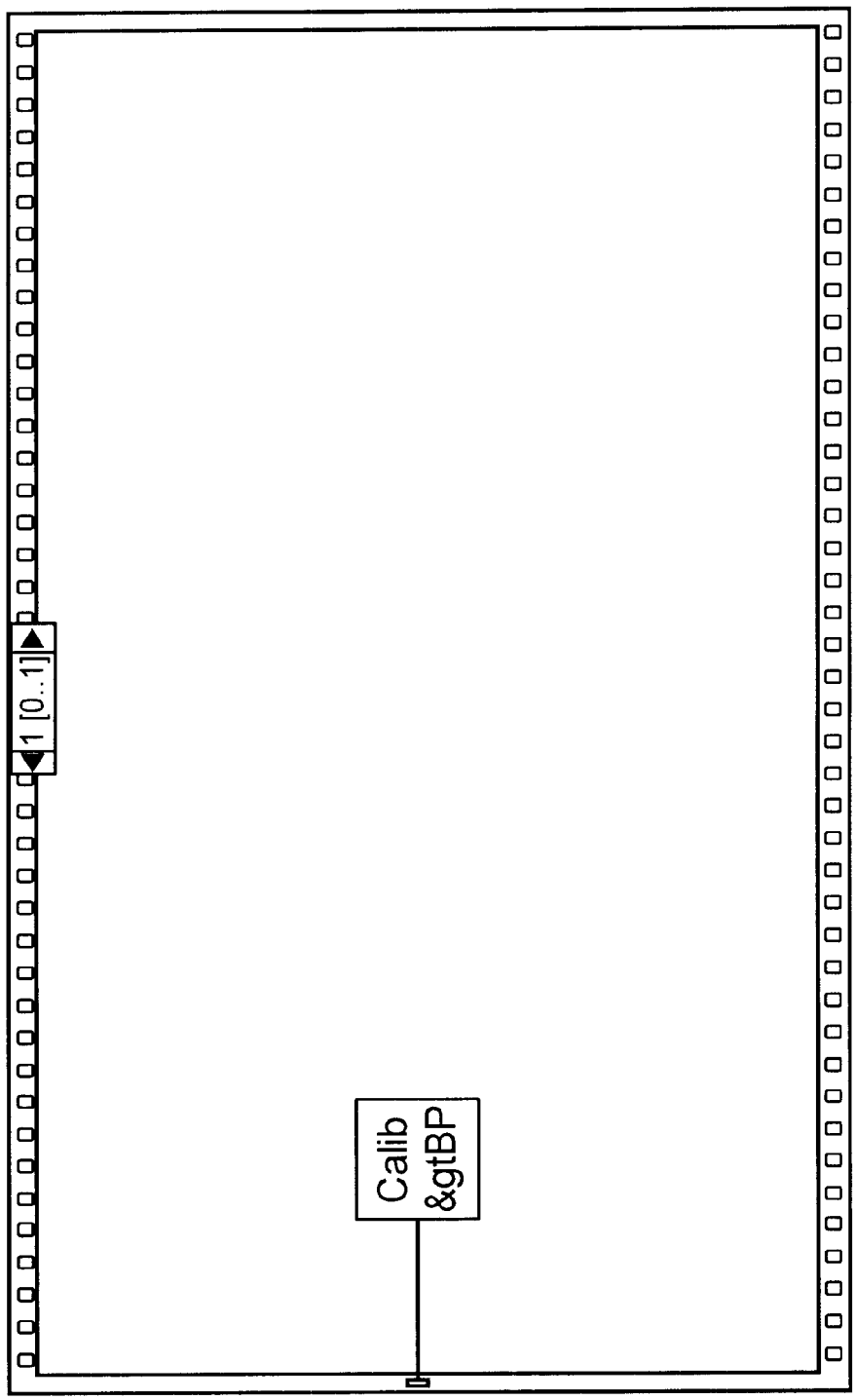
Figure 91:
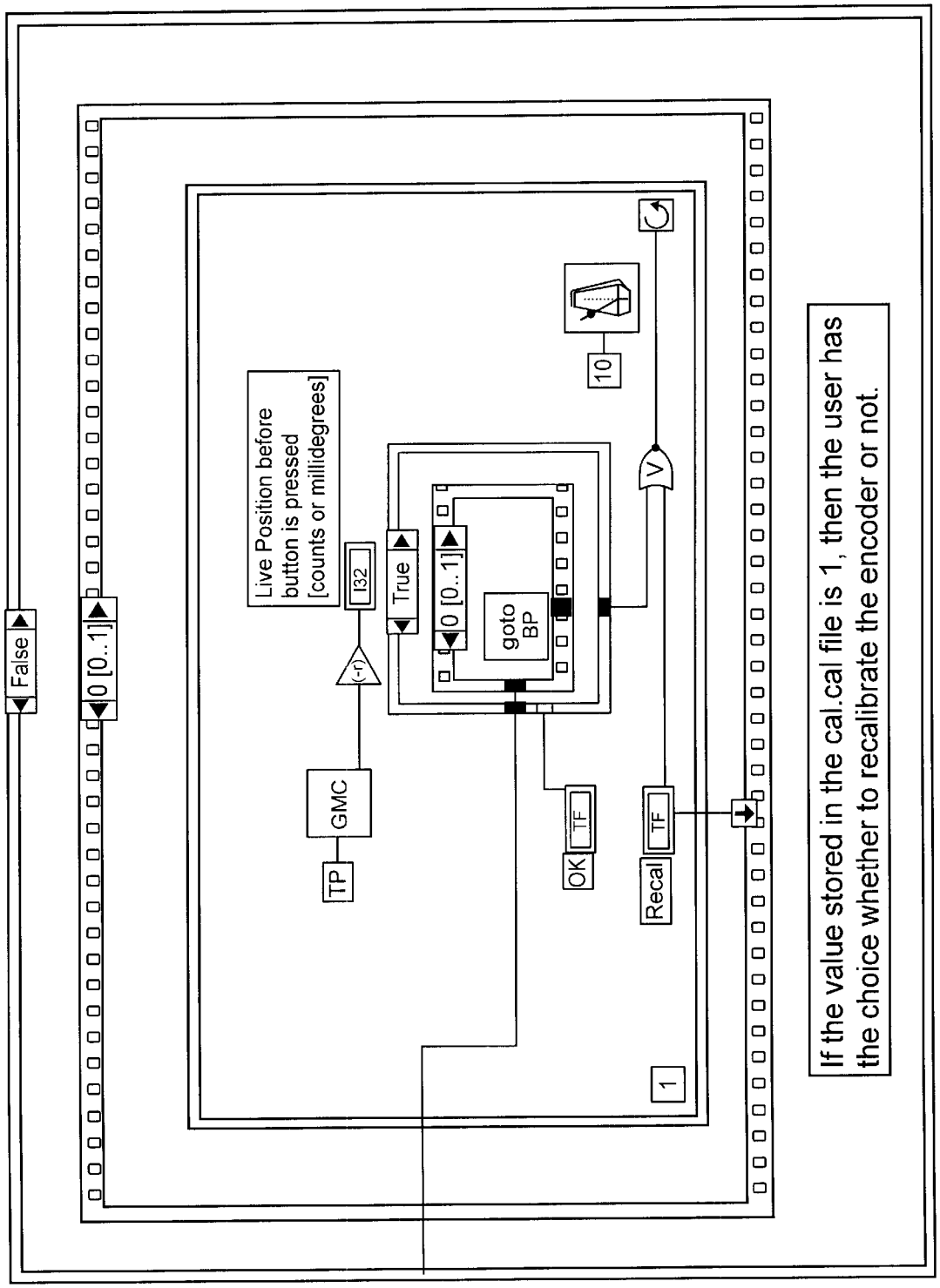
Figure 92:
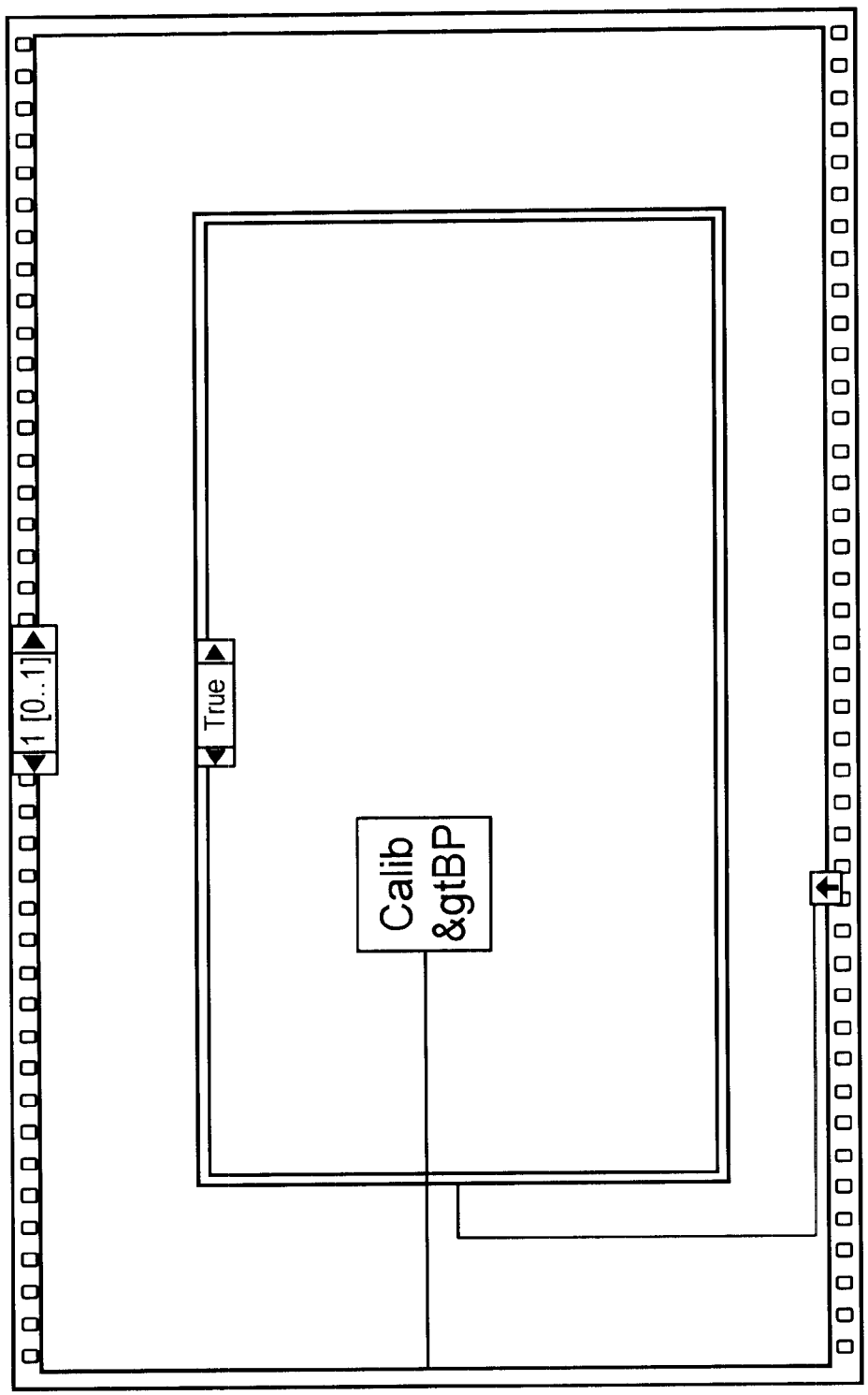
Figure 93:
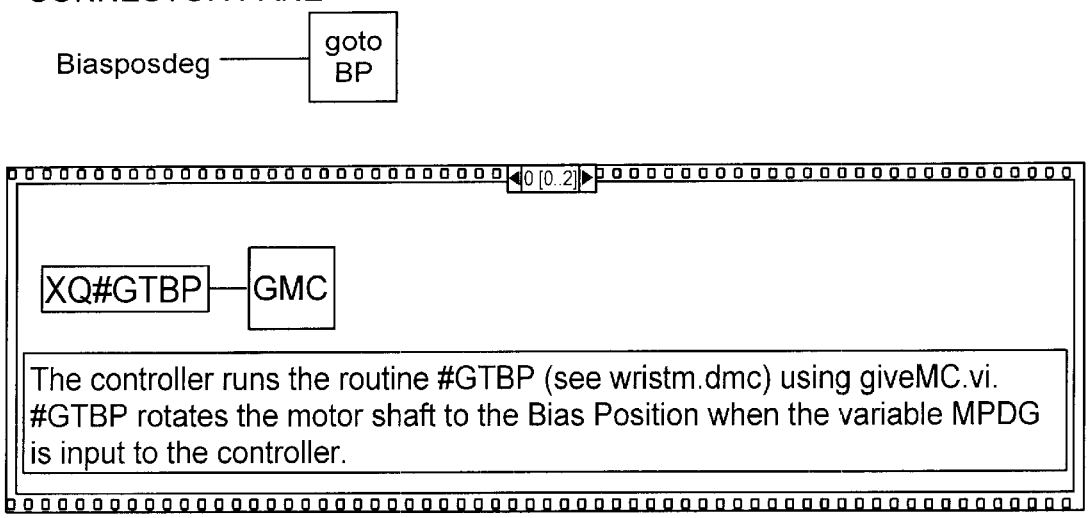
Figure 94:
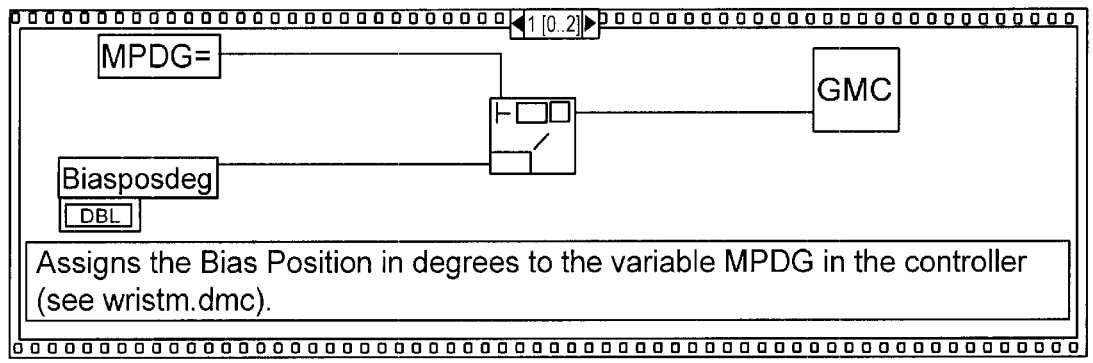
Figure 95:
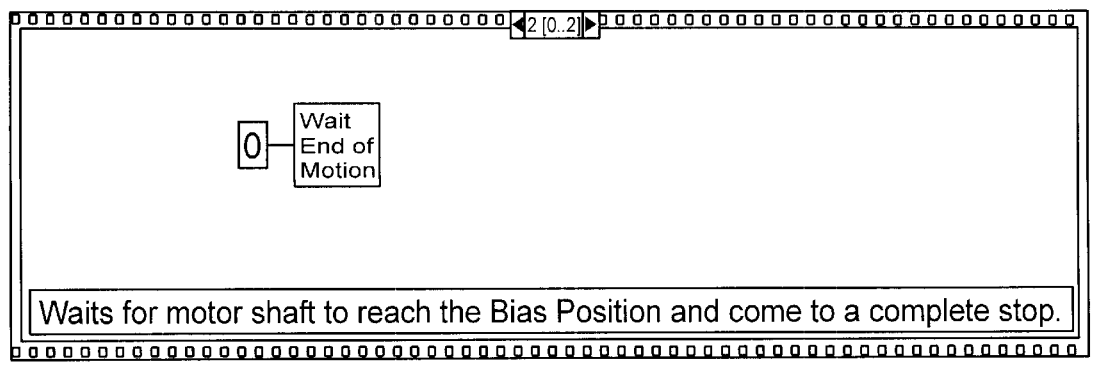
Figure 99:
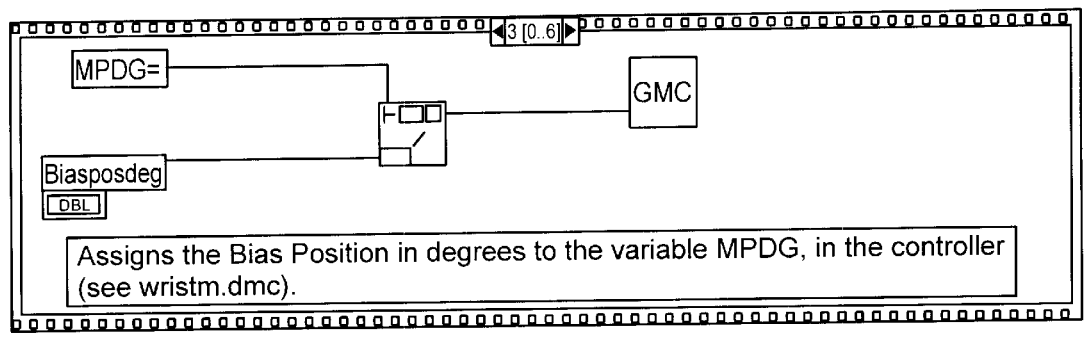
Figure 100:
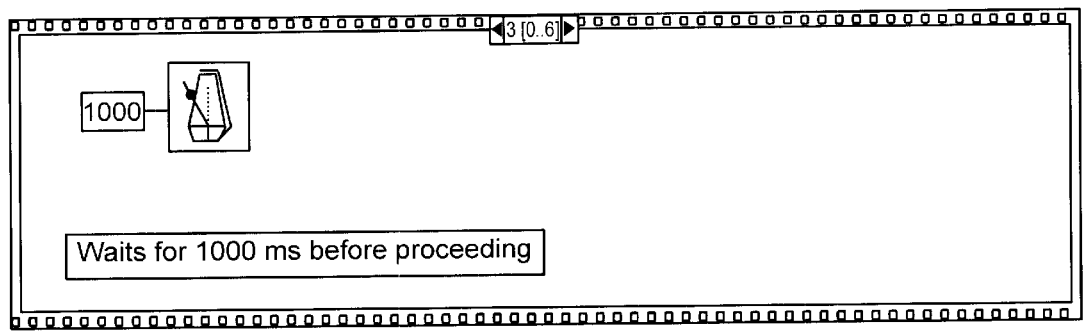
Figure 101:
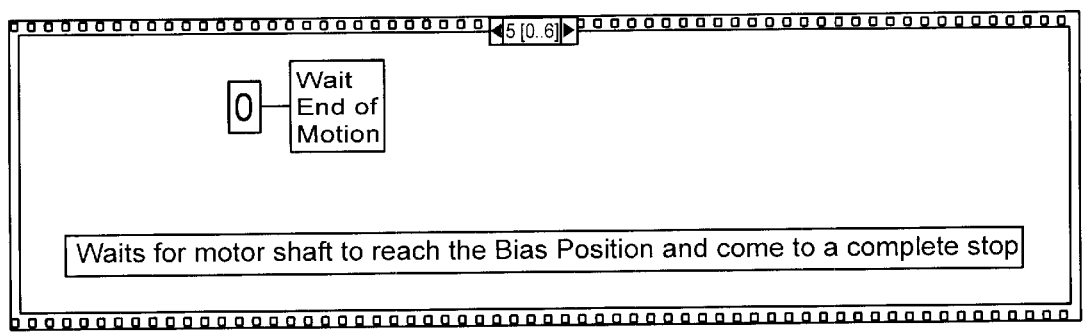
Figure 102:
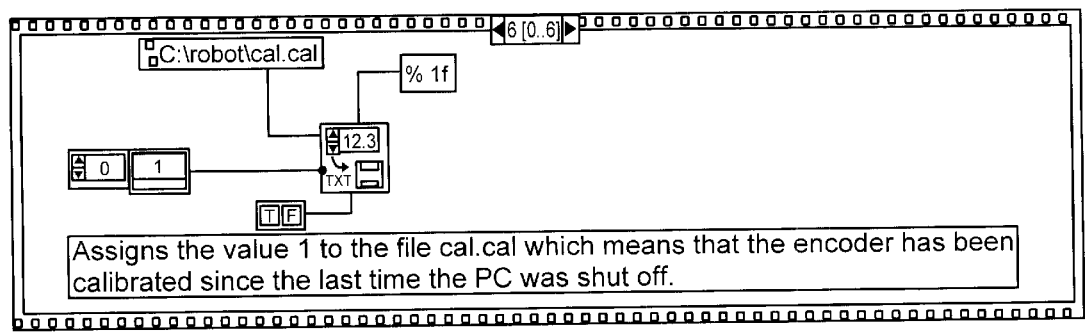
Figure 103:
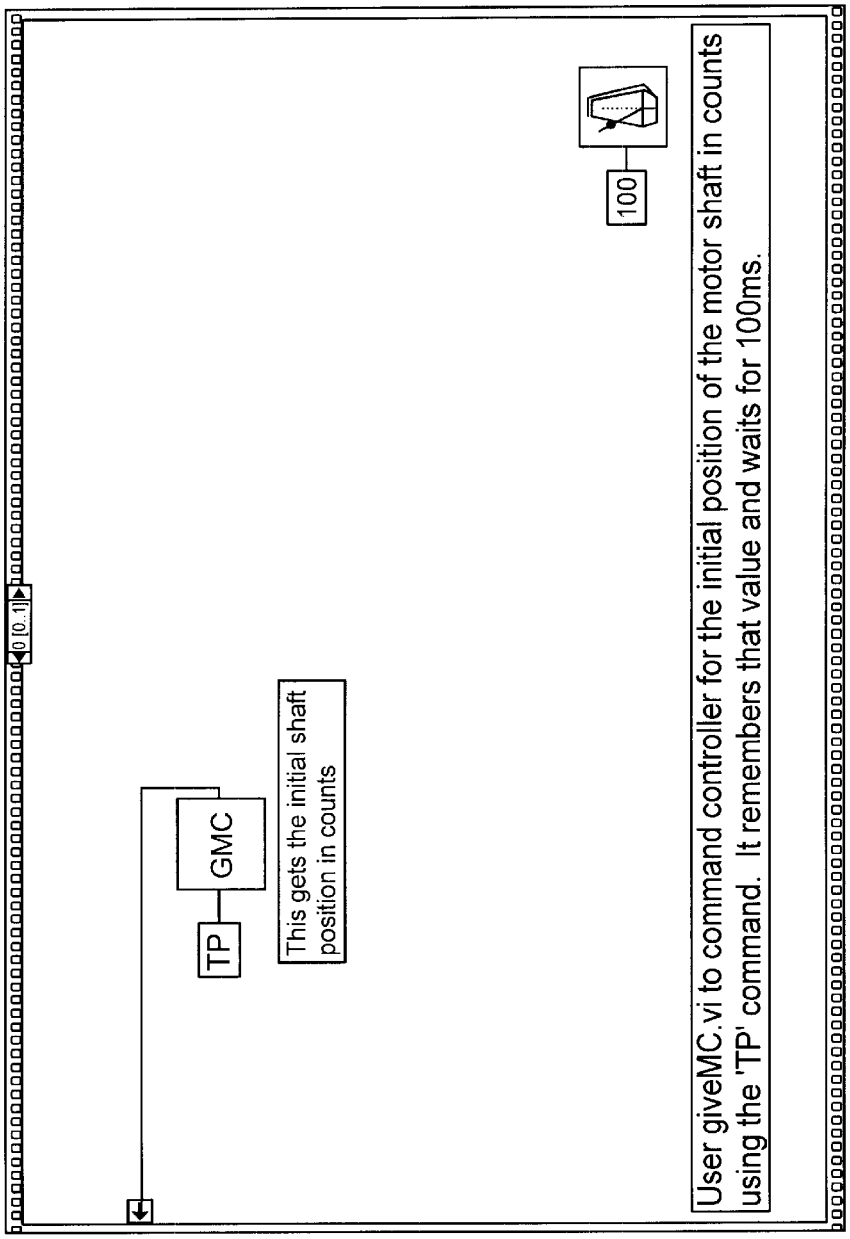
Figure 104:
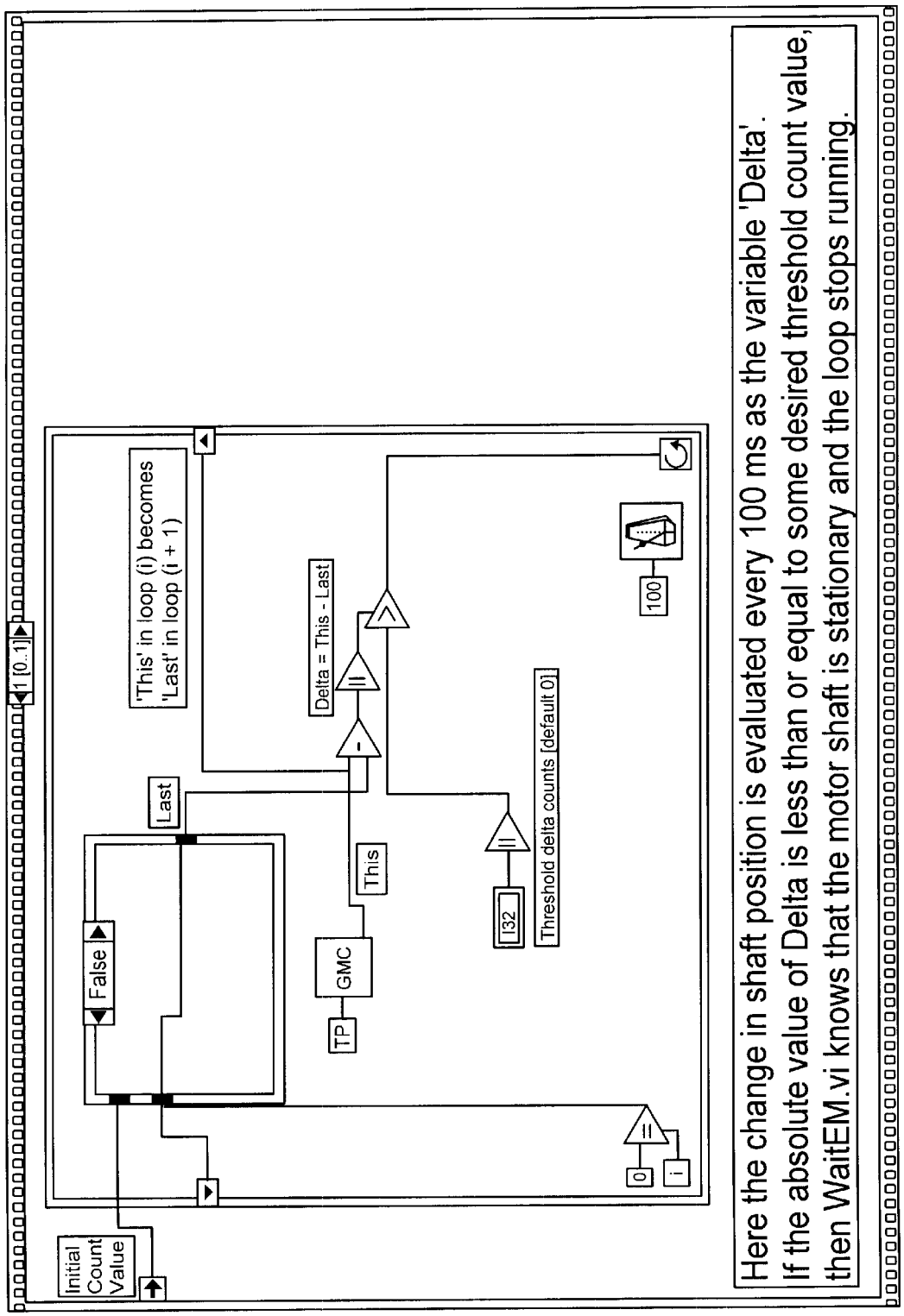
Figure 105:
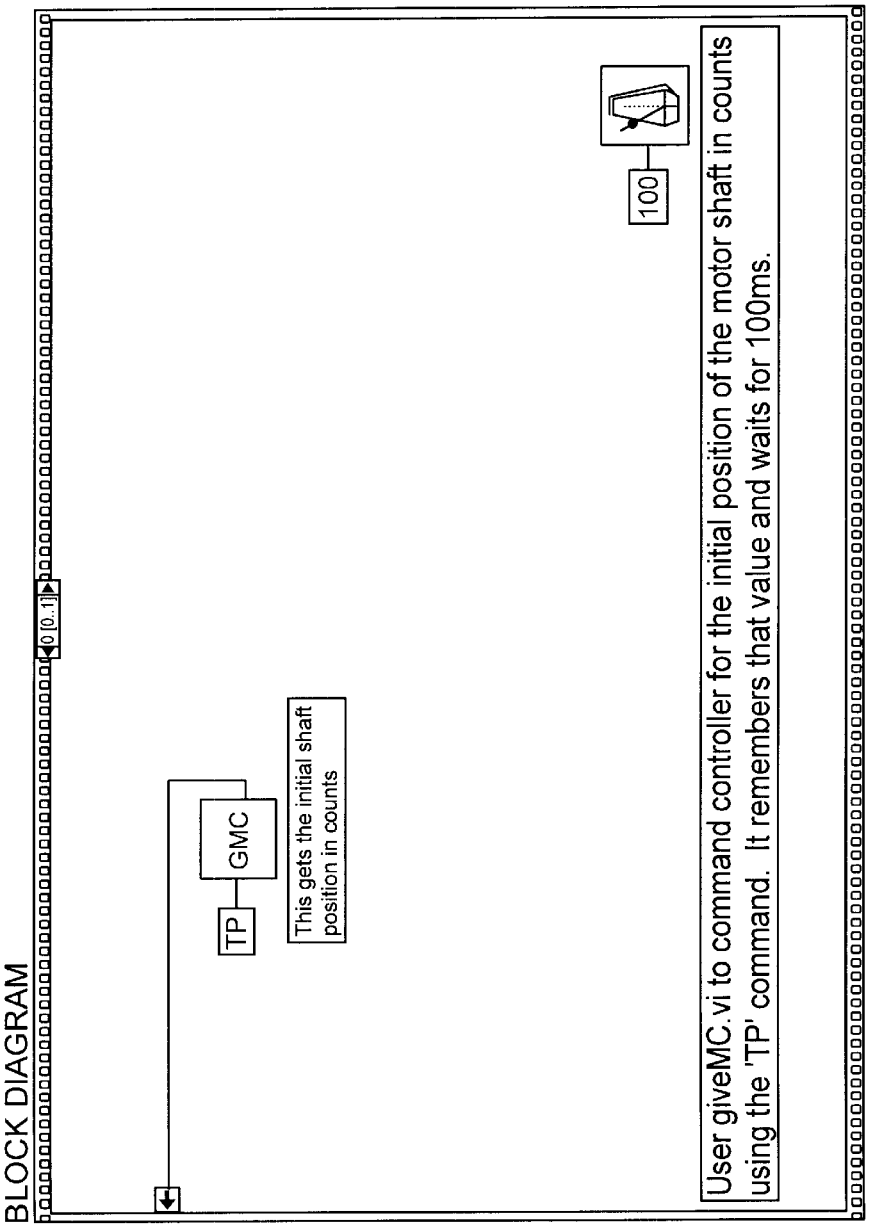
Figure 106:
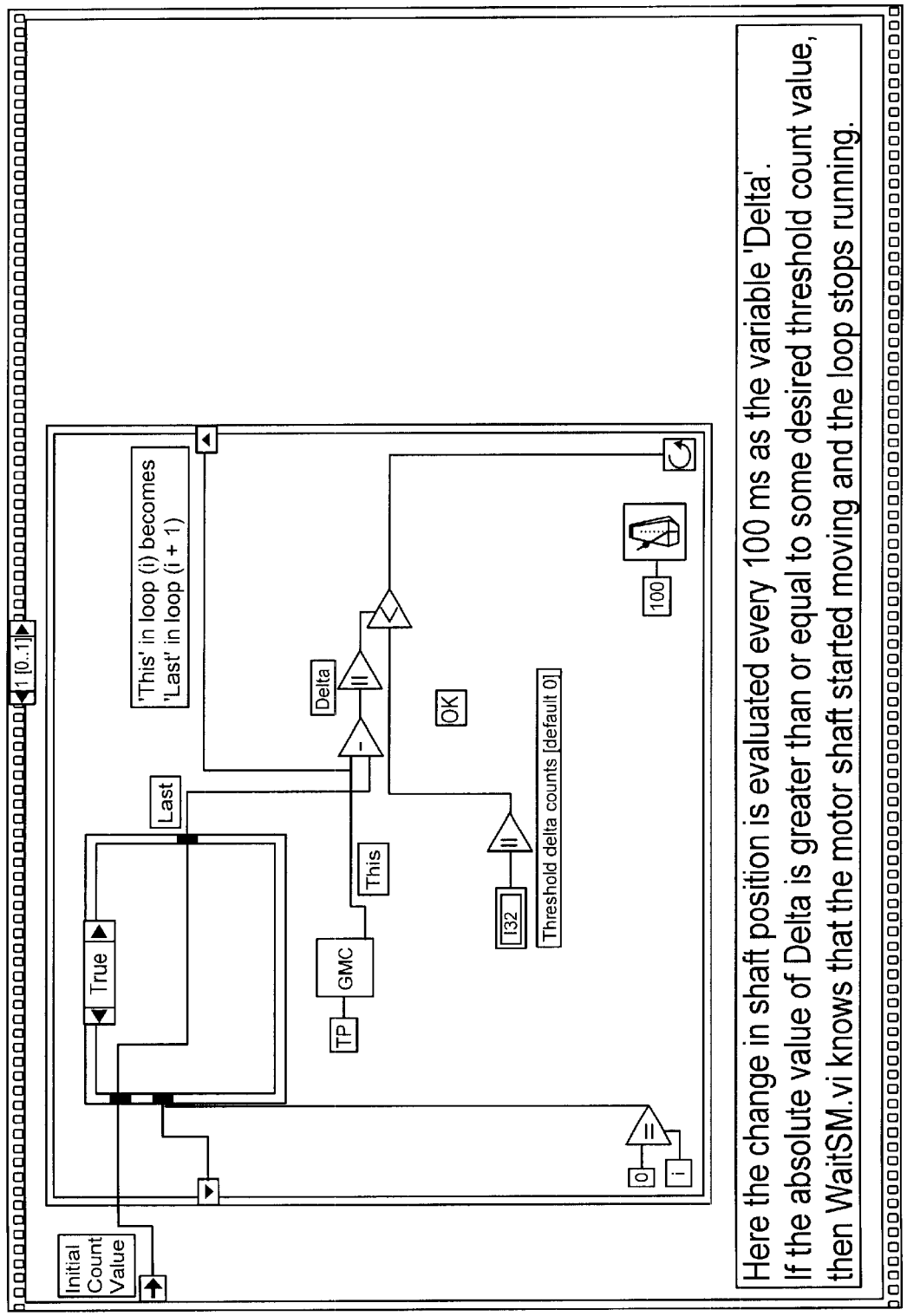
Figure 107:
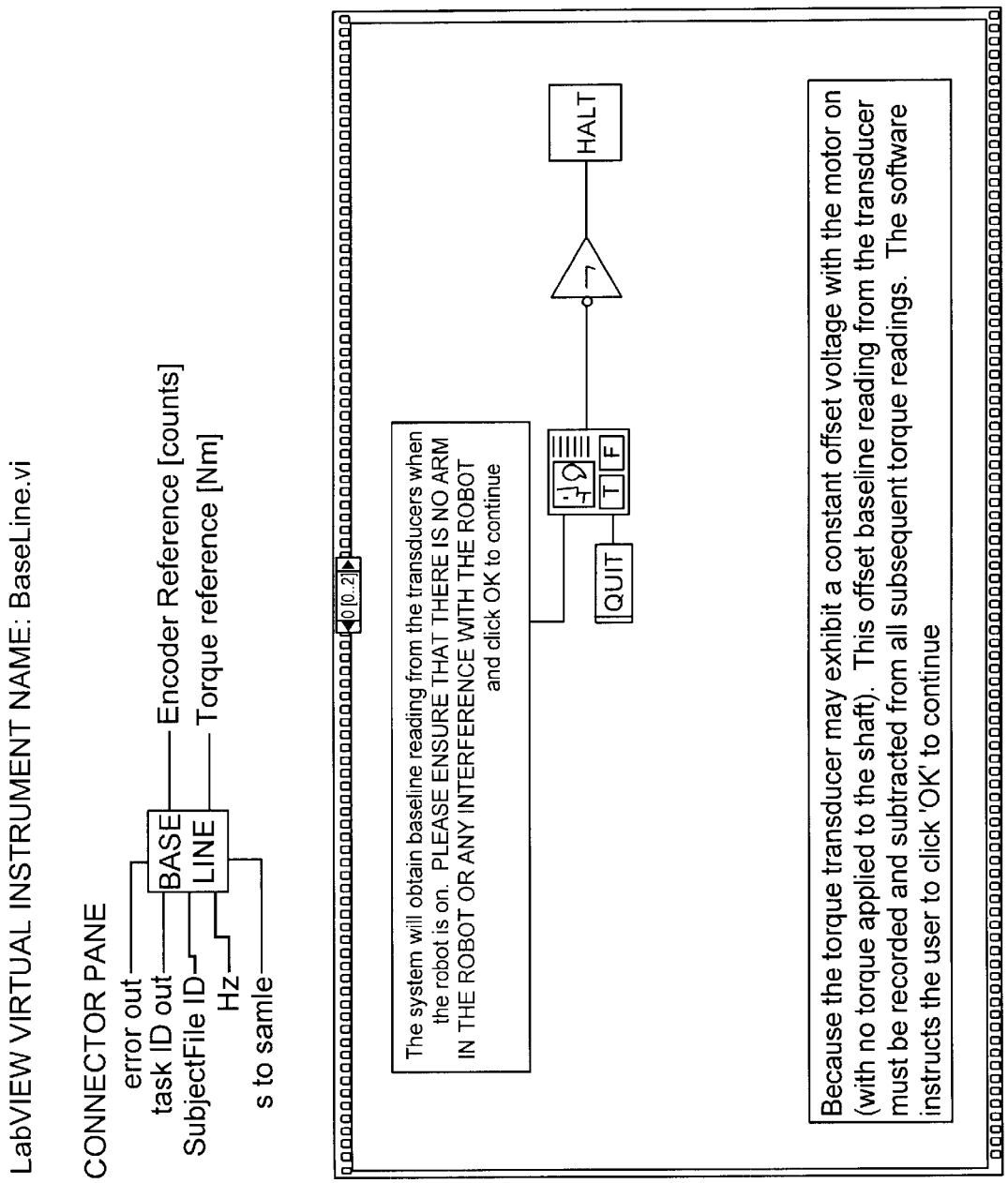
Figure 108:
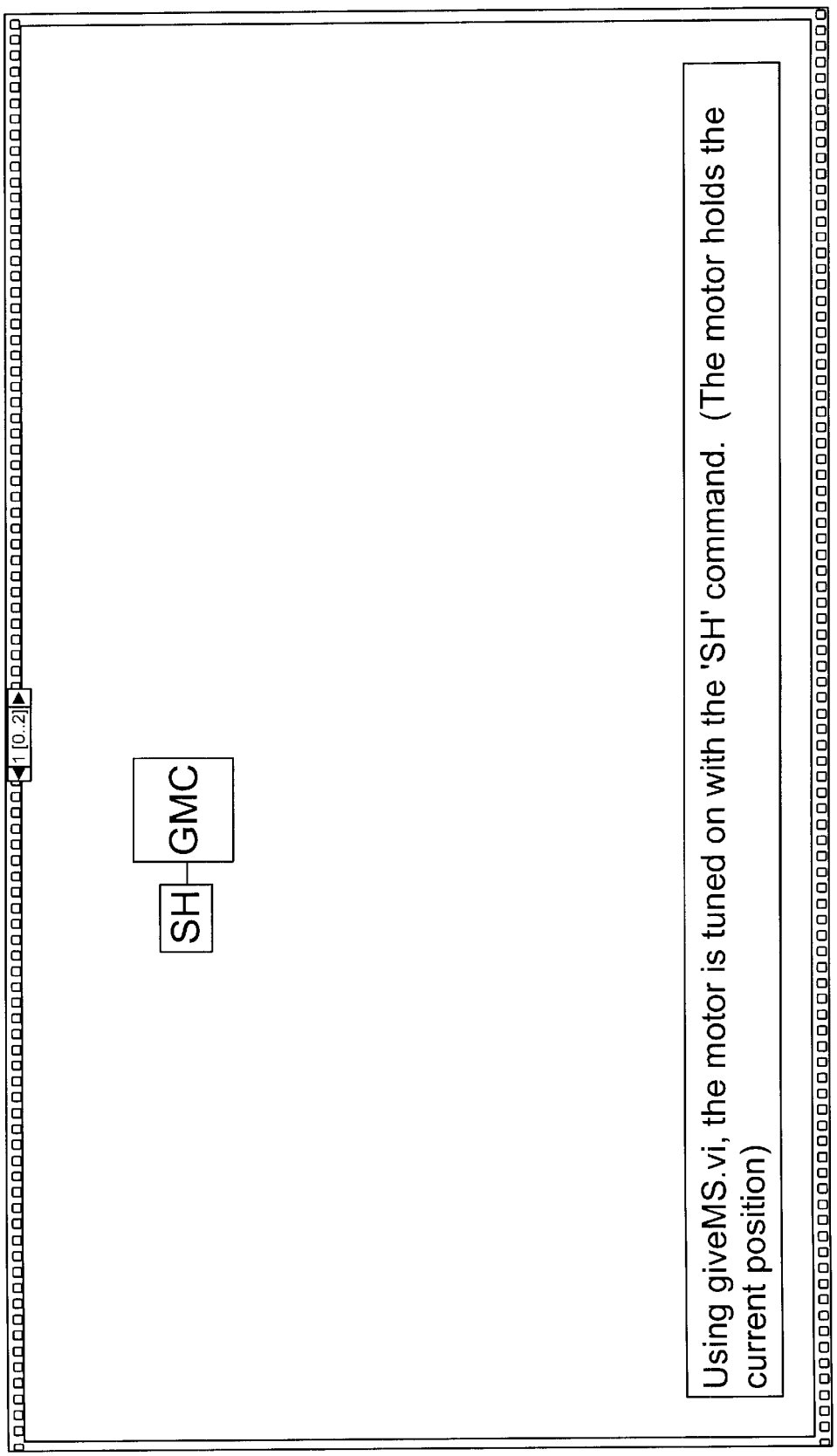
Figure 109:
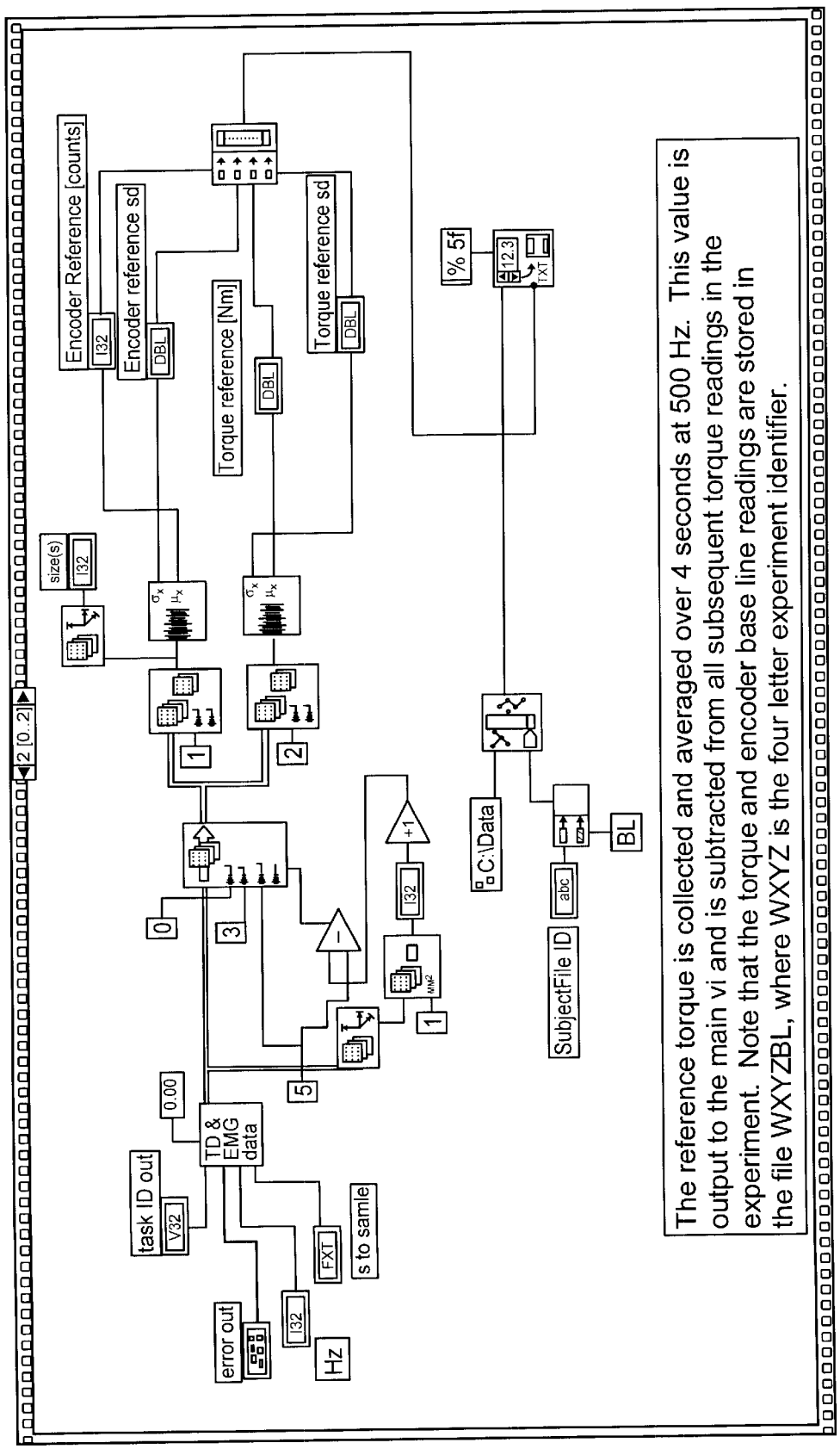
Figure 110:
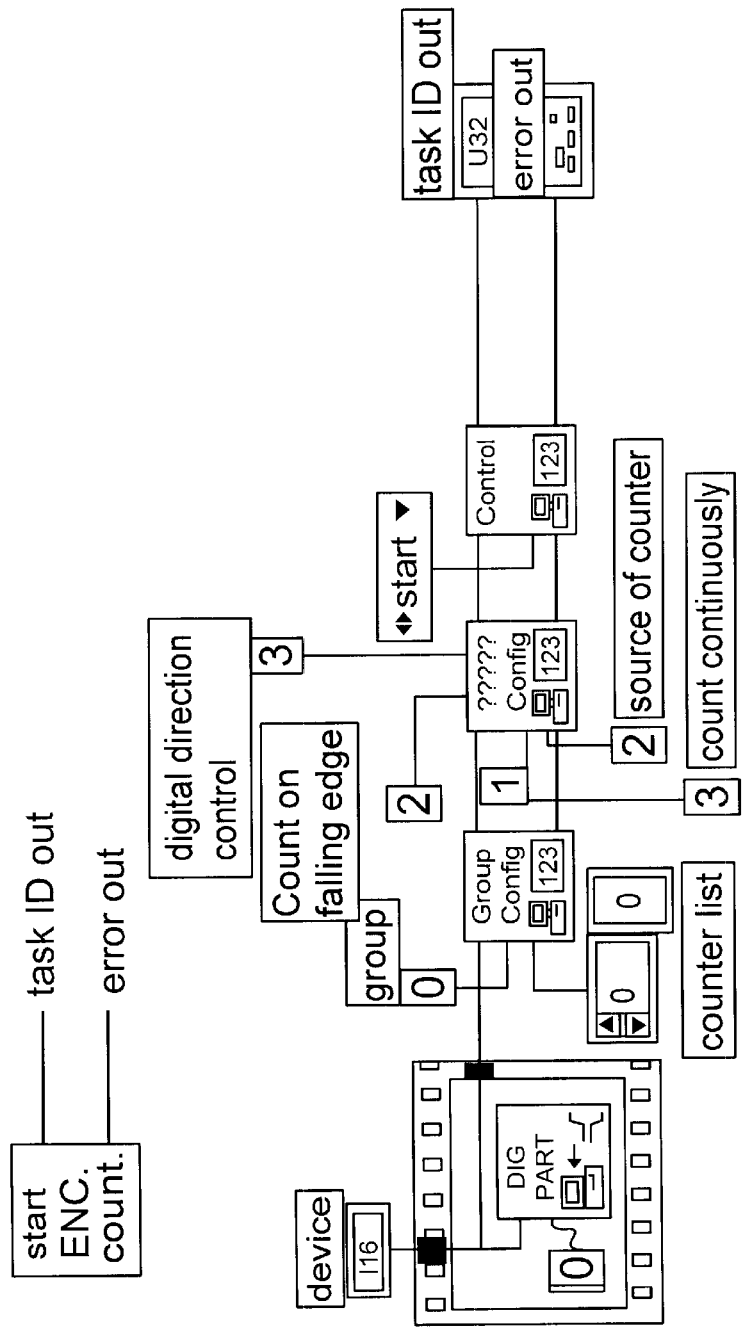
Figure 113:
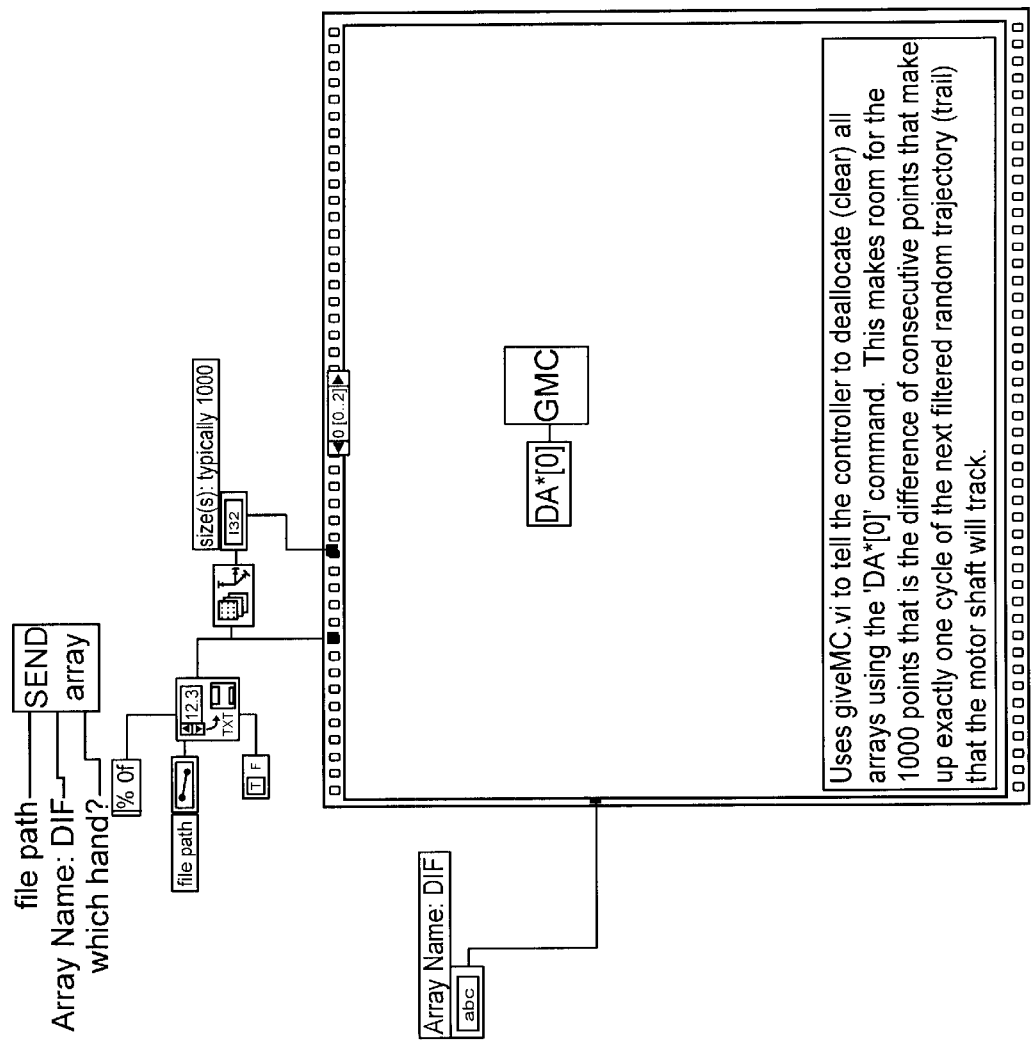
Figure 114:
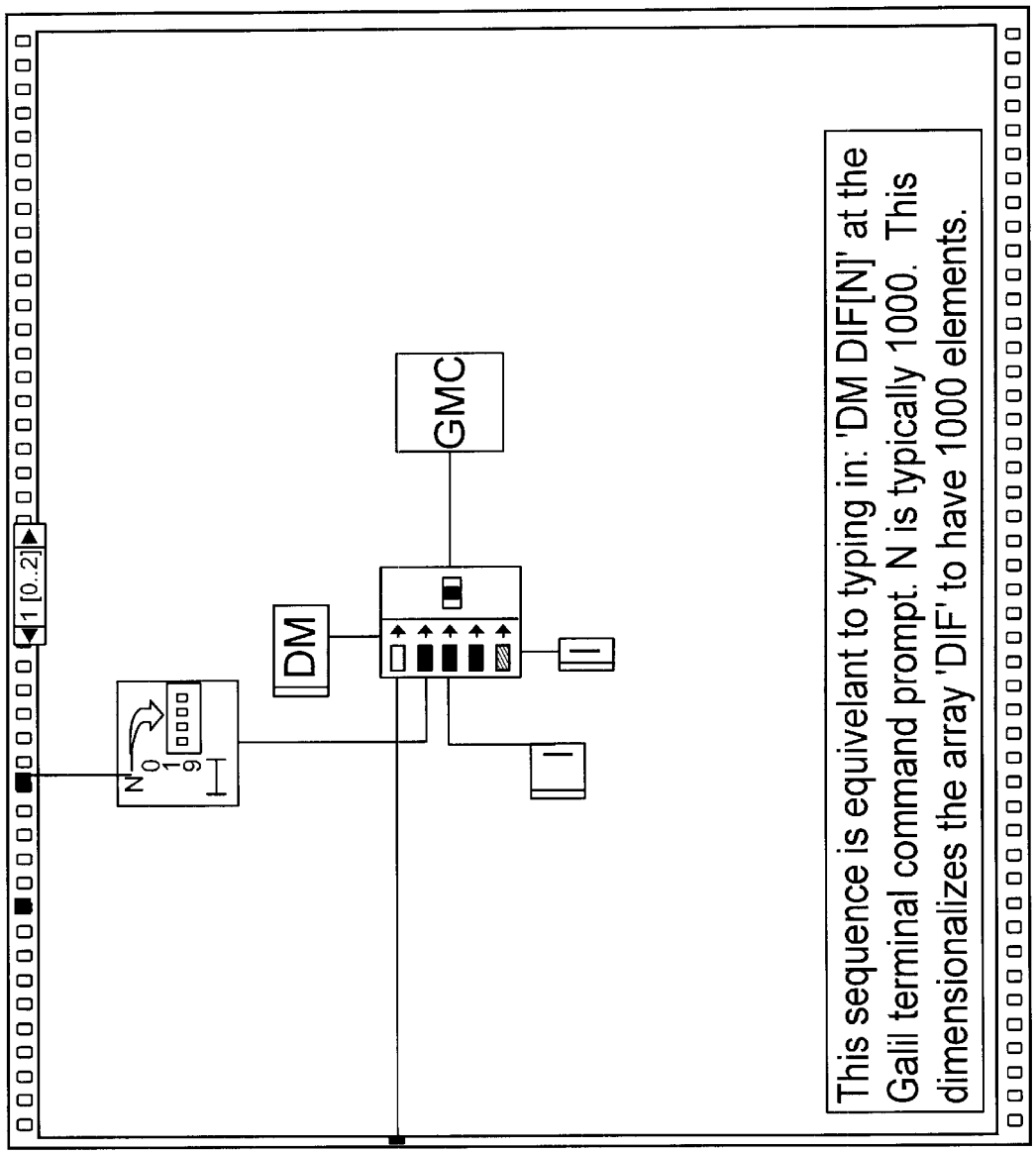
Figure 115:
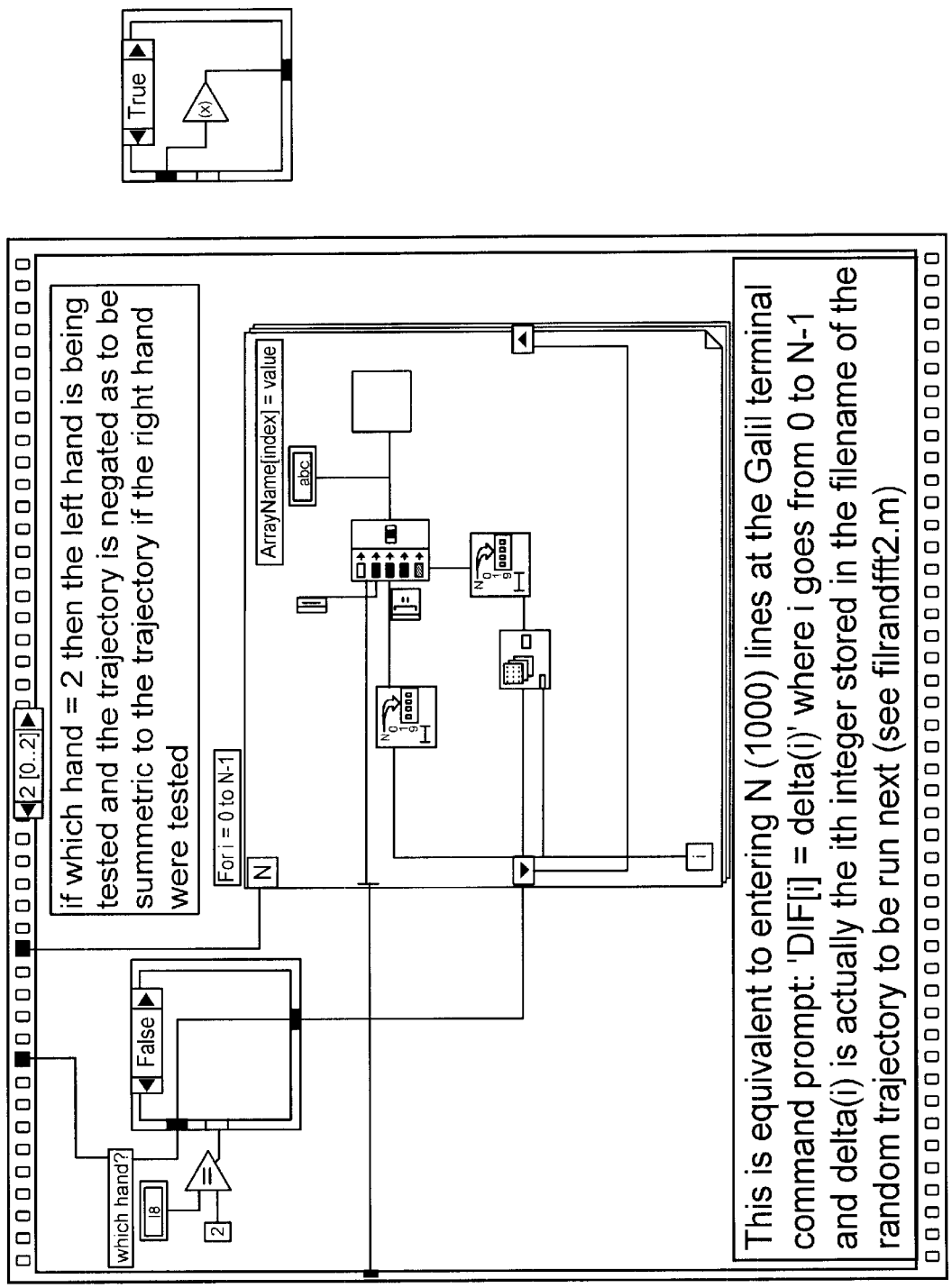
Figure 116:
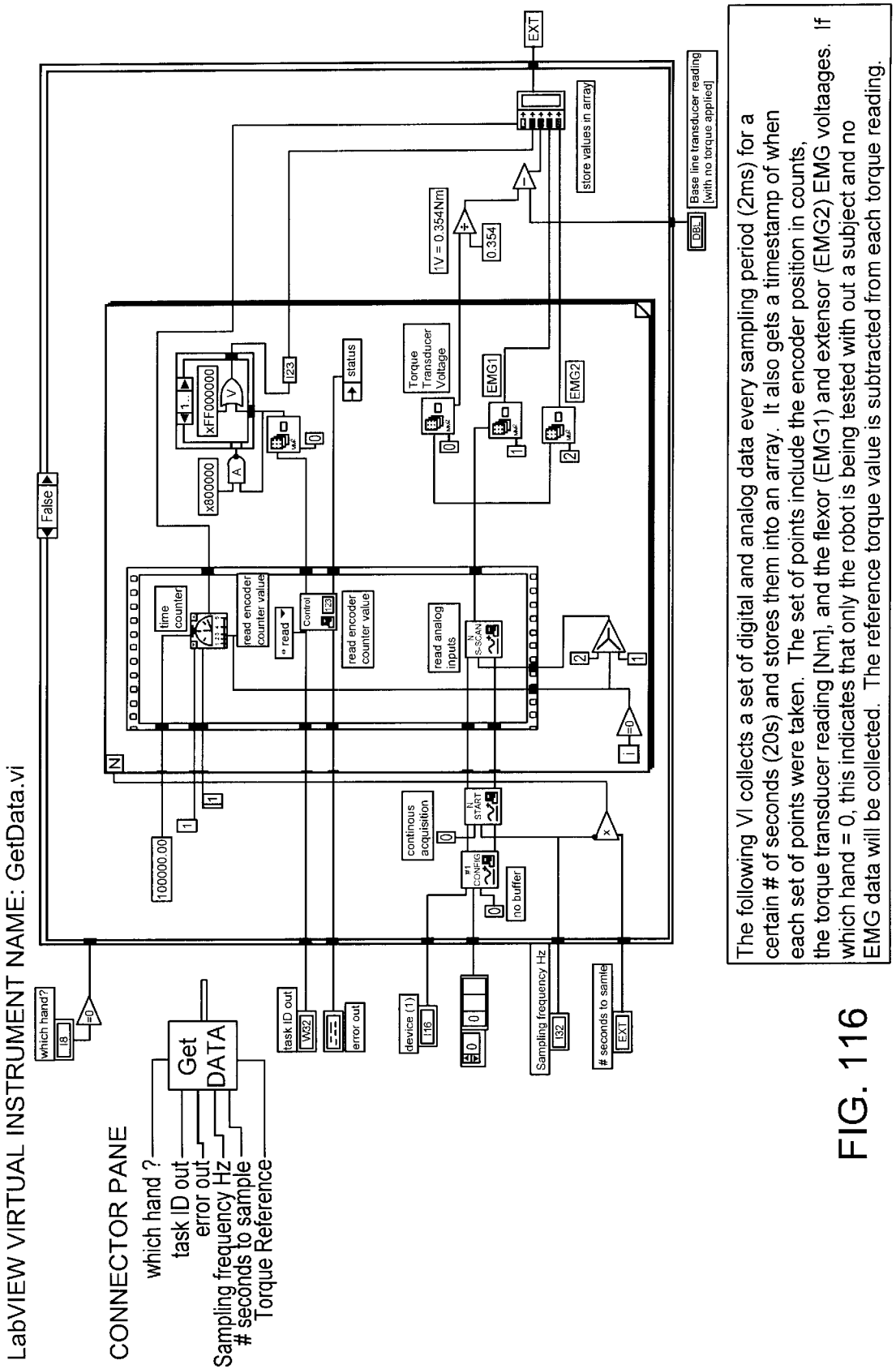
Figure 117:
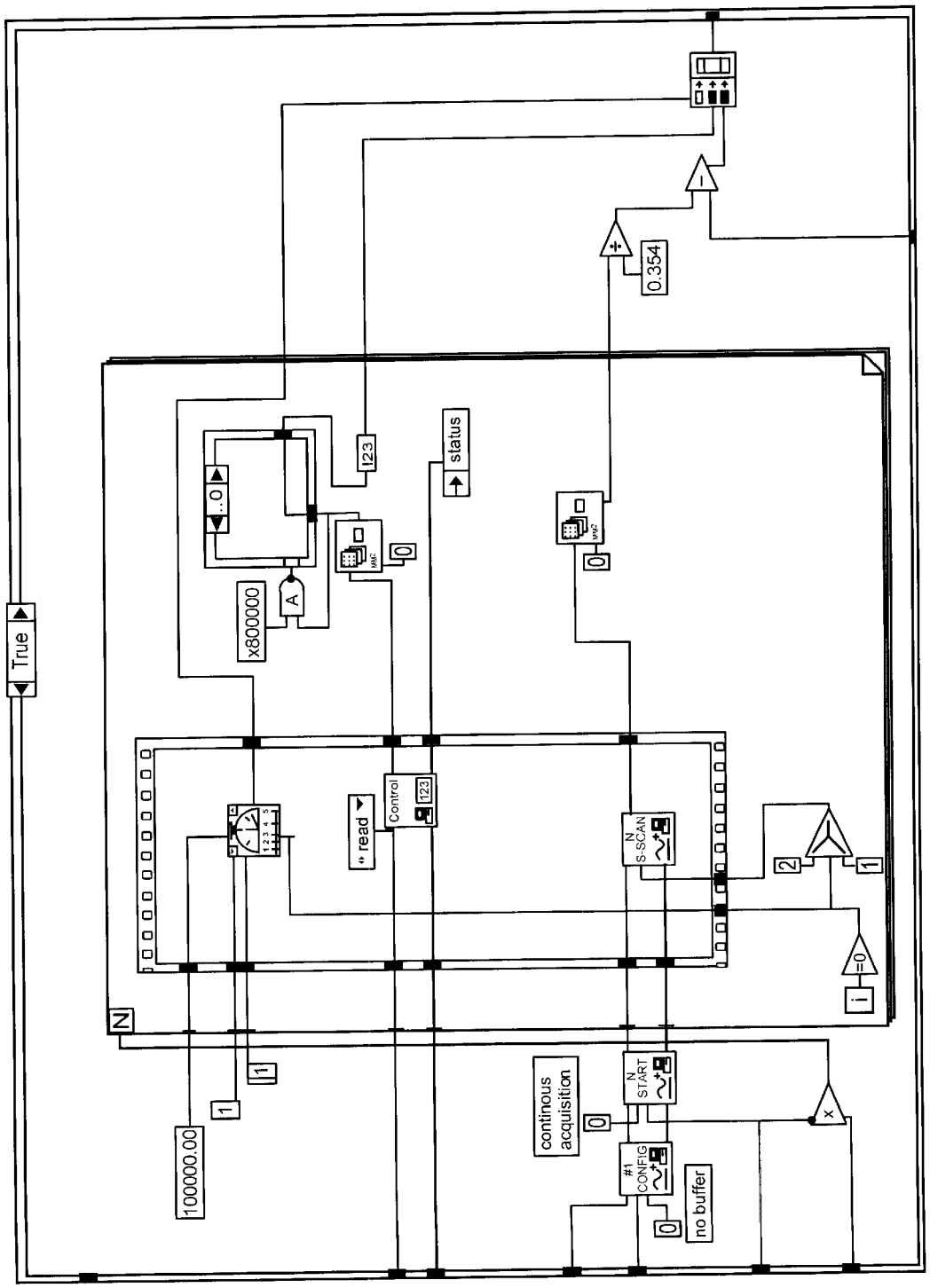
Figure 118:
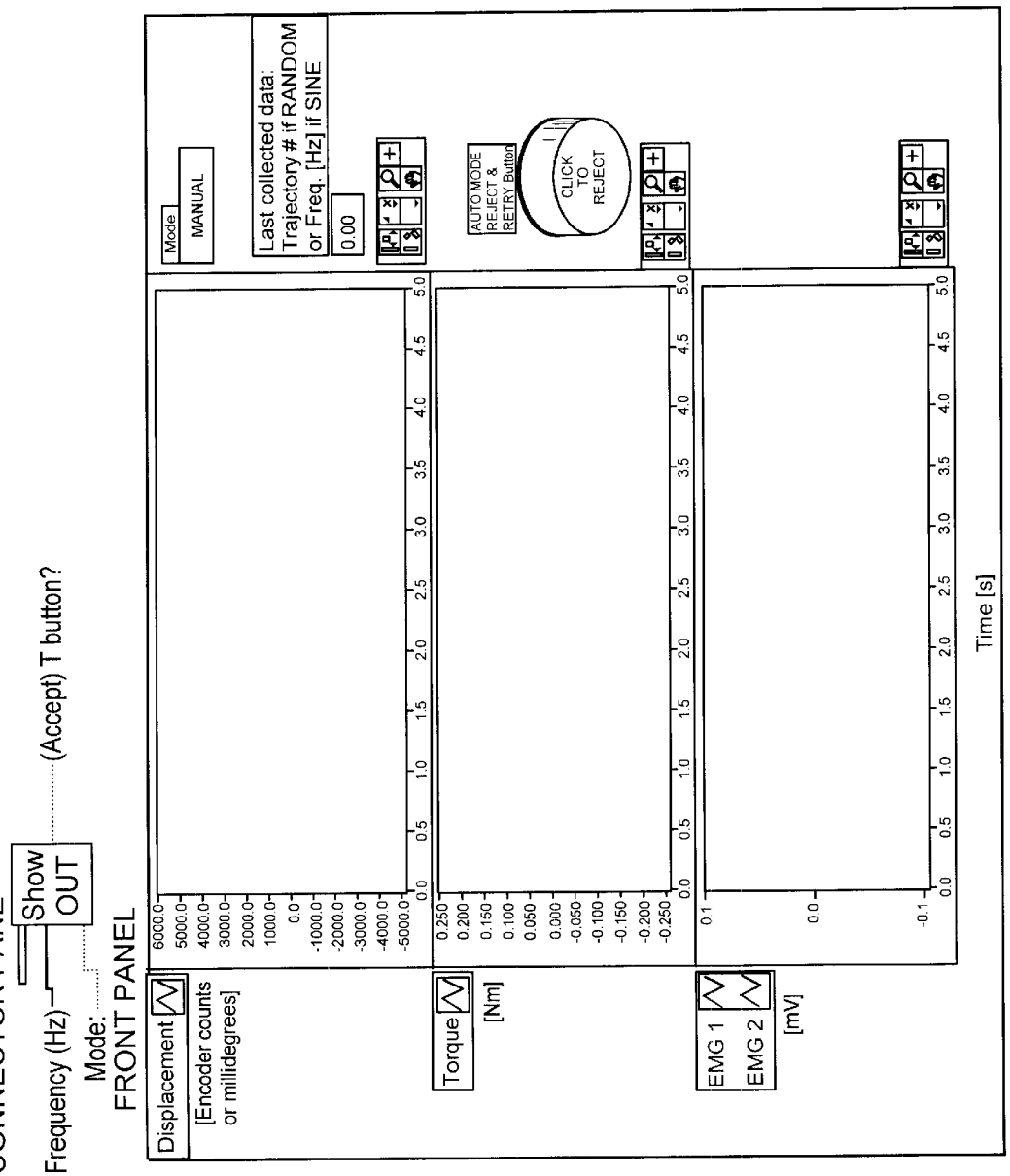
Figure 119:
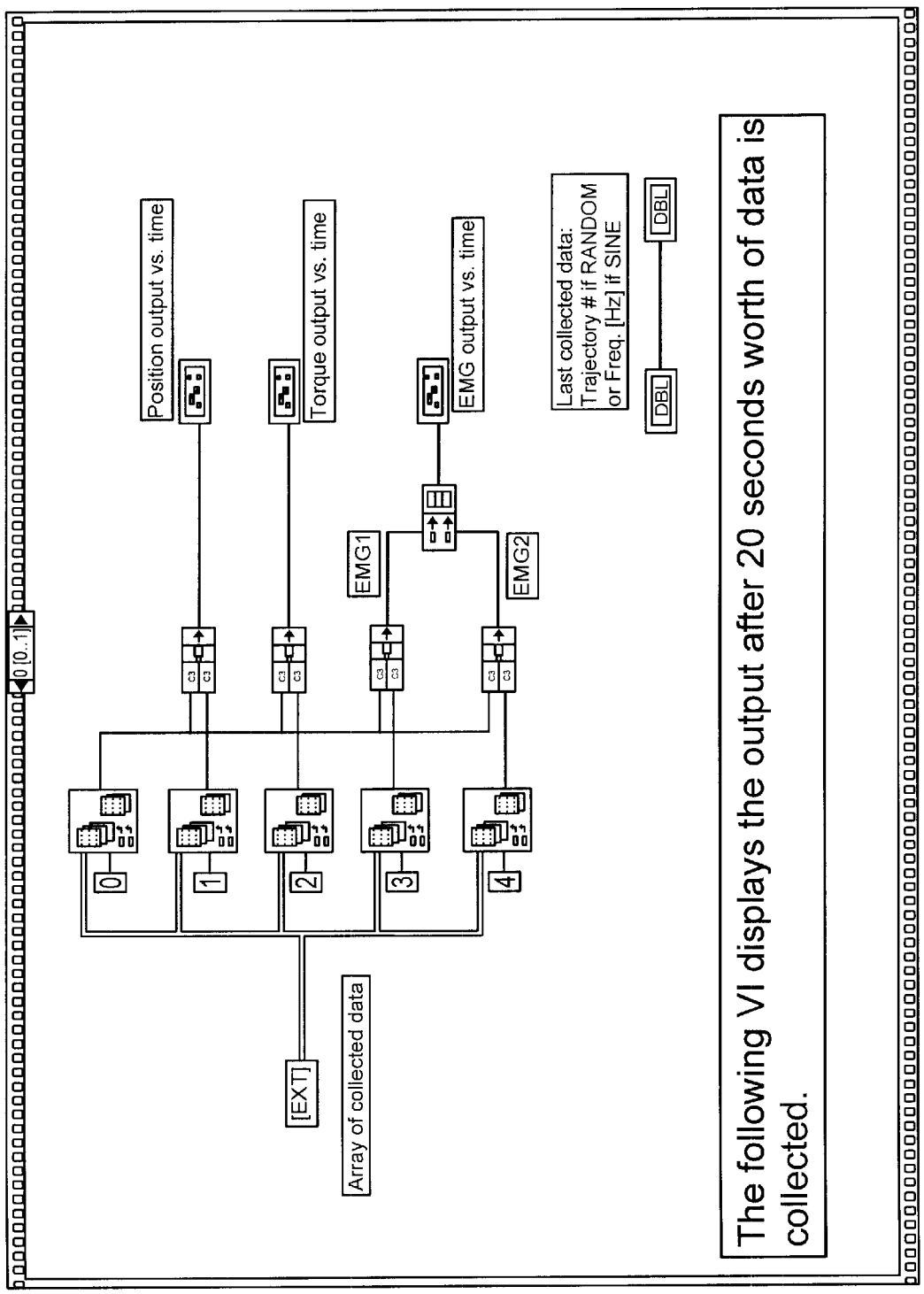
Figure 120:
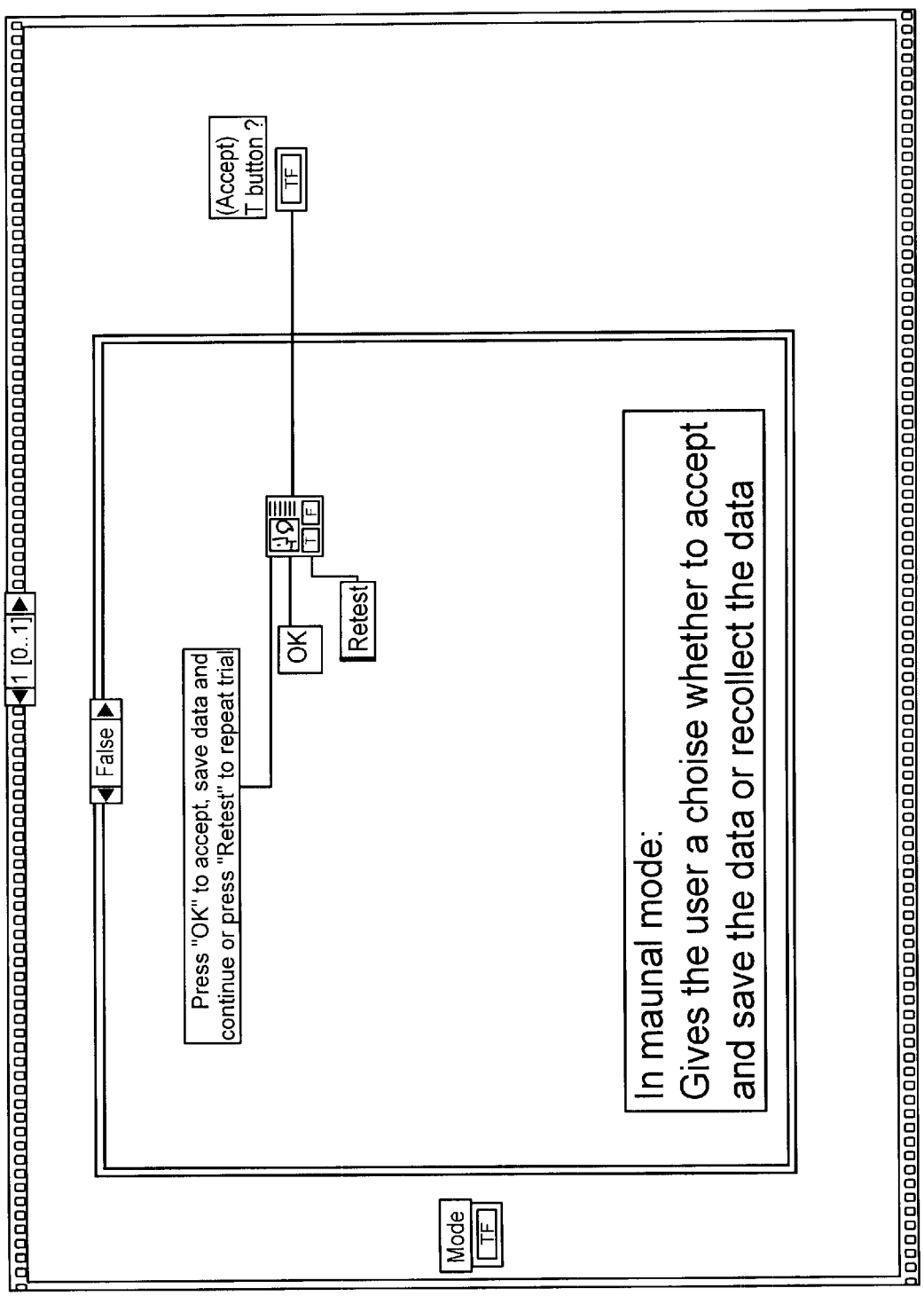
Figure 121:
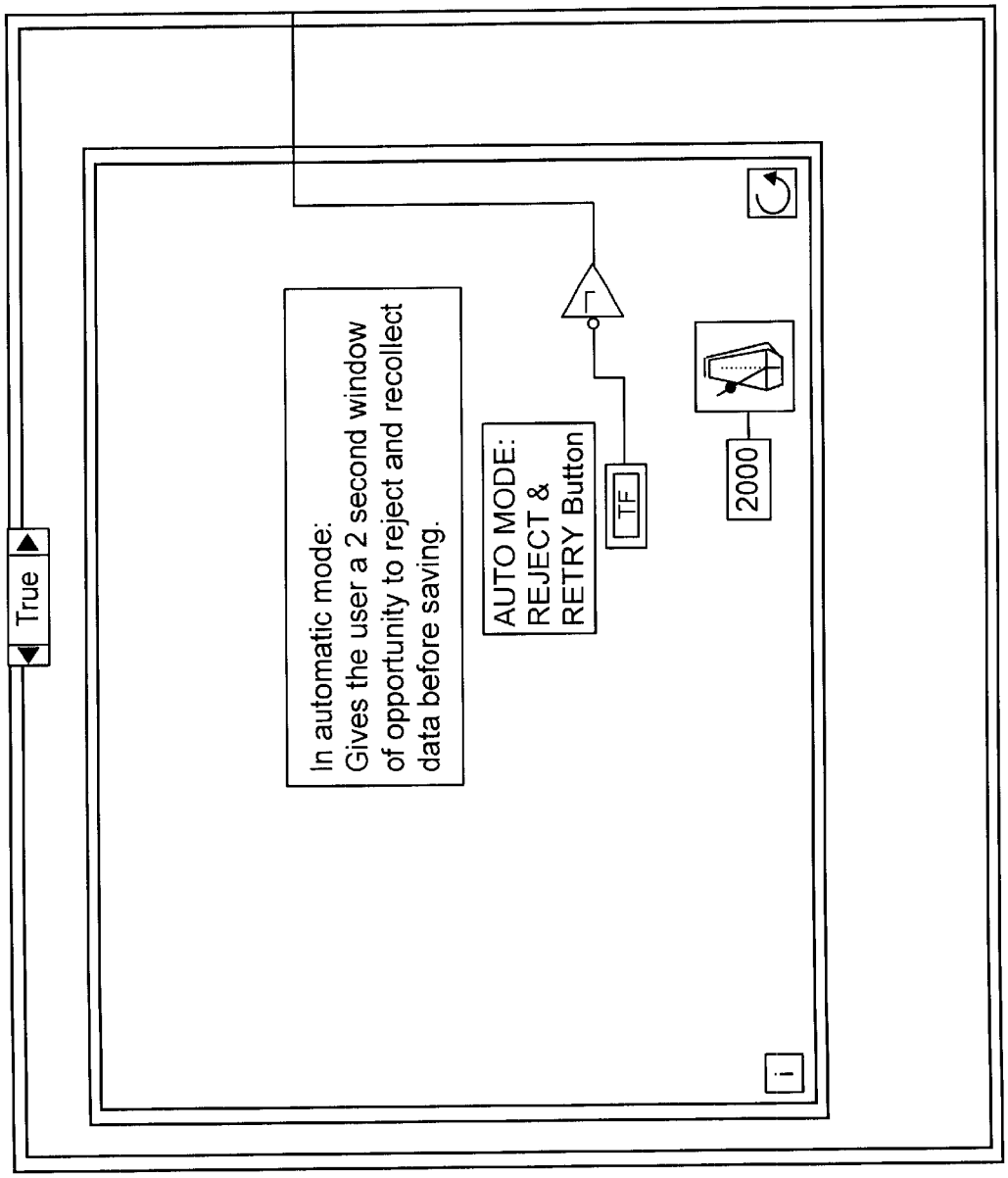
Figure 124:
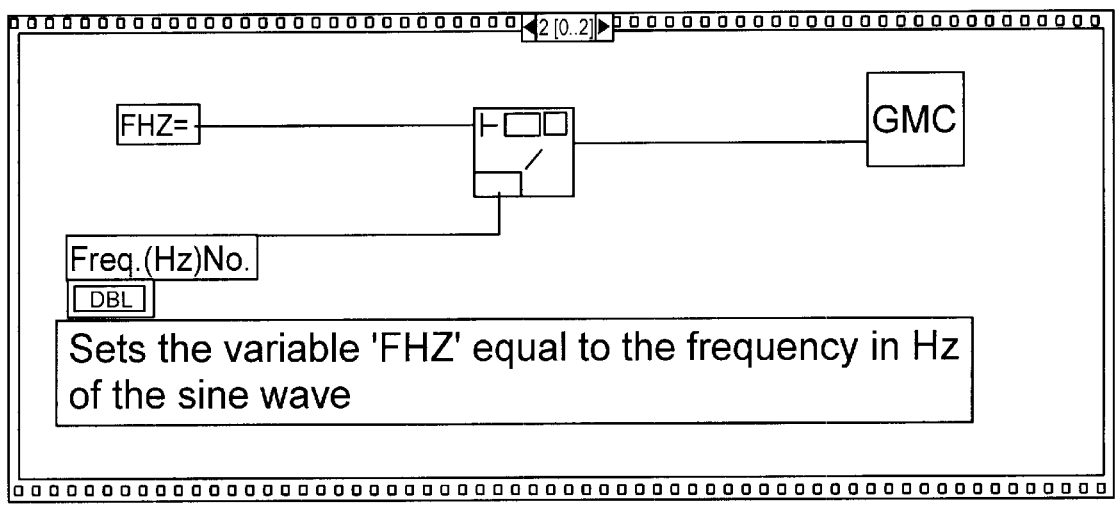
Figure 125:
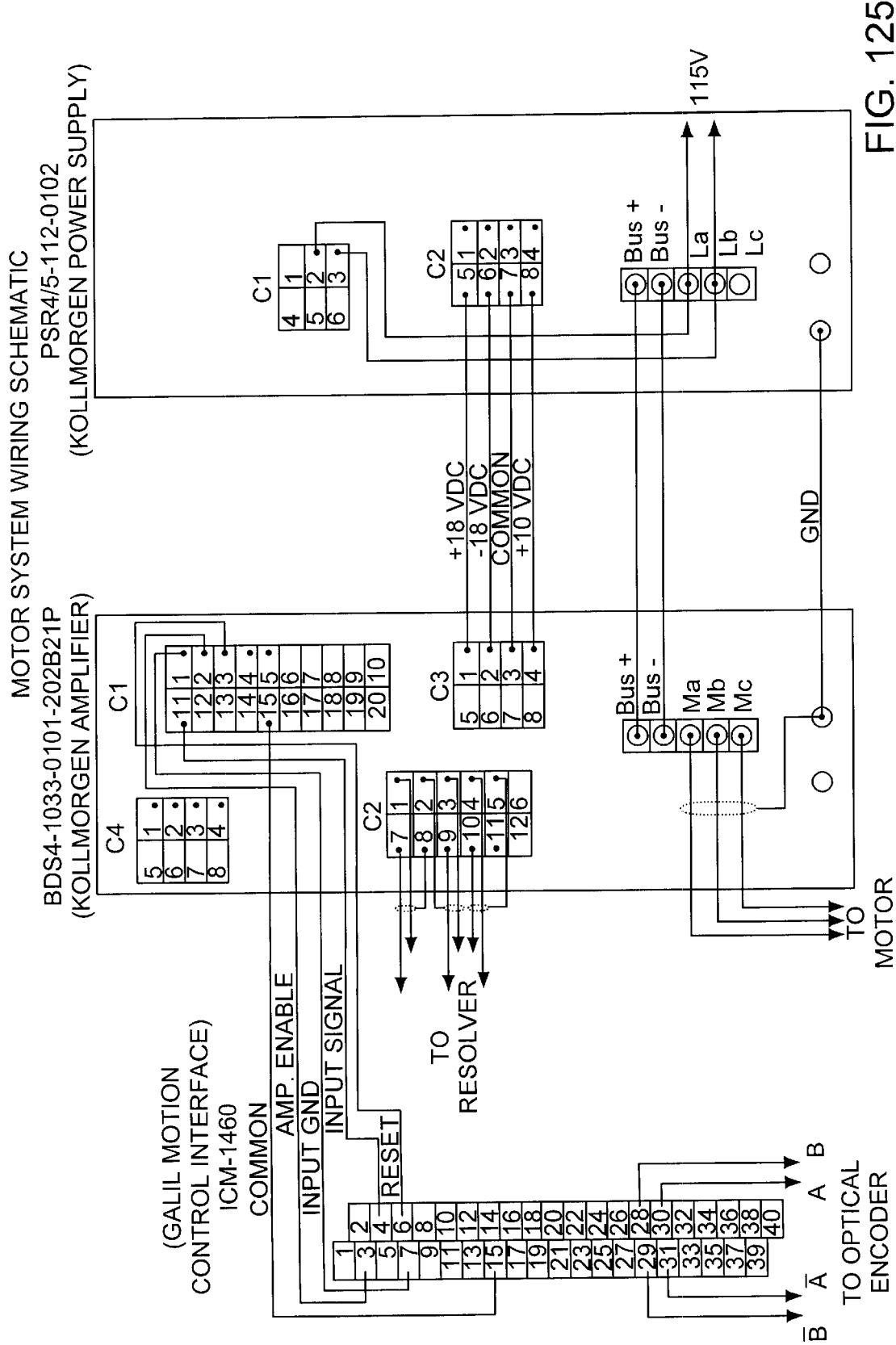
FIG. 125 shows one embodiment of the wiring schematic of the motor system in accordance with the present invention
Figure 126B:
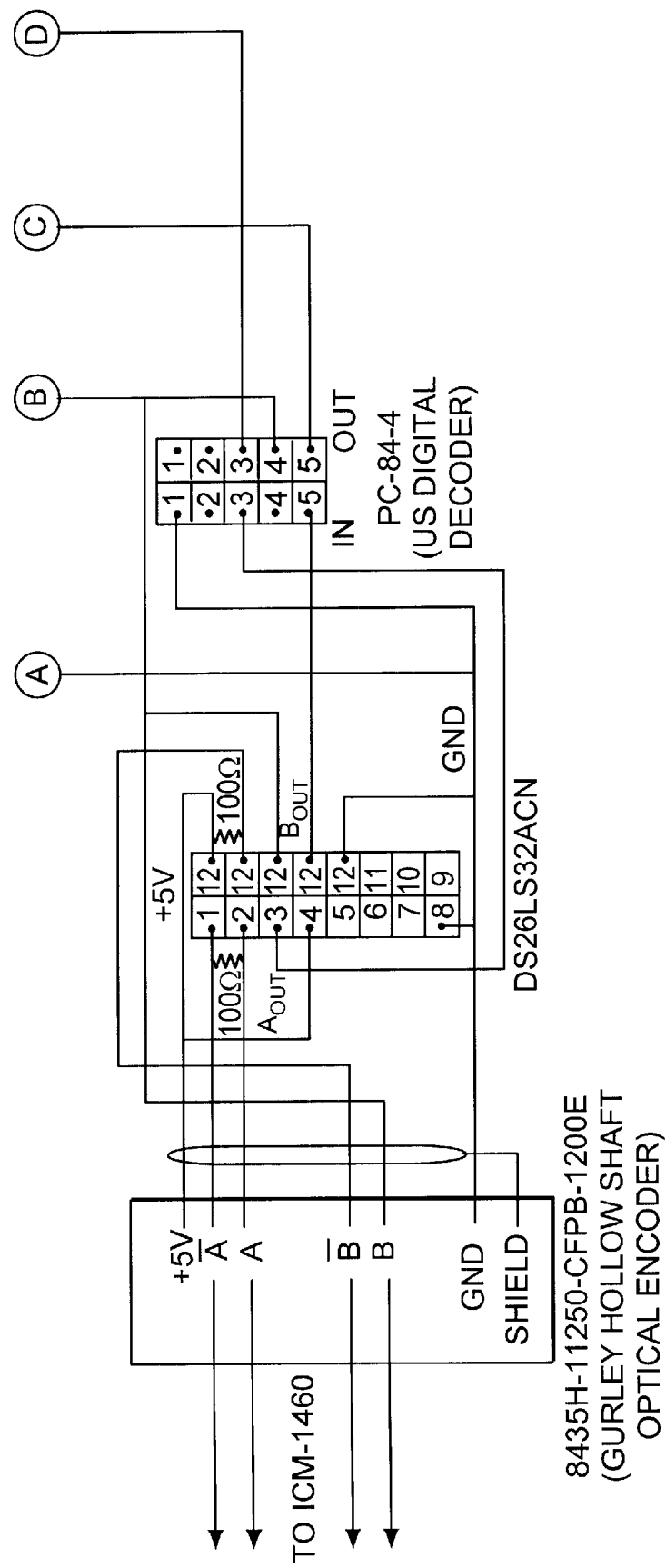
FIG. 126 shows one embodiment of the wiring schematic from the sensors to the data acquisition board in accordance with the present invention.

The average and standard deviation (denoted by the height of the error bars) of $\tau_{off}$, $\tilde{K}_H$ and $\tilde{B}_H$ values across all control adults for each trail are shown in FIG. 56. The eleventh bar shows the overall average and standard deviation across all control adults, across all ten trials.

Table 5 below shows the average and standard deviation of $\tau_{off}$, $\tilde{K}_H$ and $\tilde{B}_H$ values across all ten FIG. 56. Table 6 below shows the range of average $\tau_{off}$, $\tilde{K}_H$ and $\tilde{B}_H$ values across all ten trials in the group of adults with hemiplegic spasticity.

TABLE 5

| Hand tested (both at bias of 30 degrees flexion) | $\tilde{\tau}_{off}$ [N * m]: Torque offset towards extension | $\tilde{K}_H$ [N * m/rad]: Stiffness | $\tilde{B}_H$ [N * m * s/rad]: Viscosity |
|---|---|---|---|
| Unaffected | 0.213 ± 0.0877 | 2.062 ± 0.820 | 0.0709 ± 0.0318 |
| Affected | −0.593 ± 0.471 | 3.858 ± 1.648 | 0.0992 ± 0.0447 |

TABLE 6

| Hand tested (both at bias of 30 degrees flexion) | $\tilde{\tau}_{off}$ [N * m]: Torque offset towards extension | $\tilde{K}_H$ [N * m/rad]: Stiffness | $\tilde{B}_H$ [N * m * s/rad]: Viscosity |
|---|---|---|---|
| Unaffected | 0.144 to 0.281 | 1.220 to 2.857 | 0.0343 to 0.0916 |
| Affected | −1.1008 to −0.161 | 2.606 to 6.284 | 0.0694 to 0.166 |

Tables 5 and 6 show that at the bias position of 30 degrees flexion, the average parameter values of the unaffected or less affected arms of the hemiplegic population are still somewhat higher than when compared to the control population. This demonstrates that the tone of the less affected side of the patient group in the is still greater on average than what would be seen in the control group, though this difference is of course greater when comparing the severely affected side of the hemiplegic population with the control population. This is a fairer comparison since subjects in the control group have no known neurological disorders. When comparing the hemiplegic subjects to the controls, the observation of the negation of sign and increase in magnitude of the average torque offset values, $\tau_{off}$ across the ten trials shown by the 11$^{th}$ bars are extremely significant (p=3.0*10$^{-10}$). The increase in average stiffness, $\tilde{K}_H$ and viscosity, $\tilde{B}_H$ values across the ten trials when compared across populations are also extremely significant (p=1.5*10$^{-8}$ and p=6.5*10$^{-5}$ respectively).

On average, the stiffness and viscosity values across all trials of the control group were 1.305 N*m/rad and 0.0512 N*m*s/rad respectively. The corresponding stiffness and viscosity values of the severely affected side of the hemiplegic population were 3.858 N*m/rad and 0.0992 N*m*s/rad respectively. These elevated values when compared to those of the control group are extremely significant (p=1.5*10$^{-8}$ for stiffness and p=6.5*10$^{-5}$ for viscosity).

While the device and method have been described in detail for use in quantifying muscle tone, particularly in the wrist, in a spastic patient, the invention is not so limited. Rather, the device and method are useful on both the upper and lower extremities including, for example, the ankle. Thus, for example, the device could be modified to suit the leg and ankle accordingly. Further, the method and device can be used to measure muscle tone in the non-spastic patient. For example, the method and device can be used to measure rigidity in a patient. Further, the method and device could be used in analyzing a patient's muscle tone in line with, for example, physical therapy that the patient is undergoing to regain control of the muscles in the legs after a spinal accident.

Although a preferred embodiment of the invention has been described using specific terms, such description is for illustrative purposes only, and it is to be understood that changes and variations may be made without departing from the spirit or scope of the following claims.

What is claimed is:

1. A method for quantifying muscle tone in a patient comprising the steps of:
    moving the patient's wrist in a non-sinusoidal and non ramp trajectory and determining the stiffness, viscosity and inertial parameters using the following relationship $$\tau_s(t) = K_H \theta(t) + B_H \dot{\theta}(t) + J_T \ddot{\theta}(t) + \tau_{off}$$

where $\tau_s$ is the total torque, $\tau_{off}$ is the offset torque, $K_H$ and $B_H$ are the angular stiffness and viscosity of the combined flexor and extensor muscle groups that act on the joint, $J_T$ is the combined inertia of the oscillating appendage, $\theta$ is the angular displacement of the system, and $$\dot{\theta} \text{ and } \ddot{\theta}$$

are the velocity and acceleration.

2. A method of quantifying muscle tone in a patient comprising the steps of:
    driving the patient's wrist is in arbitrary trajectory that is neither sinusoidal nor ramp;
    controlling the trajectory θ(t);
    measuring the torque response τ(t); and
    determining the stiffness $K_H$, viscosity $B_H$, and inertial $J_T$ parameters using the relationship $$\tau_s(t) = K_H \theta(t) + B_H \dot{\theta}(t) + J_T \ddot{\theta}(t) + \tau_{off}$$

wherein where $\tau_s$ is the total torque, $\tau_{off}$ is the offset torque, $K_H$ and $B_H$ are the angular stiffness and viscosity of the combined flexor and extensor muscle groups that act on the joint, $J_T$ is the combined inertia of the oscillating appendage, θ is the angular displacement of the system, and $$\dot{\theta} \text{ and } \ddot{\theta}$$

are the velocity and acceleration.

3. A device for quantifying muscle tone in a patient comprising:
    an electromechanical system that drives the wrist of a patient with an arbitrary trajectory that is neither sinusoidal nor ramp, wherein the system includes:
    a housing having a top surface;
    a hand support on the top surface of the housing for holding the hand in a desired position;
    an arm support on the top surface of the housing for holding the arm in a desired position relative to the hand;

a motor coupled to the hand support such that the motor moves back and fourth tracking the desired trajectory and wherein the motor causes the hand to move in the desired trajectory; and an automated feedback controller for varying the torque, speed and direction of the motor.

4. The device of claim 3, wherein a discrete set of finite data points defining the trajectory is input into the controller, and wherein the motor tracks these data points.

5. The device of claim 3, wherein the hand securing mechanism comprises at least a pair of vertical bars extending upwards from the top surface of the housing and being spaced apart so the hand can be placed between the pair of vertical bars.

6. The device of claim 5, wherein the vertical bars have padding or a cushion on their outer surface.

7. The device of claim 6, wherein the padding or cushion is removable and varies in thickness for adapting the device to various sized hands.

8. The device of claim 6, wherein the padding or cushion is compressible and expandable to accommodate hands of varying sizes.

9. The device of claim 5, wherein the vertical bars are slidably attached to the housing so that the vertical bars are movable towards each other and away from each other and locked into a desired position for accommodating varying sized hands.

10. The device of claim 3, further comprising an arm securing mechanism to secure the arm in place.

11. The device of claim 3 further comprising an optical encoder for converting motion of the device and wrist into a series of digital pulses.

12. The device of claim 3 further comprising an amplifier for amplifying the command voltage from the controller into either a voltage or a current to the motor.

* * * * *